US011964977B2

(12) United States Patent
Koolman et al.

(10) Patent No.: US 11,964,977 B2
(45) Date of Patent: Apr. 23, 2024

(54) ANTHELMINTIC HETEROCYCLIC COMPOUNDS

(71) Applicants: Boehringer Ingelheim Animal Health USA Inc., Duluth, GA (US); BOEHRINGER INGELHEIM PHARMA GMBH & CO. KG, Ingelheim am Rhein (DE)

(72) Inventors: Hannes Fiepko Koolman, Biberach an der Riss (DE); Bart Herlé, Biberach an der Riss (DE); Alan Long, Biberach an der Riss (DE)

(73) Assignee: Boehringer Ingelheim Animal Health USA Inc., Duluth, GA (US)

( * ) Notice: Subject to any disclaimer, the term of this patent is extended or adjusted under 35 U.S.C. 154(b) by 0 days.

(21) Appl. No.: 17/324,288

(22) Filed: May 19, 2021

(65) Prior Publication Data

US 2021/0380591 A1 Dec. 9, 2021

Related U.S. Application Data

(60) Provisional application No. 63/031,656, filed on May 29, 2020.

(51) Int. Cl.
*A61K 31/5025* (2006.01)
*A61P 33/10* (2006.01)
*C07D 487/04* (2006.01)

(52) U.S. Cl.
CPC ............ *C07D 487/04* (2013.01); *A61P 33/10* (2018.01)

(58) Field of Classification Search
None
See application file for complete search history.

(56) References Cited

U.S. PATENT DOCUMENTS 4,464,372 A 8/1984 Bristol et al.
5,434,150 A 7/1995 Austel et al.
6,900,208 B2 5/2005 Salvati et al.
6,911,543 B2 6/2005 Walker et al.
7,030,112 B2 4/2006 Salvati et al.
7,153,854 B2 12/2006 Abe et al.
7,300,932 B2 11/2007 Fox et al.
7,306,631 B2 12/2007 Glenn, Jr. et al.
7,420,056 B2 9/2008 Kuehnert et al.
7,456,192 B2 11/2008 Imbert et al.
7,723,336 B2 5/2010 Vaccaro et al.
7,893,085 B2 2/2011 Savy et al.
7,919,628 B2 4/2011 Hachtel et al.
7,956,068 B2 6/2011 Carson et al.
7,964,204 B2 6/2011 Lahm et al.
8,030,327 B2 10/2011 Sato et al.
8,252,795 B2 8/2012 Fink et al.
8,431,593 B2 4/2013 Hutchison et al.
8,450,354 B2 5/2013 Mjalli et al.
8,772,301 B2 7/2014 Hardy et al.
9,023,850 B2 5/2015 Lahm et al.
9,556,169 B2 1/2017 Chatterjee et al.
9,718,816 B2 8/2017 Chesworth et al.
9,802,961 B2 10/2017 Clark et al.
9,868,749 B2 1/2018 Alexander et al.
9,873,703 B2 1/2018 Ali et al.
10,138,248 B2 11/2018 Buesking et al.
2004/0242587 A1 12/2004 Fu
2006/0074102 A1 4/2006 Cusack et al.
2007/0027093 A1 2/2007 Ogawa et al.
2007/0275962 A1 11/2007 Koul et al.
2011/0105457 A1 5/2011 Taniyama et al.
2011/0195933 A1 8/2011 Katz et al.
2011/0206607 A1 8/2011 Olsson et al.
2011/0245274 A1 10/2011 Nanchen et al.
2012/0065200 A1 3/2012 Barbosa et al.
2012/0083476 A1 4/2012 Breitenbucher et al.
2012/0219500 A1 8/2012 Sakurai et al.
2013/0071415 A1 3/2013 Babu et al.
2013/0203692 A1 8/2013 Soll et al.
2014/0045826 A1 2/2014 Shakespeare et al.
2014/0066434 A1 3/2014 Shakespeare
2015/0126523 A1 5/2015 Meng
2016/0106102 A1 4/2016 Kuebbeler et al.
2016/0333012 A1 11/2016 Chatterjee et al.
2017/0369486 A1 12/2017 Acharya et al.
2018/0230157 A1 8/2018 Bacon et al.
2019/0071447 A1 3/2019 Kohler et al.
2019/0233425 A1 8/2019 Bayly et al.
2019/0352275 A1 11/2019 Meldrum et al.
2020/0024264 A1 1/2020 Hubsch et al.
2020/0237771 A1 7/2020 Hallur et al.
2022/0047569 A1 2/2022 Kazmi et al.

FOREIGN PATENT DOCUMENTS

CL 202100033 7/2021
CL 202201662 6/2022
(Continued)

OTHER PUBLICATIONS

Database Registry Chemical Abstracts Service, Columbus, Ohio, Accession No. RN 2415490-08-1, Entered STN: May 1, 2020.*
(Continued)

*Primary Examiner* — Samantha L Shterengarts

(57) ABSTRACT

This invention provides for compounds of the formula:

(I)

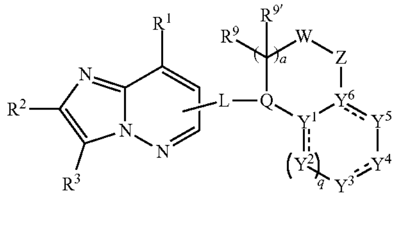

wherein the variables are defined herein, or salt thereof, compositions comprising these compounds, and method for the treatment, control or prevention of a parasitic infestation or infection in an animal in need thereof by administering an effective amount of these compounds to said animal.

41 Claims, No Drawings

(56) References Cited

FOREIGN PATENT DOCUMENTS

| | | | |
|---|---|---|---|
| CL | 202201739 | | 6/2022 |
| CL | 202202346 | | 8/2022 |
| EP | 1277754 | B1 | 7/2005 |
| EP | 3078664 | A1 | 10/2016 |
| EP | 3643711 | A1 | 4/2020 |
| JP | 2009203214 | A | 9/2009 |
| JP | 2011140452 | A | 7/2011 |
| JP | 2012012299 | A | 1/2012 |
| JP | 2016505529 | A | 2/2016 |
| WO | 2000053602 | A1 | 9/2000 |
| WO | 2005/066177 | A1 | 7/2005 |
| WO | 2006004191 | A1 | 1/2006 |
| WO | 2007123855 | A2 | 11/2007 |
| WO | 2008019309 | A1 | 2/2008 |
| WO | 2010017046 | A1 | 2/2010 |
| WO | 2011058109 | A1 | 5/2011 |
| WO | 2011075591 | A1 | 6/2011 |
| WO | 2011137587 | A1 | 11/2011 |
| WO | 2011146401 | A1 | 11/2011 |
| WO | 2012100342 | A1 | 8/2012 |
| WO | 2012107533 | A1 | 8/2012 |
| WO | 2014078802 | A1 | 5/2014 |
| WO | 2015066277 | A1 | 5/2015 |
| WO | 2017093180 | A1 | 6/2017 |
| WO | 2017125898 | A1 | 7/2017 |
| WO | 2017/178416 | A1 | 10/2017 |
| WO | 2018/087036 | A1 | 5/2018 |
| WO | 2018/197401 | A1 | 11/2018 |
| WO | 2019/002132 | A1 | 1/2019 |
| WO | 2019/025341 | A1 | 2/2019 |
| WO | 2019/115768 | A1 | 6/2019 |
| WO | 2019/215182 | A1 | 11/2019 |
| WO | 2020/014068 | A1 | 1/2020 |
| WO | 2020002124 | A1 | 1/2020 |
| WO | 2020012336 | A1 | 1/2020 |
| WO | 2020/083971 | A1 | 4/2020 |
| WO | 2020/131629 | A1 | 6/2020 |
| WO | 2020/131631 | A1 | 6/2020 |
| WO | 2020/191091 | A1 | 9/2020 |
| WO | 2020219871 | A1 | 10/2020 |
| WO | 2020/247747 | A1 | 12/2020 |
| WO | 2021/018839 | A1 | 2/2021 |
| WO | 2021030379 | A1 | 2/2021 |
| WO | 2021032934 | A1 | 2/2021 |
| WO | 2021/127443 | A1 | 6/2021 |
| WO | 2021122906 | A1 | 6/2021 |
| WO | 2021122911 | A1 | 6/2021 |
| WO | 2021/130731 | A1 | 7/2021 |
| WO | 2021/173713 | A1 | 9/2021 |
| WO | 2021204930 | A1 | 10/2021 |
| WO | 2021231571 | A1 | 11/2021 |
| WO | 2022106469 | A2 | 5/2022 |
| WO | 2022117783 | A1 | 6/2022 |
| WO | 2022122987 | A1 | 6/2022 |
| WO | 2022122988 | A1 | 6/2022 |
| WO | 2022152918 | A1 | 7/2022 |

OTHER PUBLICATIONS

Database Registry [Online], May 1, 2020 (May 1, 2020), Life Chemicals Inc.: "Imidazo[1,2-b]pyridazine-6-carboxamide, N-(1,2,3,4-tetrahydro-1-naphthalenyl)-", XP055837558, Database accession No. 2415490-08-1 compound with the Registry No. 2415490-08-1.

Preston, "Low cost whole-organism screening of compounds for anthelmintic activity", International Journal for Parasitology, vol. 45, pp. 333-343, 2015.

Database Registry (Online) Chemical Abstracts Service, Columbus, Ohio, US; Jul. 17, 2016, XP002799055, Database accession No. 1953874-77-5, 2-Benzofurancarboxamide,3,4,7-trimethyl-N-(octahydro-4-benzofuranyl)-.

Database Registry (Online) Chemical Abstracts Service, Columbus, Ohio, US; Oct. 15, 2017, XP002799056, Database accession No. 2134947-60-5, 2-Benzofurancarboxamide,3,4,7-trimethyl-N-(4,5,6,7-tetrahydro-1-methyl-1H-indazol-4-yl)-.

Database Registry (Online) Chemical Abstracts Service, Columbus, Ohio, US; Aug. 15, 2011, XP002799057, Database accession No. 1318005-39-8, 2-Benzofurancarboxamide, N-(6-bromo-3,4-dihydro-2H-1-benzopyran-4-yl)-3,7-dimethyl-.

Database Registry (Online) Chemical Abstracts Service, Columbus, Ohio, US; Dec. 23, 2015, XP002799058, Database accession No. 1835595-46-4, 2-Benzofurancarboxamide, N-(6-amino-1,2,3,4-tetrahydro-1-haphthalenyl)-3,4,7-trimethyl-, hydrochloride (1:1).

Database Registry (Online) Chemical Abstracts Service, Columbus, Ohio, US; Nov. 18, 2018, XP002799059, Database accession No. 2249355-47-1, 2-Benzofurancarboxamide, N-(6,7-dihydro-5H-pyrrolo[1,2-a]imidazol-7-yl)-3,7-dimethyl-.

Database Registry (Online) Chemical Abstracts Service, Columbus, Ohio, US; Jul. 4, 2016, XP002799060, Database accession No. 1944784-28-4, 2-Benzofurancarboxamide, 5-bromo-7-methyl-N-(4,5,6,7-tetrahydro-2-methyl-2H-indazol-4-yl)-.

* cited by examiner

ANTHELMINTIC HETEROCYCLIC COMPOUNDS

CROSS REFERENCE TO RELATED APPLICATIONS

This application claims the benefit of priority to U.S. Provisional Application No. 63/031,656 filed May 29, 2020, which is incorporated herein by reference in its entirety.

FIELD OF THE INVENTION

This patent application relates to new antiparasitic compounds, compositions comprising the compounds, processes for their preparation, and methods of using the compounds to control parasites that harm animals and humans.

BACKGROUND OF THE INVENTION

Animals, such as mammals and birds, are often susceptible to parasite infestations. These parasites may be ectoparasites, such as fleas and ticks. Animals and humans also suffer from endoparasitic infections including, for example, helminthiasis which is most frequently caused by a group of parasitic worms described as nematodes or roundworms. These parasites cause severe economic losses in pigs, sheep, horses, and cattle as well as affecting companion animals (e.g. cats and dogs) and poultry. Other parasites include those which occur in the gastrointestinal tract of animals and humans such as *Ancylostoma, Necator, Ascaris, Strongyloides, Trichinella, Capillaria, Toxocara, Toxascaris, Trichuris* and *Enterobius*. Other parasites which are found in the blood or other tissues and organs include filarial worms and the extra intestinal stages of *Strongyloides* and *Trichinella.*

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period." L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet. Parasitol.* 2005 Oct. 24 133(2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al., (*Vet. Parasitol.* 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. Heartworm Preventive Resistance. Is it Possible, vol. 37. Bulletin of the American Heartworm Society, pp. 5). Thus, there is an ongoing need to develop new anthelmintic agents with improved activity against *Dirofilaria immitis* and other endoparasites.

WO 2017/178416 A1 provides pyrazolopyrimidine derivatives for the control, treatment and/or prevention of helminths. WO 2018/197401 A1 provides bicyclic pyrazole derivatives for the control, treatment and/or prevention of helminths. WO 2018/087036 A1 provides quinolone-3-carboxamide derivatives for the control, treatment and/or prevention of helminths. WO 2019/025341 provides quinoline compounds for the treatment, control and/or prevention of helminth infections and WO 2019/002132 A1 azaquinone derivatives for the control, treatment and/or prevention of helminths. All these publications are to Bayer Animal Health GmbH and are incorporated herein by reference in their entirety.

More recently WO 2020/014068 A1 (incorporated herein by reference) describes anthelmintic heterocyclic compounds that were found to be active against *Dirofilaria immitis.*

It is expressly noted that citation or identification of any document in this application is not an admission that such document is available as prior art to the present description. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the description.

SUMMARY OF THE INVENTION

The present application provides for novel anthelmintic and antiparasitic heterocyclic compounds with improved activity against endoparasites and ectoparasites. The application is also directed to compositions comprising the compounds, methods and uses of the compounds for eradicating, controlling, and/or preventing a parasitic infection and/or infestation in animals including humans. The compounds may be administered to animals, particularly mammals, fish and birds, to prevent and/or treat parasitic infections.

An aspect of the present invention includes a compound of Formula (I):

(I)

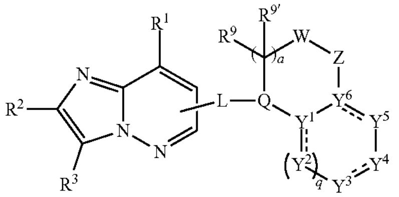

a stereoisomer, tautomer, N-oxide, hydrate, solvate, or salt thereof, wherein variables $R^1$, $R^2$, $R^3$, $R^9$, $R^{9'}$, $Y^1$, $Y^2$, $Y^3$, $Y^4$, $Y^5$, $Y^6$, L, Q, W, Z, a and q are defined herein, and the dashed bonds (- - - -) signifies a single or double bond.

The invention also includes a veterinarily acceptable composition comprising a compound of Formula (I) and a veterinarily acceptable carrier and a method of controlling parasites, including helminths, comprising administering the compound, or the veterinarily acceptable composition thereof, to an animal in need thereof. An embodiment of the invention also includes the use of the compound of Formula (I) for eradicating, controlling, and/or preventing a parasitic infection and/or infestation in animals or humans. The compounds of the invention may be administered to animals, particularly mammals, fish and birds, to prevent and/or treat parasitic infections and/or infestations.

The compound and compositions comprising the compound are highly effective for the treatment and/or prophylaxis of internal parasites in mammals, fish and birds, and in particular, cats, dogs, horses, chickens, pigs, sheep and cattle, with the aim of substantially ridding these hosts of endoparasites.

In an embodiment, compounds of Formula (I) and compositions comprising said compounds are substantially effective against endoparasites, such as filariae (e.g. heartworm), and hookworms, whipworms and roundworms of the digestive tract of animals and humans. In certain embodiments, compounds of Formula (I) and compositions comprising said compounds are effective against *Dirofilaria immitis* (heartworm) isolates that are less sensitive to treatment with macrocyclic lactones. In another embodiment, the compounds and compositions of the invention are effective for treating and/or preventing infections of animals with nematodes that are less sensitive to treatment with commercially available or known active agents.

In an embodiment, the description includes a combination of a compound of Formula (I) with at least a second active agent, which may broaden the scope of protection afforded to animals against endoparasites and/or ectoparasites.

Another embodiment includes a method for the treatment and/or prevention of a parasitic infection and/or infestation in an animal comprising administering a compound of Formula (I) to the animal. Another embodiment includes a use of a compound of Formula (I) for the treatment and/or prevention of a parasitic infection and/or infestation in an animal and the use of the compound of Formula (I) in the preparation of a medicament for the treatment and/or prevention of a parasitic infection in an animal.

Thus, the invention includes the following non-limiting embodiments:

(a) a compound of Formula (I) or a pharmaceutically or a veterinarily acceptable salt thereof, which is an active endoparasiticide and in some cases is also active against ectoparasites;

(b) a veterinary composition comprising a parasiticidally effective amount of a compound of Formula (I), or a pharmaceutically or veterinarily acceptable salt thereof, in combination with a pharmaceutically or veterinarily acceptable carrier or diluent;

(c) a veterinary composition comprising a parasiticidally effective amount of a compound of Formula (I), or a pharmaceutically or veterinarily acceptable salt thereof, in combination with one or more additional active agents (i.e., active ingredient not encompassed by Formula (I)) and a pharmaceutically or veterinarily acceptable carrier or diluent;

(d) a method for treating a parasitic infection and/or infestation in or on an animal comprising administering a parasiticidally effective amount a compound of Formula (I), or a pharmaceutically or veterinarily acceptable salt thereof, optionally with one or more additional active agents (i.e., active ingredient not encompassed by Formula (I)), to the animal in need thereof;

(e) a method for the prevention of a parasitic infection and/or infestation of an animal, which comprises administering a parasiticidally effective amount of a compound of Formula (I), or a pharmaceutically or a veterinarily acceptable salt thereof, optionally with one or more additional active agents (i.e., active ingredient not encompassed by Formula (I)), to the animal in need thereof;

(f) the use of a compound of Formula (I), or a pharmaceutically or a veterinarily acceptable salt thereof, optionally with one or more additional active agents (i.e., active ingredient not encompassed by Formula (I)), for the treatment and/or prevention of a parasitic infection and possibly also a parasitic infestation in an animal;

(g) a use of a compound of Formula (I), or a pharmaceutically or veterinarily acceptable salt thereof, optionally with one or more additional active agents (i.e., active ingredient not encompassed by Formula (I)), for the manufacture of a veterinary medicament for the treatment and/or prevention of a parasitic infection and/or infestation in an animal; and (h) a process for the preparation of a compound of Formula (I).

These and other embodiments are disclosed or are obvious from and encompassed by, the following Detailed Description.

Definitions

It is noted that in this disclosure and particularly in the claims and/or paragraphs, terms such as "comprises", "comprised", "comprising" and the like can be interpreted as "includes", "included", "including", and the like; and that terms such as "consisting essentially of" and "consists essentially of" are interpreted as allowing for elements not explicitly recited, but excluding elements that are found in the prior art or that affect a basic or novel characteristic of the invention.

Terms used herein will have their customary meanings in the art unless otherwise specified. The organic moieties mentioned in the definitions of the variables of the compounds e.g., the compound of formula (I) are like the term halogen—i.e., collective terms for individual listings of the individual group members—fluoro, chloro, bromo and iodo with respect to halogen. The prefix Cn-Cm indicates in each case the possible number of carbon atoms in the group from an integer n to another integer m.

In the present specification and claims the term "including but not limited to" is equivalent to "included".

The term "compound of Formula (I)" includes any stereoisomer, tautomer, N-oxide, hydrate, solvate, or salt thereof.

By the term "optionally substituted" is meant a radical that is optionally substituted by one or more of the following moieties: halogen, hydroxyl, alkyl, haloalkyl, carboxyl, acyl, acyloxy, alkylcarbonyl, haloalkylcarbonyl, alkoxycarbonyl, haloalkoxycarbonyl, aminocarbonyl, alkylaminocarbonyl, dialkylaminocarbonyl, haloalkylaminocarbonyl, dihaloalkylaminocarbonyl, amino, alkyl- or dialkylamino, amido, arylamino, alkoxy, haloalkoxy, aryloxy, nitro, cyano, azido, thiol, thioamide, imino, amidine, guanidine, carbonate, silyl, silyl ether, $SF_5$, sulfonic acid, sulfate, sulfonyl, alkoxysulfonyl, sulfanyl, sulfinyl, sulfamoyl, sulfoximine, sulfinimine, sulfonimidamide, sulfonediimine, ester, phosphonyl, phosphinyl, phosphoryl, phosphine, phosphonamidate, phosphinamidate, phosphinate, phosphine oxide, thioester, thioether, acid halide, anhydride, oxime, hydrazine, carbamate, phosphonic acid, phosphate, phosphonate, aryl, and heteroaryl.

In some embodiments, the term "optionally substituted" includes substitution of a core group with halogen (chloro, fluoro, bromo, iodo), $C_1$-$C_6$-alkyl, $C_1$-$C_6$-haloalkyl, 3- to 8-membered cycloalkyl, amino, $C_1$-$C_6$-alkylamino, $C_1$-$C_6$-dialkylamino, $C_1$-$C_6$-alkoxy, $C_1$-$C_6$-haloalkoxy, cyano, nitro, $SF_5$, acetyl, $C_1$-$C_6$-alkoxy carbonyl, $C_1$-$C_6$-haloalkoxycarbonyl, $C_1$-$C_6$-alkyl carbonyl, $C_1$-$C_6$-haloalkylcarbonyl, aminocarbonyl, $C_1$-$C_6$-alkylaminocarbonyl, $C_1$-$C_6$-dialkylaminocarbonyl, $C_1$-$C_6$-haloalkylaminocarbonyl, $C_1$-$C_6$-dihaloalkylaminocarbonyl, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, phenyl, 5- or 6-membered heteroaryl, 5- or 6-membered heterocyclyl.

In other embodiments, the term "optionally substituted" includes substitution of a core group with halogen (chloro, fluoro, bromo, iodo), $C_1$-$C_3$-alkyl, $C_1$-$C_3$-haloalkyl, 3- to 8-membered cycloalkyl, amino, $C_1$-$C_3$-alkylamino, $C_1$-$C_3$-dialkylamino, $C_1$-$C_3$-alkoxy, $C_1$-$C_3$-haloalkoxy, cyano, nitro, $SF_5$, acetyl, $C_1$-$C_3$-alkoxy carbonyl, $C_1$-$C_3$-haloalkoxycarbonyl, $C_1$-$C_3$-alkylcarbonyl, $C_1$-$C_3$-haloalkylcarbonyl, aminocarbonyl, $C_1$-$C_3$-alkylaminocarbonyl, $C_1$-$C_3$-dialkylaminocarbonyl, $C_1$-$C_3$-haloalkylaminocarbonyl, $C_1$-$C_3$-dihaloalkylaminocarbonyl, $C_1$-$C_3$-alkylthio, $C_1$-$C_3$-alkylsulfinyl, $C_1$-$C_3$-alkylsulfonyl, $C_1$-$C_3$-haloalkylthio, $C_1$-$C_3$-haloalkylsulfinyl, $C_1$-$C_3$-haloalkylsulfonyl, phenyl, 5- or 6-membered heteroaryl, 5- or 6-membered heterocyclyl.

In certain embodiments, the term "optionally substituted" includes substitution by halogen (chloro, fluoro, bromo and iodo), methyl, ethyl, propyl, butyl, cyclopropyl, cyclobutyl, cyclopentyl, cyclohexyl, hydroxyl, thiol, amino, methylamino, ethylamino, propylamino, butylamino, dimethylamino, diethylamino, methoxy, ethoxy, propoxy, $CF_3$, $CF_2CF_3$, $—OCF_3$, $—OCF_2CF_3$, $—SCH_3$, $—SCF_3$, $—S(O)CH_3$, $—S(O)CF_3$, $—S(O)_2CH_3$, $—S(O)_2CF_3$, morpholino, piperidinyl, pyridyl and phenyl.

In some embodiments the compounds may be substituted with a viable functional group that does not inhibit the biological activity of the compounds of the description, either unprotected, or protected as necessary, as known to those skilled in the art, for example, as taught in Greene and Wuts, Protective Groups in Organic Synthesis, John Wiley and Sons, Third Edition, 1999, hereby incorporated by reference. For avoidance of doubt, "optionally substituted alkyl" includes haloalkyl and hydroxyalkyl.

Unless otherwise stated, "alkyl" means, either alone or in combination with a heteroatom, e.g., alkoxy, thioalkyl, alkylamino, and the like, saturated straight, branched, primary, secondary or tertiary hydrocarbons, including those having 1 to 12 atoms. In some embodiments, alkyl groups will include $C_1$-$C_{10}$, $C_1$-$C_8$, $C_1$-$C_6$, $C_1$-$C_4$ or $C_1$-$C_3$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

"Carbocyclic" groups are cyclic groups composed exclusively of carbon. The carbocyclic groups include both aromatic rings such as phenyl and non-aromatic rings such as cycloalkyl rings including cyclopropyl, cyclobutyl, cyclopentyl, cyclohexyl, and the like, and include those with 3 to 14 carbon atoms having single or multiple fused rings.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$, $C_2$-$C_4$, or $C_3$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "Alkenyl" groups may include more than one double bond in the chain. Examples of alkenyl or a specific range thereof include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkynyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

The term "alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, —$SF_5$, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, $(—CH_2—)_n$, where n is 1-12 and where "aryl" is as defined above.

The term "heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Heteroaryl groups will typically include a 5- or 6-membered aromatic ring. Such heteroaryl groups can have a single ring (e.g., pyridyl or furyl) or multiple fused rings provided that the point of attachment is through a heteroaryl ring atom.

Examples of heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl, or pyrrolopyrimidyl. Heteroaryl rings may be unsubstituted or substituted by one or more moieties as described for aryl above.

The term "heterocyclyl," "heterocyclic" or "heterocyclo" refers to fully saturated or partially unsaturated, but non-aromatic cyclic groups, for example, 3 to 7 membered monocyclic, 7 to 11 membered bicyclic, or 10 to 15 membered tricyclic ring systems, which have one or more oxygen, sulfur, silicon or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Bicyclic and tricyclic carbocyclic or heterocyclic ring systems include spirocyclic systems in which at least two of the rings in the system are connected through a single carbon atom. The spirocyclic ring systems will include a combination of from 3- to 8-membered carbocyclic and/or heterocyclic ring systems joined at a common carbon atom. Thus, the spirocyclic ring systems may include a 3-membered ring bonded to another 3-membered ring (either carbocyclic or heterocyclic) to an 8-membered ring bonded to another 8-membered ring and all the combinations of different ring sizes between. The heterocyclic ring component of a spirocyclic ring system will include one or two heteroatoms selected from N, O, Si or S.

The term "alkylthio" refers to alkyl-S—, where "alkyl" is as defined above. In some embodiments, the alkyl component of the alkylthio group will include $C_1$-$C_{10}$, $C_1$-$C_8$, $C_1$-$C_6$, $C_1$-$C_4$ or $C_1$-$C_3$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio", "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(═O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$, $C_1$-$C_4$ or $C_1$-$C_3$ alkyl groups. Examples include, but are not limited to, —SO—$CH_3$, —SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylsulfinyl," "alkynylsulfinyl," "haloalkylsulfinyl," "haloalkenylsulfinyl," and "haloalkynylsulfinyl" refer to the groups alkenyl-S(═O)—, alkynyl-S(═O)—, and haloalkyl-S(═O)—, haloalkenyl-S(═O)—, and haloalkynyl-S(═O)—, where the terms "alkenyl," "alkynyl," "haloalkyl," "haloalkenyl," and "haloalkynyl" are as defined above.

The term "alkylsulfonyl" refers to the group alkyl-S(═O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —$SO_2$—$CH_3$, —$SO_2$—$C_2H_5$, n-propylsulfonyl, —$SO_2$—$CH(CH_3)_2$, n-butylsulfonyl, 1-methylpropylsulfonyl, 2-methylpropylsulfonyl, —$SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The terms "alkenylsulfonyl," "alkynylsulfonyl," "haloalkylsulfonyl," "haloalkenylsulfonyl," and "haloalkynylsulfonyl" refer to the groups alkenyl-S(═O)$_2$—, alkynyl-S(═O)$_2$—, and haloalkyl-S(═O)$_2$—, haloalkenyl-S(═O)$_2$—, and haloalkynyl-S(═O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

The terms "alkylcarbonyl", "alkoxycarbonyl", "alkylaminocarbonyl", and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl", "haloalkylaminocarbonyl", and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

DETAILED DESCRIPTION

An embodiment of the present invention includes a compound of Formula (I):

(I)

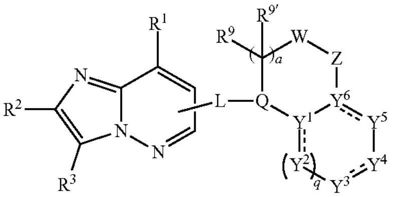

wherein:

L is L1, L2, L3, L4, L5, L6, L7, L8, L9, L10, L11, L12, L13, L14 or L15:

(L1)

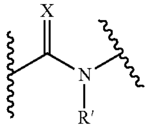

, (L2)

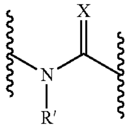

, (L3)

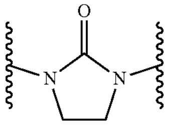

, (L4)

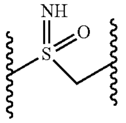

, (L5)

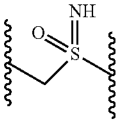

, (L6)

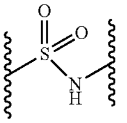

, (L7)

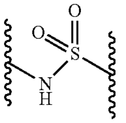

, (L8)

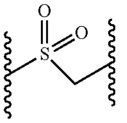

, (L9)

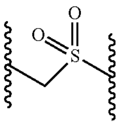

,

-continued (L10)

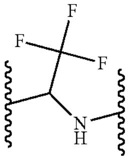

, (L11)

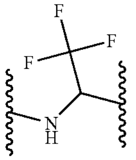

, (L12)

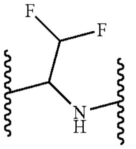

, (L13)

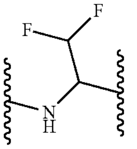

, (L14)

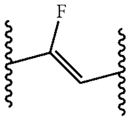

, (L15)

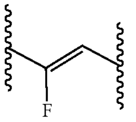

,

R' is hydrogen, optionally substituted alkyl, optionally substituted cycloalkyl, or optionally substituted aryl;

$R^1$ is hydrogen, cyano, halo, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted alkenyl, optionally substituted alkynyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, $—SO_p$ (optionally substituted alkyl or haloalkyl), $—SF_5$, or $—NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^2$ is hydrogen, cyano, halo, hydroxyl, optionally substituted alkyl, optionally substituted alkoxy, optionally substituted alkoxyalkyl, optionally substituted aminoalkyl, optionally substituted alkylaminoalkyl, optionally substituted dialkylaminoalkyl, optionally substituted alkenyl, optionally substituted alkynyl, optionally substituted aryl; optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —$SO_p$ (optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is hydrogen, optionally substituted alkyl, optionally substituted alkenyl, optionally substituted alkynyl, optionally substituted cycloalkyl, optionally substituted cycloalkenyl, optionally substituted alkylcarbonyl, optionally substituted alkoxycarbonyl, aminocarbonyl, optionally substituted alkylaminocarbonyl, optionally substituted dialkylaminocarbonyl, —$S(O)_p$ (optionally substituted alkyl), —$SF_5$, optionally substituted heterocyclyl, optionally substituted 6- to 10-membered aryl, optionally substituted 5- to 10-membered heteroaryl, a spirocyclic heterocyclyl-carbocyclyl group, a spirocyclic heterocyclyl-heterocyclyl group, a spirocyclic carbocyclyl-carbocyclyl group, a spirocyclic carbocyclyl-heterocyclyl group or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ and $R^{4'}$ are independently in each occurrence, hydrogen, halogen, cyano, nitro, hydroxyl, optionally substituted alkyl, optionally substituted alkenyl, optionally substituted alkynyl, optionally substituted alkoxy, optionally substituted alkoxyalkyl, optionally substituted aminoalkyl, optionally substituted alkylaminoalkyl, optionally substituted dialkylaminoalkyl, optionally substituted cycloalkyl, optionally substituted cycloalkoxy, optionally substituted alkylcarbonyl, optionally substituted alkoxycarbonyl, optionally substituted aminocarbonyl, optionally substituted alkylaminocarbonyl, optionally substituted di(alkyl)aminocarbonyl, optionally substituted alkylcarbonyloxy, optionally substituted alkylcarbonylamino, optionally substituted aryl, optionally substituted heteroaryl, —$SF_5$, —$SO_p$ (optionally substituted alkyl or haloalkyl); or $R^4$ together with $R^{4'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H or optionally substituted alkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^8$ is hydrogen, halogen, alkyl, haloalkyl, cycloalkyl, alkenyl or alkynyl;

$R^9$ and $R^{9'}$ are independently hydrogen, halo, $C_1$-$C_4$-alkyl, $C_1$-$C_4$-haloalkyl, $C_1$-$C_4$-alkoxy, $C_1$-$C_4$-haloalkoxy or cycloalkoxy, or $R^9$ together with $R^{9'}$ form a 2-6-membered chain optionally containing one or two heteroatoms selected from the group consisting of N, O, Si and S to form carbocyclic or heterocyclic ring together with the carbon atom to which they are attached, wherein the carbon or nitrogen atoms in the chain may be optionally substituted;

Q is C—$R^8$ or N;

X is O, S or N—R';

$Y^1$ and $Y^6$ are each independently N, C, or —$CR^4$—;

$Y^2$, $Y^3$, $Y^4$ and $Y^5$ are each independently N, NR', S, O, —$CR^4$— or $CR^4R^{4'}$;

W is $CR^5R^6$, O, $SO_p$, or N—$R^7$,

Z is $CR^5R^6$, O, $SO_p$, or N—$R^7$, wherein $R^5$ and $R^6$ are independently in each occurrence hydrogen, halo, $C_1$-$C_4$-alkyl, $C_1$-$C_4$-haloalkyl, $C_1$-$C_4$-alkoxy, $C_1$-$C_4$-haloalkoxy or cycloalkoxy, or $R^5$ together with $R^6$ form a 2-6-membered chain optionally containing one or two heteroatoms selected from the group consisting of N, O, Si and S to form carbocyclic or heterocyclic ring together with the carbon atom to which they are attached, and wherein each carbon or nitrogen in said carbocyclic or heterocyclic ring may be optionally substituted;

$R^7$ is hydrogen or $C_1$-$C_4$-alkyl; and wherein at most three of $Y^1$, $Y^2$, $Y^3$, $Y^4$, $Y^5$ and $Y^6$ are heteroatoms;

a is 0 or 1;

q is 0 or 1;

p is independently in each occurrence is 0, 1, or 2; and the dashed bonds (- - - -) signifies a single or double bond;

a stereoisomer, tautomer, N-oxide, hydrate, solvate, or salt thereof.

In another embodiment, the invention provides a compound of Formula (I)

wherein:

R' is hydrogen, $C_1$-$C_6$-alkyl, $C_1$-$C_6$-haloalkyl, optionally substituted $C_3$-$C_8$-cycloalkyl, or optionally substituted phenyl;

$R^1$ is hydrogen, cyano, halo, hydroxyl, $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, optionally substituted aryl, optionally substituted aryloxy, optionally substituted heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl, —$SF_5$, —$SO_p$ (optionally substituted $C_1$-$C_6$-alkyl or $C_1$-$C_6$-haloalkyl), or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^2$ is hydrogen, cyano, halo, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$ (optionally substituted $C_1$-$C_6$-alkyl or $C_1$-$C_6$-haloalkyl), $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkenyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SF_5$, —$S(O)_p$($C_1$-$C_6$-alkyl or $C_1$-$C_6$-haloalkyl), optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ and $R^{4'}$ are independently in each occurrence, hydrogen, halogen, cyano, nitro, hydroxyl, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted $C_1$-$C_6$-alkylcarbonyl, optionally substituted $C_1$-$C_6$-alkoxycarbonyl, optionally substituted aminocarbonyl, $C_1$-$C_6$-alkylaminocarbonyl, di($C_1$-$C_6$-alkyl)aminocarbonyl, optionally substituted $C_1$-$C_6$-alkylcarbonyloxy, optionally substituted $C_1$-$C_6$-alkylcarbonylamino, optionally substituted phenyl, optionally substituted 5- or 6-membered heteroaryl, —$SF_5$, —$SO_p$ (optionally substituted $C_1$-$C_6$-alkyl or $C_1$-$C_6$-haloalkyl); or $R^4$ together with $R^{4'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^8$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl; and L, Q, X, $Y^1$, $Y^2$, $Y^3$, $Y^4$, $Y^5$, $Y^6$, W, Z, $R^5$, $R^6$, $R^7$, $R^9$, $R^{9'}$, a, q, p and the dashed bonds (- - - -) are as defined above for the compound of Formula (I).

In one embodiment, L is L1. In another embodiment, L is L2. In another embodiment, L is L3. In another embodiment, L is L4. In another embodiment, L is L5. In another embodiment, L is L6. In another embodiment, L is L7. In another embodiment, L is L8. In another embodiment, L is L9. In another embodiment, L is L10. In another embodiment, L is L11. In another embodiment, L is L12. In another embodiment, L is L13. In another embodiment, L is L14. In another embodiment, L is L15.

In some embodiments:

$R^1$ is hydrogen, cyano, optionally substituted $C_1$-$C_4$-alkyl, optionally substituted $C_1$-$C_4$-alkoxy, optionally substituted $C_1$-$C_4$-alkenyl, optionally substituted $C_1$-$C_4$-alkynyl, optionally substituted $C_3$-$C_8$-cycloalkyl, optionally substituted $C_3$-$C_8$-cycloalkenyl, optionally substituted, saturated or partially unsaturated 5-, 6-, or 7-membered heterocycle group, optionally substituted aryl, optionally substituted heteroaryl, optionally substituted aryloxy, optionally substituted $C_1$-$C_4$-alkylcarbonyl, optionally substituted $C_1$-$C_4$-alkoxycarbonyl, optionally substituted aminocarbonyl, optionally substituted $C_1$-$C_4$-alkylaminocarbonyl, optionally substituted $C_1$-$C_4$-dialkylaminocarbonyl, optionally substituted alkyl-$SO_p$—, haloalkyl-$SO_p$—, amino, —NH-optionally substituted $C_1$-$C_4$-alkyl, or —$NR^aR^b$, wherein $R^a$ and $R^b$ are independently optionally substituted alkyl; or $R^a$ and $R^b$ may form, with the nitrogen to which they are attached, a 3-, 4-5-, 6-, 7-, or 8-membered-heterocyclyl group, which may include one to three additional heteroatoms selected from the group consisting of N, O and S and may be optionally substituted;

R' is hydrogen or $C_1$-$C_4$-alkyl;

$R^2$ is hydrogen, halogen, cyano, nitro, —OH, optionally substituted $C_1$-$C_4$-alkyl, optionally substituted $C_1$-$C_4$-alkoxy, optionally substituted $C_3$-$C_8$-cycloalkyl, optionally substituted $C_3$-$C_8$-cycloalkenyl, -amino, NH-optionally substituted $C_1$-$C_4$-alkyl, —$SF_5$, or —$NR^aR^b$, wherein $R^c$ and $R^d$ are independently optionally substituted $C_1$-$C_4$-alkyl; or $R^a$ and $R^b$ may form, with the nitrogen to which they are attached, a 3-, 4-, 5-, 6-, 7-, or 8-membered heterocyclyl group, which may be optionally substituted, $SO_p$ (optionally substituted $C_1$-$C_4$-alkyl or haloalkyl);

$R^3$ is $C_1$-$C_4$-alkyl, $C_3$-$C_6$-cycloalkyl, optionally substituted $C_5$-$C_7$-cycloalkenyl, 4- to 6-membered-heterocyclyl, 6- to 10-membered aryl, 5- to 10-membered heteroaryl, each of which may be optionally substituted with 1, 2, or 3 substituents;

$R^4$ and $R^{4'}$ are independently hydrogen, halogen, cyano, nitro, —OH, optionally substituted $C_1$-$C_4$-alkyl, optionally substituted $C_1$-$C_4$-alkoxy, optionally substituted $C_3$-$C_8$-cycloalkyl, -amino, NH-optionally substituted $C_1$-$C_4$-alkyl, —$SF_5$; or $R^4$ together with $R^{4'}$ together form a 2-6-membered chain optionally containing one or two heteroatoms selected from the group consisting of O, Si and S, or containing the group NR', to form carbocyclic or heterocyclic ring together with the carbon atom to which they are attached; or —$NR^cR^d$, wherein $R^c$ and $R^d$ are independently optionally substituted $C_1$-$C_4$-alkyl; or $R^c$ and $R^d$ may form, with the nitrogen to which they are attached, a 3-, 4-, 5-, 6-, 7-, or 8-membered heterocyclyl group, which may be optionally substituted, $SO_p$ (optionally substituted $C_1$-$C_4$-alkyl or haloalkyl.

In some embodiments, $R^1$ is hydrogen.

In some embodiments, $R^1$ is $C_1$-$C_4$-alkyl, $C_1$-$C_4$-haloalkyl, amino, $C_1$-$C_4$-alkylamino, or di-($C_1$-$C_4$-alkyl) amino.

In another embodiment, $R^1$ is halogen.

In another embodiment, $R^1$ is $C_1$-$C_4$-alkyl-$SO_p$—, $C_1$-$C_4$-haloalkyl-$SO_p$— or —$SF_5$.

In other embodiments, $R^1$ is hydroxy-$C_1$-$C_4$-alkyl, $C_1$-$C_4$-alkoxy-$C_1$-$C_4$-alkyl, $C_1$-$C_4$-haloalkoxy-$C_1$-$C_4$-alkyl or $C_1$-$C_4$-haloalkoxy-$C_1$-$C_4$-haloalkyl.

In another embodiment, $R^1$ is methyl, ethyl, propyl, butyl, pentyl, isopropyl (i-Pr), tert-butyl (t-butyl), prop-1-en-2-yl, 2-fluoroprop-2-yl, 1,1-difluoroethyl or 2-hydroxyprop-2-yl.

In another embodiment, $R^1$ is $C_1$-$C_3$-alkoxy or $C_1$-$C_3$-haloalkoxy.

In another embodiment, $R^1$ is $OCH_3$ or $OCH_2CH_3$.

In another embodiment, $R^1$ is $OCF_3$ or $SCF_3$.

In another embodiment, $R^1$ is $CF_3$, —$CH_2CF_3$, —$CHFCF_3$ or —$CF_2CF_3$.

In some embodiments, $R^1$ is $C_2$-$C_4$-alkenyl or $C_2$-$C_4$-haloalkenyl.

In some embodiments, $R^1$ is optionally substituted cyclopentyl or optionally substituted cyclohexyl.

In other embodiments, $R^1$ is cyclopropyl or cyclobutyl.

In some embodiments, $R^1$ is an optionally substituted, saturated or unsaturated 6-membered heterocyclyl group.

In one embodiment, $R^1$ is —$NR^aR^b$, wherein $R^a$ and $R^b$ are independently hydrogen or $C_1$-$C_6$ alkyl. In another embodiment $R^1$ is —$NR^aR^b$, wherein $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O and S and may be optionally substituted.

In another embodiment, $R^1$ is $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl.

In some embodiments, $R^1$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^1$ is optionally substituted phenyl.

In some embodiments, $R^1$ is aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, pyranyl, dihydropyranyl, tetrahydropyranyl, thiopyranyl, dihydrothiopyranyl, tetrahydrothiopyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^1$ is aziridinyl, azetidinyl, oxetanyl, pyrrolidinyl, pyrrolyl, or morpholinyl, all of which are optionally substituted by one or more halogen.

In some embodiments, $R^2$ is hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, $R^2$ is hydrogen, methyl, ethyl, n-propyl, iso-propyl, n-butyl, sec-butyl, iso-butyl or tert-butyl.

In another embodiment, $R^2$ is hydrogen, $CF_3$, —$CH_2CF_3$, —$CHFCF_3$ or —$CF_2CF_3$.

In some embodiments, $R^2$ is hydrogen.

In some embodiments, $R^2$ is halogen.

In another embodiment, $R^2$ is fluoro or chloro.

In another embodiment, $R^2$ is hydrogen, $C_1$-$C_4$-alkoxy, $C_1$-$C_4$-haloalkoxy or $S(O)_p$($C_1$-$C_4$-alkyl or $C_1$-$C_4$-haloalkyl) where p is 0, 1 or 2.

In another embodiment, $R^2$ is methoxy, ethoxy, propoxy or butoxy.

In another embodiment, $R^2$ is methylthio, ethylthio, propylthio or butylthio.

In another embodiment, $R^2$ is —$OCF_3$ or —$SCF_3$.

In some embodiments, $R^2$ is $C_1$-$C_4$-alkenyl or $C_1$-$C_4$-haloalkenyl.

In some embodiments, $R^2$ is optionally substituted cyclopentyl or optionally substituted cyclohexyl.

In some embodiments, $R^2$ is an optionally substituted, saturated or unsaturated 6-membered heterocyclyl group.

In some embodiments, $R^2$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^2$ is optionally substituted phenyl.

In other embodiments, $R^2$ is phenyl substituted with 1, 2, or 3 substituents, which are independently halo, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^2$ is a 5- or 6-membered heteroaryl with 1 or 2 substituents, which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In one embodiment, $R^2$ is pyridinyl optionally substituted with halo, cyano, nitro, $C_1$-$C_3$-alkyl, $C_1$-$C_3$-haloalkyl, $C_1$-$C_3$-alkoxy, $C_1$-$C_3$-haloalkoxy or ($C_1$-$C_3$-alkyl or $C_1$-$C_3$-haloalkyl)$S(O)_p$.

In some embodiments, $R^2$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^2$ is aziridinyl, azetidinyl, oxetanyl, pyrrolidinyl, pyrrolyl, or morpholinyl, all of which are optionally substituted by one or more halogen.

In some embodiments, $R^3$ is 6- to 10-membered aryl optionally substituted with 1, 2, 3, 4 or 5 substituents.

In some embodiments, $R^3$ is $C_1$-$C_4$-alkyl or $C_1$-$C_4$-haloalkyl.

In some embodiments, $R^3$ is methyl, ethyl, n-propyl, n-butyl, iso-propyl, tert-butyl, sec-butyl or iso-butyl.

In other embodiments, $R^3$ is $CF_3$, $—CH_2CF_3$, $—CHFCF_3$ or $—CF_2CF_3$.

In some embodiments, $R^3$ is optionally substituted $C_3$-$C_8$-cycloalkyl. In yet other embodiments, $R^3$ is optionally substituted $C_3$-$C_6$-cycloalkyl. In yet other embodiments, $R^3$ is optionally substituted $C_3$-$C_8$-cycloalkenyl or $C_3$-$C_6$-cycloalkenyl. In some embodiments, $R^3$ is optionally substituted cyclopentyl or cyclohexyl. In other embodiments, $R^3$ is optionally substituted cyclopropyl or cyclobutyl.

In one embodiment, $R^3$ is cyclohexyl optionally substituted by one or more halo, $C_1$-$C_3$-alkyl or $C_1$-$C_3$-haloalkyl. In another embodiment, $R^3$ is cyclohexyl substituted by 1 or 2 fluoro, chloro or $CF_3$.

In some embodiments, $R^3$ is optionally substituted piperidinyl, morpholinyl, tetrahydrofuranyl or dihydrofuranyl. In some embodiments, $R^3$ is piperidinyl, morpholinyl, tetrahydrofuranyl or dihydrofuranyl substituted with one or more halo, $C_1$-$C_6$-alkyl or $C_1$-$C_6$-haloalkyl. In another embodiment, $R^3$ is piperidinyl, morpholinyl, tetrahydrofuranyl or dihydrofuranyl substituted with one or more methyl, chloro or fluoro.

In some embodiments, $R^3$ is 5- to 10-membered heteroaryl optionally substituted with 1, 2, 3, 4 or 5 substituents. In one embodiment, the 5- to 10-membered heteroaryl is pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl or pyrrolopyrimidyl.

In other embodiments, $R^3$ is an optionally substituted spirocyclic heterocyclyl-carbocyclyl group, an optionally substituted spirocyclic heterocyclyl-heterocyclyl group, an optionally substituted spirocyclic carbocyclyl-carbocyclyl group or an optionally substituted spirocyclic carbocyclyl-heterocyclyl group. In other embodiments, $R^3$ is a 5- to 11-membered optionally substituted spirocyclic heterocyclyl-carbocyclyl group, a 5- to 11-membered optionally substituted spirocyclic heterocyclyl-heterocyclyl group, a 5- to 11-membered optionally substituted spirocyclic carbocyclyl-carbocyclyl group or a 5- to 11-membered optionally substituted spirocyclic carbocyclyl-heterocyclyl group. Non-limiting examples of spirocyclic carbocyclyl-carbocyclyl, spirocyclic carbocyclyl-heterocyclyl and spirocyclic heterocyclyl-heterocyclyl groups are shown below for illustration.

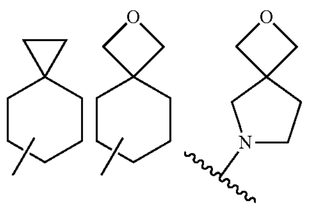

However, it will be apparent to persons skilled in the art that the second ring of the spirocyclic group may be joined at any available carbon of the first ring. It will also be understood that the first ring of the spirocyclic group may be bonded to the molecule at any available atom. Thus, the present invention includes 3-, 4-, 5-, 6- and 7-membered carbocyclic or heterocyclic rings as defined herein joined to a second 3-, 4-, 5-, 6- and 7-membered carbocyclic or heterocyclic ring at any available carbon atom of the first ring.

In some embodiments, $R^3$ is phenyl substituted with 1 to 4 substituents. In another embodiment, $R^3$ is phenyl substituted by 1 to 3 substituents. In yet another embodiment, $R^3$ is phenyl substituted by 1 or 2 substituents. In some embodiments, $R^3$ is phenyl substituted by 1, 2, 3 or 4 substituents which are independently halo, cyano, nitro, alkylsulfonyl, haloalkylsulfonyl, alkyl, alkenyl, alkynyl, cycloalkyl, cycloalkenyl, phenyl, substituted phenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is para-substituted phenyl.

In some embodiments, $R^3$ is meta-substituted phenyl.

In some embodiments, $R^3$ is ortho-substituted phenyl.

In some embodiments, $R^3$ is halophenyl.

In some embodiments, $R^3$ is haloalkylphenyl.

In some embodiments, $R^3$ is haloalkoxyphenyl.

In some embodiments, $R^3$ is phenyl substituted with 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2,3-disubstituted phenyl.

In some embodiments, $R^3$ is 2,4-disubstituted phenyl.

In some embodiments, $R^3$ is 2,5-disubstituted phenyl.

In some embodiments, $R^3$ is a 2,6-disubstituted phenyl.

In some embodiments, $R^3$ is a 3,5-disubstituted phenyl.

In other embodiments, $R^3$ is a 3,4-disubstitued phenyl.

In other embodiments, $R^3$ is a 3,6-disubstituted phenyl.

In some embodiments, $R^3$ is dihalophenyl, e.g., dichloro; difluoro; or chloro, fluoro.

In some embodiments, $R^3$ is 2,3-dihalophenyl.

In some embodiments, $R^3$ is chlorophenyl. In another embodiment, $R^3$ is fluorophenyl. In another embodiment, $R^3$ dichlorophenyl. In another embodiment, $R^3$ is difluorophenyl. In yet another embodiment, $R^3$ is 3,5-dichlorophenyl. In another embodiment, $R^3$ is 3,5-difluorophenyl. In another embodiment, $R^3$ is 2,6-dichlorophenyl. In another embodiment, $R^3$ is 2,6-difluorophenyl.

In some embodiments, $R^3$ is phenyl substituted with halo and haloalkyl.

In some embodiments, $R^3$ is phenyl substituted with halo and haloalkoxy.

In some embodiments, $R^3$ is phenyl substituted with haloalkyl and haloalkoxy.

In some embodiments, $R^3$ is phenyl substituted with 3 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is trihalophenyl, e.g., trichloro; trifluoro; or chloro, chloro, fluoro, or fluoro, fluoro, chloro.

In some embodiments, $R^3$ is phenyl substituted with 2 halo and haloalkyl.

In some embodiments, $R^3$ is phenyl substituted with 2 halo and haloalkoxy.

In some embodiments, $R^3$ is phenyl substituted with 1 haloalkyl, 1 halo, and 1 haloalkoxy.

In some embodiments, $R^3$ is phenyl substituted with 1 halo and 2 haloalkyl.

In some embodiments, $R^3$ is 5-membered heteroaryl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 6-membered heteroaryl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 3-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 4-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^3$ is 4-pyridyl which is unsubstituted or substituted with 1 or 2 chloro or fluoro. In yet another embodiment $R^3$ is 3-pyridyl which is unsubstituted or substituted with 1 or 2 chloro or fluoro.

In other embodiments, $R^3$ is an optionally substituted 3- to 7-membered heterocycle. In some embodiments, $R^3$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In another embodiment, $R^3$ may be a heterocyclic, bridged bicyclic group, which may be optionally substituted.

In some embodiments, $R^4$ and/or $R^{4'}$ are hydrogen.

In some embodiments, each $R^4$ and/or $R^{4'}$ are independently hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, each $R^4$ and/or $R^{4'}$ are independently hydrogen, methyl, ethyl, n-propyl, iso-propyl, n-butyl, sec-butyl, iso-butyl or tert-butyl.

In another embodiment, $R^4$ and/or $R^{4'}$ are independently hydrogen, $CF_3$, $—CH_2CF_3$, $—CHFCF_3$ or $—CF_2CF_3$.

In some embodiments, $R^4$ and/or $R^{4'}$ are independently hydrogen or halogen.

In another embodiment, $R^4$ and/or $R^{4'}$ are independently hydrogen, fluoro or chloro.

In another embodiment, $R^4$ and/or $R^{4'}$ are independently hydrogen, $C_1$-$C_4$-alkoxy, $C_1$-$C_4$-haloalkoxy or $S(O)_p$($C_1$-$C_4$-alkyl or $C_1$-$C_4$-haloalkyl), where p is 0, 1 or 2.

In another embodiment, $R^4$ and/or $R^{4'}$ are independently hydrogen, methoxy, ethoxy, propoxy or butoxy.

In another embodiment, $R^4$ and/or $R^{4'}$ are independently hydrogen, methylthio, ethylthio, propylthio or butylthio.

In another embodiment, $R^4$ and/or $R^{4'}$ are independently hydrogen, $—OCF_3$ or $—SCF_3$.

In some embodiments, $R^4$ and/or $R^{4'}$ are independently hydrogen, $C_1$-$C_4$-alkenyl or $C_1$-$C_4$-haloalkenyl.

In some embodiments, $R^4$ and/or $R^{4'}$ are independently hydrogen, $C_1$-$C_4$-alkylcarbonyl or $C_1$-$C_4$-alkoxycarbonyl.

In other embodiments, $R^4$ and/or $R^{4'}$ are independently hydrogen, $C_1$-$C_4$-alkylcarbonylamino.

In some embodiments, $R^4$ and/or $R^{4'}$ are independently hydrogen, optionally substituted cyclopentyl or optionally substituted cyclohexyl.

In some embodiments, $R^4$ and/or $R^{4'}$ are independently hydrogen, optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^4$ and/or $R^{4'}$ are independently hydrogen, optionally substituted phenyl.

In other embodiments, $R^4$ and/or $R^{4'}$ are independently hydrogen, phenyl substituted with 1, 2, or 3 substituents, which are independently halo, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In other embodiments, $R^4$ and/or $R^{4'}$ are independently hydrogen, a 5- or 6-membered heteroaryl with 1 or 2 substituents, which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ and/or $R^{4'}$ are independently hydrogen, optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^4$ and $R^{4'}$ are independently hydrogen, aziridinyl, azetidinyl, oxetanyl, pyrrolidinyl, pyrrolyl, or morpholinyl, all of which are optionally substituted by one or more halogen.

In one embodiment, $R^8$ is H. In another embodiment, $R^8$ is $C_1$-$C_3$-alkyl or $C_1$-$C_3$-haloalkyl.

In one embodiment, $R^9$ and $R^{9'}$ are each hydrogen. In another embodiment, $R^9$ and $R^{9'}$ together form a 2- to 6-membered chain to form a spiroxyclic ring substituent together with the carbon atom to which they are attached. In another embodiment, $R^9$ and $R^{9'}$ together form a 2- to 5-membered chain to form a spiroxyclic ring substituent together with the carbon atom to which they are attached. In another embodiment, $R^9$ and $R^{9'}$ together form a 2- to 4-membered chain to form a spiroxyclic ring substituent together with the carbon atom to which they are attached. In another embodiment, $R^9$ and $R^{9'}$ together form a 2- or 3-membered chain to form a spiroxyclic ring substituent together with the carbon atom to which they are attached. In another embodiment, $R^9$ and $R^{9'}$ together form a 2-membered chain to form a spiroxyclic ring substituent together with the carbon atom to which they are attached.

In some embodiments, a is 0.

In some embodiments, a is 1.

In some embodiments, Q is N.

In other embodiments, Q is C—$R^8$.

In some embodiments, X is O.

In some embodiments, X is S.

In some embodiments, X is NR'.

In some embodiments, W is $CH_2$.

In other embodiments, W is $C(C_1\text{-}C_3\text{-alkyl})_2$ or $C(C_1\text{-}C_3\text{-haloalkyl})_2$;

In other embodiments, W is $C(CH_3)_2$, $C(C_2H_5)_2$ or $C(CF_3)_2$

In some embodiments, Z is $CH_2$.

In some embodiments, Z is O.

In some embodiments, Z is $SO_p$.

In some embodiments, Z is $SO_2$.

In other embodiments, Z is SO.

In some embodiments, Z is NH.

In other embodiments, Z is $N(C_1\text{-}C_3\text{-alkyl})$ or $N(C_1\text{-}C_3\text{-haloalkyl})$ In some embodiments, the compound of Formula (I) is the compound of Formula (I-1):

(I-1)

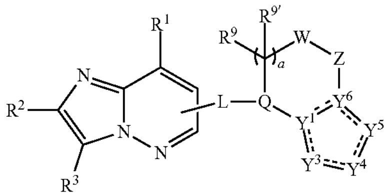

wherein variables L, $R^1$, $R^2$, $R^3$, $R^9$, $R^{9'}$, $Y^1$, $Y^3$, $Y^4$, $Y^5$, $Y^6$, Q, W, Z and a are as defined for formula (I).

In one embodiment of Formula (I-1), W is $CH_2$ and Z is O. In one embodiment, Q is N. In another embodiment, Q is C—$R^8$. In another embodiment of Formula (I-1), W is $CH_2$ and Z is $CH_2$. In another embodiment of Formula (I-1), W is $CR^5R^6$ wherein $R^5$ and $R^6$ are $C_1\text{-}C_3$-alkyl or $C_1\text{-}C_3$-haloalkyl and Z is O. In another embodiment of Formula (I-1), W is $CR^5R^6$ and Z is $CR^5R^6$, wherein each $R^5$ and $R^6$ are independently $C_1\text{-}C_3$-alkyl or $C_1\text{-}C_3$-haloalkyl. In another embodiment of Formula (I-1), W is $CR^5R^6$ wherein $R^5$ and $R^6$ together form a 2- to 5-membered chain to form a ring and Z is O. In another embodiment, a is 0 and Z is O. In another embodiment, a is 0, Z is O and W is $CH_2$.

In one embodiment of Formula (I-1), $Y^3$ is S. In another embodiment of Formula (I-1), $Y^5$ is S. In another embodiment, $Y^3$ is N. In another embodiment $Y^5$ is N. In another embodiment of Formula (I-1), $Y^5$ is N and $Y^3$ is S. In yet another embodiment of Formula (I-1), $Y^5$ is S and $Y^3$ is N. In another embodiment of Formula (I-1), $Y^6$ and $Y^3$ are each N. In another embodiment of Formula (I-1), $Y^6$ is N and $Y^3$ is N. In another embodiment, $Y^1$ is N and $Y^5$ is N.

In some embodiments, the compound of Formula (I) is the compound of formula (I-2):

(I-2)

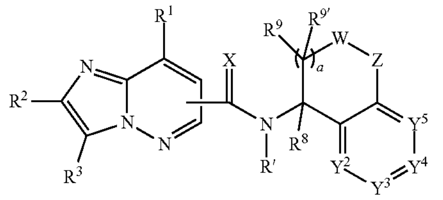

wherein variables $R^1$, $R^2$, $R^3$, R', $R^8$, $R^9$, $R^{9'}$, $Y^2$, $Y^3$, $Y^4$, $Y^5$, X, W, Z and a are as defined for formula (I).

In other embodiments, the compound of Formula (I) is the compound of Formula (I-3) below:

(I-3)

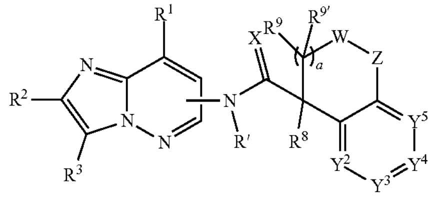

wherein variables $R^1$, $R^2$, $R^3$, R', $R^8$, $R^9$, $R^{9'}$, $Y^2$, $Y^3$, $Y^4$, $Y^5$, X, W, Z and a are as defined for formula (I).

In other embodiments, the compound of Formula (I) is the compound of Formula (I-4):

(I-4)

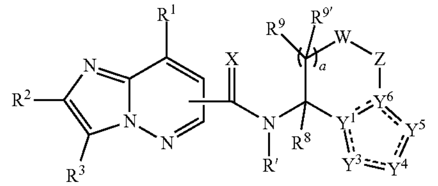

wherein variables $R^1$, $R^2$, $R^3$, R', $R^8$, $R^9$, $R^{9'}$, $Y^1$, $Y^3$, $Y^4$, $Y^5$, $Y^6$, X, W, Z and a are as defined for formula (I).

In another embodiment, the compound of Formula (I) is the compound of Formula (I-5):

(I-5)

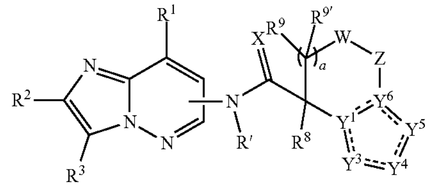

wherein variables $R^1$, $R^2$, $R^3$, R', $R^8$, $R^9$, $R^{9'}$, $Y^1$, $Y^3$, $Y^4$, $Y^5$, $Y^6$, X, W, Z and a are as defined for formula (I).

In some embodiments, the compound of formula (I) is the compound of formula (Ia):

(Ia)

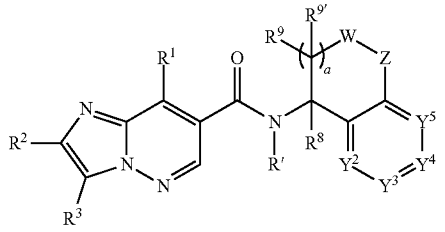

wherein variables $R^1$, $R^2$, $R^3$, R', $R^8$, $R^9$, $R^{9'}$, W, Z, $Y^2$, $Y^3$, $Y^4$, $Y^5$ and a are as defined for formula (I).

In some embodiments, the compound of formula (I) is the compound of formula (Ib):

(Ib)

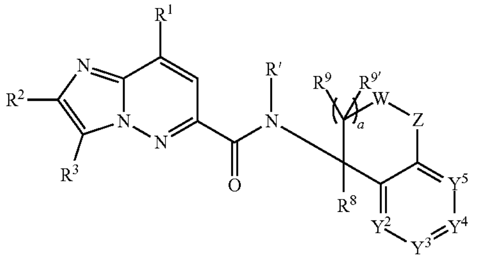

wherein variables $R^1$, $R^2$, $R^3$, R', $R^8$, $R^9$, $R^{9'}$, $Y^2$, $Y^3$, $Y^4$, $Y^5$, W, Z and a are as defined for formula (I).

In some embodiments, the compound of formula (I) is the compound of formula (Ic):

(Ic)

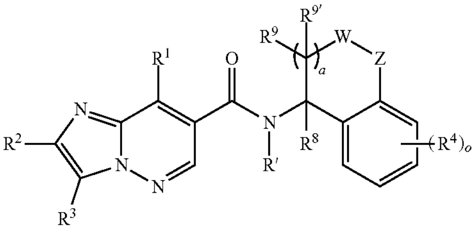

wherein variables $R^1$, $R^2$, $R^3$, R', $R^8$, $R^9$, $R^{9'}$, $R^4$, W, Z and a are as defined for formula (I); and o is 0, 1, 2, 3 or 4.

In other embodiments, the compound of formula (I) is the compound of formula (Id):

(Id)

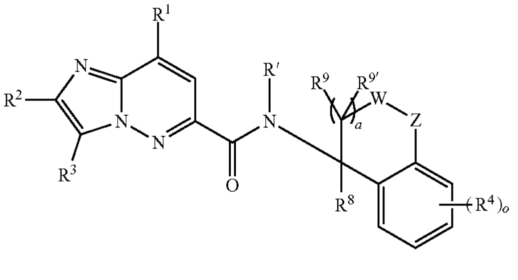

wherein variables $R^1$, $R^2$, $R^3$, R', $R^8$, $R^9$, $R^{9'}$, $R^4$, W, Z and a are as defined for formula (I); and o is 0, 1, 2, 3 or 4.

In other embodiments, the compound of formula (I) is the compound of formula (Ie):

(Ie)

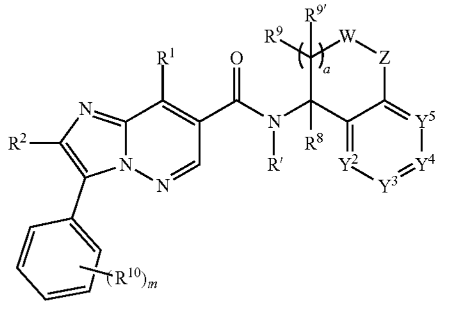

wherein variables $R^1$, $R^2$, R', $R^8$, $R^9$, $R^{9'}$, $Y^2$, $Y^3$, $Y^4$, $Y^5$, W, Z and a are as defined for formula (I); m is 0, 1, 2, 3 or 4; and each $R^{10}$ is cyano, halo, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$ (optionally substituted $C_1$-$C_6$-alkyl or $C_1$-$C_6$-haloalkyl), where p is 0, 1 or 2, $SF_5$, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered heterocyclyl group, which may include one to three additional heteroatoms selected from the group consisting of N, O, Si and S and may be optionally substituted.

In one embodiment of formula (Ie), $R^{10}$ is halo. In another embodiment, $R^{10}$ is chloro. In yet another embodiment, $R^{10}$ is fluoro. In another embodiment, $R^{10}$ is chloro or fluoro and m is 1, 2 or 3. In yet another embodiment, $R^{10}$ is fluoro and m is 2. In another embodiment, $R^{10}$ is chloro and m is 2. In another embodiment, $R^{10}$ is fluoro or chloro, m is 2 and the fluoro or chloro are substituted are the 3- and 5-positions of the phenyl ring. In another embodiment, $R^{10}$ is fluoro or chloro, m is 2 and the fluoro or chloro are substituted at the 2- and 6-positions.

In other embodiments, the compound of formula (I) is the compound of formula (If):

(If)

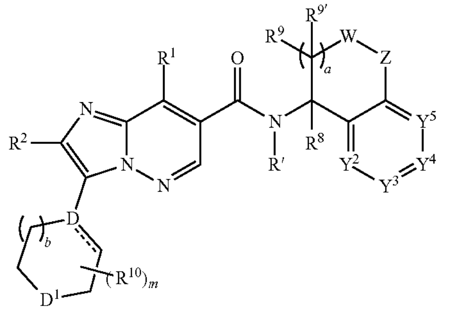

wherein variables $R^1$, $R^2$, R', $R^8$, $R^9$, $R^{9'}$, $R^4$, $R^{4'}$, $Y^2$, $Y^3$, $Y^4$, $Y^5$, W, Z and a are as defined for formula (I); $R^{10}$ and m are as defined for formula (Ie); b is 0 or 1; the dashed bond (- - - -) signifies a single or double bond; D is N, $SiR^{11}$, where $R^{11}$ is $C_1$-$C_6$alkyl or $C_1$-$C_6$haloalkyl, C or C—$R^4$; $D^1$ is N, O, $SiR^{11}R^{12}$, where $R^{11}$ and $R^{12}$ are independently $C_1$-$C_6$alkyl or $C_1$-$C_6$haloalkyl, —$CR^4R^{4'}$, $S(O)_p$, where p is 0, 1 or 2, or $D^1$ is $CR^4R^{4'}$, wherein $R^4$ and $R^{4'}$ together form a 2- to 5-membered chain optionally substituted with one heteroatom in the chain to form a spirocyclic group.

In some embodiments, the present invention provides compounds of formula (If), wherein the dashed bond is a single bond.

In some embodiments, the present invention provides compounds of formula (If), wherein the dashed bond is a double bond.

In some embodiments, the present invention provides compounds of formula (If), wherein D is CH, C-halo or N.

In some embodiments, the present invention provides compounds of formula (If), wherein D is C, CH, C—F or N.

In some embodiments, the present invention provides compounds of formula (If), wherein $D^1$ is $CR^4R^{4'}$, wherein $R^4$ and $R^{4'}$ together form a 2- to 5-membered chain optionally with one heteroatom in the chain to form a spirocyclic group.

In some embodiments, the present invention provides compounds of formula (If), wherein $D^1$ is $CH_2$, independently C-$(halo)_2$, CH($C_1$-$C_3$-alkyl) or CH($C_1$-$C_3$-haloalkyl).

In some embodiments, the present invention provides compounds of formula (If), wherein $D^1$ is $CH_2$, independently $CF_2$, $CH(CH_3)$ or $CH(CF_3)$.

In some embodiments, the present invention provides compounds of formula (If), wherein $D^1$ is O, S, S(O) or $S(O)_2$.

In some embodiments, the present invention provides compounds of formula (If), wherein D is CH or C-halo; and $D^1$ is $CH_2$.

In some embodiments, the present invention provides compounds of formula (If), wherein D is N; and $D^1$ is $CH_2$, O or S.

In another embodiment, the present invention provides compounds of formula (If), wherein D is N and $D^1$ is $SiR^{11}R^{12}$. In another embodiment of formula (If), D is $CH_2$ and $D^1$ is $SiR^{11}R^{12}$. In yet another embodiment, D is N and $D^1$ is $Si(CH_3)_2$.

In some embodiments, the present invention provides compounds of formula (If), wherein the dashed line is a double bond; D is C; and $D^1$ is $CH_2$, $CF_2$, O or S.

In some embodiments, the present invention provides compounds of formula (If), wherein D is N; and $D^1$ is $CR^4R^{4'}$, wherein $R^4$ and $R^{4'}$ together form a 2- to 4-membered chain optionally with one oxygen in the chain to form a spirocyclic group.

In some embodiments, the present invention provides compounds of formula (If), wherein D is CH; and $D^1$ is $CR^4R^{4'}$, wherein $R^4$ and $R^{4'}$ together form a 2- to 4-membered chain optionally with one oxygen in the chain to form a spirocyclic group.

In some embodiments, the present invention provides compounds of formula (If), wherein D is C and the dashed bond signify a double bond; and $D^1$ is $CR^4R^{4'}$, wherein $R^4$ and $R^{4'}$ together form a 2- to 4-membered chain optionally with one oxygen in the chain to form a spirocyclic group.

It will be appreciated by persons of skill in the art that in Formulae (Ic) and (Id) above, where variable $R^4$ is indicated to be present as substituents on the aromatic rings (e.g. $(R^4)_o$ groups, where o is 0, 1, 2, 3 or 4), they will represent non-hydrogen substituents since in embodiments where o is 0, $R^4$ will not be present. The same principle applies to variable $R^{10}$ in the compounds of formula (Je) and (If).

In other embodiments, the invention provides compounds of formula (Ia), wherein variables $R^1$, $R^2$, $R^3$, $R^1$, $R^4$, $R^9$, $R^{9'}$, W, Z, $R^8$ and a are as defined for formula (I) above, and $Y^2$, $Y^3$, $Y^4$ and $Y^5$ are as shown in Table 1:

(Ia)

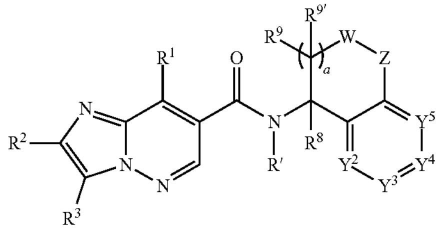

TABLE 1

| Formula | $Y^2$ | $Y^3$ | $Y^4$ | $Y^5$ |
|---|---|---|---|---|
| Ia-1 | $CR^4$ | $CR^4$ | $CR^4$ | $CR^4$ |
| Ia-2 | N | $CR^4$ | $CR^4$ | $CR^4$ |
| Ia-3 | $CR^4$ | N | $CR^4$ | $CR^4$ |
| Ia-4 | $CR^4$ | $CR^4$ | N | $CR^4$ |
| Ia-5 | $CR^4$ | $CR^4$ | $CR^4$ | N |
| Ia-6 | N | N | $CR^4$ | $CR^4$ |
| Ia-7 | $CR^4$ | N | N | $CR^4$ |
| Ia-8 | $CR^4$ | $CR^4$ | N | N |
| Ia-9 | N | $CR^4$ | N | $CR^4$ |
| Ia-10 | $CR^4$ | N | $CR^4$ | N |
| Ia-11 | N | $CR^4$ | $CR^4$ | N |

In other embodiments, the invention provides compounds of formula (Ib), wherein variables $R^1$, $R^2$, $R^3$, $R^4$, R', $R^9$, $R^{9'}$, W, Z, $R^8$ and a are as defined for formula (I) above, and $Y^2$, $Y^3$, $Y^4$ and $Y^5$ are as shown in Table 2:

(Ib)

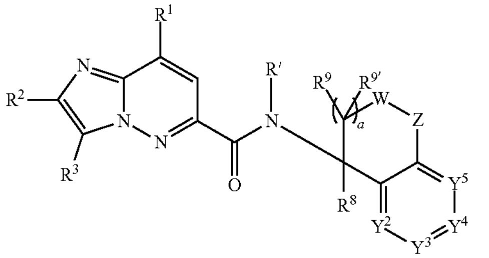

TABLE 2

| Formula | $Y^2$ | $Y^3$ | $Y^4$ | $Y^5$ |
|---|---|---|---|---|
| Ib-1 | $CR^4$ | $CR^4$ | $CR^4$ | $CR^4$ |
| Ib-2 | N | $CR^4$ | $CR^4$ | $CR^4$ |
| Ib-3 | $CR^4$ | N | $CR^4$ | $CR^4$ |
| Ib-4 | $CR^4$ | $CR^4$ | N | $CR^4$ |
| Ib-5 | $CR^4$ | $CR^4$ | $CR^4$ | N |
| Ib-6 | N | N | $CR^4$ | $CR^4$ |
| Ib-7 | $CR^4$ | N | N | $CR^4$ |
| Ib-8 | $CR^4$ | $CR^4$ | N | N |
| Ib-9 | N | $CR^4$ | N | $CR^4$ |
| Ib-10 | $CR^4$ | N | $CR^4$ | N |
| Ib-11 | N | $CR^4$ | $CR^4$ | N |

In some embodiment, the present invention provides compounds of formulae (I-1), (I-2), (I-3), (I-4), (I-5), (Ia), (Ib), (Ic), (Id), (Ie) or (If), wherein each $R^2$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae (I-1), (I-2), (I-3), (I-4), (I-5), (Ia), (Ib), (Ic), (Id), (Ie) or (If), wherein each $R^2$ is independently H, chloro, fluoro, methyl, ethyl, n-propyl, iso-propyl, n-butyl, sec-butyl, iso-butyl or tert-butyl.

In some embodiment, the present invention provides compounds of formulae (I-1), (I-2), (I-3), (I-4), (I-5), (Ia), (Ib), (Ic), (Id), (Ie) or (If), wherein each $R^2$ is independently H, $CF_3$, —$CH_2CF_3$, —$CHFCF_3$ or —$CF_2CF_3$.

In some embodiment, the present invention provides compounds of formulae (I-1), (I-2), (I-3), (I-4), (I-5), (Ia), (Ib), (Ic), (Id), (Ie) or (If), wherein each $R^2$ is independently H, methoxy, ethoxy, propoxy or butoxy.

In some embodiment, the present invention provides compounds of formulae (I-1), (I-2), (I-3), (I-4), (I-5), (Ia), (Ib), (Ic), (Id), (Ie) or (If), wherein each $R^2$ is independently H, —$OCF_3$ or —$SCF_3$.

In some embodiment, the present invention provides compounds of formulae (I-1), (I-2), (I-3), (I-4), (I-5), (Ia), (Ib), (Ie) or (If), wherein each $R^4$ and/or $R^{4'}$ are independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae (I-1), (I-2), (I-3), (I-4), (I-5), (Ia), (Ib), (Ie) or (If), wherein each $R^4$ and/or $R^{4'}$ are independently H, chloro, fluoro, methyl, ethyl, n-propyl, iso-propyl, n-butyl, sec-butyl, iso-butyl or tert-butyl.

In some embodiment, the present invention provides compounds of formulae (I-1), (I-2), (I-3), (I-4), (I-5), (Ia), (Ib), (Ie) or (If), wherein each $R^4$ and/or $R^{4'}$ are independently H, $CF_3$, —$CH_2CF_3$, —$CHFCF_3$ or —$CF_2CF_3$.

In some embodiment, the present invention provides compounds of formulae (I-1), (I-2), (I-3), (I-4), (I-5), (Ia), (Ib), (Ie) or (If) wherein each $R^4$ and/or $R^{4'}$ are independently H, methoxy, ethoxy, propoxy or butoxy.

In some embodiment, the present invention provides compounds of formulae (I-1), (I-2), (I-3), (I-4), (I-5), (Ia), (Ib), (Ie) or (If), wherein each $R^4$ and/or $R^{4'}$ are independently H, —$OCF_3$ or —$SCF_3$.

In other embodiments, the invention provides compounds of formulae (I-2), (I-3), (I-4), (I-5), (Ia), (Ib), (Ic), (Id), (Ie) or (If), wherein R' and $R^8$ are independently H or $C_1$-$C_3$-alkyl.

In other embodiments, the invention provides compounds of formulae (Ia) to (If), wherein a is 1, W is $CH_2$ and Z is O.

In other embodiments, the invention provides compounds of formulae (I-1), (I-2), (I-3), (I-4), (I-5), (Ia), (Ib), (Ic), (Id), (Ie) or (If), wherein $R^1$ is $C_1$-$C_6$-alkyl, $C_1$-$C_6$-haloalkyl, hydroxy-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_1$-$C_6$-haloalkoxy, $C_2$-$C_6$-alkenyl, $C_2$-$C_6$-haloalkenyl, optionally substituted $C_3$-$C_8$-cycloalkyl, optionally substituted 3- to 7-membered heterocyclyl, or —$NR^aR^b$, wherein $R^a$ and $R^b$ are independently H or optionally substituted $C_1$-$C_6$-alkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae (I-1), (I-2), (I-3), (I-4), (I-5), (Ia), (Ib), (Ic) or (Id), wherein $R^3$ is $C_1$-$C_6$-alkyl, $C_1$-$C_6$-haloalkyl, optionally substituted $C_3$-$C_8$-cycloalkyl, optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae (I-1), (I-2), (I-3), (I-4), (I-5), (Ia), (Ib), (Ic) or (Id) above, wherein $R^3$ is optionally substituted phenyl. In another embodiment compounds of formulae (I-1), (I-2), (I-3), (I-4), (I-5), (Ia), (Ib), (Ic) or (Id) are provided, wherein $R^3$ is phenyl substituted with one or more halogen. In yet another embodiment, compounds of formulae (I-1), (I-2), (I-3), (I-4), (I-5), (Ia), (Ib), (Ic) or (Id) are provided, wherein $R^3$ is phenyl substituted with 1 halogen. In another embodiment, compounds of formulae (I-1), (I-2), (I-3), (I-4), (I-5), (Ia), (Ib), (Ic) or (Id) are provided, wherein $R^3$ is phenyl substituted with two halogen. In yet another embodiment, compounds of formulae (I-1), (I-2), (I-3), (I-4), (I-5), (Ia), (Ib), (Ic) or (Id) are provided, wherein $R^3$ is phenyl substituted with three or four halogen.

In another embodiment, compounds of formulae (I-1), (I-2), (I-3), (I-4), (I-5), (Ia), (Ib), (Ic) or (Id) are provided, wherein $R^3$ is phenyl substituted with one or more chloro or fluoro. In yet another embodiment, compounds of formulae (I-1), (I-2), (I-3), (I-4), (I-5), (Ia), (Ib), (Ic) or (Id) are provided, wherein $R^3$ is phenyl substituted with 1 chloro or fluoro. In another embodiment, compounds of formulae (I-1), (I-2), (I-3), (I-4), (I-5), (Ia), (Ib), (Ic) or (Id) are provided, wherein $R^3$ is phenyl substituted with two chloro or fluoro. In yet another embodiment, compounds of formulae (I-1), (I-2), (I-3), (I-4), (I-5), (Ia), (Ib), (Ic) or (Id) are provided, wherein $R^3$ is phenyl substituted with three or four chloro or fluoro.

In other embodiments, the invention provides compounds of formulae (I-2), (I-3), (I-4), (I-5), (Ia), (Ib), (Ic), (Id), (Ie) or (If), wherein R' and $R^8$ are independently H or $C_1$-$C_3$-alkyl; W is $CH_2$, Z is O and a is 1.

In other embodiments of formulae (I), (I-2), (I-3), (Ia), (Ib) and (Ie) each of $Y^2$, $Y^3$, $Y^4$, $Y^5$ are CH.

In other embodiments of formulae (I), (I-2), (I-3), (Ia), (Ib) and (Ie) each of $Y^2$, $Y^3$, $Y^4$, $Y^5$ are each independently CH or $CR^4$, where $R^4$ is a non-hydrogen substituent.

In other embodiments of formulae (I-1), (I-4) and (I-5) each of $Y^3$, $Y^4$ and $Y^5$ are CH.

In other embodiments of formulae (I), (I-2), (I-3), (Ia), (Ib) and (Ie) each of $Y^2$, $Y^3$, $Y^4$, $Y^5$ are independently CH or C-halogen.

In any of the embodiments of formulae (I), (I-1), (I-2), (I-3), (I-4), (I-5), (Ia), (Ib), (Ic), (Id), (Ie) and (If) above, a is 1, W is —$CH_2$—, and Z is O.

In any of the embodiments of formulae (I), (I-1), (I-2), (I-3), (I-4), (I-5), (Ia), (Ib), (Ic), (Id), (Ie) and (If) above, $R^1$ is $C_1$-$C_4$-alkyl, $C_1$-$C_4$ alkenyl, $C_1$-$C_4$-cycloalkyl, amino, $C_1$-$C_4$-alkylamino, di($C_1$-$C_4$-alkyl)amino, morpholino, pyranyl, tetrahydropyranyl, or dihydropyranyl.

In any of the embodiments of formulae (I), (I-1), (I-2), (I-3), (I-4), (I-5), (Ia), (Ib), (Ic), (Id), (Ie) and (If) above, an $R^4$ is, independently of other $R^4$, a halogen, cyano, $C_1$-$C_4$-alkyl, $C_1$-$C_4$ haloalkyl, $C_1$-$C_4$-cycloalkyl, amino, $C_1$-$C_4$-alkylamino, di($C_1$-$C_4$-alkyl)amino, or phenyl optionally substituted 1 or 2 times by halo or $C_1$-$C_4$-alkyl.

In other embodiments, the present invention includes the compounds of formula (I), wherein the group:

In other embodiments, the present invention provides compounds of formulae (I) shown in Table 3 below, wherein L, $R^1$, $R^2$ and $R^3$ are defined in the table, X is O, R' is hydrogen, and wherein the group

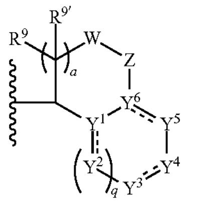

is one of the following Ring Systems:

Ring System A

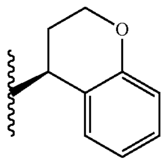

;

Ring System B

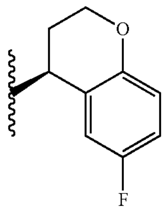

;

-continued

Ring System C

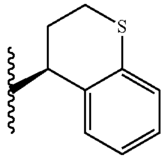

;

Ring System D

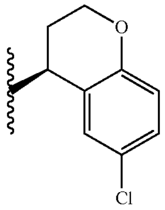

;

Ring System E

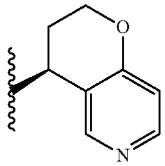

;

Ring System F

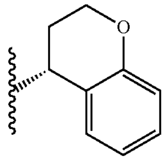

;

Ring System G

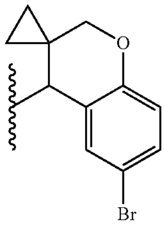

;

Ring System H

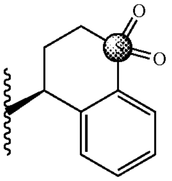

;

Ring System I

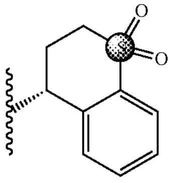

;

Ring System J

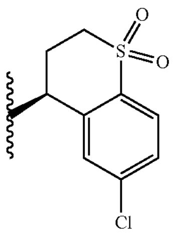

;

-continued
Ring System K
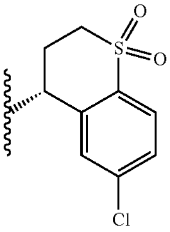
;
Ring System L
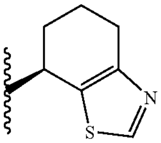
;
Ring System M
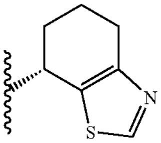
;
Ring System N
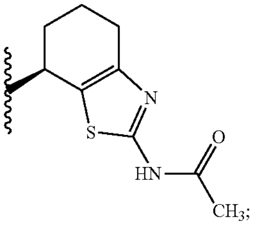
Ring System O
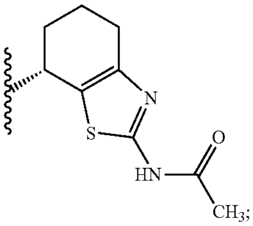
Ring System P
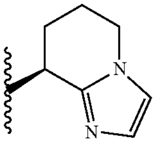
;
Ring System Q
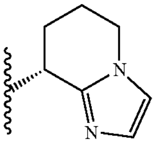
;
Ring System R
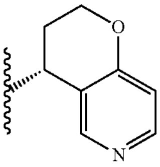
;
-continued
Ring System S
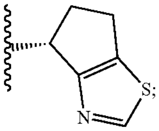
Ring System T
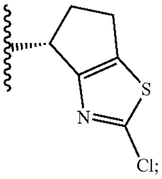
Ring System U
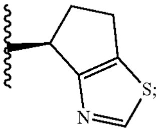
Ring System V
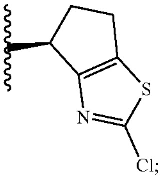
Ring System W
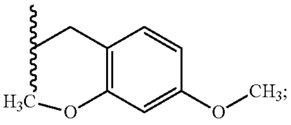
Ring System X
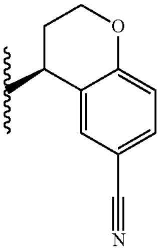
;
Ring System Y
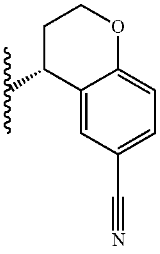
;
Ring System Z
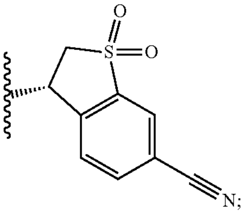

-continued
Ring System AA
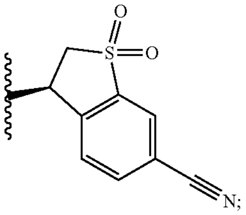
Ring System AB
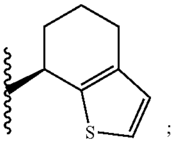
Ring System AC
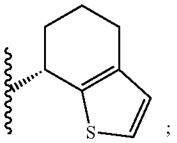
Ring System AD
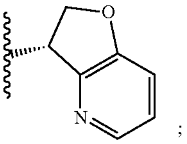
Ring System AE
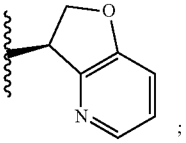
Ring System AF
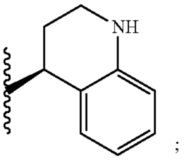
Ring System AG
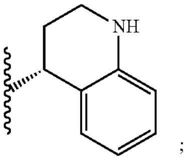
Ring System AH
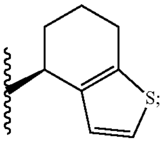
Ring System AJ
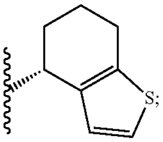
-continued
Ring System AK
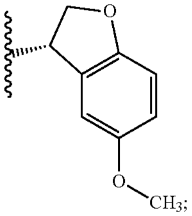
Ring System AL
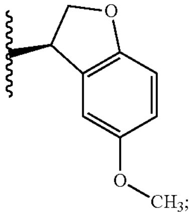
Ring System AM
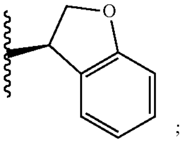
Ring System AN
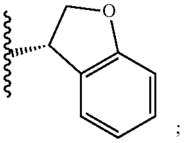
Ring System AO
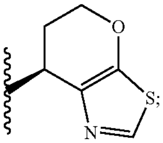
Ring System AP
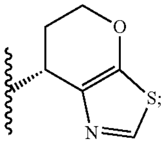
Ring System AQ
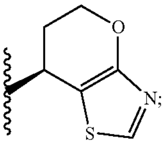
Ring System AR
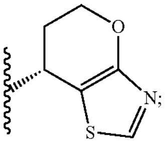
Ring System AS
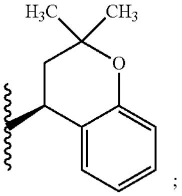

-continued

Ring System AT

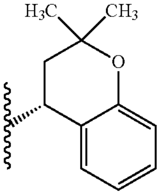

;

Ring System AU

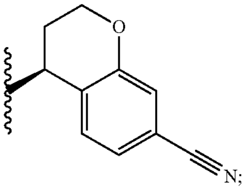

Ring System AV

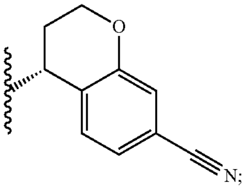

Ring System AW

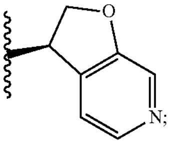

Ring System AX

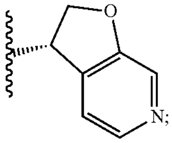

Ring System AY

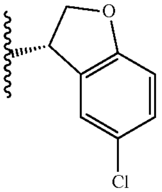

;

Ring System AZ

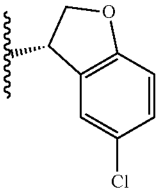

;

-continued

Ring System AAA

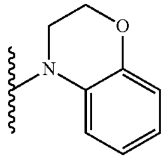

;

In Table 3, "Me" represents methyl, the expression "3,5-di-F-Ph" represents the 3,5-difluorophenyl group; "3,5-di-Cl-Ph" represents 3,5-dichlorophenyl; "2,3,5-tri-F-Ph" represents 2,3,5-trifluorophenyl; "3-F-Ph" represents 3-fluorophenyl; "2,6-di-F-Ph" represents 2,6-difluorophenyl; 2,6-di-Cl-Ph" represents 2,6-dichlorophenyl; "2,4-di-F-Ph" represents 2,4-difluorophenyl; "4-F-Ph" represents 4-fluorophenyl; "3-Cl-4-F-Ph" represents 3-chloro-4-fluorophenyl; "3-Cl-Ph" represents 3-chlorophenyl; "2,3-di-F-Ph" represents 2,3-difluorophenyl; and so on;

prop-1-en-2-yl represents the group;

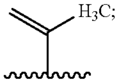 [SMILES: *C(=C)C]

2-F-prop-2-yl represents the group

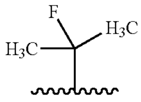

1,1-difluoroethyl represents the group

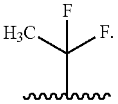

Formula (I)

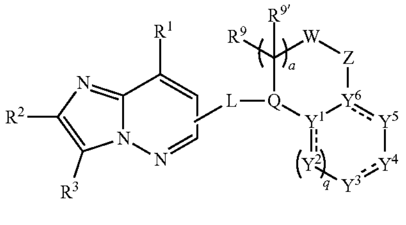

TABLE 3

| Cmpd. # | L | $R^1$ | $R^2$ | $R^3$ | Ring System | ESI-MS |
|---|---|---|---|---|---|---|
| 271 | L1 | i-Pr | Me | 3,5-di-Cl—Ph | A | 596 $[M + H]^+$ |

TABLE 3-continued

| Cmpd. # | L | $R^1$ | $R^2$ | $R^3$ | Ring System | ESI-MS |
|---|---|---|---|---|---|---|
| 326 | L1 | i-Pr | Me | 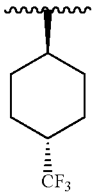 | A | 502 $[M + H]^+$ |
| 327 | L1 | i-Pr | Me | 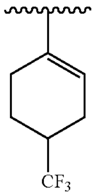 | A | 500 $[M + H]^+$ |
| 326-0 | L1 | i-Pr | Me | 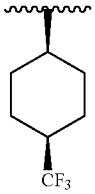 | A | 502 $[M + H]^+$ |
| 324 | L1 | i-Pr | Me | 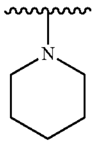 | A | 435 $[M + H]^+$ |
| 325 | L1 | i-Pr | Me | 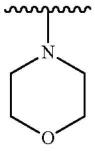 | A | 437 $[M + H]^+$ |
| 323 | L1 | i-Pr | Me | t-Bu | A | 408 $[M + H]^+$ |
| 175 | L1 | i-Pr | Me | 3,5-di-F—Ph | A | 463 $[M + H]^+$ |
| A407 | L1 | i-Pr | Me | 2,6-di-F—Ph | A | 463 $[M + H]^+$ |
| A406 | L1 | i-Pr | Me | 2,6-di-Cl—Ph | A | 495 $[M + H]^+$ |
| A413 | L1 | i-Pr | Me | 2,4-di-F—Ph | A | 463 $[M + H]^+$ |
| A408 | L1 | 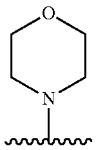 | Me | 3,5-di-Cl—Ph | A | 538 $[M + H]^+$ |
| A412 | L1 | i-Pr | Me | 4-F—Ph | A | 445 $[M + H]^+$ |
| A410 | L1 | i-Pr | Me | 3-Cl-4-F—Ph | A | 479 $[M + H]^+$ |
| A411 | L1 | i-Pr | Me | 3,5-di-Cl—Ph | C | 511 $[M + H]^+$ |
| A409 | L1 | $—N(CH_3)_2$ | Me | 3,5-di-Cl—Ph | A | 496 $[M + H]^+$ |
| A414 | L1 | i-Pr | Me | 3,5-di-Cl—Ph | D | 529 $[M + H]^+$ |
| 306 | L1 | t-Bu | Me | 3,5-di-Cl—Ph | A | 510 $[M + H]^+$ |

TABLE 3-continued

| Cmpd. # | L | $R^1$ | $R^2$ | $R^3$ | Ring System | ESI-MS |
|---|---|---|---|---|---|---|
| 297 | L1 | t-Bu | Me | 3,5-di-Cl—Ph | B | 528 $[M + H]^+$ |
| 365 | L1 | i-Pr | Me | cyclopropyl | A | 391 $[M + H]^+$ |
| 371 | L1 | i-Pr | Me | 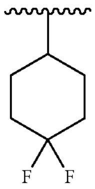 | A | 470 $[M + H]^+$ |
| 370 | L1 | i-Pr | Me | 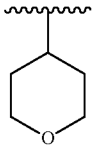 | A | 436 $[M + H]^+$ |
| 366 | L1 | i-Pr | Me | CN | A | 376 $[M + H]^+$ |
| 369 | L1 | i-Pr | Me | 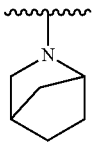 | A | 447 $[M + H]^+$ |
| 308 | L1 | prop-1-en-2-yl | Me | 3,5-di-Cl—Ph | B | 512 $[M + H]^+$ |
| 364 | L1 | i-Pr | Me | 3,5-di-Cl—Ph | E | 470 $[M + H]^+$ |
| 352 | L1 | i-Pr | H | 3,5-di-Cl—Ph | A | 481 $[M + H]^+$ |
| 320-0 | L1 | i-Pr | Me | 3,5-di-F—Ph | F | 463 $[M + H]^+$ |
| 345 | L1 | i-Pr | Me | 2,3,5-tri-F—Ph | A | 481 $[M + H]^+$ |
| 344 | L1 | i-Pr | Me | 2,3,5-tri-F—Ph | B | 499 $[M + H]^+$ |
| 294 | L1 | i-Pr | Me | 3,5-di-Cl—Ph | B | 514 $[M + H]^+$ |
| 320 | L2 | i-Pr | Me | 3,5-di-F—Ph | A | 463 $[M + H]^+$ |
| 277 | L1 | 2-F-prop-2-yl | Me | 3,5-di-F—Ph | A | 481 $[M + H]^+$ |
| 323-0 | L1 | i-Pr | Me | $—CH_2CH(CH_3)_2$ | A | 407 $[M + H]^+$ |
| 298-0 | L1 | t-Bu | $CF_3$ | 3-Cl—Ph | B | 548 $[M + H]^+$ |
| 299-0 | L1 | t-Bu | $CF_3$ | 3-Cl—Ph | A | 530 $[M + H]^+$ |
| 299 | L1 | t-Bu | $CF_3$ | 3,5-di-Cl—Ph | B | 582 $[M + H]^+$ |
| 298 | L1 | t-Bu | $CF_3$ | 3,5-di-Cl—Ph | A | 564 $[M + H]^+$ |
| 304-0 | L1 | i-Pr | 3,5-di-Cl—Ph | Cl | B | 535 $[M + H]^+$ |
| 321 | L1 | i-Pr | 4-F—Ph | 3,5-di-F—Ph | A | 544 $[M + H]^+$ |
| 322 | L1 | i-Pr | Me | 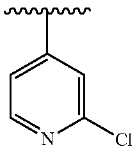 [SMILES: *c1ccnc(Cl)c1] | A | 463 $[M + H]^+$ |
| 304 | L1 | i-Pr | Cl | 3,5-di-Cl—Ph | B | 535 $[M + H]^+$ |

TABLE 3-continued

| Cmpd. # | L | $R^1$ | $R^2$ | $R^3$ | Ring System | ESI-MS |
|---|---|---|---|---|---|---|
| 307 | L1 | prop-1-en-2-yl | Me | 3,5-di-F—Ph | B | 478 $[M + H]^+$ |
| 296 | L1 | i-Pr | $CF_3$ | 3,5-di-Cl—Ph | B | 568 $[M + H]^+$ |
| 295 | L1 | i-Pr | $CF_3$ | 3,5-di-Cl—Ph | A | 550 $[M + H]^+$ |
| 293 | L1 | i-Pr | Me | 2,3-di-Cl—Ph | B | 514 $[M + H]^+$ |
| 276 | L1 | i-Pr | $CF_3$ | 3,5-di-F—Ph | A | 517 $[M + H]^+$ |
| 274 | L1 | i-Pr | Me | 2,3-di-Cl—Ph | A | 496 $[M + H]^+$ |
| 273 | L1 | i-Pr | Me | 3-F—Ph | A | 446 $[M + H]^+$ |
| 272 | L1 | i-Pr | Me | 3-Cl-5-F—Ph | A | 480 $[M + H]^+$ |
| 275 | L1 | i-Pr | Me | 3,5-di-F—Ph | B | 481 $[M + H]^+$ |
| 279 | L1 | prop-1-en-2-yl | Me | 3,5-di-F—Ph | A | 461 $[M + H]^+$ |
| 174 | L1 | H | H | 2,6-di-F—Ph | A | 407 $[M + H]^+$ |
| A400 | L1 | 1,1-difluoroethyl | Me | 3,5-di-Cl—Ph | A | 517 $[M + H]^+$ |
| A401 | L1 | $CF_3$ | Me | 3,5-di-Cl—Ph | A | 521 $[M + H]^+$ |
| 373 | L1 | i-Pr | Me | 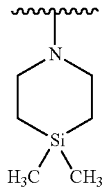 | A | 479 $[M + H]^+$ |
| 372-0 | L1 | i-Pr | Me | 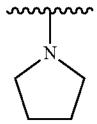 | A | 421 $[M + H]^+$ |
| A402 | L1 | i-Pr | Me | 3,5-di-Cl—Ph | G | 599 $[M + H]^+$ |
| A403 | L1 | i-Pr | —$CH_2OH$ | 3,5-di-Cl—Ph | A | 511 $[M + H]^+$ |
| A404 | L1 | i-Pr | —$CF_2CF_3$ | 3,5-di-Cl—Ph | A | 599 $[M + H]^+$ |
| 394 | L1 | —$OCH_3$ | H | 3,5-di-Cl—Ph | A | 470 $[M + H]^+$ |
| 398 | L1 | —$OCH_2CH_3$ | H | 3,5-di-Cl—Ph | A | 484 $[M + H]^+$ |
| A405 | L1 | —$CHF_2$ | Me | 3,5-di-Cl—Ph | A | 503 $[M + H]^+$ |
| 573 | L1 | t-Bu | Cl | 2,3,5-tri-F—Ph | A | 515 $[M + H]^+$ |
| 559 | L1 | i-Pr | —CN | 3,5-di-Cl—Ph | A | 504 $[M + H]^+$ |
| 614 | L1 | t-Bu | Me | 3,5-di-Cl—Ph | AAA | 510 $[M + H]^+$ |
| 451 | L1 | —$N(CH_3)_2$ | $CF_3$ | 3,5-di-Cl—Ph | A | 550 $[M + H]^+$ |
| 572 | L1 | t-Bu | Cl | 2,5-di-Cl-4-F—Ph | A | 547 $[M + H]^+$ |
| 528 | L1 | i-Pr | Me | 2,5-di-Cl-4-F—Ph | A | 513 $[M + H]^+$ |
| 571 | L1 | t-Bu | Cl | 2,4,5-tri-F—Ph | A | 515 $[M + H]^+$ |
| 574 | L1 | t-Bu | Cl | 2,3-di-Cl-5-F—Ph | A | 547 $[M + H]^+$ |
| A415 | L1 | i-Pr | Me | 3,5-di-Cl—Ph | H | 543 $[M + H]^+$ |
| A416 | L1 | i-Pr | Me | 3,5-di-Cl—Ph | I | 543 $[M + H]^+$ |

TABLE 3-continued

| Cmpd. # | L | $R^1$ | $R^2$ | $R^3$ | Ring System | ESI-MS |
|---|---|---|---|---|---|---|
| A417 | L1 | i-Pr | Me | 3,5-di-Cl—Ph | J | 578 $[M + H]^+$ |
| A418 | L1 | i-Pr | Me | 3,5-di-Cl—Ph | K | 578 $[M + H]^+$ |
| A419 | L1 | i-Pr | Me | 3,5-di-Cl—Ph | L | 500 $[M + H]^+$ |
| A420 | L1 | i-Pr | Me | 3,5-di-Cl—Ph | M | 500 $[M + H]^+$ |
| 560 | L1 | i-Pr | $—CHF_2$ | 3,5-di-Cl—Ph | A | 530 $[M + H]^+$ |
| 305 | L1 | i-Pr | $—CHF_2$ | 3,5-di-Cl—Ph | B | 548 $[M + H]^+$ |
| A421 | L1 | 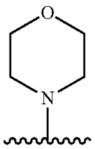 | Me | 2,6-di-Cl-4-F | A | 556 $[M + H]^+$ |
| A422 | L1 | 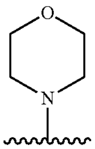 | Me | 2,3,5-tri-F—Ph | A | 524 $[M + H]^+$ |
| 420 | L1 | t-Bu | Cl | 3,5-di-Cl—Ph | A | 572 $[M + H + CH_3CN]^+$ |
| A423 | L1 | i-Pr | Me | 3,5-di-Cl—Ph | N | 557 $[M + H]^+$ |
| A424 | L1 | i-Pr | Me | 3,5-di-Cl—Ph | O | 557 $[M + H]^+$ |
| 523 | L1 | t-Bu | Me | 2,6-di-Cl-4-F—Ph | A | 527 $[M + H]^+$ |
| A425 | L1 | i-Pr | Me | 3,5-di-Cl—Ph | P | 483 $[M + H]^+$ |
| A426 | L1 | i-Pr | Me | 3,5-di-Cl—Ph | Q | 483 $[M + H]^+$ |
| 526 | L1 | t-Bu | Me | 2,3-di-Cl-5-F—Ph | A | 527 $[M + H]^+$ |
| 527 | L1 | i-Pr | Me | 2,4,6-tri-F—Ph | A | 481 $[M + H]^+$ |
| 524 | L1 | t-Bu | Me | 2,4,6-tri-F—Ph | A | 495 $[M + H]^+$ |
| 525 | L1 | t-Bu | Me | 2,3,5-tri-F—Ph | A | 495 $[M + H]^+$ |
| 414-0 | L2 | i-Pr | Me | 3,5-di-Cl—Ph | R | 496 $[M + H]^+$ |
| 514 | L2 | i-Pr | Me | 3,5-di-Cl—Ph | E | 496 $[M + H]^+$ |
| A427 | L1 | i-Pr | Me | 3,5-di-Cl—Ph | S | 487 $[M + H]^+$ |
| A428 | L1 | i-Pr | Me | 3,5-di-Cl—Ph | T | 522 $[M + H]^+$ |
| A429 | L1 | i-Pr | Me | 3,5-di-Cl—Ph | U | 487 $[M + H]^+$ |
| A430 | L1 | i-Pr | Me | 3,5-di-Cl—Ph | V | 522 $[M + H]^+$ |
| 418 | L1 | t-Bu | H | 3,5-di-Cl—Ph | A | 495 $[M + H]^+$ |
| 513 | L2 | i-Pr | Me | 3,5-di-Cl—Ph | A | 495 $[M + H]^+$ |
| 513-0 | L2 | i-Pr | Me | 3,5-di-Cl—Ph | F | 496 $[M + H]^+$ |
| 511 | L1 | 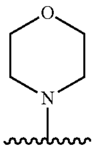 | H | 3,5-di-Cl—Ph | A | 524 $[M + H]^+$ |

TABLE 3-continued

| Cmpd. # | L | $R^1$ | $R^2$ | $R^3$ | Ring System | ESI-MS |
|---|---|---|---|---|---|---|
| 512 | L1 | —$N(CH_3)_2$ | H | 3,5-di-Cl—Ph | A | 482 [M + H]$^+$ |
| A431 | L1 | i-Pr | Me | 3,5-di-Cl—Ph | W | 513 [M + H]$^+$ |
| 450 | L1 | 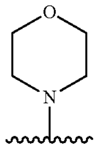 | $CF_3$ | 3,5-di-Cl—Ph | A | 592 [M + H]$^+$ |
| A432 | L1 | i-Pr | Me | 3,5-di-Cl—Ph | X | 520 [M + H]$^+$ |
| A473 | L1 | i-Pr | Me | 3,5-di-Cl—Ph | Y | 520 [M + H]$^+$ |
| A433 | L1 | i-Pr | Me | 3,5-di-Cl—Ph | Z | 554 [M + H]$^+$ |
| A434 | L1 | i-Pr | Me | 3,5-di-Cl—Ph | AA | 554 [M + H]$^+$ |
| A435 | L1 | i-Pr | Me | 3,5-di-Cl—Ph | AB | 499 [M + H]$^+$ |
| A436 | L1 | L1 | i-Pr | Me | N/A (H) | 363 [M + H]$^+$ |
| A437 | L1 | i-Pr | Me | 3,5-di-Cl—Ph | AC | 499 [M + H]$^+$ |
| A438 | L1 | i-Pr | Me | 3,5-di-Cl—Ph | AD | 482 [M + H]$^+$ |
| A439 | L1 | i-Pr | Me | 3,5-di-Cl—Ph | AF | 494 [M + H]$^+$ |
| A440 | L1 | i-Pr | Me | 3,5-di-Cl—Ph | AG | 494 [M + H]$^+$ |
| A441 | L1 | i-Pr | Me | 3,5-di-Cl—Ph | AH | 499 [M + H]$^+$ |
| A442 | L1 | i-Pr | Me | 3,5-di-Cl—Ph | AE | 482 [M + H]$^+$ |
| A443 | L1 | i-Pr | Me | 3,5-di-Cl—Ph | AJ | 499 [M + H]$^+$ |
| A445 | L1 | i-Pr | Me | 3,5-di-Cl—Ph | AK | 511 [M + H]$^+$ |
| A446 | L1 | i-Pr | Me | 3,5-di-Cl—Ph | AL | 511 [M + H]$^+$ |
| A447 | L1 | i-Pr | Me | 3,5-di-Cl—Ph | AM | 482 [M + H]$^+$ |
| A448 | L1 | i-Pr | Me | 3,5-di-Cl—Ph | AO | 502 [M + H]$^+$ |
| A449 | L1 | i-Pr | Me | 3,5-di-Cl—Ph | AQ | 502 [M + H]$^+$ |
| A450 | L1 | i-Pr | Me | 3,5-di-Cl—Ph | AR | 502 [M + H]$^+$ |
| A451 | L1 | i-Pr | Me | 3,5-di-Cl—Ph | AP | 502 [M + H]$^+$ |
| A452 | L1 | i-Pr | Me | 3,5-di-Cl—Ph | AS | 523 [M + H]$^+$ |
| A472 | L1 | i-Pr | Me | 3,5-di-Cl—Ph | AT | 523 [M + H]$^+$ |
| A453 | L1 | i-Pr | Me | 3,5-di-Cl—Ph | AN | 482 [M + H]$^+$ |
| A454 | L1 | i-Pr | Me | 3,5-di-Cl—Ph | AU | 520 [M + H]$^+$ |
| 419 | L1 | i-Pr | Cl | 3,5-di-Cl—Ph | A | 558 [M + $CH_3CN$]$^+$ |
| 397-0 | L1 | $OCH_2CH{=}CH_2$ | Me | 3,5-di-Cl—Ph | A | 495 [M + H]$^+$ |
| A455 | L1 | i-Pr | Me | 3,5-di-Cl—Ph | AW | 482 [M + H]$^+$ |
| A456 | L1 | i-Pr | Me | 3,5-di-Cl—Ph | AX | 482 [M + H]$^+$ |
| A457 | L1 | i-Pr | Me | 3,5-di-Cl—Ph | AY | 515 [M + H]$^+$ |
| A458 | L1 | i-Pr | Me | 3,5-di-Cl—Ph | AZ | 515 [M + H]$^+$ |
| 395 | L1 | —$OCHF_2$ | Me | 3,5-di-Cl—Ph | A | 568 [M + $CH_3CN$+Na]$^+$ |

TABLE 3-continued

| Cmpd. # | L | $R^1$ | $R^2$ | $R^3$ | Ring System | ESI-MS |
|---|---|---|---|---|---|---|
| A459 | L1 | 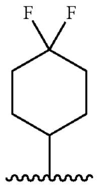 | Me | 3,5-di-Cl—Ph | A | 570 $[M + H]^+$ |
| A464 | L1 | —$N(CH_3)_2$ | Me | 2,6-di-Cl-4-F—Ph | A | 514 $[M + H]^+$ |
| A462 | L1 | —$N(CH_3)_2$ | Me | 2,4,6-tri-F—Ph | A | 481 $[M + H]^+$ |
| A463 | L1 | —$N(CH_3)_2$ | Me | 2,3-di-Cl-5-F—Ph | A | 514 $[M + H]^+$ |
| A460 | L1 | —$N(CH_3)_2$ | Me | 2,3,5-tri-F—Ph | A | 481 $[M + H]^+$ |
| A461 | L1 | —$N(CH_3)_2$ | Me | 2,3,5-tri-Cl—Ph | A | 531 $[M + H]^+$ |
| 558 | L1 | i-Pr | —$C(O)CH_3$ | 3,5-di-Cl—Ph | A | 523 $[M + H]^+$ |

For avoidance of doubt, each of the compounds presented in Table 3 has been prepared.

Stereoisomers and Polymorphic Forms

It will be appreciated by those of skill in the art that the compound may exist and be isolated in optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the description may include one or more chiral centers, which results in a theoretical number of optically active isomers. In the present case, the compounds of formula (I) include at least one chiral center at the carbon atom bearing variable $R^8$ when Q is C—$R^8$. Where compounds of the description include n chiral centers, the compounds may comprise up to $2^n$ optical isomers. Thus, the compounds of the present invention include at least 2 enantiomers which are encompassed by the invention. The description encompasses the specific enantiomers or diastereomers of each compound as well as mixtures of different enantiomers and/or diastereomers of the compounds that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compound may also be present in different solid forms such as different crystalline forms or in the form of an amorphous solid. The description includes different crystalline forms as well as amorphous forms of the compound.

In addition, the compound may exist as hydrates or solvates, in which a certain stoichiometric amount of water or a solvent is associated with the molecule in the crystalline form. The hydrates and solvates of the compound are also the subject of the description.

Salts

In addition to the neutral compound, salt forms of the compound are also active against endoparasites. The term "veterinarily acceptable salt" is used throughout the specification to describe any salts of the compounds that are acceptable for administration for veterinary applications, and which provides an active compound upon administration.

In cases where compounds are sufficiently basic or acidic to form stable non-toxic acid or base salts, the compound may be in the form of a veterinarily or agriculturally acceptable salt. Veterinarily acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^{''}$) as well as substituted ammonium cations, in which one or more of the hydrogen atoms are replaced by alkyl or aryl groups are encompassed by the description.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartrate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compound can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the description.

Processes for the Preparation of the Compounds

The compounds of Formula (I) or pharmaceutically or a veterinarily acceptable salts thereof may be prepared by adopting schemes 1 and 2 below and the procedures in the examples:

Scheme 1

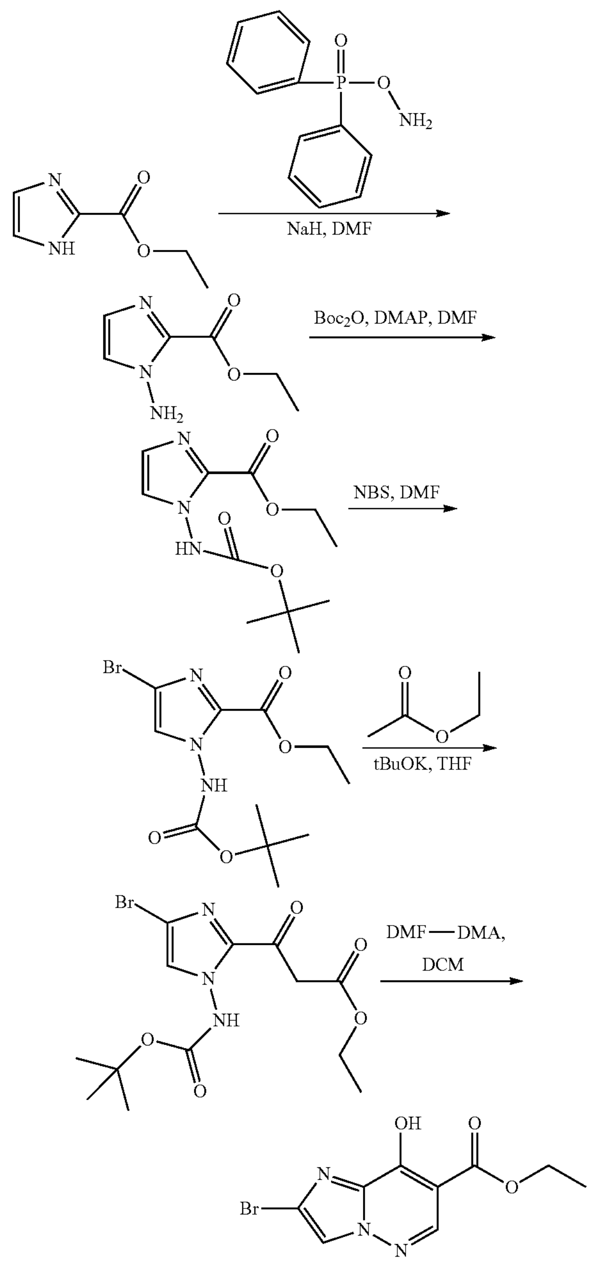

Scheme 2

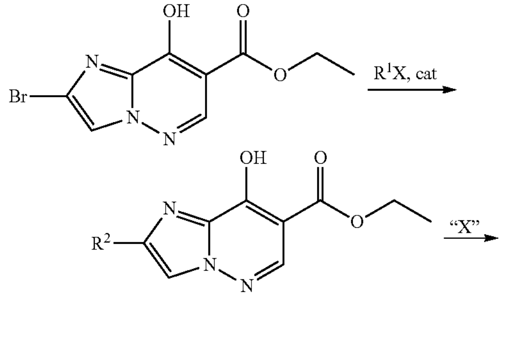

-continued

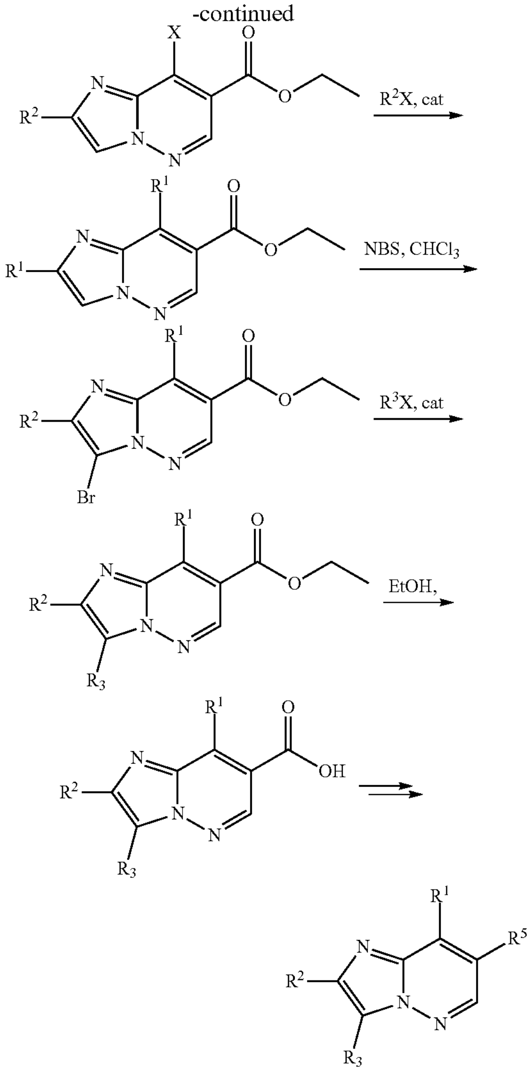

In scheme 2 variables $R^1$, $R^2$ and $R^3$ represent the groups defined in formula (I) above and may be introduced by a metal-catalyzed cross-coupling reaction. Examples include the Heck reaction, the Negishi coupling reaction, the Stille cross-coupling reaction, the Suzuki reaction, and others well known in the art. Variable $R^5$ represents the linker L bonded to one of the bicyclic rings shown in formula (I) at this position of the bicyclic core. It is well within the skill level of a person of ordinary skill in the art to adapt these schemes to synthesize a specific compound of the invention. Moreover, the starting materials are either readily available or can be made via known procedures.

Veterinary Compositions

The compound and compositions comprising the compound are useful for the prevention and/or treatment of parasitic infections or infestations in animals. The compositions of the description comprise an effective amount of a compound or a veterinarily acceptable salt thereof, in combination with a veterinarily acceptable carrier or diluent and optionally a non-active excipient. The compositions may be in a variety of solid and liquid forms which are suitable for various forms of application or administration to an animal. For example, the veterinary compositions comprising the compound may be in compositions suitable for oral administration, injectable administration, including subcutaneous and parenteral administration, and topical administration (e.g. spot-on or pour-on), dermal or subdermal administration. The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compound to protect companion animals such as dogs and cats from endoparasites is particularly useful.

As discussed above, the compositions of the description may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench compositions, dispersible powders or granules, premixes, syrups or elixirs, enteric compositions or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, granulating and disintegrating agents, binding agents, and lubricating agents. The tablets may be uncoated, or they may be coated by known techniques to delay disintegration and absorption in the gastrointestinal tract and thereby provide a sustained action over a longer period. They may also be coated by the technique described in U.S. Pat. Nos. 4,256,108; 4,166,452; and 4,265,874 (all incorporated herein by reference in their entirety) to form osmotic therapeutic tablets for controlled release.

Oral compositions include hard gelatin capsules. Capsules may also be soft gelatin capsules, wherein the active ingredient is mixed with water or water-miscible solvents, or an oil medium.

In one embodiment, the compound may be administered in chewable tablet compositions or soft chewable compositions such as those described in US 2013/0203692 A1, US 2010/0087492, US 2006/0222684, US 2004/0151759, U.S. Pat. No. 7,955,632, all incorporated herein by reference. The veterinary compositions may be in the form of a soft chewable composition ("soft chew"), which is palatable and acceptable to the animal. In addition to the active ingredient (s), the soft chews of the description may include one or more of the following components known in the art for these dosage forms: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

The compositions may also contain other inert ingredients such as antioxidants, preservatives, or pH stabilizers. These compounds are well known in the composition art. Antioxidants may be added to the compositions of the description to inhibit degradation of the active agents.

The compositions of the description may also include one or more lubricants and/or processing aids. In some cases, the lubricant/processing aid may also behave as a solvent, and accordingly, there some of the components of the inventive compositions may have dual functions.

Many flavoring agents may be used in the compositions of the description to improve the palatability of the oral veterinary compositions. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the description, the active composition may be administered via a drench, and may be administered either topically or orally. Drench compositions are those in which the liquid-containing compositions of the description are administered to the mouth or throat of the animal or poured onto the skin or coat of the animal.

The compositions of the description may also be in the form of oil-in-water or water-in-oil emulsions which may include emulsifying agents known in the art. The emulsions may also contain sweetening agents, bittering agents, flavoring agents, and/or preservatives.

In one embodiment, the composition of the description may be in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase.

Oily suspensions may be formulated by suspending the active ingredient in a vegetable oil. The oily suspensions may contain a thickening agent. Sweetening agents, bittering agents, and flavoring agents may be added to provide a palatable oral preparation. These compositions may be preserved by the addition of an antioxidant, or other known preservatives.

Aqueous suspensions may contain the active material in admixture with excipients suitable for the manufacture of aqueous suspensions. The aqueous suspensions may also contain one or more preservatives, one or more coloring agents, one or more flavoring agents, and one or more sweetening agents and/or bittering agents.

Dispersible powders and granules suitable for preparation of an aqueous suspension by the addition of water may provide the active ingredient in admixture with a dispersing or wetting agent, suspending agent and one or more preservatives. Additional excipients, for example, sweetening, bittering, flavoring and coloring agents, may also be present.

Syrups and elixirs may be formulated with sweetening agents. Such compositions may also contain a demulcent, a preservative, flavoring agent(s) and/or coloring agent(s).

In another embodiment of the description, the composition may be in paste form. Examples of embodiments in a paste form include, but are not limited to, those described in U.S. Pat. Nos. 6,787,342 and 7,001,889 (each of which are incorporated herein by reference). In addition to the compounds of the description, the paste may further contain fumed silica; a viscosity modifier; a carrier; optionally, an absorbent; and optionally, a colorant, stabilizer, surfactant, or preservative.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent.

In addition, sterile, fixed oils may be conventionally employed as a solvent or suspending medium.

Topical, dermal and subdermal compositions may include, by way of non-limiting example, emulsions, creams, ointments, gels, pastes, powders, shampoos, pour-on compositions, ready-to-use compositions, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. Spot-on compositions are typically applied in a localized region which refers to an area other than the entire animal. In one embodiment, the location may be between the shoulders. In another embodiment the topical composition may be administered as a stripe on the surface of the animal, e.g. a stripe from head to tail of the animal.

Pour-on compositions are described in U.S. Pat. No. 6,010,710, also incorporated herein by reference. Pour-on compositions may be advantageously oily, and generally comprise a diluent or vehicle and also a solvent (e.g. an organic solvent) for the active ingredient if the latter is not soluble in the diluent. In other embodiments, pour-on compositions may comprise water-miscible organic solvents.

The solvent will be used in proportion with the concentration of the active agent compound and its solubility in this solvent. It will be sought to have the lowest possible volume. The vehicle makes up the difference to 100%.

In another embodiment of the description, an emollient and/or spreading and/or film-forming agent may be added to the topical composition.

In another embodiment of the description, the composition may be in ready-to-use solution form as is described in U.S. Pat. No. 6,395,765, incorporated herein by reference. In addition to the compounds of the description, the ready-to-use solution may contain a crystallization inhibitor and an organic solvent or a mixture of organic solvents. In some embodiments, water may be included with the organic solvent.

The composition may also comprise an antioxidizing agent intended to inhibit oxidation in air, this agent may be present in a proportion of about 0.005 to about 1% (w/v), about 0.01 to about 0.1%, or about 0.01 to about 0.05%.

The composition excipients discussed above are well known to the practitioner in this art and may be obtained commercially or through known techniques. These compositions are generally prepared by simple mixing of the constituents as defined above; advantageously, the starting point is to mix the active material in the main solvent and then the other ingredients or adjuvants are added.

The volume of the composition applied will depend on the type of animal and the size of the animal as well as the strength of the composition and the potency of the active agents. In one embodiment, an amount of about 0.1 to about 20 ml of the composition may be applied to the animal. In other embodiment for the volume, the volume may be about 0.1 to about 10 ml, about 0.1 to about 5 ml, about 0.5 ml to about 10 ml, or about 0.3 to about 3 ml.

Spot-on compositions may be prepared by dissolving the active ingredients into the pharmaceutically or veterinary acceptable vehicle. Alternatively, the spot-on composition may be prepared by encapsulation of the active ingredient to leave a residue of the therapeutic agent on the surface of the animal. These compositions will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the description, the compound of Formula (I) may be present in the composition at a concentration of about 0.05 to about 50% weight/weight. In other embodiments, the compound of Formula (I) may be present in a concentration of about 0.1 to about 30% (w/w). In other embodiments, the compound of Formula (I) may be present in a concentration of about 0.5 to about 30% (w/w), about 1 to about 20% (w/w) or about 0.05 to about 10% (w/w). In other embodiments, the compound of Formula (I) may be present in a concentration of about 10 to about 50% (w/w), about 10 to about 30% (w/w), about 10 to about 20% (w/w). In yet another embodiment, the compound of Formula (I) may be present in a concentration of about 1 to 10% (w/w) or about 5 to about 15% (w/w). In another embodiment of the description, the active agent may be present in the composition as a concentration from about 0.1 to about 2% w/w. In yet another embodiment of the description, the active agent may be present in the composition as a concentration from about 0.25 to about 1.5% w/w. In still another embodiment of the description, the active agent may be present in the composition as a concentration about 1% w/w.

Methods of Treatment

As discussed above, the compound of Formula (I) are effective against endoparasites and may be used to treat and/or prevent parasitic infections in animals. In one embodiment, the present description provides a method of treating and/or preventing an endoparasite infection in or on an animal (e.g. a mammal or bird) comprising administering an endoparasiticidally effective amount of a compound of formula (I), or veterinarily acceptable salts thereof, or a composition of the description, to the animal.

The present description also provides a use of the compound of Formula (I) in the preparation of a medicament for the treatment and/or prevention of parasitic infections in animals. The present description also provides the compound of Formula (I) for use in the treatment and/or prevention of a parasitic infection in animals.

In certain embodiments, the compound of Formula (I) may also effective against ectoparasites and may be used to treat and/or prevent ectoparasitic infestations on animals. In another embodiment, the present description provides a method of treating and/or preventing an ectoparasitic infestation on an animal (e.g. a mammal or bird) comprising administering an ectoparasiticidally effective amount of a compound of formula (I), or veterinarily acceptable salts thereof, or a composition of the description, to the animal.

Also provided is the use of the compound of Formula (I) in the preparation of a medicament for the treatment and/or prevention of an ectoparasitic infestation in animals. The present description also provides a compound of Formula (I) for use in the treatment and/or prevention of an ectoparasitic infestation on animals.

In another embodiment, the description provides a method for treating and/or preventing an endoparasitic infection and an ectoparasitic infestation in and on an animal, comprising administering a composition comprising an effective amount of a compound of formula (I) in combination with an effective amount of at least a second active agent, or veterinarily acceptable salts thereof, to the animal.

The compound of Formula (I) in combination with at least a second active agent for use in the treatment and/or prevention of an endoparasitic infection and an ectoparasitic infestation is also provided herein. In addition, the use of the compound of Formula (I) in combination with at least a second active agent in the preparation of a medicament for the preparation of a medicament for the treatment and/or prevention of an endoparasitic infection and an ectoparasitic infestation is provided.

In still another embodiment of the description, a method is provided for the treatment and/or prevention of a parasitic infestation at a locus, which comprises administering or applying a parasiticidally effective amount of a compound of formula (I), or veterinarily acceptable salts thereof, to the locus. With respect to animal health applications, "locus" is intended to mean a habitat, breeding ground, area, material or environment in which a parasite is growing or may grow, excluding in or on an animal.

In another embodiment, the description provides methods and uses of the compound for controlling pests in plants and crops or for protecting wood-containing structures.

In some embodiments, the animals which can be treated are mammals that include but are not limited to humans, cats, dogs, cattle, chickens, cows, bison, deer, goats, horses, llamas, camels, pigs, sheep and yaks. In one embodiment of the description, the mammals treated are humans, cats or dogs.

In one embodiment of the description, the compounds of Formula (I) have been found to have superior efficacy against endoparasites, and in particular against endoparasites that are resistant to active agents of the macrocyclic lactone class. In one embodiment, the compounds and compositions of the description are effective for controlling *Haemonchus contortus, Ostertagia circumcincta* and *Trichostrongylus colubriformis* in mammals or birds.

In another embodiment, the description provides a method for the treatment or prevention of a parasitic infestation or infection in an animal, comprising administering an effective amount of an anthelmintic compound of the description in combination with an effective amount of activators of invertebrate GABA receptors including an avermectin or milbemycin to the animal in need thereof.

In another embodiment, the invention provides use of the compound of Formula (I) in the manufacture of a medicament for the treatment or prevention of a parasitic infestation or infection in an animal. In yet another embodiment, the invention provides a compound of Formula (I) for use in treating or preventing a parasitic infection or infestation in an animal.

Avermectins that may be used in combination with the compounds of the description include, but are not limited to abamectin, dimadectin, doramectin, emamectin, eprinomectin, ivermectin, latidectin, lepimectin, and selamectin Milbemycins compounds that may be used in combination with the compounds of the description include, but are not limited to, milbemectin, milbemycin D, moxidectin and nemadectin. Also included are the 5-oxo and 5-oxime derivatives of said avermectins and milbemycins.

In one embodiment, the compounds and compositions of the description may be used for treating and/or preventing an endoparasitic infection of the following parasite: Anaplocephala (*Anoplocephala*), *Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In a particularly preferred embodiment of the description, the compounds and compositions of the description are used to treat and/or prevent an infection by *Dirofilaria immitis*. The compounds have been found to be highly effective against *D. immitis* microfilaria and L4 larvae. Thus, the compounds may be used to protect animals from developing heartworm disease by killing the immature stages of *D. immitis* before they can develop into adult worms. In one embodiment, the compound and compositions comprising the compounds may be used to prevent the development of heartworm disease by killing immature stages of *D. immitis* that are resistant to macrocyclic lactones. In another embodiment the compounds and compositions of the description are used to treat and/or prevent an infection by *Dirofilaria repens* or *Dirofilaria hongkongensis*.

In another embodiment of the description, the parasite is *Haemonchus contortus, Ostertagia circumcincta, Trichostrongylus axei, Trichostrongylus colubriformis, Cooperia curticei, Nematodirus battus* and combinations thereof.

In another embodiment for treatment against both endoparasites and ectoparasites when combined with ectoparasiticidal agents, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., Otodectes spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include, but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In another embodiment of the description, the compounds and compositions of the description are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the description can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of *Blattaria*, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Coch/iomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinellafrit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, Arion spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furca-*

*tus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephalafestina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, Acronicta major, *Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the description, the compounds and compositions of the description can be applied against a single pest or combinations thereof.

Mixtures with Other Active Agents

In another embodiment, the compositions comprising the compounds of Formula (I) may also include other veterinary therapeutic agents. Veterinary pharmaceutical agents that may be included in the compositions of the description are well-known in the art (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/− clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium·calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprazole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the description, arylpyrazole compounds such as phenylpyrazoles may be included in the veterinary compositions of the description. Arylpyrazoles are known in the art and may be suitable for combination with the compound of Formula (I) in the compositions of the description. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the description, one or more macrocyclic lactones, which act as an acaricide, an anthelmintic agent and/or an insecticide, can be included in the compositions of the description in combination with the compound. For the avoidance of doubt, the term "macrocyclic lactone" as used herein includes both naturally occurring and synthetic or semisynthetic avermectin and milbemycin compounds.

The macrocyclic lactones that may be used in the compositions of the description include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, New Jersey (1996). Latidectin is described in the "International Non-proprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the description comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the description provides a veterinary composition comprising an effective amount of at least one of abamectin, emamectin, eprinomectin, ivermectin, doramectin or selamectin, or a combination thereof. In still another embodiment, the veterinary compositions of the description comprise an effective amount of at least one of ivermectin, milbemectin, milbemycin oxime or moxidectin, or a combination thereof.

In another embodiment of the description, a composition comprising a compound of Formula (I) in combination with a class of acaricide or insecticides known as insect growth regulators (IGRs) are provided. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the description may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one. In another embodiment, the compositions of the description comprise a compound of formula (I) in combination with methoprene or pyriproxyfen and a pharmaceutically acceptable carrier.

In another embodiment, the compositions of the description include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl) phenylurea.

In some embodiments, the compositions of the description may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the description may include an imidazothiazole compounds including, but not limited to, tetramisole, levamisole and butamisole.

In still other embodiments, the compositions of the description may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the description may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the description including, but not limited to, arecoline in various salt forms, bunamidine, niclosamide, nitroscanate, paromomycin, paromomycin II, praziquantel and epsiprantel.

In yet other embodiments, the compositions of the description may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, an antiparasitic agent that can be included in the veterinary composition containing a compound of formula (I) can be a biologically active peptide or protein including, but not limited to, depsipeptides other than the compound. These include PF1022A or analogs thereof and emodepside. Other cyclic depsipeptide compounds that may be included in the compositions comprising a compound of Formula (I) are those described in WO 2016/187534 A1 and WO 2017/116702 A1, both incorporated herein by reference. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the description may comprise an active agent from the neonicotinoid class of parasiticides. The neonicotinoids bind and inhibit insect specific nicotinic acetylcholine receptors. In one embodiment, the neonicotinoid insecticidal agent that can be combined with a compound of Formula (I) in a composition of the description is imidacloprid. Agents of this class are described, for example, in U.S. Pat. No. 4,742,060 or in EP 0 892 060 (both incorporated herein by reference). In another embodiment, the compositions of the description may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the description, the compound of Formula (I) can be combined with the compositions of the description is a semicarbazone, such as metaflumizone.

In another embodiment, the compositions of the description may advantageously include one or more isoxazoline compounds known in the art. Isoxazoline active agents are highly effective against a variety of ectoparasites and combination with the compound of Formula (I) would expand the scope of efficacy against these parasites. Particularly useful isoxazoline active agents that can be combined with the compound include afoxolaner (including the substantially pure active enantiomer, esafoxolaner), sarolaner, fluralaner (including substantially pure active enantiomer), lotilaner and tigolaner. These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, 9,221,835, US 2011/0144349, U.S. Pat. No. 8,053,452; US 2010/0137612, U.S. Pat. No. 8,410,153, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, US 2015/0126523, WO 2010/003923, WO 2010/003877, WO 2010/072602, WO 2014/134236, WO 2017/147352, U.S. Pat. Nos. 7,897,630, 7,951,828, WO 2020/007704 A1, WO 2021/028479 A1, WO 2014/122083 A1, WO 2016/177619 A1, WO 2014/012975 A1, WO 2015/078846 A1, WO 2015/078847 A1, WO 2015/150302 A1, WO 2015/181139 A1 and WO 2016/026789 A1, all of which are incorporated herein by reference in their entirety.

In another embodiment of the description, nodulisporic acid and its derivatives may be added to the compositions of the description. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the description. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the description may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621, which is also incorporated herein by reference. Aryloazol-2-yl cyanoethylamino active agents, which are systemically-acting against endoparasites, may be used in combination with the compound in veterinary compositions of the description.

The compositions of the description may also include paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds is a known class of compounds that include a spirodioxepino indole core with activity against certain parasites (see *Tett. Lett.* 1981, 22, 135*; J. Antibiotics* 1990, 43, 1380, and *J. Antibiotics* 1991, 44, 492). In addition, the structurally related marcfortine family of compounds, such as marcfortines A-C, are also known and may be combined with the compositions of the description (see *J Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety.

In another embodiment of the description, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the description. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the description, may be produced via fermentation by conventional techniques known in the art. Other spinosyn compounds that may be used in the compositions of the description are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than the compound of formula (I) described above) is included in the dosage units of the description in an amount of between about 0.1 μg and about 1000 mg. Typically, the active agent may be included in an amount of about 10 μg to about 500 mg, about 10 μg to about 400 mg, about 1 mg to about 300 mg, about 10 mg to about 200 mg or about 10 mg to about 100 mg. More typically the additional active agent will be present in an amount of about 5 mg to about 50 mg in the compositions of the description.

The concentration of the additional active agent in the compositions of the description will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.10% to about 1% (w/w).

In other embodiments, the additional active agent will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the description, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the description where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 μg/kg to about 200 μg/kg or about 0.1 mg/kg to about 1 mg/kg of weight of animal.

In addition to the other active agents mentioned above, combinations of two or more active agents may be used with the compounds of the description in a composition to treat a desired spectrum of pests and parasites. It would be well within the skill level of the practitioner to decide which individual compound can be used in the inventive composition to treat a particular infection of an insect.

The invention will now be further described by way of the following non-limiting examples.

EXAMPLES

Preparation Examples

The Examples that follow are intended to only illustrate the present invention without restricting it. The compounds of Formula (I) or pharmaceutically or a veterinarily acceptable salts thereof may be prepared by adopting one of the following reaction schemes. The starting materials for their preparation may be commercially available or can be prepared by methods known by persons of skill in the art and as described in the literature or may be an intermediate in any other of the schemes described herein. It will be appreciated that the following procedures may be modified by persons of skill in the art to prepare additional compounds according to the invention. For example, a person of skill in the art will understand that replacement of certain starting materials or the use of different intermediates will enable the preparation of different compounds of Formula (I).

The terms "ambient temperature" and "room temperature" are used interchangeably and designate a temperature of about 20° C. Although the following subject matter is described in some detail by way of illustration and example for purposes of clarity of understanding, it will be understood by those skilled in the art that certain changes and modifications can be practiced within the scope of the Examples.

List of Abbreviations

ACN acetonitrile
AIBN azobisisobutyronitrile
BINAP (2,2'-Bis(diphenylphosphino)-1,1'-binaphthyl)
BSA bovine serum albumin
BOC tert-butoxycarbonyl BOP—Cl Bis(2-oxo-3-oxazolidinyl)phosphinic chloride
DAST Diethylaminosulfur trifluoride
DCC N,N'-Dicyclohexylcarbodiimide solution
DCM dichloromethane
DEAD Diethyl azodicarboxylate
DIEA diisopropylethylamine
DMF N,N-dimethylformamide
DMAP 4-(Dimethylamino)pyridine
DMSO dimethylsulfoxide
EDAC N-(3-Dimethylaminopropyl)-N'-ethylcarbodiimide hydrochloride
EDCI 1-Ethyl-3-(3-dimethylaminopropyl)carbodiimide
ES electrospray
EtOAc or EA ethyl acetate
HATU 1-[bis(dimethylamino)methylene]-1H-1,2,3-triazolo[4,5 b]pyridinium 3-oxide hexafluorophosphate
HOBt or HOBT 1-hydroxybenzotriazole
KHMDS potassium hexamethyldisilazide, more precisely potassium bis(trimethylsilyl)amide
MeOH methanol
m-CPBA m-Chloroperbenzoic acid
NMO N-Methylmorpholine-N-oxide
o/n over night
PE petroleum ether
$Pd(dtbpf)Cl_2$ Dichloro[1,1'-bis (di-tert-butylphosphino) ferrocene] palladium(II)
$Pd_2dba_3$ Tris(dibenzylideneacetone)dipalladium(O)
$Pd(dppf)Cl_2$ [1,1'-Bis(diphenylphosphino)ferrocene]dichloropalladium(II), complex with dichloromethane
TBAF tert-butyl ammonium fluoride
TfO triflate
THE tetrahydrofuran
TLC thin-layer chromatography Some examples of Formula (I) are derived after separation of racemic mixtures and obtained as enantiomerically pure products. The stereochemistry is in some cases arbitrarily assigned and the respective compound characterized by analytical methods as described below:

Method A

| Gradient/ Solvent Time [min] | % Sol [scCO$_2$] | % Sol [MeOH 20 mM NH$_3$] | Flow [ml/min] | Temp [° C.] | Back pressure [PSI] |
|---|---|---|---|---|---|
| 0.0 | 75.0 | 25.0 | 2.0 | 40.0 | 2175.0 |
| 4.0 | 75.0 | 25.0 | 2.0 | 40.0 | 2175.0 |

CHIRAL ART ® Cellulose SJ_3 x 100 mm_3 μm (Agilent)

Method B

| Gradient/ Solvent Time [min] | % Sol [scCO$_2$] | % Sol [MeOH 20 mM NH$_3$] | Flow [ml/min] | Temp [° C.] | Back pressure [PSI] |
|---|---|---|---|---|---|
| 0.0 | 85.0 | 15.0 | 2.0 | 40.0 | 2175.0 |
| 4.0 | 85.0 | 15.0 | 2.0 | 40.0 | 2175.0 |

CHIRAL ART ® Cellulose SJ_3 x 100 mm_3 μm (Agilent)

Method C

| Gradient/ Solvent Time [min] | % Sol [scCO$_2$] | % Sol [MeOH 20 mM NH$_3$] | Flow [ml/min] | Temp [° C.] | Back pressure [PSI] |
|---|---|---|---|---|---|
| 0.0 | 80.0 | 20.0 | 2.0 | 40.0 | 2175.0 |
| 4.0 | 80.0 | 20.0 | 2.0 | 40.0 | 2175.0 |

CHIRAL ART ® Cellulose SJ_3 x 100 mm_3 μm (Agilent)

Method D

| Gradient/ Solvent Time [min] | % Sol [scCO$_2$] | % Sol IPA 20 mM NH$_3$] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

CHIRAL ART ® Cellulose SB_4.6 x 250 mm_5 μm (Agilent)

Method E

| Gradient/ Solvent Time [min] | % Sol [scCO$_2$] | % Sol IPA [MeOH 20 mM NH$_3$] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

CHIRAL ART ® Cellulose SB_4.6 x 250 mm_5 μm (Agilent)

Preparation Example 1: The following example compounds can be synthesized by adopting the subsequent schemes 3 and 4 shown below for compound 175 by someone skilled in the art: 271, 272, 273, 274, 275, 276, 279, 293, 294, 295, 296, 304, 305, 307, 308, 322, 344, 345, 364, 527, 528, A402, A403, A404, A406, A407, A410, A411, A412, A413, A414, A415, A416, A417, A418, 419, A419, A420, A423, A424, A425, A426, A428, A429, A430, A431, A432, A433, A434, A435, A436, A437, A438, A439, A440, A441, A442, A443, A445, A446, A447, A448, A451, A452, A453, A454, A455, A456, A457, A458, A460, A472, 560.

Scheme 3

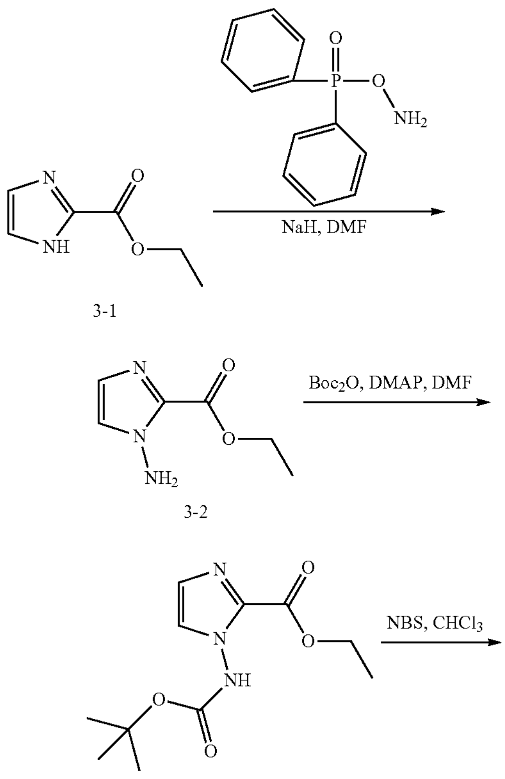

3-1

3-2

3-3

-continued
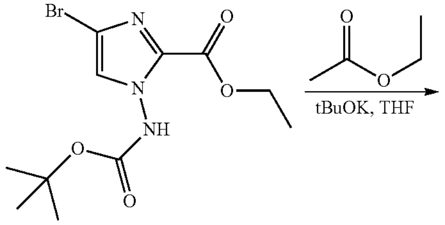
3-4
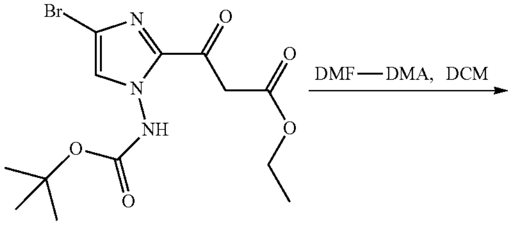
3-5
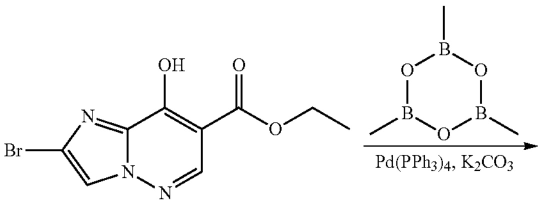
3-6
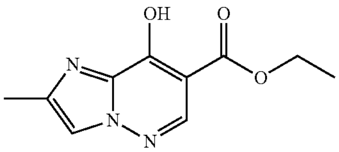
3-7
Scheme 4
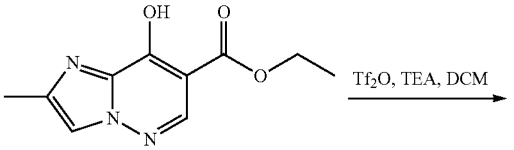
3-7
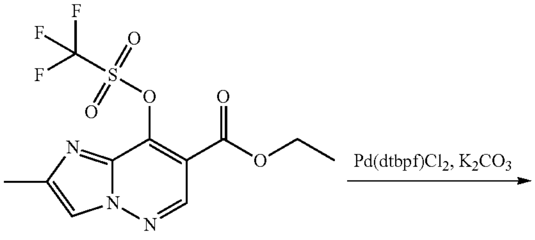
4-1
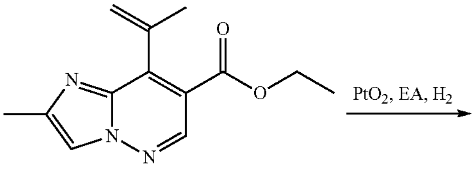
4-2
-continued
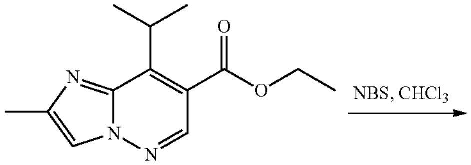
4-3
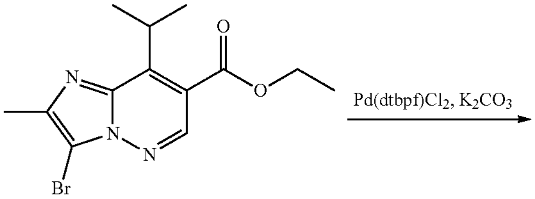
4-4
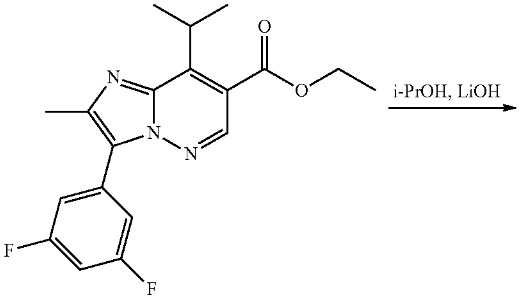
4-5
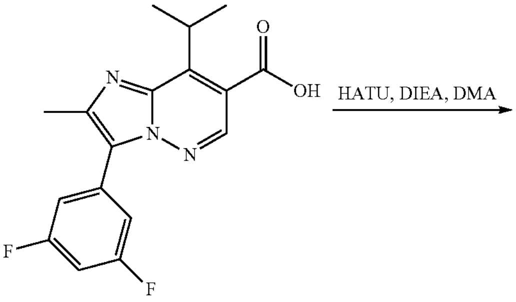
4-6
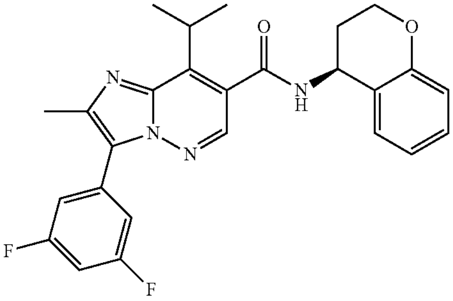
175

1. Synthesis of ethyl 1-aminoimidazole-2-carboxylate

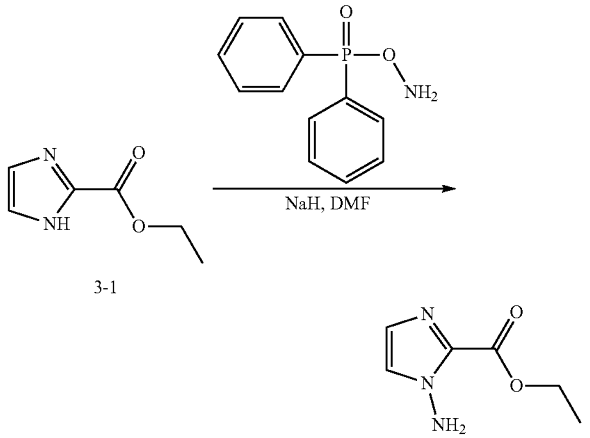

3-1

3-2

Into a 3000-mL 3-necked round-bottom flask, was placed DMF (2000 mL), ethyl 1H-imidazole-2-carboxylate (3-1, 50.0 g, 356.7 mmol, 1.0 equiv). This was followed by the addition of NaH (21.0 g, 875.0 mmol, 2.4 equiv), in portions at room temperature. To this was added amino diphenylphosphinate (119.0 g, 510.2 mmol, 1.4 equiv), in portions at 0° C. The resulting solution was stirred for 3 hr at room temperature. The resulting mixture was concentrated under vacuum. The solids were filtered off. The resulting mixture was concentrated under vacuum. The residue was applied onto a silica gel column with dichloromethane/methanol (10:1). This resulted in 40 g (72.2%) of ethyl 1-aminoimidazole-2-carboxylate (3-2) as a white solid.

2. Synthesis of ethyl 1-[(tert-butoxycarbonyl)amino]imidazole-2-carboxylate (3-3)

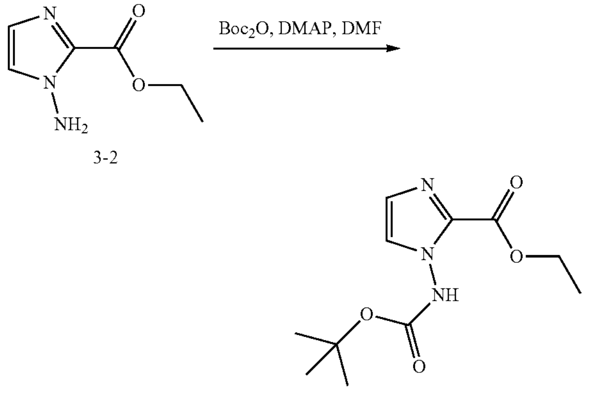

3-2

3-3

Into a 500-mL round-bottom flask, was placed DMF (200.0 mL), ethyl 1-aminoimidazole-2-carboxylate (3-2, 35.0 g, 225.5 mmol, 1.0 equiv), $Boc_2O$ (63.9 g, 293.2 mmol, 1.3 equiv), DMAP (13.7 g, 112.7 mmol, 0.5 equiv). The resulting solution was stirred for 2 hr at 80° C. The reaction was then quenched by the addition of 500 mL of water. The resulting solution was extracted with 3×200 mL of ethyl acetate and the organic layers combined and dried over anhydrous sodium sulfate and concentrated under vacuum. The residue was applied onto a silica gel column with ethyl acetate/petroleum ether (1:3). This resulted in 28 g (48.6%) of ethyl 1-[(tert-butoxycarbonyl)amino]imidazole-2-carboxylate (3-3) as a white solid.

3. Synthesis of ethyl 4-bromo-1-[(tert-butoxycarbonyl)amino]imidazole-2-carboxylate (3-4)

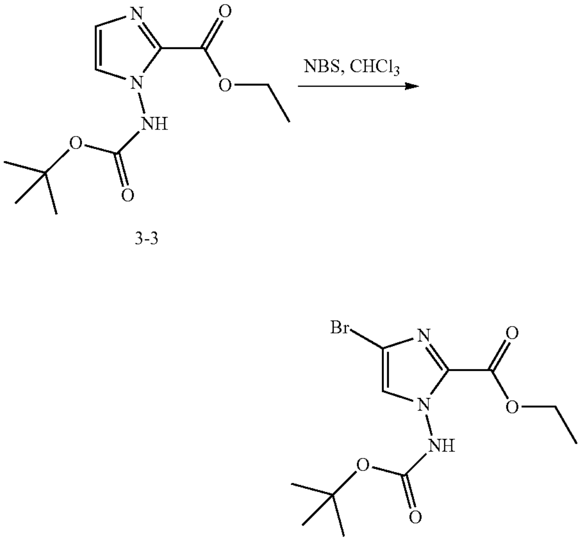

3-3

3-4

Into a 250-mL round-bottom flask, was placed DMF (100.0 mL), ethyl 1-[(tert-butoxycarbonyl)amino]imidazole-2-carboxylate (3-3, 15.0 g, 58.7 mmol, 1.0 equiv), NBS (10.4 g, 58.8 mmol, 1.0 equiv). The resulting solution was stirred for 1 days at room temperature. The reaction was then quenched by the addition of 300 mL of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1:4). This resulted in 12 g (61.1%) of ethyl 4-bromo-1-[(tert-butoxycarbonyl)amino]imidazole-2-carboxylate (3-4) as colorless oil.

4. Synthesis of ethyl 3-[4-bromo-1-[(tert-butoxycarbonyl)amino]imidazol-2-yl]-3-oxopropanoate (3-5)

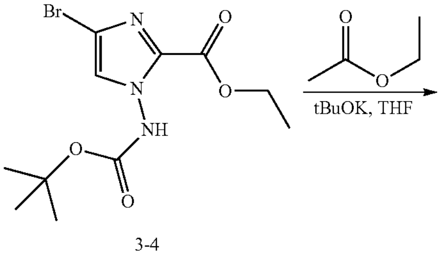

3-4

-continued

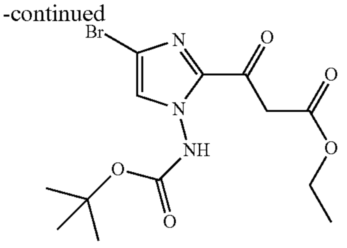

3-5

Into a 1000-mL 3-necked round-bottom flask, was placed THF (400.0 mL), ethyl 4-bromo-1-[(tert-butoxycarbonyl) amino]imidazole-2-carboxylate (3-4, 12.0 g, 35.9 mmol, 1.0 equiv). This was followed by the addition of t-BuOK (60.0 g, 534.7 mmol, 14.9 equiv), in portions at 0° C. in 30 min. To this was added ethyl acetate (32.0 g, 363.2 mmol, 10.1 equiv) dropwise with stirring at 0° C. The resulting solution was stirred for 2 hr at room temperature. The reaction was then quenched by the addition of HCl (1M). The resulting solution was extracted with 3×50 mL of ethyl acetate and the organic layers combined and dried over anhydrous sodium sulfate and concentrated under vacuum. This resulted in 6.5 g (48.1%) of ethyl 3-[4-bromo-1-[(tert-butoxycarbonyl) amino]imidazol-2-yl]-3-oxopropanoate (3-5) as yellow oil.

5. Synthesis of ethyl 2-bromo-8-hydroxyimidazo[1,2-b]pyridazine-7-carboxylate (3-6)

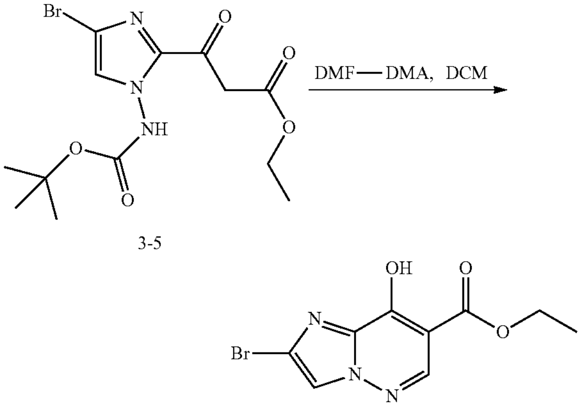

3-5

3-6

Into a 100-mL round-bottom flask, was placed DCM (30.0 mL), ethyl 3-[4-bromo-1-[(tert-butoxycarbonyl)amino]imidazol-2-yl]-3-oxopropanoate (3-5, 6.5 g, 17.2 mmol, 1.0 equiv), DMF-DMA (5.00 mL, 37.3 mmol, 2.2 equiv). The resulting solution was stirred for 2 hr at room temperature. The resulting mixture was concentrated under vacuum. The crude product was purified by Flash-Prep-HPLC with the following conditions (IntelFlash-1): Column, C18 silica gel; mobile phase, $H_2O$:ACN=90:10 increasing to $H_2O$: ACN=50:50 within 15 min; Detector, 254 nm. This resulted in 3.3 g (66.7%) of ethyl 2-bromo-8-hydroxyimidazo[1,2-b]pyridazine-7-carboxylate (3-6) as a white solid.

6. Synthesis of ethyl 8-hydroxy-2-methylimidazo[1,2-b]pyridazine-7-carboxylate (3-7)

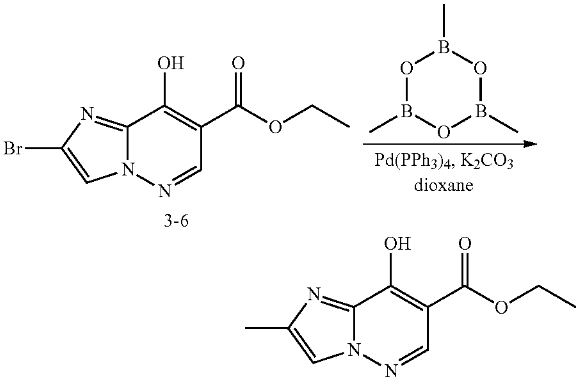

3-6

3-7

Into a 250-mL round-bottom flask purged and maintained with an inert atmosphere of nitrogen, was placed dioxane (60.0 mL), ethyl 2-bromo-8-hydroxyimidazo[1,2-b] pyridazine-7-carboxylate (3-6, 3.0 g, 10.5 mmol, 1.0 equiv), trimethyl-1,3,5,2,4,6-trioxatriborinane (2.6 g, 20.9 mmol, 2.0 equiv), $Pd(PPh_3)_4$ (1.2 g, 1.0 mmol, 0.1 equiv), $K_2CO_3$ (4.3 g, 31.3 mmol, 3.0 equiv). The resulting solution was stirred for 4 hr at 100 degrees C. The resulting mixture was concentrated under vacuum. The residue was applied onto a silica gel column with ethyl acetate/petroleum ether (1:2). This resulted in 2 g (86.2%) of ethyl 8-hydroxy-2-methyl-imidazo[1,2-b]pyridazine-7-carboxylate (3-7) as a yellow solid.

7. Synthesis of ethyl 2-methyl-8-(trifluoromethanesulfonyloxy)imidazo[1,2-b]pyridazine-7-carboxylate (4-1)

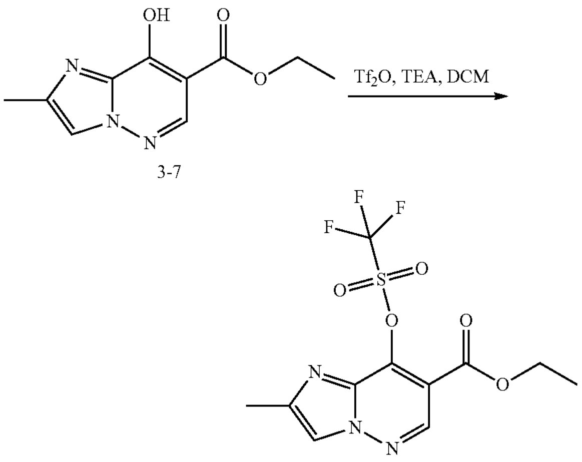

3-7

4-1

Into a 50-mL round-bottom flask purged and maintained with an inert atmosphere of nitrogen, was placed DCM (20.0 mL), ethyl 8-hydroxy-2-methylimidazo[1,2-b]pyridazine-7-carboxylate (3-7, 200.0 mg, 0.9 mmol, 1.0 equiv), TEA (457.0 mg, 4.5 mmol, 5.0 equiv). This was followed by the addition of $Tf_2O$ (765.6 mg, 2.7 mmol, 3.0 equiv) dropwise with stirring at −78 degrees C. The resulting solution was stirred for 1 hr at −50 degrees C. The reaction was then quenched by the addition of water/ice. The resulting solution was extracted with 3×20 mL of dichloromethane and the organic layers combined and dried over anhydrous sodium sulfate and concentrated under vacuum. This resulted in 200 mg (62.6%) of ethyl 2-methyl-8-(trifluoromethanesulfonyloxy)imidazo[1,2-b]pyridazine-7-carboxylate (4-1) as brown oil.

8. Synthesis of ethyl 2-methyl-8-(prop-1-en-2-yl) imidazo[1,2-b]pyridazine-7-carboxylate (4-2)

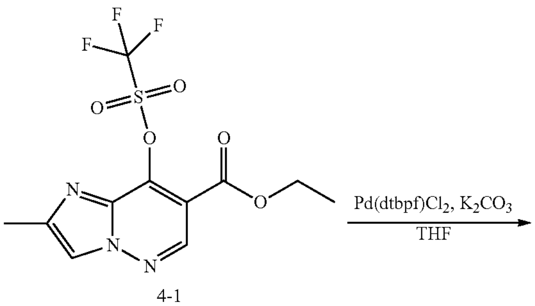

4-1

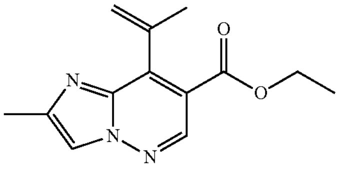

4-2

Into a 50-mL round-bottom flask purged and maintained with an inert atmosphere of nitrogen, was placed THE (10.0 mL), $H_2O$ (2.0 mL), ethyl 2-methyl-8-(trifluoromethanesulfonyloxy)imidazo[1,2-b]pyridazine-7-carboxylate (4-1, 200.0 mg, 0.6 mmol, 1.0 equiv), 4,4,5,5-tetramethyl-2-(prop-1-en-2-yl)-1,3,2-dioxaborolane (179.0 mg, 1.0 mmol, 1.9 equiv), $Pd(dtbpf)Cl_2$ (37.2 mg, 0.06 mmol, 0.10 equiv), $K_2CO_3$ (234.0 mg, 1.7 mmol, 3.0 equiv). The resulting solution was stirred for 2 hr at room temperature. The resulting mixture was concentrated under vacuum. The residue was applied onto a silica gel column with ethyl acetate/petroleum ether (1:4). This resulted in 90 mg (64.8%) of ethyl 2-methyl-8-(prop-1-en-2-yl)imidazo[1,2-b]pyridazine-7-carboxylate (4-2) as a white solid.

9. Synthesis of ethyl 8-isopropyl-2-methylimidazo [1,2-b]pyridazine-7-carboxylate

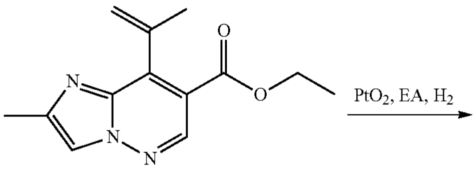

4-2

-continued

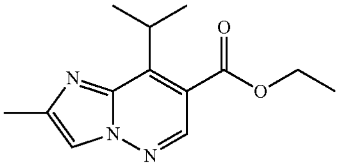

4-3

Into a 50-mL round-bottom flask, was placed EA (5.0 mL), ethyl 2-methyl-8-(prop-1-en-2-yl)imidazo[1,2-b]pyridazine-7-carboxylate (4-2, 90.0 mg, 0.4 mmol, 1.0 equiv), $PtO_2$ (30.00 mg, 0.1 mmol, 0.4 equiv), and an atmosphere of $H_2$ (g) by balloon. The resulting solution was stirred for 1 hr at 50° C. The solids were filtered out. The resulting mixture was concentrated under vacuum. This resulted in 90 mg (99.2%) of ethyl 8-isopropyl-2-methylimidazo[1,2-b]pyridazine-7-carboxylate (4-3) as a white solid.

10. Synthesis of ethyl 3-bromo-8-isopropyl-2-methylimidazo[1,2-b]pyridazine-7-carboxylate

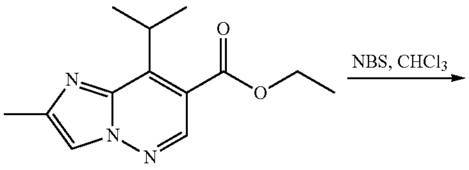

4-3

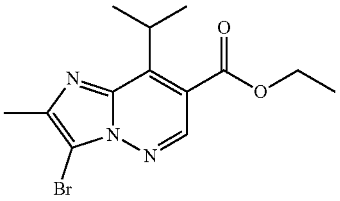

4-4

Into a 50-mL round-bottom flask, was placed $CHCl_3$ (10.0 mL), ethyl 8-isopropyl-2-methylimidazo[1,2-b]pyridazine-7-carboxylate (4-3, 90.0 mg, 0.4 mmol, 1.0 equiv), NBS (90.0 mg, 0.5 mmol, 1.4 equiv). The resulting solution was stirred for 1 hr at 80 degrees C. The reaction was then quenched by the addition of 10 mL of water. The resulting solution was extracted with 3×10 mL of dichloromethane and the organic layers combined and dried over anhydrous sodium sulfate and concentrated under vacuum. This resulted in 100 mg (crude) of ethyl 3-bromo-8-isopropyl-2-methylimidazo[1,2-b]pyridazine-7-carboxylate (4-4) as a white solid.

11. Synthesis of ethyl 3-(3,5-difluorophenyl)-8-isopropyl-2-methylimidazo[1,2-b]pyridazine-7-carboxylate (4-5)

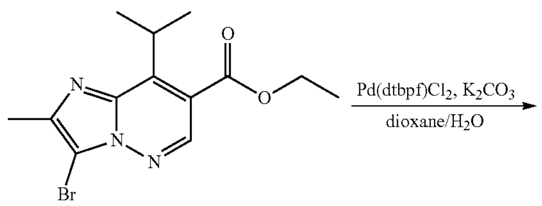

4-4

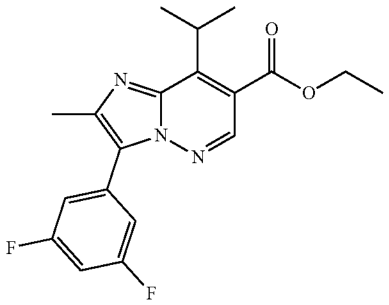

4-5

Into a 50-mL round-bottom flask purged and maintained with an inert atmosphere of nitrogen, was placed dioxane (10.0 mL), $H_2O$ (3.0 mL), ethyl 3-bromo-8-isopropyl-2-methylimidazo[1,2-b]pyridazine-7-carboxylate (4-4, 90.0 mg, 0.3 mmol, 1.0 equiv), 3,5-difluorophenylboronic acid (87.5 mg, 0.5 mmol, 2.0 equiv), Pd(dtbpf)$Cl_2$ (18.0 mg, 0.03 mmol, 0.1 equiv), $K_2CO_3$ (114.6 mg, 0.829 mmol, 3.0 equiv). The resulting solution was stirred for 3 hr at 100° C. The resulting mixture was concentrated under vacuum. The residue was applied onto a silica gel column with ethyl acetate/petroleum ether (1:3). This resulted in 80 mg (80.7%) of ethyl 3-(3,5-difluorophenyl)-8-isopropyl-2-methylimidazo[1,2-b]pyridazine-7-carboxylate (4-5) as a yellow solid.

12. Synthesis of 3-(3,5-difluorophenyl)-8-isopropyl-2-methylimidazo[1,2-b]pyridazine-7-carboxylic Acid (4-6)

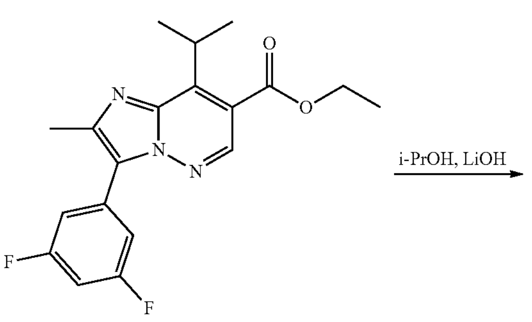

4-5

-continued

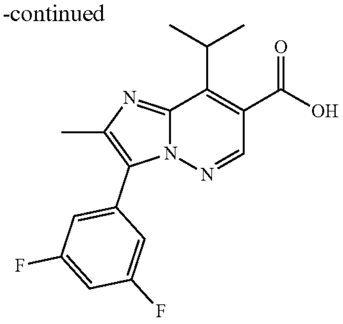

4-6

Into a 50-mL round-bottom flask, was placed $H_2O$ (1.0 mL), i-PrOH (5.0 mL), ethyl 3-(3,5-difluorophenyl)-8-isopropyl-2-methylimidazo[1,2-b]pyridazine-7-carboxylate (4-5, 80 mg, 0.2 mmol, 1.0 equiv), $LiOH \cdot H_2O$ (28.0 mg, 0.7 mmol, 3.0 equiv). The resulting solution was stirred for 2 hr at 50° C. The pH value of the solution was adjusted to 4 with HCl (2M). The resulting solution was extracted with 3×20 mL of ethyl acetate and the organic layers combined and dried over anhydrous sodium sulfate and concentrated under vacuum. This resulted in 60 mg (90%) of 3-(3,5-difluorophenyl)-8-isopropyl-2-methylimidazo[1,2-b]pyridazine-7-carboxylic acid (4-6) as a white solid.

13. Synthesis of 3-(3,5-difluorophenyl)-N-[(4S)-3,4-dihydro-2H-1-benzopyran-4-yl]-8-isopropyl-2-methylimidazo[1,2-b]pyridazine-7-carboxamide (compound 175)

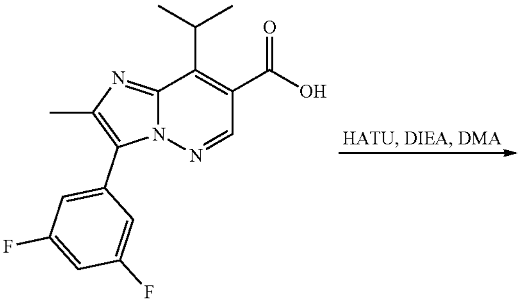

4-6

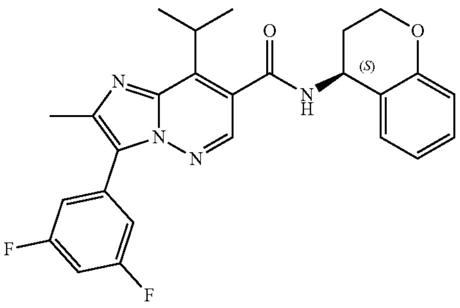

175

Into a 50-mL round-bottom flask, was placed DMA (5.0 mL), 3-(3,5-difluorophenyl)-8-isopropyl-2-methylimidazo[1,2-b]pyridazine-7-carboxylic acid (4-6, 60.0 mg, 0.2 mmol, 1.0 equiv), (4S)-3,4-dihydro-2H-1-benzopyran-4-amine (57.2 mg, 0.4 mmol, 2.1 equiv), HATU (138.0 mg, 0.4 mmol, 2.0 equiv), DIEA (70.0 mg, 0.5 mmol, 3.0 equiv). The resulting solution was stirred for 1 hr at room temperature. The mixture was purified by Flash-Prep-HPLC with the following conditions (IntelFlash-1): Column, C18 silica gel; mobile phase, $H_2O$:ACN=60:40 increasing to $H_2O$:ACN=10:90 within 25; Detector, 220 nm. This resulted in 38.6 mg (46.0%) of 3-(3,5-difluorophenyl)-N-[(4S)-3,4-dihydro-2H-1-benzopyran-4-yl]-8-isopropyl-2-methylimidazo[1,2-b]pyridazine-7-carboxamide (175) as a white solid (300 MHz, CD3OD, ppm) δ 8.33 (s, 1H), 7.41-7.33 (m, 3H), 7.21-7.16 (m, 1H), 7.06-6.97 (m, 1H), 6.95-6.92 (m, 1H), 6.82 (d, J=8.1 Hz, 1H), 5.32 (t, J=5.1 Hz, 1H), 4.33-4.25 (m, 2H), 3.70-3.65 (m, 1H), 2.62 (s, 3H), 2.33-2.28 (m, 1H), 2.23-2.19 (m, 1H), 1.62 (t, J=6.6 Hz, 6H).

Preparation Example 2: Similarly to the process described in Preparation Example 1, the process depicted in Schemes 5-7 below may be used to prepare compound 271:

Scheme 5

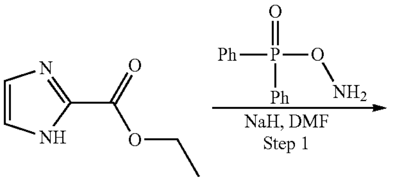

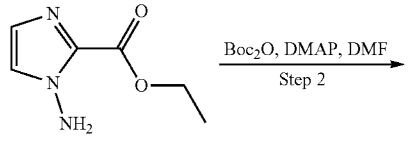

3-2

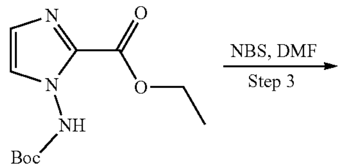

3-3

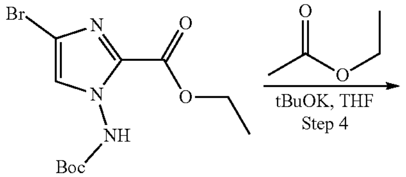

3-4

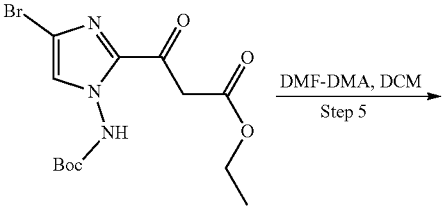

3-5

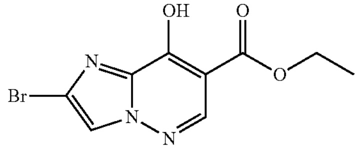

3-6

Scheme 6

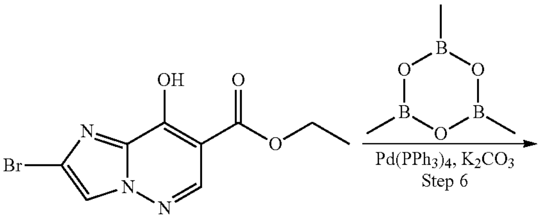

3-6

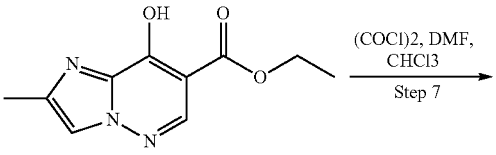

3-7

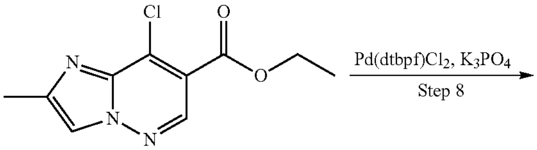

271-1

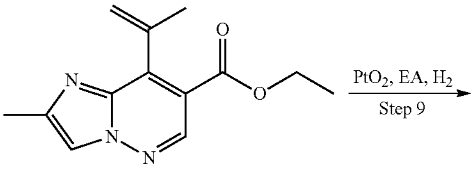

4-2

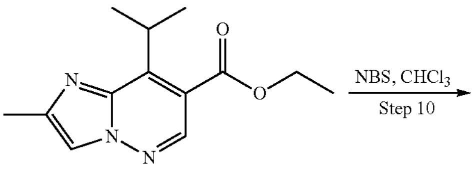

4-3

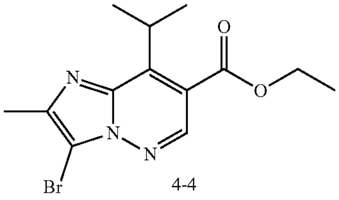

4-4

Scheme 7

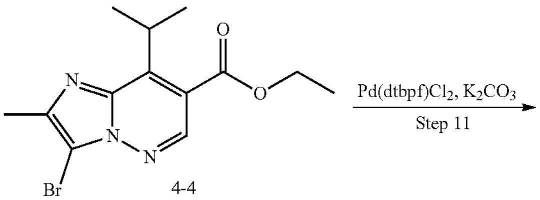

4-4

-continued

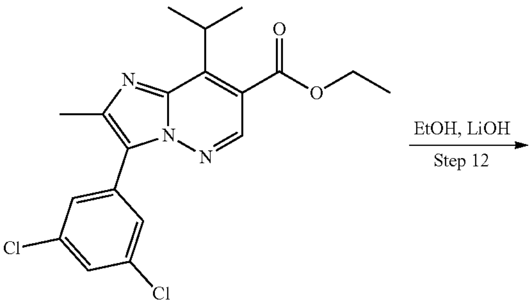

271-2

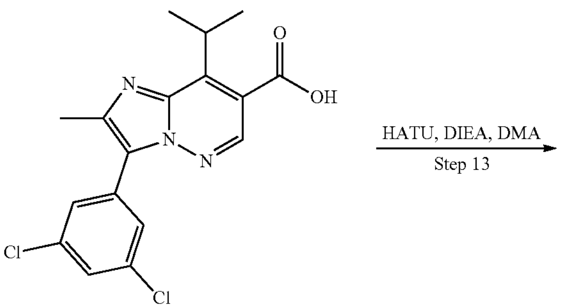

271-3

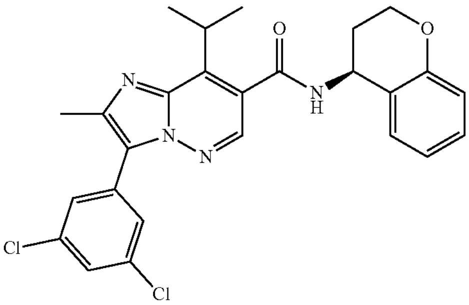

271

The process in Schemes 3-7 described above may be modified according to methods known to persons of skill in the art to incorporate different functional groups in the core structure. For example, intermediate 3-6 may be reacted with an alternate coupling partner to introduce a different $R^2$ substituent. Similarly, intermediates 4-1, 271-1 and 4-4 may be reacted with alternate compounds to introduce different $R^1$ and $R^3$ substituents.

1. Synthesis of ethyl 1-aminoimidazole-2-carboxylate (3-2)

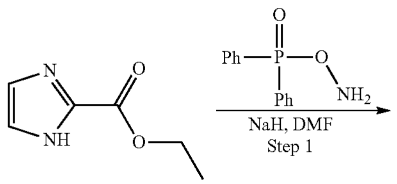

-continued

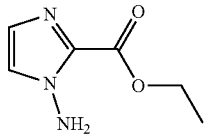

3-2

Into a 5-L round-bottom flask, was placed DMF (4000.00 mL, 51687.010 mmol, 144.87 equiv), ethyl 1H-imidazole-2-carboxylate (50.00 g, 356.781 mmol, 1.00 equiv). This was followed by the addition of NaH (21.00 g, 875.083 mmol, 2.45 equiv), in portions at room temperature in 30 min. To this was added amino diphenylphosphinate (120.00 g, 514.564 mmol, 1.44 equiv), in portions at room temperature. The resulting solution was stirred for 2 hr at room temperature. The resulting mixture was dried with nitrogen (blowing nitrogen). The residue was dissolved in 2000 mL of EA. The solids were filtered out. The filtrate was concentrated under vacuum. This resulted in 42 g (75.87%) of ethyl 1-aminoimidazole-2-carboxylate (3-2) as a white solid.

2. Synthesis of ethyl 1-[(tert-butoxycarbonyl) amino]imidazole-2-carboxylate (3-3)

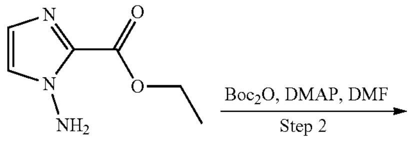

3-2

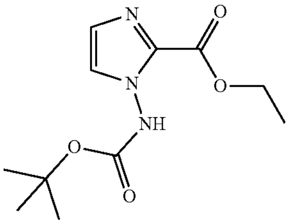

3-3

Into a 1000-mL round-bottom flask, was placed DMF (500.00 mL, 6460.876 mmol, 28.64 equiv), ethyl 1-amino-imidazole-2-carboxylate (35.00 g, 225.578 mmol, 1.00 equiv), $Boc_2O$ (73.30 g, 335.858 mmol, 1.49 equiv), DMAP (13.78 g, 112.796 mmol, 0.50 equiv). The resulting solution was stirred for 2 hrs at 80 degrees C. The reaction was then quenched by the addition of water/ice. The resulting solution was extracted with 3×500 mL of ethyl acetate and the organic layers combined and washed with 2×500 ml of $H_2O$, 1×500 ml of brine. Organic Layer was dried over anhydrous sodium sulfate and concentrated under vacuum. The residue was applied onto a silica gel column with ethyl acetate/petroleum ether (1:2). This resulted in 30 g (52.10%) of ethyl 1-[(tert-butoxycarbonyl)amino]imidazole-2-carboxylate (3-3) as a white solid.

3. Synthesis of ethyl 4-bromo-1-[(tert-butoxycarbonyl)amino]imidazole-2-carboxylate (3-4)

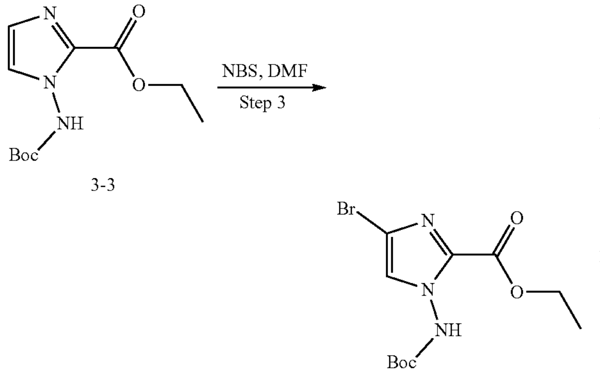

3-3

3-4

Into a 1000-mL round-bottom flask, was placed DMF (400.00 mL, 5168.701 mmol, 26.39 equiv), ethyl 1-[(tert-butoxycarbonyl)amino]imidazole-2-carboxylate (50.00 g, 195.868 mmol, 1.00 equiv), NBS (40.00 g, 0.225 mmol). The resulting solution was stirred overnight at room temperature. The reaction was then quenched by the addition of water/ice. The resulting solution was extracted with 3×100 mL of ethyl acetate and the organic layers combined and washed with 2×500 ml of $H_2O$, 1×500 ml of brine. Organic Layer was dried over anhydrous sodium sulfate and concentrated under vacuum. The residue was applied onto a silica gel column with ethyl acetate/petroleum ether (1:1). This resulted in 30 g (45.83%) of ethyl 4-bromo-1-[(tert-butoxycarbonyl)amino]imidazole-2-carboxylate (3-4) as yellow oil.

4. Synthesis of ethyl 3-[4-bromo-1-[(tert-butoxycarbonyl)amino]imidazol-2-yl]-3-oxopropanoate (3-5)

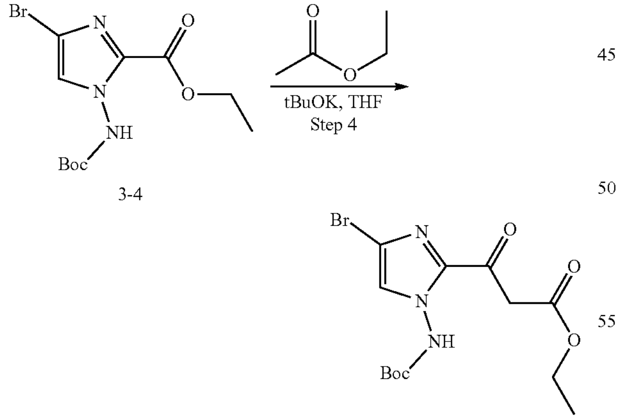

3-4

3-5

Into a 1000-mL 3-necked round-bottom flask, was placed THE (500.00 mL, 6171.495 mmol, 58.92 equiv), ethyl 4-bromo-1-[(tert-butoxycarbonyl)amino]imidazole-2-carboxylate (35.00 g, 104.737 mmol, 1.00 equiv), EA (93.50 g, 1061.233 mmol, 10.13 equiv). This was followed by the addition of t-BuOK (170.00 g, 1514.989 mmol, 14.46 equiv), in portions at 0 degrees C. The resulting solution was stirred for 1 hr at room temperature. The reaction was then quenched by the addition of $NH_4Cl$ (aq.). The resulting solution was extracted with 3×300 mL of ethyl acetate and the organic layers combined and dried over anhydrous sodium sulfate and concentrated under vacuum. The residue was dissolved in 500 ml of hexane. The solids were collected by filtration. This resulted in 22 g (55.83%) of ethyl 3-[4-bromo-1-[(tert-butoxycarbonyl)amino]imidazol-2-yl]-3-oxopropanoate (3-5) as a white solid.

5. Synthesis of ethyl 2-bromo-8-hydroxyimidazo[1,2-b]pyridazine-7-carboxylate (3-6)

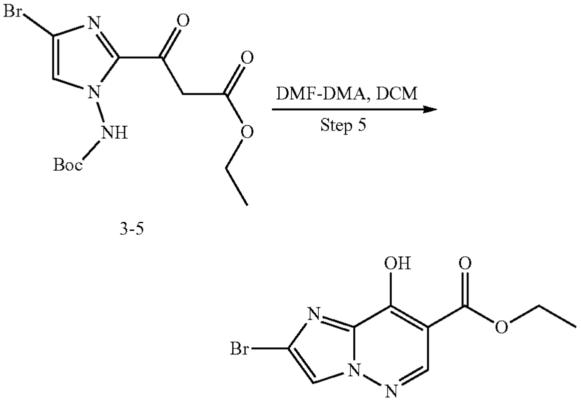

3-5

3-6

Into a 100-mL round-bottom flask, was placed DCM (30.00 mL, 471.901 mmol, 27.31 equiv), ethyl 3-[4-bromo-1-[(tert-butoxycarbonyl)amino]imidazol-2-yl]-3-oxopropanoate (6.50 g, 17.278 mmol, 1.00 equiv), DMF-DMA (5.00 mL, 37.344 mmol, 2.16 equiv). The resulting solution was stirred for 2 hr at room temperature. The resulting mixture was concentrated under vacuum. The crude product was purified by Flash-Prep-HPLC with the following conditions (IntelFlash-1): Column, C18 silica gel; mobile phase, $H_2O$ (0.1% TFA):ACN=90:10 increasing to $H_2O$ (0.1% TFA):ACN=50:50 within 15 min; Detector, 254 nm. This resulted in 3.3 g (66.76%) of ethyl 2-bromo-8-hydroxyimidazo[1,2-b]pyridazine-7-carboxylate (3-6) as a white solid.

6. Synthesis of ethyl 8-hydroxy-2-methylimidazo[1,2-b]pyridazine-7-carboxylate (3-7)

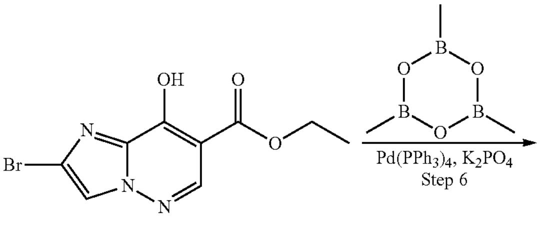

3-6

-continued

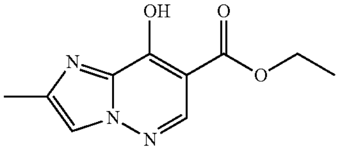

3-7

Into a 250-mL round-bottom flask purged and maintained with an inert atmosphere of nitrogen, was placed dioxane (100.0 mL, 1180.408 mmol, 67.54 equiv), ethyl 2-bromo-8-hydroxyimidazo[1,2-b]pyridazine-7-carboxylate (5.00 g, 17.477 mmol, 1.00 equiv), trimethyl-1,3,5,2,4,6-trioxatriborinane (6.60 g, 52.577 mmol, 3.01 equiv), $Pd(PPh_3)_4$ (2.00 g, 1.731 mmol, 0.10 equiv), $K_3PO_4$ (7.20 g, 52.096 mmol, 2.98 equiv). The resulting solution was stirred for 4 hrs at room temperature. The resulting mixture was concentrated under vacuum. The crude product was purified by Flash-Prep-HPLC with the following conditions (IntelFlash-1): Column, C18 silica gel; mobile phase, $H_2O$ (0.1% $NH_3{\cdot}H_2O$): ACN=100:0 increasing to $H_2O$ (0.1% $NH_3{\cdot}H_2O$):ACN=50:50 within 10 min; Detector, 254 nm. This resulted in 0.75 g (25.6%) of ethyl 8-hydroxy-2-methylimidazo[1,2-b]pyridazine-7-carboxylate (3-7) as a yellow solid.

7. Synthesis of ethyl 8-chloro-2-methylimidazo[1,2-b]pyridazine-7-carboxylate (271-1)

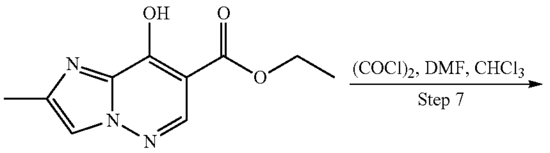

3-7

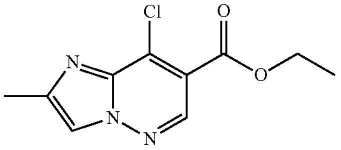

271-1

Into a 100-mL round-bottom flask, was placed $CHCl_3$ (20.00 mL, 247.952 mmol, 18.28 equiv), ethyl 8-hydroxy-2-methylimidazo[1,2-b]pyridazine-7-carboxylate (3.00 g, 13.561 mmol, 1.00 equiv), oxalyl chloride (6.00 g, 47.274 mmol, 3.49 equiv), DMF (0.10 mL). The resulting solution was stirred for 2 hrs at 80 degrees C. The resulting mixture was concentrated under vacuum. This resulted in 3.6 g (crude) of ethyl 8-chloro-2-methylimidazo[1,2-b]pyridazine-7-carboxylate (271-1) as a yellow solid.

8. Synthesis of ethyl 2-methyl-8-(prop-1-en-2-yl)imidazo[1,2-b]pyridazine-7-carboxylate (4-2)

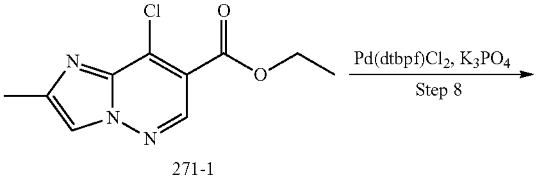

271-1

-continued

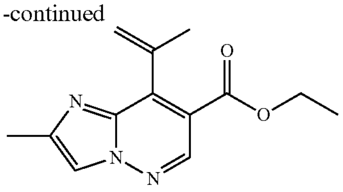

4-2

Into a 100-mL round-bottom flask purged and maintained with an inert atmosphere of nitrogen, was placed THF (30.00 mL, 370.290 mmol, 88.74 equiv), $H_2O$ (5.00 mL, 277.542 mmol, 66.52 equiv), ethyl 8-chloro-2-methylimidazo[1,2-b]pyridazine-7-carboxylate (1.00 g, 4.173 mmol, 1.00 equiv), 4,4,5,5-tetramethyl-2-(prop-1-en-2-yl)-1,3,2-dioxaborolane (2.11 g, 12.557 mmol, 3.01 equiv), Pd(dtbpf)$Cl_2$ (410.00 mg, 0.629 mmol, 0.15 equiv), $K_3PO_4$ (2.66 g, 12.531 mmol, 3.00 equiv). The resulting solution was stirred for 2 hrs at 70 degrees C. The resulting mixture was concentrated under vacuum. The residue was applied onto a silica gel column with ethyl acetate/petroleum ether (1:2). This resulted in 500 mg (48.85%) of ethyl 2-methyl-8-(prop-1-en-2-yl)imidazo[1,2-b]pyridazine-7-carboxylate (4-2) as yellow oil.

9. Synthesis of ethyl 8-isopropyl-2-methylimidazo[1,2-b]pyridazine-7-carboxylate (4-3)

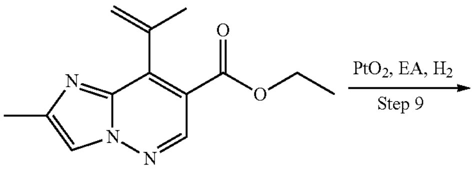

4-2

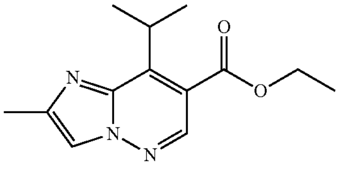

4-3

Into a 50-mL round-bottom flask, was placed EA (5.00 mL, 0.057 mmol, 0.03 equiv), ethyl 2-methyl-8-(prop-1-en-2-yl)imidazo[1,2-b]pyridazine-7-carboxylate (500.00 mg, 2.038 mmol, 1.00 equiv), $PtO_2$ (100.00 mg, 0.440 mmol, 0.22 equiv), to the above $H_2$ (g) was introduced in. The resulting solution was stirred for 2 hrs at 50 degrees C. The solids were filtered out. The filtrate was concentrated under vacuum. This resulted in 350 mg (69.43%) of ethyl 8-isopropyl-2-methylimidazo[1,2-b]pyridazine-7-carboxylate (4-3) as yellow oil.

10. Synthesis of ethyl 3-bromo-8-isopropyl-2-methylimidazo[1,2-b]pyridazine-7-carboxylate (4-4)

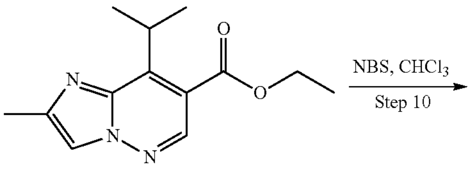

4-3

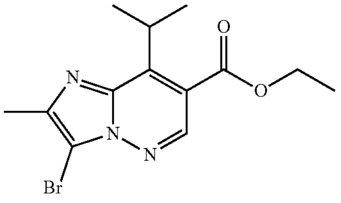

4-4

Into a 50-mL round-bottom flask, was placed $CHCl_3$ (5.00 mL, 61.988 mmol, 47.90 equiv), ethyl 8-isopropyl-2-methylimidazo[1,2-b]pyridazine-7-carboxylate (320.00 mg, 1.294 mmol, 1.00 equiv), NBS (253.70 mg, 1.425 mmol, 1.10 equiv). The resulting solution was stirred for 1 hr at 80 degrees C. The resulting mixture was concentrated under vacuum. The residue was applied onto a silica gel column with ethyl acetate/petroleum ether (1:5). This resulted in 350 mg (82.92%) of ethyl 3-bromo-8-isopropyl-2-methylimidazo[1,2-b]pyridazine-7-carboxylate (4-4) as yellow oil.

11. Synthesis of ethyl 3-(3,5-dichlorophenyl)-8-isopropyl-2-methylimidazo[1,2-b]pyridazine-7-carboxylate (271-2)

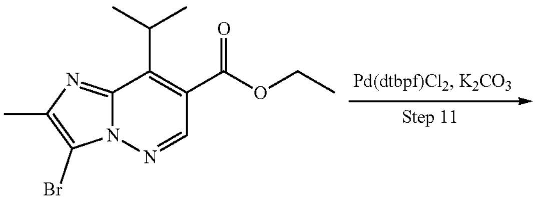

4-4

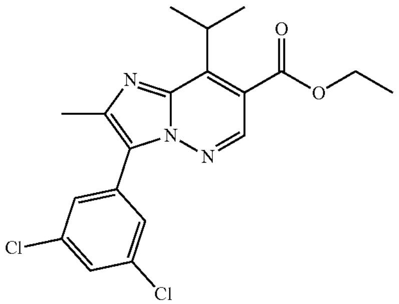

271-2

Into a 8-mL round-bottom flask purged and maintained with an inert atmosphere of nitrogen, was placed THE (1.00 mL, 12.343 mmol, 44.74 equiv), $H_2O$ (0.20 mL, 11.102 mmol, 40.24 equiv), ethyl 3-bromo-8-isopropyl-2-methylimidazo[1,2-b]pyridazine-7-carboxylate (90.00 mg, 0.276 mmol, 1.00 equiv), 3,5-dichlorophenylboronic acid (53.17 mg, 0.279 mmol, 1.01 equiv), Pd(dtbpf)$Cl_2$ (17.98 mg, 0.028 mmol, 0.10 equiv), $K_2CO_3$ (75.88 mg, 0.549 mmol, 1.99 equiv). The resulting solution was stirred for 2 hrs at 50° C. The resulting mixture was concentrated under vacuum. The residue was applied onto a silica gel column with ethyl acetate/petroleum ether (1:4). This resulted in 70 mg (64.67%) of ethyl 3-(3,5-dichlorophenyl)-8-isopropyl-2-methylimidazo[1,2-b]pyridazine-7-carboxylate (271-2) as colorless oil.

12. Synthesis of 3-(3,5-dichlorophenyl)-8-isopropyl-2-methylimidazo[1,2-b]pyridazine-7-carboxylic acid (271-3)

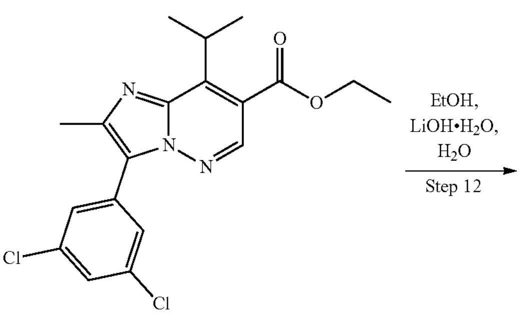

271-3

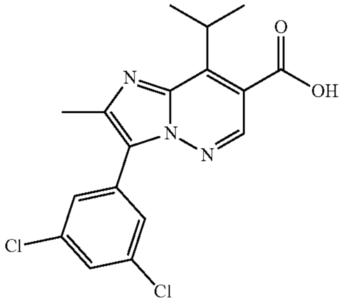

271-3

Into a 50-mL round-bottom flask, was placed $H_2O$ (0.50 mL, 27.754 mmol, 155.53 equiv), EtOH (2.00 mL, 0.043 mmol, 0.24 equiv), ethyl 3-(3,5-dichlorophenyl)-8-isopropyl-2-methylimidazo[1,2-b]pyridazine-7-carboxylate (70.00 mg, 0.178 mmol, 1.00 equiv), LiOH·$H_2O$ (22.50 mg, 0.536 mmol, 3.00 equiv). The resulting solution was stirred for 1 hr at room temperature. The pH value of the solution was adjusted to 5 with HCl (6 mol/L). The resulting solution was extracted with 3×20 mL of ethyl acetate and the organic layers combined and dried over anhydrous sodium sulfate and concentrated under vacuum. This resulted in 50 mg (76.93%) of 3-(3,5-dichlorophenyl)-8-isopropyl-2-methylimidazo[1,2-b]pyridazine-7-carboxylic acid (271-3) as yellow oil.

Synthesis of 3-(3,5-dichlorophenyl)-N-[(4S)-3,4-dihydro-2H-1-benzopyran-4-yl]-8-isopropyl-2-methylimidazo[1,2-b]pyridazine-7-carboxamide (Compound 271)

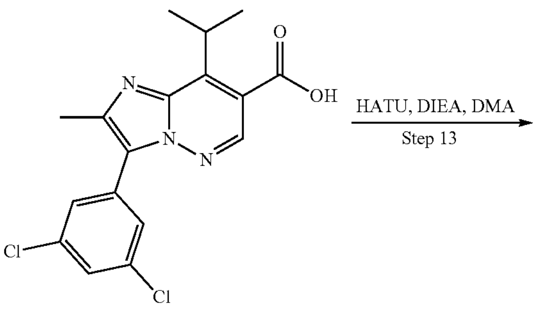

271-3

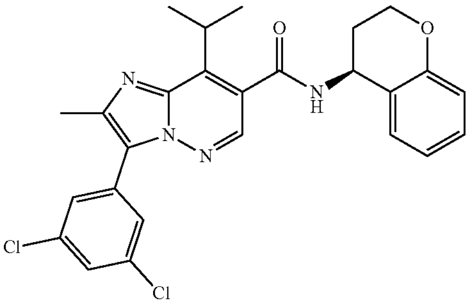

271

Into a 50-mL round-bottom flask, was placed DMA (1.00 mL, 10.755 mmol, 87.05 equiv), 3-(3,5-dichlorophenyl)-8-isopropyl-2-methylimidazo[1,2-b]pyridazine-7-carboxylic acid (45.00 mg, 0.124 mmol, 1.00 equiv), (4S)-3,4-dihydro-2H-1-benzopyran-4-amine (29.30 mg, 0.196 mmol, 1.59 equiv), HATU (93.90 mg, 0.247 mmol, 2.00 equiv), DIEA (47.80 mg, 0.370 mmol, 2.99 equiv). The resulting solution was stirred for 1 hr at room temperature. The crude mixture was purified by Flash-HPLC with the following conditions (IntelFlash-1): Column, C18 silica gel; mobile phase, $H_2O$ (0.1% $NH_3 \cdot H_2O$):ACN=50:50 increasing to $H_2O$ (0.1% $NH_3 \cdot H_2O$):ACN=10:90 within 20 min; Detector, 254 nm. This resulted in 42.2 mg (68.95%) of 3-(3,5-dichlorophenyl)-N-[(4S)-3,4-dihydro-2H-1-benzopyran-4-yl]-8-isopropyl-2-methylimidazo[1,2-b]pyridazine-7-carboxamide (271) as a white solid.

$^1$H NMR (300 MHz, $CDCl_3$, ppm) δ 8.29 (s, 1H), 7.59 (d, J=1.9 Hz, 2H), 7.43 (t, J=1.9 Hz, 1H), 7.34-7.18 (m, 2H), 6.97 (td, J=7.5, 1.2 Hz, 1H), 6.89 (dd, J=8.2, 1.2 Hz, 1H), 6.15 (d, J=7.6 Hz, 1H), 5.38 (q, J=5.6 Hz, 1H), 4.40-4.36 (m, 1H), 4.28-4.14 (m, 1H), 3.78-3.73 (m, 1H), 2.64 (s, 3H), 2.44-2.41 (m, 1H), 2.26-2.22 (m, 1H), 1.65 (t, J=6.7 Hz, 6H); (ES, m/z): 495 $[M+H]^+$.

As noted above, the following compounds may be prepared according to schemes 3 to 7:

| Compound | $^1$H NMR Spectra |
|---|---|
| 272 | (300 MHz, CDCl3, ppm) δ 8.30 (s, 1H), 7.49 (s, 1H), 7.37-7.30 (m, 2H), 7.29-7.21 (m, 1H), 7.20-7.15 (m, 1H), 6.99-6.94 (m, 1H), 6.89 (d, J = 8.4 Hz, 1H), 6.19 (d, J = 7.5 Hz, 1H), 5.38 (q, J = 6.9 Hz, 1H), 4.37-4.35 (m, 1H), 4.25-4.14 (m, 1H), 3.79-3.74 (m, 1H), 2.64 (s, 3H), 2.43-2.40 (m, 1H), 2.26-2.21 (m, 1H), 1.64 (t, J = 6.6 Hz, 6H) |
| 273 | (300 MHz, CDCl3, ppm) δ 8.31 (s, 1H), 7.53-7.40 (m, 3H), 7.40-7.31 (m, 1H), 7.29-7.17 (m, 2H), 6.99-6.93 (m, 1H), 6.88 (d, J = 8.4 Hz, 1H), 6.26 (d, J = 7.2 Hz, 1H), 5.38 (q, J = 7.2 Hz, 1H), 4.39-4.33 (m, 1H), 4.25-4.20 (m, 1H), 3.78-3.73 (m, 1H), 2.63 (s, 3H), 2.44-2.37 (m, 1H), 2.26-2.23 (m, 1H), 1.63 (t, J = 6.9 Hz, 6H) |
| 274 | (300 MHz, CDCl3, ppm) δ 8.24 (d, J = 2.4 Hz, 1H), 7.64 (dd, J = 7.2, 2.1 Hz, 1H), 7.41-7.35 (m, 2H), 7.33-7.29 (m, 1H), 7.27-7.20 (m, 1H), 6.98-6.93 (m, 1H), 6.90-6.87 (m, 1H), 6.20 (d, J = 7.5 Hz, 1H), 5.38 (q, J = 7.2 Hz, 1H), 4.37-4.34 (m, 1H), 4.27-4.13 (m, 1H), 3.79-3.74 (m, 1H), 2.47 (s, 3H), 2.41-2.39 (m, 1H), 2.27-2.20 (m, 1H), 1.69-1.63 (m, 6H) |
| 275 | (300 MHz, DMSO-d6, ppm) δ 9.16 (d, J = 8.4 Hz, 1H), 8.53 (s, 1H), 7.51-7.47 (m, 2H), 7.36-7.30 (m, 1H), 7.16 (dd, J = 9.3, 2.7 Hz, 1H), 7.08-7.01 (m, 1H), 6.83 (dd, J = 9.0, 4.8 Hz, 1H), 5.24 (q, J = 7.2 Hz, 1H), 4.28-4.22 (m, 2H), 3.62-3.57 (m, 1H), 2.57 (s, 3H), 2.30-2.16 (m, 1H), 2.11-1.95 (m, 1H), 1.55 (t, J= 7.4 Hz, 6H) |
| 276 | (300 MHz, CDCl3, ppm) δ 8.36 (s, 1H), 7.28-7.22 (m, 2H), 7.19-7.16 (m, 2H), 7.03-6.95 (m, 2H), 6.91-6.88 (m, 1H), 6.09 (d, J = 7.2 Hz, 1H), 5.39 (q, J = 7.5 Hz, 1H), 4.41-4.35 (m, 1H), 4.24-4.17 (m, 1H), 3.77-3.72 (m, 1H), 2.44-2.39 (m, 1H), 2.28-2.24 (m, 1H), 1.68 (t, J = 6.9 Hz, 6H) |
| 279 | (300 MHz, DMSO-d6, ppm) δ 8.99 (d, J = 8.4 Hz, 1H), 8.60 (s, 1H), 7.58-7.43 (m, 2H), 7.43-7.25 (m, 2H), 7.24-7.12 (m, 1H), 6.93 (t, J = 6.9 Hz, 1H), 6.79 (d, J = 8.1 Hz, 1H), 5.45 (s, 1H), 5.26-5.16 (m, 2H), 4.30-4.17 (m, 2H), 2.55 (s, 3H), 2.30 (s, 3H), 2.23-2.09 (m, 1H), 2.00-1.95 (m, 1H) |
| 293 | (300 MHz, CDCl3, ppm) δ 8.16 (d, J = 3.6 Hz, 1H), 7.60 (dd, J = 7.5, 1.5 Hz, 1H), 7.40-7.29 (m, 2H), 6.99-6.89 (m, 2H), 6.83-6.79 (m, 1H), 6.24-6.22 (m, 1H), 5.36-5.33 (m, 1H), 4.34-4.28 (m, 1H), 4.19-4.11 (m, 1H), 3.79-3.74 (m, 1H), 2.46 (s, 3H), 2.39-2.30 (m, 1H), 2.23-2.07 (m, 1H), 1.72-1.58 (m, 6H) |
| 294 | (300 MHz, CDCl3, ppm) δ 8.27 (s, 1H), 7.58 (d, J = 1.8 Hz, 2H), 7.42 (t, J = 1.8 Hz, 1H), 7.01-6.90 (m, 2H), 6.84-6.80 (m, 1H), 6.31 (br s, 1H), 5.39-5.34 (m, 1H), 4.36-4.30 (m, 1H), 4.24-4.17 (m, 1H), 3.79-3.75 (m, 1H), 2.63 (s, 3H), 2.42-2.36 (m, 1H), 2.22-2.16 (m, 1H), 1.64 (t, J = 6.6 Hz, 6H) |

-continued

| Compound | $^1$H NMR Spectra |
|---|---|
| 295 | (300 MHz, CDCl3, ppm) δ 8.37 (s, 1H), 7.53-7.51 (m, 3H), 7.26-7.23 (m, 1H), 7.02-6.95 (m, 1H), 6.92-6.89 (m, 1H), 6.06 (d, J = 7.2 Hz, 1H), 5.43-5.37 (s, 1H), 4.42-4.35 (m, 1H), 4.24-4.17 (m, 1H), 3.77-3.70 (m, 1H), 2.47-2.41 (m, 1H), 2.27-2.22(m, 1H), 1.68 (t, J = 6.6 Hz, 6H) |
| 296 | (300 MHz, CDCl3, ppm) δ 8.37 (s, 1H), 7.53-7.51 (m, 3H), 7.00-6.93 (m, 2H), 6.88-6.83 (m, 1H), 6.04 (d, J = 7.8 Hz, 1H), 5.43-5.37 (m, 1H), 4.38-4.33 (m, 1H), 4.26-4.12 (m, 1H), 3.76-3.71 (m, 1H), 1.68 (t, J = 6.9 Hz, 6H) |
| 304 | (300 MHz, CDCl3, ppm) δ 8.40 (s, 1H), 8.16 (s, 2H), 7.42 (t, J = 2.1 Hz, 1H), 7.03-6.93 (m, 2H), 6.88-6.83 (m, 1H), 6.06 (d, J = 7.8 Hz, 1H), 5.48-5.32 (m, 1H), 4.39-4.33 (m, 1H), 4.24-4.18 (m, 1H), 3.76-3.69 (m, 1H), 2.46-2.39 (m, 1H), 2.29-2.18 (m, 1H), 1.72-1.68 (m, 6H) |
| 305 | (400 MHz, Chloroform-d, ppm) δ : 8.37 (s, 1H), 7.66 (s, 2H), 7.55 (s, 1H), 7.01-6.84 (m, 4H), 6.10 (d, J = 8.3 Hz, 1H), 5.35 (d, J = 8.3 Hz, 1H), 4.39-4.34 (m, 1H), 4.26-4.15 (m, 1H), 3.81-3.74 (m, 1H), 2.44-2.38 (m, 1H), 2.21-2.20 (m, 1H), 1.70-1.55 (m, 6H) |
| 307 | (300 MHz, CDCl3, ppm): δ 8.86 (s, 1H), 7.33-7.30 (m, 2H), 7.04-6.80 (m, 5H), 5.69 (s, 1H), 5.50-5.30 (m, 2H), 4.35-4.30 (m, 1H), 4.25-4.00 (m, 1H), 2.68 (s, 3H), 2.45-2.25 (m, 4H), 2.20-2.10 (m, 1H) |
| 308 | (300 MHz, Chloroform-d, ppm): δ 8.84 (s, 1H), 7.63 (s, 2H), 7.46 (s, 1H), 7.02-6.78 (m, 4H), 5.68 (s, 1H), 5.45-5.31 (m, 2H), 4.37-4.30 (m, 1H), 4.21-4.07 (m, 1H), 2.66 (s, 3H), 2.45-2.30 (m, 4H), 2.20-2.10 (m, 1H) |
| 322 | (300 MHz, Chloroform-d, ppm): δ 8.52 (d, J = 5.1 Hz, 1H), 8.32 (s, 1H), 7.80 (s, 1H), 7.70-7.60 (m, 1H), 7.40-7.20 (m, 2H), 7.05-6.95 (m, 1H), 6.93-6.87 (m, 1H), 6.20-6.00 (m, 1H), 5.45-5.30 (m, 1H), 4.45-4.35 (m, 1H), 4.30-4.15 (m, 1H), 3.83-3.74 (m, 1H), 2.71 (s, 3H), 2.52-2.37 (m, 1H), 2.30-2.15 (m, 1H), 1.75-1.65 (m, 6H) |
| 344 | (300 MHz Chloroform-d, ppm): δ 8.23 (s, 1H), 7.14-6.91 (m, 4H), 6.90-6.75 (m, 1H), 6.10 (d, J = 7.8 Hz, 1H), 5.45-5.31 (m, 1H), 4.45-4.32 (m, 1H), 4.30-4.10 (m, 1H), 3.85-3.65 (m, 1H), 2.54 (s, 3H), 2.44-2.30 (m, 1H), 2.24-2.17 (m, 1H), 1.67 (t, J = 6.6 Hz, 6H) |
| 345 | (300 MHz, Chloroform-d, ppm): δ 8.23 (s, 1H), 7.28-7.20 (m, 2H), 7.10-7.00 (m, 2H), 6.99-6.93 (m, 1H), 6.90-6.87 (m, 1H), 6.11 (d, J = 7.2 Hz, 1H), 5.40-5.30 (m, 1H), 4.40-4.34 (m, 1H), 4.24-4.15 (m, 1H), 3.85-3.74 (m, 1H), 2.53 (s, 3H), 2.50-2.35 (m, 1H), 2.30-2.15 (m, 1H), 1.66 (t, J = 6.6 Hz, 6H) |
| 364 | (300 MHz, Chloroform-d, ppm): δ 8.47 (s, 1H), 8.34-8.24 (m, 2H), 7.60 (d, J = 1.8 Hz, 2H), 7.42 (t, J = 1.8 Hz, 1H), 6.79 (d, J = 5.7 Hz, 1H), 6.55-6.40 (m, 1H), 5.47-5.40 (m, 1H), 4.49-4.41 (m, 1H), 4.40-4.25 (m, 1H), 3.82-3.70 (m, 1H), 2.64 (s, 3H), 2.50-2.25 (m, 2H), 1.68-1.64 (m, 6H) |
| 527 | (300 MHz DMSO-d6, ppm): δ 8.08 (s, 1H), 7.15-7.44(m, 3H), 7.00-6.79(m, 2H), 6.10-6.21 (m, 1H), 5.36-5.43 (m, 1H), 4.30-4.49 (m, 1H), 4.10-4.18 (m, 1H), 2.40-2.38 (m, 4H), 2.28-2.26 (m, 1H), 1.80 (bs, 9H) |
| 528 | (300 MHz, DMSO-d6, ppm) δ 9.18 (d, J = 8.1 Hz, 1H), 8.37 (s, 1H), 7.79 (d, J = 8.7 Hz, 2H), 7.32 (d, J = 7.5 Hz, 1H), 7.17 (t, J = 7.5 Hz, 1H), 6.92 (t, J = 7.5 Hz, 1H), 6.79 (d, J = 8.1 Hz, 1H), 5.26-5.20 (m, 1H), 4.30-4.14 (m, 2H), 3.61-3.51 (m, 1H), 2.30 (s, 3H), 2.22-2.17 (m, 1H), 2.08-2.01 (m, 1H), 1.59-1.56 (m, 6H) |
| A402 | (400 MHz, DMSO-d6, ppm) δ 9.19 (d, J = 8.62 Hz, 1H) 8.46 (s, 1H) 7.77 (d, J = 1.90 Hz, 2H) 7.68 (t, J = 1.96 Hz, 1H) 7.45 (d, J = 2.41 Hz, 1H) 7.36 (dd, J = 8.68, 2.47 Hz, 1H) 6.83 (d, J = 8.74 Hz, 1H) 4.81 (d, J = 8.62 Hz, 1H) 4.29 (d, J = 11.28 Hz, 1H) 3.72-3.76 (m, 1H) 3.48-3.58 (m, 1H) 2.54 (s, 3H) 1.54 (dd, J = 8.36, 7.10 Hz, 6H) 0.89-0.99 (m, 1H) 0.75 (dt, J = 9.03, 4.67 Hz, 1H) 0.66-0.72 (m, 1H) 0.59-0.66 (m, 1H) |
| A403 | (400 MHz, DMSO-d6) δ ppm 9.14 (d, J = 8.11 Hz, 1H) 8.56 (s, 1H) 7.96 (d, J = 1.90 Hz, 2H) 7.69 (t, J = 1.90 Hz, 1H) 7.34 (d, J = 7.10 Hz, 1H) 7.18 (t, J = 7.69 Hz, 1H) 6.93 (t, J = 7.16 Hz, 1H) 6.80 (d, J = 8.24 Hz, 1H) 5.19-5.29 (m, 1H) 4.65 (s, 2H) 4.18-4.33 (m, 2H) 3.57-3.66 (m, 1H) 2.13-2.27 (m, 1H) 1.97-2.13 (m, 1H) 1.55 (dd, J = 10.77, 6.97 Hz, 6H) |
| A404 | (400 MHz, DMSO-d6) δ ppm 9.18 (d, J = 8.11 Hz, 1 H) 8.66 (s, 1 H) 7.84 (t, J = 1.90 Hz, 1H) 7.68 (d, J = 1.90 Hz, 2H) 7.33 (d, J = 6.97 Hz, 1H) 7.17 (t, J = 7.77 Hz, 1H) 6.92 (t, J = 7.17 Hz, 1H) 6.80 (d, J = 8.11 Hz, 1H) 5.21-5.27 (m, 1H) 4.25-4.31 (m, 1H) 4.18-4.25 (m, 1H) 3.58 (dt, J = 13.94, 6.97 Hz, 1H) 2.17-2.25 (m, 1H) 2.00-2.08 (m, 1H) 1.54 (dd, J = 11.79) |
| A406 | (400 MHz, DMSO-d6, ppm) δ 9.15 (d, J = 7.98 Hz, 1H), 8.34 (s, 1H), 7.66-7.71 (m, 2H), 7.57-7.64 (m, 1H), 7.31 (d, J = 6.97 Hz, 1H), 7.16 (t, J = 7.66 Hz, 1H), 6.91 (t, J = 7.15 Hz, 1H), 6.78 (d, J = 8.27 Hz, 1H), 5.19-5.25 (m, 1H), 4.18-4.30 (m, 2H), 3.35-3.61 (m, 3H), 2.56-2.66 (m, 1H), 2.15-2.32 (m, 1H), 2.01-2.09 (m, 1H), 1.51-1.59 (m, 6H) |
| A407 | (400 MHz, DMSO-d6, ppm) δ 9.12 (d, J = 8.11 Hz, 1H), 8.39 (s, 1H), 7.62-7.70 (m, 1H), 7.14-7.36 (m, 4H), 6.91 (t, J = 7.19 Hz, 1H), 6.79 (d, J = 8.11 Hz, 1H), 5.23 (br d, J = 7.48 Hz, 1H), 4.17-4.32 (m, 2H), 3.51-3.62 (m, 1H), 2.03-2.39 (m, 5H), 1.57-1.54 (m, 6H) |
| A410 | (400 MHz, DMSO-d6, ppm) δ 9.11 (d, J = 8.11 Hz, 1H), 8.44-8.52 (m, 1H), 7.93 (m, 1H), 7.15-7.73 (m, 4H), 6.92 (m, 1H), 6.76-6.80 (m, 1H), 4.04-5.27 (m, 4H), 3.52-3.66 (m, 1H), 2.51-2.53 (m, 2H), 2.36-2.46 (m, 1H), 1.98-2.26 (m, 2H), 1.46-1.61 (m, 5H) |

-continued

| Compound | $^1$H NMR Spectra |
|---|---|
| A411 | (400 MHz, DMSO-d6, ppm) δ ppm 9.14 (d, J = 8.24 Hz, 1H) 8.47 (s, 1H) 7.77 (d, J = 1.90 Hz, 2H) 7.68 (t, J = 1.90 Hz, 1H) 7.37 (d, J = 7.73 Hz, 1H) 7.07-7.19 (m, 3H) 5.22-5.29 (m, 1H) 3.57-3.64 (m, 3H) 3.03-3.20 (m, 2H) 2.54 (s, 3H) 2.14 -2.31 (m, 2H) 1.55 (br d, J = 6.97 Hz, 3H) 1.52 (br d, J = 6.97 Hz, 3H) |
| A412 | (400 MHz, DMSO-d6, ppm) δ 9.10 (d, J = 8.11 Hz, 1H), 8.40 (s, 1H), 6.77-7.76 (m, 9H), 5.19-5.28 (m, 1H), 3.55-4.66 (m, 5H), 2.00-2.49 (m, 2H), 1.52-1.56 (m, 6H) |
| A413 | (400 MHz, DMSO-d6, ppm) δ 9.11 (d, J = 7.98 Hz, 1H), 8.37 (s, 1H), 7.63-7.71 (m, 1H), 7.46 (m, 1H), 7.26-7.34 (m, 2H), 7.16 (t, J = 7.74 Hz, 1H), 6.92 (t, J = 7.41 Hz, 1H), 6.79 (d, J = 7.60 Hz, 1H), 5.23 (br d, J = 7.73 Hz, 1H), 4.25 (m, 2H), 3.37-3.67 (m, 3H), 2.35-2.46 (m, 1H), 2.16-2.26 (m, 1H), 2.04 (br s, 1H), 1.56-1.53 (m, 6H) |
| A414 | (400 MHz, DMSO-d6, ppm) δ 9.15 (d, J = 7.98 Hz, 1H) 8.54 (s, 1H) 7.78 (d, J = 1.90 Hz, 2H) 7.68 (t, J = 1.90 Hz, 1H) 7.35 (d, J = 2.41 Hz, 1H) 7.22 (dd, J = 8.74, 2.66 Hz, 1H) 6.84 (d, J = 8.74 Hz, 1H) 5.23 (q, J = 6.42 Hz, 1H) 3.88-4.34 (m, 2H) 3.60 (spt, J = 6.91 Hz, 1H) 2.55 (s, 3 H) 1.94-2.24 (m, 2H) 1.55 (dd, J = 10.39, 6.97 Hz, 6H) |
| A415 | (400 MHz, DMSO-d6) δ ppm 9.35 (d, J = 8.62 Hz, 1H), 8.57 (s, 1H), 7.57-7.85 (m, 7H), 5.52 (m, 1H), 3.57-3.81 (m, 3H), 2.53-2.69 (m, 4H), 1.55-1.50 (m, 7H) |
| A416 | (400 MHz, DMSO-d6, ppm) δ 9.35 (d, J = 8.62 Hz, 1H), 8.57 (s, 1H), 7.57-7.85 (m, 7H), 5.52 (m, 1H), 3.57-3.81 (m, 3H), 2.53-2.69 (m, 4H), 1.55-1.50 (m, 7H) |
| A417 | (400 MHz, DMSO-d6, ppm) δ 9.37 (d, J = 8.36 Hz, 1H), 8.61 (s, 1H), 7.78-7.89 (m, 3H), 7.61-7.71 (m, 3H), 5.48-5.55 (m, 1H), 3.57-3.84 (m, 3H), 2.54-2.68 (m, 5H), 1.58 (d, J = 6.97 Hz, 3H), 1.54 (br d, J = 6.84 Hz, 3H) |
| A418 | (400 MHz, DMSO-d6, ppm) δ 9.37 (d, J = 8.36 Hz, 1H), 8.61 (s, 1H), 7.78-7.89 (m, 3H), 7.61-7.71 (m, 3H), 5.48-5.55 (m, 1H), 3.57-3.84 (m, 3H), 2.54-2.68 (m, 5H), 1.58 (d, J = 6.97 Hz, 3H), 1.54 (br d, J = 6.84 Hz, 3H) |
| 419 | (300 MHz, DMSO-d6, ppm) δ 8.50 (s, 1H), 7.83 (d, J = 7.5 Hz, 2H), 7.45-7.50 (m, 1H), 7.10-7.28 (m, 1H), 6.98-6.89 (m, 2H), 6.10-6.05 (m, 1H), 5.45-5.40 (m, 1H), 4.50-4.10 (m, 2H) 3.80-3.70 (m, 1H), 2.40-2.21 (m, 2H), 1.65-1.58 (m, 6H) |
| A419 | (400 MHz, DMSO-d6, ppm) δ 9.17 (d, J = 7.98 Hz, 1H), 8.97 (s, 1H), 8.39 (s, 1H), 7.67-7.78 (m, 3H), 5.28-5.35 (m, 1H), 3.58 (m, 1H), 2.68-2.80 (m, 2H), 2.52-2.55 (m, 3H), 1.51-2.16 (m, 10H) |
| A420 | (400 MHz, DMSO-d6, ppm) δ 9.17 (d, J = 7.98 Hz, 1H), 8.97 (s, 1H), 8.39 (s, 1H), 7.67-7.78 (m, 3H), 5.28-5.35 (m, 1H), 3.58 (m, 1H), 2.68-2.80 (m, 2H), 2.52-2.55 (m, 3H), 1.51-2.16 (m, 10H) |
| A423 | (400 MHz, DMSO-d6, ppm) δ 11.72-12.10 (m, 1H), 9.07 (d, J = 8.11 Hz, 1H), 8.37 (s, 1H), 7.66-7.79 (m, 3H), 5.21 (d, J = 6.72 Hz, 1H), 3.54-3.65 (m, 1H), 2.53-2.60 (m, 4H), 1.51-2.14 (m, 14H) |
| A424 | (400 MHz, DMSO-d6, ppm) δ 11.72-12.10 (m, 1H), 9.07 (d, J = 8.11 Hz, 1H), 8.37 (s, 1H), 7.66-7.79 (m, 3H), 5.21 (d, J = 6.72 Hz, 1H), 3.54-3.65 (m, 1H), 2.53-2.60 (m, 4H), 1.51-2.14 (m, 14H) |
| A425 | (400 MHz, DMSO-d6, ppm) δ 9.42 (d, J = 7.86 Hz, 1H), 8.57 (s, 1H), 7.67-7.81 (m, 5H), 5.45 (d, J = 6.46 Hz, 1H), 3.56-4.22 (m, 3H), 2.54-2.57 (m, 3H), 1.50-2.32 (m, 10H) |
| A426 | (400 MHz, DMSO-d6, ppm) δ 9.42 (d, J = 7.86 Hz, 1H), 8.57 (s, 1H), 7.67-7.81 (m, 5H), 5.45 (d, J = 6.46 Hz, 1H), 3.56-4.22 (m, 3H), 2.54-2.57 (m, 3H), 1.50-2.32 (m, 10H) |
| A428 | (400 MHz, DMSO-d6, ppm) δ 9.02 (d, J = 8.24 Hz, 1H), 8.39 (s, 1H), 7.67-7.80 (m, 1H), 7.67 (s, 1H), 5.40 (br d, J = 2.66 Hz, 1H), 3.36-3.70 (m, 2H), 2.76-3.16 (m, 2H), 2.53-2.57 (m, 2H), 2.50-2.67 (m, 2H), 2.08-2.39 (m, 1H), 1.23-1.55 (m, 6H) |
| A429 | 400 MHz, DMSO-d6, ppm) δ 9.00 (t, J = 4.06 Hz, 2H), 8.38 (s, 1H), 7.76 (d, J = 1.77 Hz, 1H), 7.67 (s, 1H), 5.45 (d, J = 5.07 Hz, 1H), 3.60-3.77 (m, 1H), 2.72-3.47 (m, 4H), 2.53-2.56 (m, 2H), 2.34-2.46 (m, 1H), 1.42-1.58 (m, 6H) |
| A430 | (400 MHz, DMSO-d6, ppm) δ 9.02 (d, J = 8.24 Hz, 1H), 8.39 (s, 1H), 7.67-7.80 (m, 1H), 7.67 (s, 1H), 5.40 (br d, J = 2.66 Hz, 1H), 3.36-3.70 (m, 2H), 2.76-3.16 (m, 2H), 2.53-2.57 (m, 2H), 2.50-2.67 (m, 2H), 2.08-2.39 (m, 1H), 1.23-1.55 (m, 6H) |
| A431 | (400 MHz, DMSO-d6, ppm) δ 8.82 (br t, J = 5.39 Hz, 1H) 8.40 (s, 1H) 7.77 (d, J = 1.65 Hz, 2H) 7.66-7.73 (m, 1H) 7.20 (d, J = 8.36 Hz, 1H) 6.55-6.60 (range, 1H) 6.48-6.54 (range, 1H) 4.38 (br d, J = 5.45 Hz, 2H) 3.81 (s, 3H) 3.76 (s, 3H) 3.50 (dt, J = 13.88, 6.88 Hz, 1H) 2.53 (s, 3H) 1.50 (d, J = 6.84 Hz, 6H) |
| A432 | (400 MHz, DMSO-d6, ppm) δ 9.15 (d, J = 7.86 Hz, 1H), 8.62 (s, 1H), 7.62-7.82 (m, 5H), 6.98 (d, J = 8.49 Hz, 1H), 5.26 (m, 1H), 3.77-4.43 (m, 2H), 3.34-3.70 (m, 1H), 2.33-2.43 (m, 1H), 1.98-2.31 (m, 2H), 1.55 (m, 6H) |
| A433 | (400 MHz, DMSO-d6, ppm) δ 9.55 (d, J = 7.60 Hz, 1H), 8.60 (s, 1H), 8.54 (s, 1H), 8.24 (m, 1H), 7.97 (d, J = 8.11 Hz, 1H), 7.68-7.80 (m, 3H), 5.89 (d, J = 7.10 Hz, 1H), 3.70-4.29 (m, 3H), 2.53-2.57 (m, 3H), 1.45-1.54 (m, 6H) |
| A434 | (400 MHz, DMSO-d6, ppm) δ 9.55 (d, J = 7.60 Hz, 1H), 8.60 (s, 1H), 8.54 (s, 1H), 8.24 (m, 1H), 7.97 (d, J = 8.11 Hz, 1H), 7.68-7.80 (m, 3H), 5.89 (d, J = 7.10 Hz, 1H), 3.70-4.29 (m, 3H), 2.53-2.57 (m, 3H), 1.45-1.54 (m, 6H) |

-continued

| Compound | $^1$H NMR Spectra |
|---|---|
| A435 | (400 MHz, DMSO-d6, ppm) δ 9.11 (d, J = 8.49 Hz, 1H), 8.37 (s, 1H), 7.38-7.79 (m, 4H), 6.82 (d, J = 5.07 Hz, 1H), 5.27 (d, J = 6.59 Hz, 1H), 3.36-3.67 (m, 1H), 2.53-2.62 (m, 5H), 1.52-2.14 (m, 10H) |
| A436 | (400 MHz, DMSO-d6) δ ppm 8.44 (s, 1H) 8.05 (br s, 1H) 7.80 (br s, 1H) 7.77 (d, J = 1.90 Hz, 2H) 7.68 (t, J = 1.84 Hz, 1H) 3.56-3.67 (m, 1H) 2.54 (s, 3H) 1.53 (d, J = 6.97 Hz, 6H) |
| A437 | (400 MHz, DMSO-d6, ppm) δ 9.11 (d, J = 8.49 Hz, 1H), 8.37 (s, 1H), 7.38-7.79 (m, 4H), 6.82 (d, J = 5.07 Hz, 1H), 5.27 (d, J = 6.59 Hz, 1H), 3.36-3.67 (m, 1H), 2.53-2.62 (m, 5H), 1.52-2.14 (m, 10H) |
| A438 | (400 MHz, DMSO-d6, ppm) δ 9.32 (d, J = 7.6 Hz, 1H), 8.42 (s, 1H), 8.10-8.17 (m, 3H), 7.64-7.83 (m, 1H), 7.21-7.31 (m, 2H), 5.66-5.77 (m, 1H), 4.93 (t, J = 9.4 Hz, 1H), 4.48 (m, 1H), 3.35-3.73 (m, 1H), 2.52-2.69 (m, 3H), 1.50-1.63 (m, 6H) |
| A439 | 400 MHz, DMSO-d6, ppm) δ 8.97 (d, J = 8.11 Hz, 1H), 8.44 (s, 1H), 7.66-7.79 (m, 3H), 6.94-7.17 (m, 2H), 6.52-6.63 (m, 2H), 3.88-5.17 (m, 1H), 2.53-3.60 (m, 7H), 1.44-2.33 (m, 8H) |
| A440 | 400 MHz, DMSO-d6, ppm) δ 8.97 (d, J = 8.11 Hz, 1H), 8.44 (s, 1H), 7.66-7.79 (m, 3H), 6.94-7.17 (m, 2H), 6.52-6.63 (m, 2H), 3.88-5.17 (m, 1H), 2.53-3.60 (m, 7H), 1.44-2.33 (m, 8H) |
| A441 | (400 MHz, DMSO-d6, ppm) δ 8.94 (d, J = 8.36 Hz, 1H), 8.43 (s, 1H), 7.66-7.80 (m, 3H), 6.87-7.36 (m, 2H), 5.09-5.17 (m, 1H), 3.37-3.78 (m, 1H), 2.53-2.77 (m, 5H), 2.23-2.41 (m, 1H), 1.51-2.09 (m, 9H) |
| A442 | (400 MHz, DMSO-d6, ppm) δ 9.32 (d, J = 7.6 Hz, 1H), 8.42 (s, 1H), 8.10-8.17 (m, 3H), 7.64-7.83 (m, 1H), 7.21-7.31 (m, 2H), 5.66-5.77 (m, 1H), 4.93 (t, J = 9.4 Hz, 1H), 4.48 (m, 1H), 3.35-3.73 (m, 1H), 2.52-2.69 (m, 3H), 1.50-1.63 (m, 6H) |
| A443 | (400 MHz, DMSO-d6, ppm) δ 8.94 (d, J = 8.36 Hz, 1H), 8.43 (s, 1H), 7.66-7.80 (m, 3H), 6.87-7.36 (m, 2H), 5.09-5.17 (m, 1H), 3.37-3.78 (m, 1H), 2.53-2.77 (m, 5H), 2.23-2.41 (m, 1H), 1.51-2.09 (m, 9H) |
| A445 | (400 MHz, DMSO-d6, ppm) δ 9.21 (d, J = 7.35 Hz, 1H), 8.44 (s, 1H), 7.66-7.78 (m, 3H), 7.30 (d, J = 8.24 Hz, 1H), 6.51 (m, 1H), 6.47 (d, J = 2.15 Hz, 1H), 5.65 (br d, J = 4.56 Hz, 1H), 4.81 (m, 1H), 4.40 (m, 1H), 3.56-3.74 (m, 4H), 2.52-2.55 (m, 3H), 1.50-1.59 (m, 6H) |
| A446 | (400 MHz, DMSO-d6, ppm) δ 9.21 (d, J = 7.35 Hz, 1H), 8.44 (s, 1H), 7.66-7.78 (m, 3H), 7.30 (d, J = 8.24 Hz, 1H), 6.51 (m, 1H), 6.47 (d, J = 2.15 Hz, 1H), 5.65 (br d, J = 4.56 Hz, 1H), 4.81 (m, 1H), 4.40 (m, 1H), 3.56-3.74 (m, 4H), 2.52-2.55 (m, 3H), 1.50-1.59 (m, 6H) |
| A447 | (400 MHz, DMSO-d6, ppm) δ 9.28 (d, J = 7.35 Hz, 1H), 8.46 (s, 1H), 7.66-7.79 (m, 3H), 7.43 (d, J = 7.35 Hz, 1H), 7.24 (t, J = 7.41 Hz, 1H), 6.94 (t, J = 7.41 Hz, 1H), 6.87 (d, J= 7.98 Hz, 1H), 5.72-5.80 (m, 1H), 4.80 (t, J = 9.19 Hz, 1H), 4.29-4.38 (m, 1H), 3.58 (m, 1H), 2.53-2.56 (m, 3H), 1.50-1.60 (m, 6H) |
| A448 | (400 MHz, DMSO-d6, ppm) δ 9.20 (d, J = 7.35 Hz, 1H), 8.84 (s, 1H), 8.43 (s, 1H), 7.67-7.80 (m, 3H), 5.21-5.27 (m, 1H), 4.28-4.43 (m, 2H), 3.58 (m, 1H), 2.52-2.67 (m, 3H), 2.00-2.45 (m, 2H), 1.52 (m, 6H) |
| A451 | (400 MHz, DMSO-d6, ppm) δ 9.20 (d, J = 7.35 Hz, 1H), 8.84 (s, 1H), 8.43 (s, 1H), 7.67-7.80 (m, 3H), 5.21-5.27 (m, 1H), 4.28-4.43 (m, 2H), 3.58 (m, 1H), 2.52-2.67 (m, 3H), 2.00-2.45 (m, 2H), 1.52 (m, 6H) |
| A452 | (400 MHz, DMSO-d6, ppm) δ 9.02 (d, J = 8.49 Hz, 1H), 8.53 (s, 1H), 7.78 (d, J = 1.90 Hz, 2H), 7.68 (t, J = 1.84 Hz, 1H), 7.36 (d, J = 7.73 Hz, 1H), 7.17 (t, J = 7.71 Hz, 1H), 6.92 (t, J = 7.26 Hz, 1H), 6.76 (d, J = 8.11 Hz, 1H), 5.32 (m, 1H), 3.52-3.62 (m, 1H), 2.52-2.58 (m, 3H), 2.21 (m, 1H), 1.80-1.89 (m, 1H), 1.23-1.61 (m, 12H) |
| A453 | (400 MHz, DMSO-d6, ppm) δ 9.28 (d, J = 7.35 Hz, 1H), 8.46 (s, 1H), 7.66-7.79 (m, 3H), 7.43 (d, J = 7.35 Hz, 1H), 7.24 (t, J = 7.41 Hz, 1H), 6.94 (t, J = 7.41 Hz, 1H), 6.87 (d, J = 7.98 Hz, 1H), 5.72-5.80 (m, 1H), 4.80 (t, J = 9.19 Hz, 1H), 4.29-4.38 (m, 1H), 3.58 (m, 1H), 2.53-2.56 (m, 3H), 1.50-1.60 (m, 6H) |
| A454 | (400 MHz, DMSO-d6, ppm) δ 9.17(d, J = 8.11 Hz, 1H) 8.54 (s, 1H) 7.78 (d, J = 1.77 Hz, 2H) 7.68 (t, J = 1.90 Hz, 1H) 7.54 (d, J = 7.98 Hz, 1H) 7.36 (dd, J = 7.86, 1.52 Hz, 1H) 7.31 (d, J = 1.52 Hz, 1H) 5.30 (q, J = 6.67 Hz, 1H) 4.24-4.39 (m, 2H) 3.50-3.65 (m, 1H) 2.55 (s, 3H) 2.15-2.31 (m, 1H) 1.99-2.15 (m, 1H) 1.54 (dd, J = 11.09, 6.91 Hz, 6H) |
| A455 | (400 MHz, DMSO-d6, ppm) δ 9.41 (d, J = 7.35 Hz, 1H), 8.51 (s, 1H), 8.27-8.42 (m, 2H), 7.66-7.79 (m, 4H), 5.82-5.90 (m, 1H), 4.93 (t, J = 9.38 Hz, 1H), 3.61-4.54 (m, 1H), 2.53-2.58 (m, 3H), 1.48-1.53 (m, 3H), 1.45-1.51 (m, 4H) |
| A456 | (400 MHz, DMSO-d6, ppm) δ 9.41 (d, J = 7.35 Hz, 1H), 8.51 (s, 1H), 8.27-8.42 (m, 2H), 7.66-7.79 (m, 4H), 5.82-5.90 (m, 1H), 4.93 (t, J = 9.38 Hz, 1H), 3.61-4.54 (m, 1H), 2.53-2.58 (m, 3H), 1.48-1.53 (m, 3H), 1.45-1.51 (m, 4H) |
| A457 | (400 MHz, DMSO-d6, ppm) δ 9.33 (d, J = 7.10 Hz, 1H), 8.52 (s, 1H), 7.66-7.79 (m, 3H), 7.48 (s, 1H), 7.20-7.28 (m, 1H), 6.90 (d, J = 8.49 Hz, 1H), 5.73 (br d, J = 5.20 Hz, 1H), 4.85 (t, J = 9.25 Hz, 1H), 4.43 (m, 1H), 3.35-3.63 (m, 1H), 2.53-2.56 (m, 3H), 1.50-1.53 (m, 6H) |
| A458 | (400 MHz, DMSO-d6, ppm) δ 9.33 (d, J = 7.10 Hz, 1H), 8.52 (s, 1H), 7.66-7.79 (m, 3H), 7.48 (s, 1H), 7.20-7.28 (m, 1H), 6.90 (d, J = 8.49 Hz, 1H), 5.73 (br d, J = 5.20 Hz, 1H), 4.85 (t, J = 9.25 Hz, 1H), 4.43 (m, 1H), 3.35-3.63 (m, 1H), 2.53-2.56 (m, 3H), 1.50-1.53 (m, 6H) |

-continued

| Compound | $^1$H NMR Spectra |
|---|---|
| A472 | (400 MHz, DMSO-d6, ppm) δ 9.02 (d, J = 8.49 Hz, 1H), 8.53 (s, 1H), 7.78 (d, J = 1.90 Hz, 2H), 7.68 (t, J = 1.84 Hz, 1H), 7.36 (d, J = 7.73 Hz, 1H), 7.17 (t, J = 7.71 Hz, 1H), 6.92 (t, J = 7.26 Hz, 1H), 6.76 (d, J = 8.11 Hz, 1H), 5.32 (m, 1H), 3.52-3.62 (m, 1H), 2.52-2.58 (m, 3H), 2.21 (m, 1H), 1.80-1.89 (m, 1H), 1.23-1.61 (m, 12H) |
| 560 | (400 MHz, Chloroform-d, ppm) δ+0: 8.35 (s, 1H), 7.51 (s, 2H), 7.65 (s, 1H), 7.29-7.21 (m, 2H), 7.01-6.84 (m, 3H), 6.20 (d, J = 8.3 Hz, 1H), 6.08-6.07 (m, 1H), 5.40 (d, J = 8.3 Hz, 1H), 4.39-4.34 (m, 1H), 4.21-4.15 (m, 1H), 3.71-3.64 (m, 1H), 2.44-2.39 (m, 1H), 2.26-2.20 (m, 1H), 1.65-1.54 (m, 6H) |

Preparation Example 3: The example compounds A400, A401, A405 and A459 were prepared according to scheme 8, with reactions that are adapted from known reactions in the literature. For example, see Campbell, Alison N. et al. Organic Process Research & Development (2013), 17(2), 273-281 and Stanovnik, B. et al., Tetrahedron (1967), 23(6), 2739-46.

Scheme 8

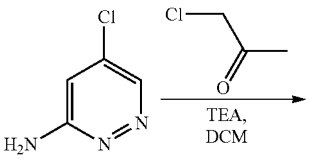

8-1

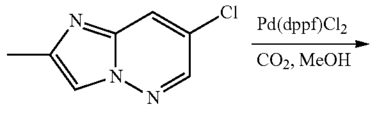

8-2

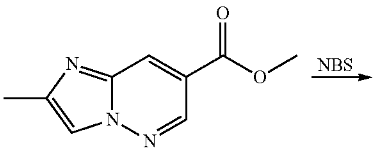

8-3

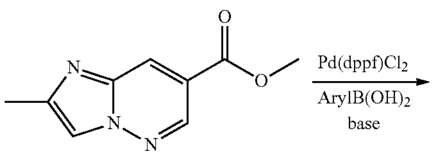

8-4

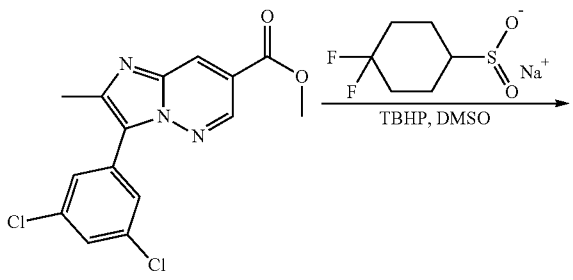

8-5

-continued

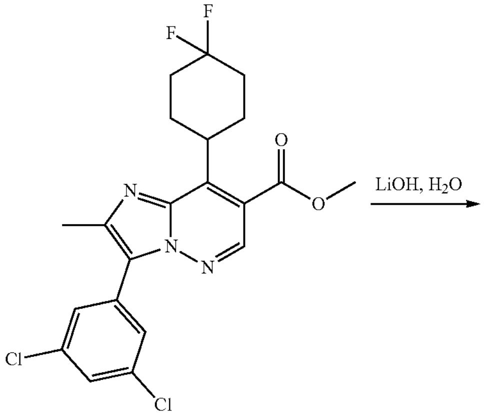

8-6

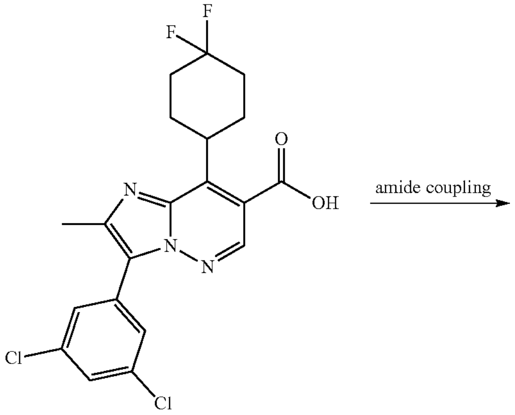

8-7

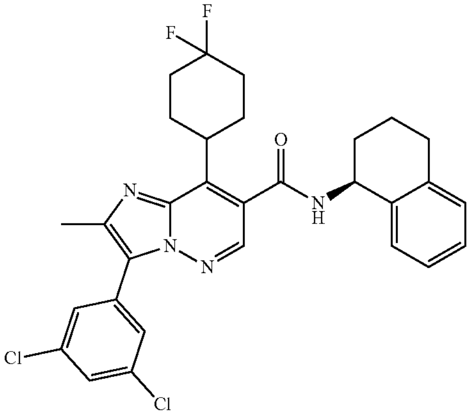

A459

Description of the Key Step: Synthesis of methyl 3-(3,5-dichlorophenyl)-8-(4,4-difluorocyclohexyl)-2-methylimidazo[1,2-b]pyridazine-7-carboxylate (8-6)

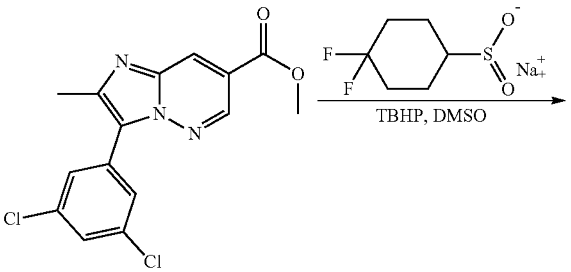

8-5

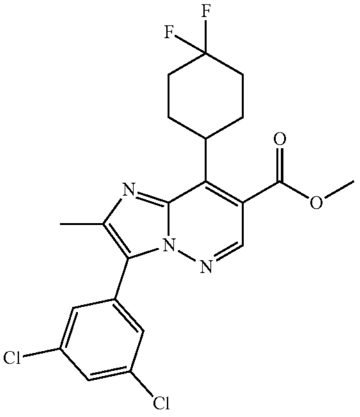

8-6

A mixture of 90 mg (0.3 mmol) methyl 3-(3,5-dichlorophenyl)-2-methylimidazo[1,2-b]pyridazine-7-carboxylate (8-5) in 5 mL DMSO was treated with 200 mg (1.0 mmol) of zinc sulfinate and the solution was cooled with an ice bath. 185 μL (1 mmol) of 2-Methyl-prop-2-yl-hydroperoxide (TBHP) was added dropwise and the reaction mixture was stirred at 50° C. for 1 h. The reaction mixture was quenched with sodium carbonate solution and extracted with EE. The organic layers were collected, dried, filtered and evaporated. The mixture was evaporated, purified by column chromatography (silica gel; CyH/EtOAc) and the solvents removed in vacuo to obtain 900 mg (74%) of the product as yellow oil. (400 MHz, DMSO-d6) δ ppm 9.11 (d, J=8.11 Hz, 1H) 8.52 (s, 1H) 7.76 (d, J=1.77 Hz, 2H) 7.66-7.71 (m, 1H) 7.39 (d, J=7.35 Hz, 1H) 7.18 (t, J=7.73 Hz, 1H) 6.89-6.95 (m, 1H) 6.80 (d, J=8.11 Hz, 1H) 5.23-5.30 (m, 1H) 4.18-4.33 (m, 2H) 2.61-2.80 (m, 3H) 2.53 (s, 3H) 2.30-2.39 (m, 1H) 2.09-2.30 (m, 3H) 1.73-1.94 (m, 4H).

The conversion of compound 8-6 into the product may be achieved as in Scheme 4 by hydrolysis of the methyl ester to the carboxylic acid followed by coupling of the acid with the desired amine.

As noted above, compounds A400, A401 and A405 are prepared by adopting the process described in Scheme 8.

| Compound | $^1$H NMR Spectra |
|---|---|
| A400 | (400 MHz, DMSO-d6) δ ppm 9.12 (d, J = 7.98 Hz, 1H) 8.69 (s, 1H) 7.79 (d, J = 1.90 Hz, 2 H) 7.71-7.75 (m, 1H) 7.34 (d, J = 7.73 Hz, 1 H) 7.18 (t, J = 7.67 Hz, 1H) 6.92 (t, J = 7.09 Hz, 1 H) 6.80 (d, J = 8.11 Hz, 1 H) 5.14-5.22 (m, 1H) 4.24-4.34 (m, 1H) 4.13-4.24 (m, 1H) 2.67 (dt, J = 3.68, 1.84 Hz, 1H) 2.56 (s, 3H) 2.27 (t, J = 19.33 Hz, 3H) 2.10-2.21 (m, 1H) 1.96-2.08 (m, 1H |
| A401 | (400 MHz, DMSO-d6) δ ppm 9.34 (d, J = 8.11 Hz, 1H) 8.84 (s, 1H) 7.80 (d, J = 1.90 Hz, 2 H) 7.74-7.77 (m, 1H) 7.33 (d, J = 7.10 Hz, 1H) 7.19 (t, J = 7.10 Hz, 1H) 6.93 (t, J = 7.03 Hz, 1H) 6.81 (d, J = 8.11 Hz, 1H) 5.16-5.23 (m, 1H) 4.23-4.33 (m, 1H) 4.14-4.23 (m, 1H) 2.58 (s, 3H) 2.16-2.27 (m, 1H) 1.98-2.07 (m, 1H) |
| A405 | (400 MHz, DMSO-d6) δ ppm 9.29 (d, J = 7.98 Hz, 1H) 8.77 (s, 1H) 7.80 (d, J = 1.90 Hz, 2H) 7.73 (d, J = 1.90 Hz, 1H) 7.60 (t, J = 52.00 Hz, 1H) 7.36 (d, J = 6.97 Hz, 1H) 7.16-7.21 (m, 1H) 6.92 (td, J = 7.45, 1.08 Hz, 1H) 6.81 (d, J = 8.11 Hz, 1H) 5.19-5.25 (m, 1H) 4.19-4.31 (m, 2H) 2.58 (s, 3H) 2.15-2.24 (m, 1H) 2.03-2.11 (m, 1H |

Preparation Example 4: The example 304-0 was prepared according to scheme 9 below. Analogously, compound 321 can be prepared by the one skilled in the art in the same manner.

Scheme 9

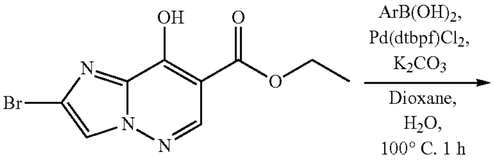

3-6

-continued

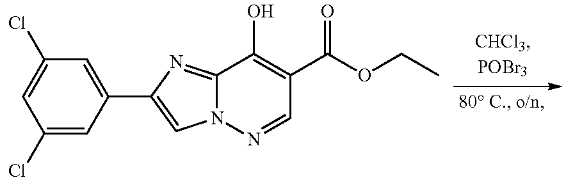

9-2

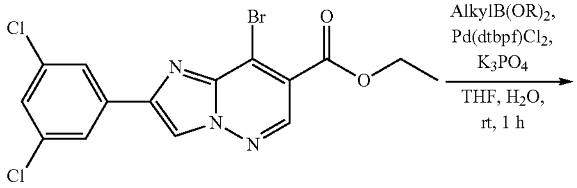

9-3

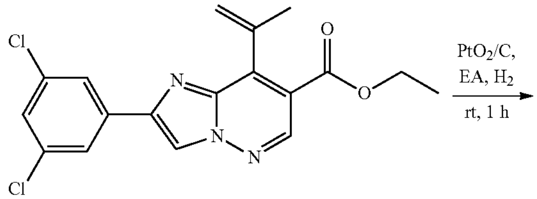

9-4

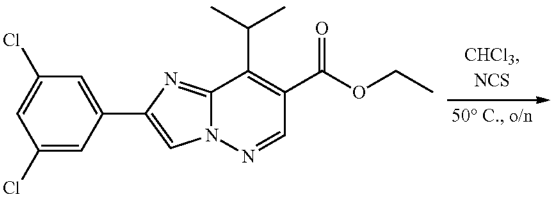

9-5

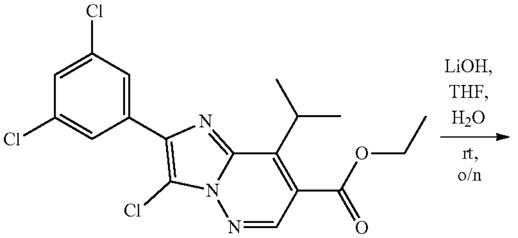

9-6

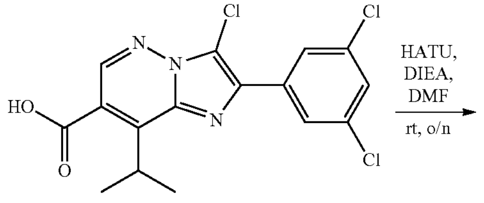

9-7

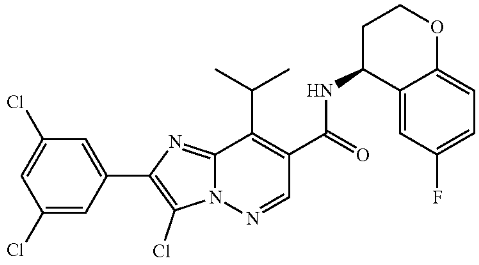

304-0

1. Synthesis of ethyl 2-(3,5-dichlorophenyl)-8-hydroxyimidazo[1,2-b]pyridazine-7-carboxylate (9-2)

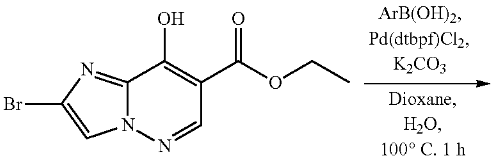

3-6

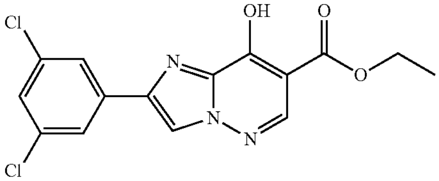

9-2

Into a 500-mL round-bottom flask purged and maintained with an inert atmosphere of nitrogen, was placed ethyl 2-bromo-8-hydroxyimidazo[1,2-b]pyridazine-7-carboxylate (3-6, 2.0 g, 0.007 mmol, 1.0 equiv), 3,5-dichlorophenylboronic acid (1.6 g, 0.008 mmol, 1.2 equiv), $K_2CO_3$ (2.1 g, 0.015 mmol, 2.2 equiv), dioxane (100.0 mL), $H_2O$ (20.0 mL), $Pd(dtbpf)Cl_2$ (0.27 g, 0.000 mmol, 0.06 equiv). The resulting solution was stirred for 1 hr at 100° C. in an oil bath. The reaction was then quenched by the addition of 100 mL of water. The solids were collected by filtration. This resulted in 2.1 g (85.3%) of ethyl 2-(3,5-dichlorophenyl)-8-hydroxyimidazo[1,2-b]pyridazine-7-carboxylate (9-2) as an off-white solid. (ES, m/z): 352 $[M+H]^+$.

2. Synthesis of ethyl 8-bromo-2-(3,5-dichlorophenyl)imidazo[1,2-b]pyridazine-7-carboxylate (9-3)

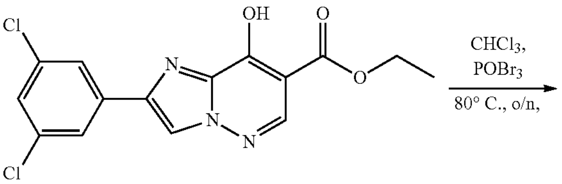

9-2

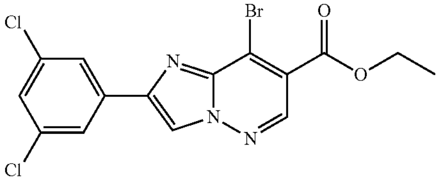

9-3

Into a 100-mL round-bottom flask purged and maintained with an inert atmosphere of nitrogen, was placed ethyl 2-(3,5-dichlorophenyl)-8-hydroxyimidazo[1,2-b]pyridazine-7-carboxylate (9-2, 2.0 g, 5.7 mmol, 1.0 equiv), $CHCl_3$ (25.0 mL), $POBr_3$ (8.14 g, 28.4 mmol, 5.0 equiv). The resulting solution was stirred for 1 overnight at 80° C. The resulting mixture was cooled to room temperature and concentrated. The residue was diluted with 50 ml of water.

The pH value of the solution was adjusted to 7-8 with $Na_2CO_3$ (saturated). The resulting solution was extracted with 3×50 mL of ethyl acetate. The combined organic layer was dried over anhydrous sodium sulfate and concentrated. The residue was applied onto a silica gel column with ethyl acetate/petroleum ether (1:10). This resulted in 810 mg (34.4%) of ethyl 8-bromo-2-(3,5-dichlorophenyl)imidazo[1,2-b]pyridazine-7-carboxylate (9-3) as an off-white solid. (ES, m/z): 414 $[M+H]^+$.

3. Synthesis of ethyl 2-(3,5-dichlorophenyl)-8-(prop-1-en-2-yl)imidazo[1,2-b]pyridazine-7-carboxylate (9-4)

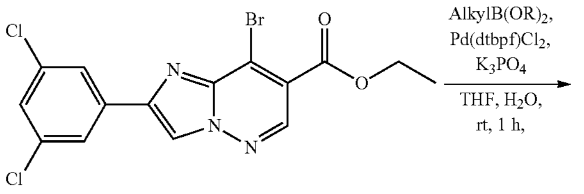

9-3

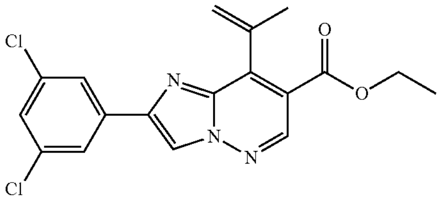

9-4

Into a 50-mL round-bottom flask purged and maintained with an inert atmosphere of nitrogen, was placed ethyl 8-bromo-2-(3,5-dichlorophenyl)imidazo[1,2-b]pyridazine-7-carboxylate (9-3, 1800.0 mg, 4.4 mmol, 1.0 equiv), $K_3PO_4$ (2761.5 mg, 13.0 mmol, 3.0 equiv), THF (20.0 mL), $H_2O$ (5.0 mL), $Pd(dtbpf)Cl_2$ (282.6 mg, 0.4 mmol, 0.1 equiv), 4,4,5,5-tetramethyl-2-(prop-1-en-2-yl)-1,3,2-dioxaborolane (801.6 mg, 4.8 mmol, 1.1 equiv). The resulting solution was stirred for 1 hr at room temperature. The reaction was then quenched by the addition of 20 mL of water. The resulting solution was extracted with 3×30 mL of ethyl acetate. The combined organic layer was dried over anhydrous sodium sulfate and concentrated. The residue was applied onto a silica gel column with ethyl acetate/petroleum ether (1:10). This resulted in 0.55 g (33.7%) of ethyl 2-(3,5-dichlorophenyl)-8-(prop-1-en-2-yl)imidazo[1,2-b]pyridazine-7-carboxylate (9-4) as an off-white solid. (ES, m/z): 376 $[M+H]^+$.

4. Synthesis of ethyl 2-(3,5-dichlorophenyl)-8-isopropylimidazo[1,2-b]pyridazine-7-carboxylate (9-5)

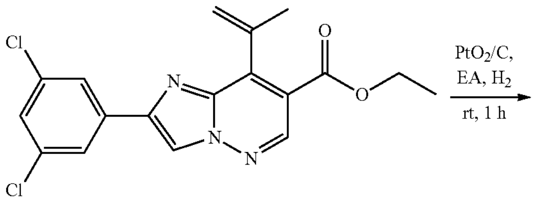

9-4

-continued

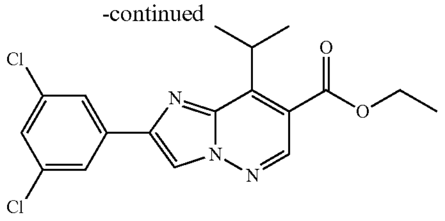

9-5

Into a 50-mL round-bottom flask purged and maintained with an inert atmosphere of $H_2$ (g), was placed ethyl 2-(3,5-dichlorophenyl)-8-(prop-1-en-2-yl)imidazo[1,2-b]pyridazine-7-carboxylate (9-4, 500.0 mg, 1.3 mmol, 1.0 equiv), EA (10.0 mL), $PtO_2$ (100.0 mg, 0.4 mmol, 0.3 equiv). The resulting solution was stirred for 1 hr at room temperature. The solids were filtered out. The filtrate was concentrated. This resulted in 450 mg (82.4%) of ethyl 2-(3,5-dichlorophenyl)-8-isopropylimidazo[1,2-b]pyridazine-7-carboxylate as an off-white solid (9-5). (ES, m/z): 378 $[M+H]^+$.

5. Synthesis of ethyl 3-chloro-2-(3,5-dichlorophenyl)-8-isopropylimidazo[1,2-b]pyridazine-7-carboxylate (9-6)

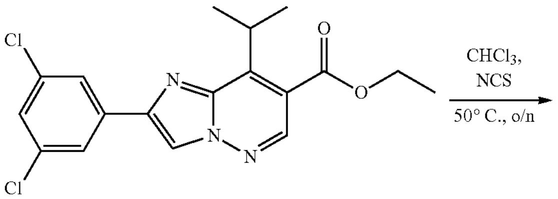

9-5

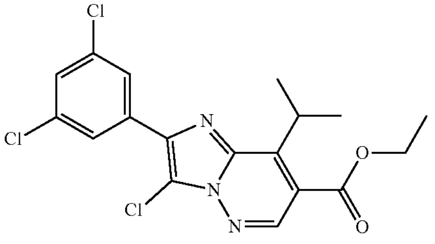

9-6

Into a 20-mL round-bottom flask purged and maintained with an inert atmosphere of nitrogen, was placed ethyl 2-(3,5-dichlorophenyl)-8-isopropylimidazo[1,2-b]pyridazine-7-carboxylate (9-5, 100.0 mg, 0.3 mmol, 1.0 equiv), $CHCl_3$ (5.0 mL), NCS (38.8 mg, 0.3 mmol, 1.1 equiv). The resulting solution was stirred for 1 overnight at 50° C. The resulting mixture was concentrated. The residue was applied on a silica gel column and eluted with EA/PE (1/20). This resulted in 106.6 mg (97.7%) of ethyl 3-chloro-2-(3,5-dichlorophenyl)-8-isopropylimidazo[1,2-b]pyridazine-7-carboxylate (9-6) as an off-white solid. (ES, m/z): 412 $[M+H]^+$.

6. Synthesis of 3-chloro-2-(3,5-dichlorophenyl)-8-isopropylimidazo[1,2-b]pyridazine-7-carboxylic Acid (9-7)

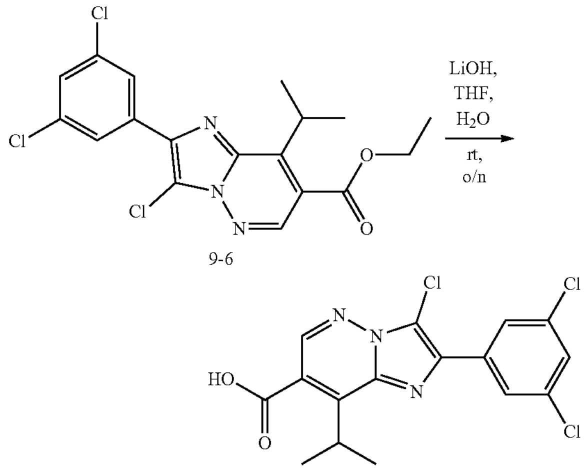

9-6

9-7

Into a 20-mL round-bottom flask purged and maintained with an inert atmosphere of nitrogen, was placed ethyl 3-chloro-2-(3,5-dichlorophenyl)-8-isopropylimidazo[1,2-b]pyridazine-7-carboxylate (9-6, 95.0 mg, 0.2 mmol, 1.0 equiv), THF (5.0 mL), $H_2O$ (1.0 mL), LiOH (27.6 mg, 1.2 mmol, 5.0 equiv). The resulting solution was stirred for 1 overnight at room temperature. The pH value of the solution was adjusted to 3-4 with HCl (1 mol/L). The resulting solution was extracted with 3×10 mL of ethyl acetate and the organic layers combined. The organic phase was dried in an oven under reduced pressure and concentrated. This resulted in 78 mg (88.1%) of 3-chloro-2-(3,5-dichlorophenyl)-8-isopropylimidazo[1,2-b]pyridazine-7-carboxylic acid (9-7) as an off-white solid. (ES, m/z): 384 $[M+H]^+$.

7. Synthesis of 3-chloro-2-(3,5-dichlorophenyl)-N-[(4S)-6-fluoro-3,4-dihydro-2H-1-benzopyran-4-yl]-8-isopropylimidazo[1,2-b]pyridazine-7-carboxamide (Compound 304)

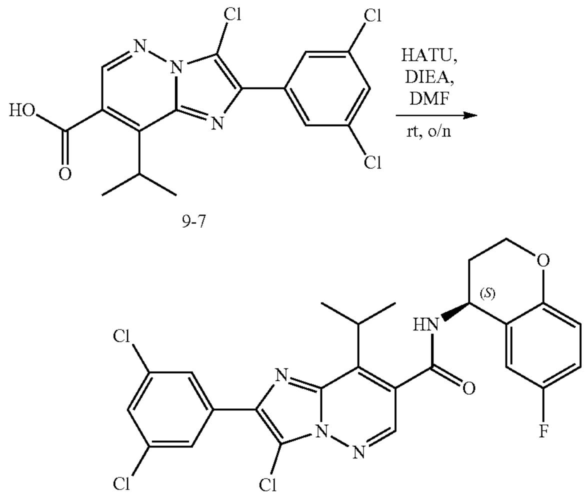

9-7

304-0

Into a 20-mL round-bottom flask purged and maintained with an inert atmosphere of nitrogen, was placed (4S)-6-fluoro-3,4-dihydro-2H-1-benzopyran-4-amine dihydrochloride (51.0 mg, 0.2 mmol, 1.2 equiv), 3-chloro-2-(3,5-dichlorophenyl)-8-isopropylimidazo[1,2-b]pyridazine-7-carboxylic acid (9-7, 68.0 mg, 0.2 mmol, 1.0 equiv), DMF (5.0 mL), DIEA (45.7 mg, 0.35 mmol, 2.0 equiv), HATU (100.8 mg, 0.3 mmol, 1.5 equiv). The resulting solution was stirred for 1 overnight at room temperature. The crude product was purified by Flash-Prep-HPLC with the following conditions (IntelFlash-1): Column, C18 silica gel; mobile phase, $ACN:H_2O=72$ increasing to $ACN:H_2O=95$ within 7; Detector, 254. This resulted in 67.7 mg (71.7%) of 3-chloro-2-(3,5-dichlorophenyl)-N-[(4S)-6-fluoro-3,4-dihydro-2H-1-benzopyran-4-yl]-8-isopropylimidazo[1,2-b]pyridazine-7-carboxamide (304-0) as an off-white solid. (300 MHz, $CDCl_3$, ppm) δ 8.36 (s, 1H), 7.83 (d, J=1.8 Hz, 2H), 7.45 (t, J=1.8 Hz, 1H), 7.02-6.93 (m, 2H), 6.87-6.83 (m, 1H), 6.06 (d, J=7.8 Hz, 1H), 5.41 (t, J=5.7 Hz, 1H), 4.38-4.32 (m, 1H), 4.24-4.16 (m, 1H), 3.73 (t, J=6.9 Hz, 1H), 2.45-2.40 (m, 1H), 2.24-2.18 (m, 1H), 1.68-1.64 (m, 6H).

Compound 321: (300 MHz, Chloroform-d, ppm): δ 8.27 (s, 1H), 7.76-7.60 (m, 2H), 7.35-7.30 (m, 1H), 7.28-7.20 (m, 1H), 7.20-7.03 (m, 4H), 7.03-6.80 (m, 3H), 6.20-5.90 (m, 1H), 5.50-5.25 (m, 1H), 4.45-4.30 (m, 1H), 4.30-4.10 (m, 1H), 3.80-3.65 (m, 1H), 2.55-2.35 (m, 1H), 2.33-2.15 (m, 1H), 1.72 (t, J=6.3 Hz, 6H)

Preparation Example 5: The example 174 was prepared according to scheme 10:

Scheme 10

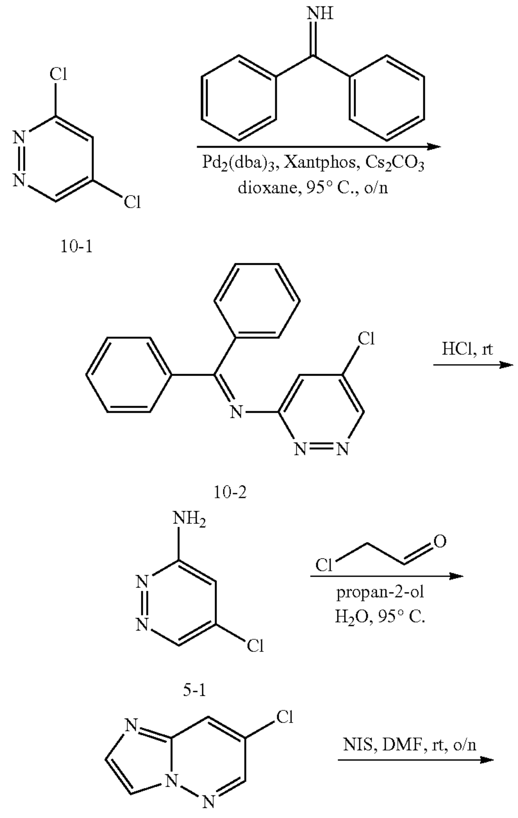

10-1

10-2

5-1

10-4

-continued

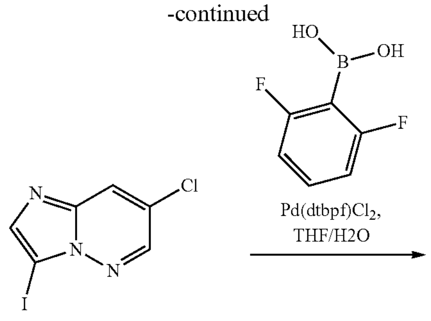

10-5

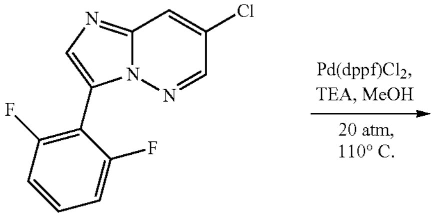

10-6

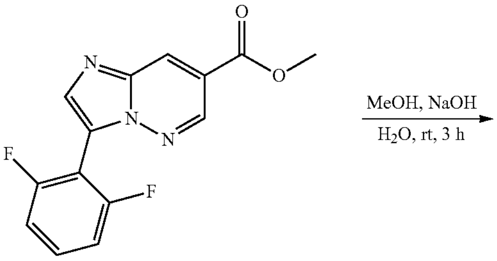

10-7

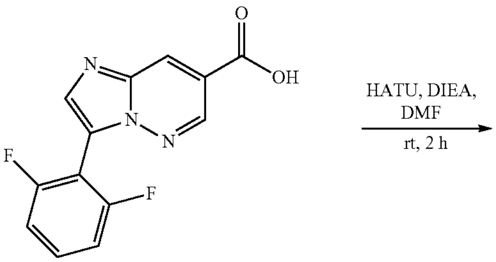

10-8

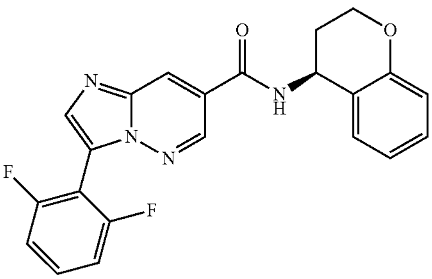

174

1. Synthesis of N-(5-chloropyridazin-3-yl)-1,1-diphenylmethanimine (10-2)

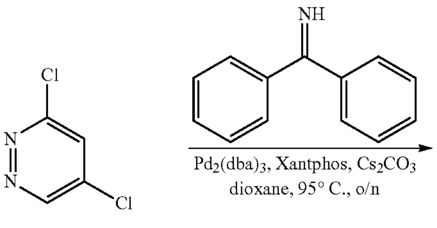

10-1

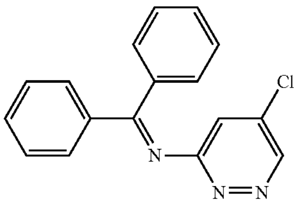

10-2

Into a 40-mL round-bottom flask purged and maintained with an inert atmosphere of nitrogen, was placed 3,5-dichloropyridazine (10-1, 500.0 mg, 3.4 mmol, 1.0 equiv), diphenylmethanimine (675.2 mg, 3.7 mmol, 1.1 equiv), XantPhos (69.9 mg, 0.12 mmol, 0.04 equiv), $Pd_2(dba)_3$ (34.7 mg, 0.06 mmol, 0.02 equiv), $Cs_2CO_3$ (2187.1 mg, 6.7 mmol, 2.0 equiv), dioxane (5 ml). The resulting solution was stirred for 3 hr at 90 degrees C. in an oil bath. The solids were filtered out. The resulting mixture was concentrated. This resulted in 3 mL (30.4%) of N-(5-chloropyridazin-3-yl)-1,1-diphenylmethanimine (10-2) as brown oil.

2. Synthesis of 5-chloropyridazin-3-amine

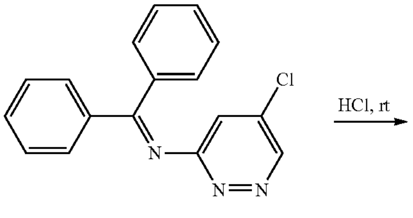

10-2

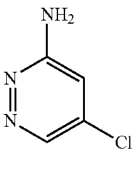

5-1

Into a 50-mL 3-necked round-bottom flask purged and maintained with an inert atmosphere of nitrogen, was placed N-(5-chloropyridazin-3-yl)-1,1-diphenylmethanimine (10-2, 10.0 mL), HCl (3M) (15.0 mL). The resulting solution was stirred for 1 hr at room temperature. The pH value of the solution was adjusted to 7 with $NaHCO_3$. The resulting mixture was concentrated. This resulted in 15 mL of 5-chloropyridazin-3-amine (5-1) as brown oil.

3. Synthesis of 7-chloroimidazo[1,2-b]pyridazine (10-4)

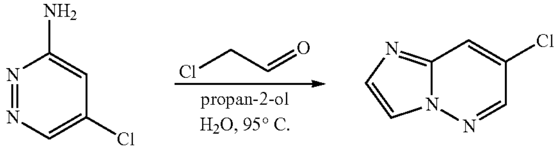

5-1

10-4

Into a 250-mL round-bottom flask, was placed 5-chloropyridazin-3-amine (5-1, 15.00 mL), chloroacetaldehyde (17.5 mL), $H_2O$ (17.5 mL), i-PrOH (25 mL). The resulting solution was stirred for 5 hr at 95° C. in an oil bath. The resulting mixture was concentrated. The pH value of the solution was adjusted to 9 with NaOH. The resulting solution was extracted with 3×50 mL of ethyl acetate, the organic layer was washed with 3×50 ml of brine. The organic phase was collected and dried over anhydrous sodium sulfate and concentrated. The residue was applied onto a silica gel column with ethyl acetate/petroleum ether (2:3). This resulted in 2.2 g (12.4%) of 7-chloroimidazo[1,2-b]pyridazine (10-4) as yellow oil.

4. Synthesis of 7-chloro-3-iodoimidazo[1,2-b]pyridazine (10-5)

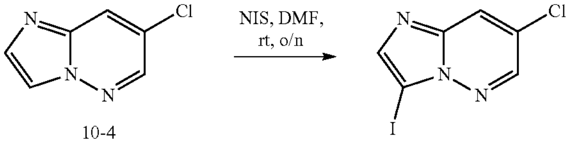

10-4

10-5

Into a 50-mL round-bottom flask, was placed 7-chloroimidazo[1,2-b]pyridazine (1.0 g, 7.0 mmol, 1.0 equiv), NIS (2.2 g, 10.0 mmol, 1.5 equiv), DMF (10 mL). The resulting solution was stirred for 1 overnight at room temperature. The reaction was then quenched by the addition of 20 mL of water. The resulting solution was extracted with 3×20 mL of ethyl acetate concentrated. The residue was applied onto a silica gel column with ethyl acetate/petroleum ether (2:1). This resulted in 800 mg (43.9%) of 7-chloro-3-iodoimidazo[1,2-b]pyridazine as yellow oil.

5. Synthesis of 7-chloro-3-(2,6-difluorophenyl)imidazo[1,2-b]pyridazine (10-6)

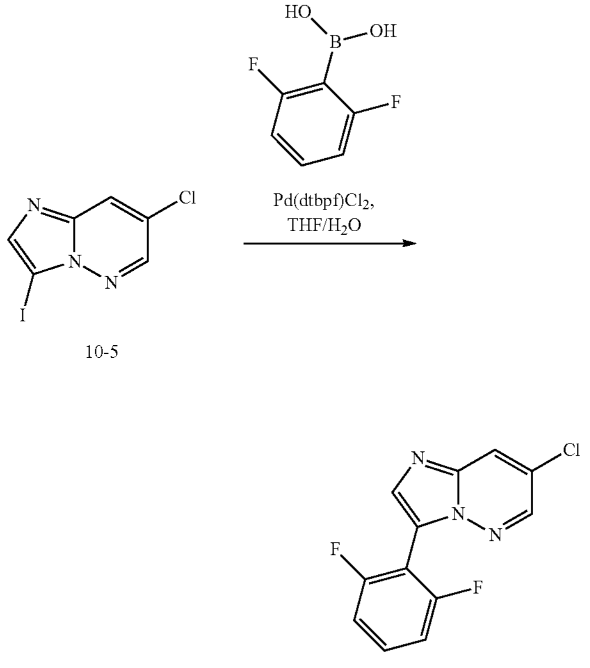

10-5

10-6

Into a 40-mL round-bottom flask purged and maintained with an inert atmosphere of nitrogen, was placed 7-chloro-3-iodoimidazo[1,2-b]pyridazine (10-5, 400.0 mg, 1.4 mmol, 1.0 equiv), 2,6-difluorophenylboronic acid (452.0 mg, 2.9 mmol, 2.0 equiv), Pd(dtbpf)$Cl_2$ (93.3 mg, 0.14 mmol, 0.1 equiv), $K_3PO_4$ (911.4 mg, 4.3 mmol, 3.0 equiv), THE (10 mL), $H_2O$ (2.5 mL). The resulting solution was stirred for 1 hr overnight at room temperature. The resulting mixture was concentrated. The residue was applied onto a silica gel column with ethyl acetate/petroleum ether (1:3). This resulted in 150 mg (39.4%) of 7-chloro-3-(2,6-difluorophenyl)imidazo[1,2-b]pyridazine (10-6) as a white solid.

6. Synthesis of methyl 3-(2,6-difluorophenyl)imidazo[1,2-b]pyridazine-7-carboxylate (10-7)

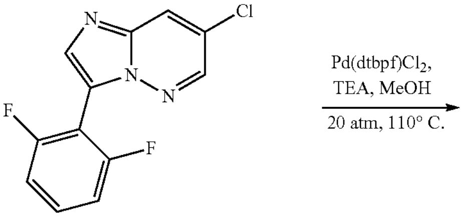

10-6

-continued

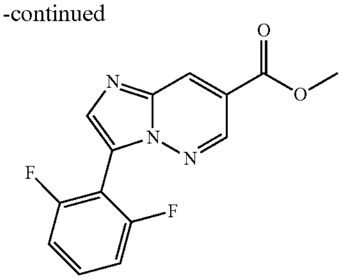

10-7

Into a 50-mL pressure tank reactor, was placed 7-chloro-3-(2,6-difluorophenyl)imidazo[1,2-b]pyridazine (10-6) 130.0 mg, 0.5 mmol, 1.0 equiv), Pd(dppf)$Cl_2$ (35.8 mg, 0.05 mmol, 0.1 equiv), TEA (148.6 mg, 1.5 mmol, 3.0 equiv), CO (20 atm), MeOH (10.00 mL). The resulting solution was stirred for 4 hr at 110° C. in an oil bath. The resulting mixture was concentrated. The residue was applied onto a silica gel column with ethyl acetate/petroleum ether (1:3). This resulted in 95 mg (67.1%) of methyl 3-(2,6-difluorophenyl)imidazo[1,2-b]pyridazine-7-carboxylate (10-7) as a white solid.

7. Synthesis of 3-(2,6-difluorophenyl)imidazo[1,2-b]pyridazine-7-carboxylic acid (10-8)

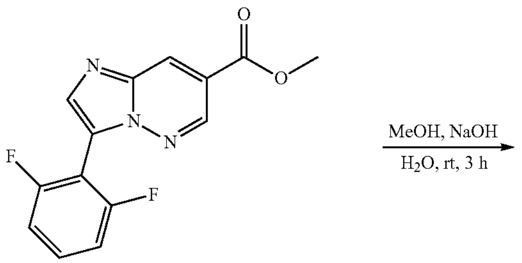

10-7

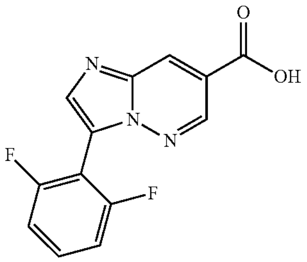

10-8

Into a 40-mL round-bottom flask, was placed methyl 3-(2,6-difluorophenyl)imidazo[1,2-b]pyridazine-7-carboxylate (10-7, 85.0 mg, 0.3 mmol, 1.0 equiv), NaOH (58.7 mg, 1.5 mmol, 5.0 equiv), MeOH (9 mL), $H_2O$ (3 mL). The resulting solution was stirred for 3 hr at room temperature. The resulting solution was diluted with 20 mL of water. The pH value of the solution was adjusted to 3-4 with HCl (3 mol/L). The resulting solution was extracted with 3×20 mL of ethyl acetate, the organic phase was collected and dried over anhydrous sodium sulfate and concentrated. This resulted in 65 mg (80.4%) of 3-(2,6-difluorophenyl)imidazo[1,2-b]pyridazine-7-carboxylic acid (10-8) as a white solid.

8. Synthesis of 3-(2,6-difluorophenyl)-N-[(4S)-3,4-dihydro-2H-1-benzopyran-4-yl]imidazo[1,2-b]pyridazine-7-carboxamide (Compound 174)

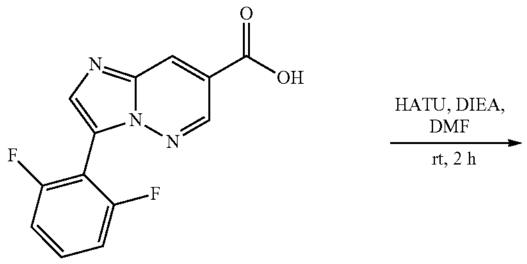

10-8

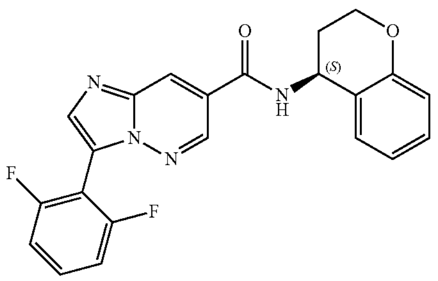

174

Into a 40-mL round-bottom flask, was placed 3-(2,6-difluorophenyl)imidazo[1,2-b]pyridazine-7-carboxylic acid (10-8, 60.0 mg, 0.2 mmol, 1.0 equiv), (4S)-3,4-dihydro-2H-1-benzopyran-4-amine (48.8 mg, 0.3 mmol, 1.5 equiv), HATU (165.79 mg, 0.436 mmol, 2 equiv), DIEA (84.5 mg, 0.6 mmol, 3.0 equiv), DMF (3 mL). The resulting solution was stirred for 2 hr at room temperature. The crude product was purified by Prep-HPLC with the following conditions (Waters-2767): Column, X-bridge RP18, 5 um, 19*100 mm; mobile phase, 0.03% ammonia in water and $CH_3CN$ (30% $CH_3CN$ up to 70% in 15 min); Detector, UV 254 nm. This resulted in 19.4 mg (21.9%) of 3-(2,6-difluorophenyl)-N-[(4S)-3,4-dihydro-2H-1-benzopyran-4-yl]imidazo[1,2-b]pyridazine-7-carboxamide (174) as a white solid. (300 MHz, $CDCl_3$, ppm) δ 8.95 (s, 1H), 8.54 (s, 1H), 7.97 (s, 1H), 7.55-7.45 (m, 1H), 7.25-7.24 (m, 1H), 7.17-7.08 (m, 4H), 6.91-6.81 (m, 2H), 5.43-5.39 (m, 1H), 4.35-4.25 (m, 2H), 2.41-2.31 (m, 1H), 2.28-2.21 (m, 1H).

Preparation Example 6: The example 277 was prepared according to scheme 11 below:

Scheme 11
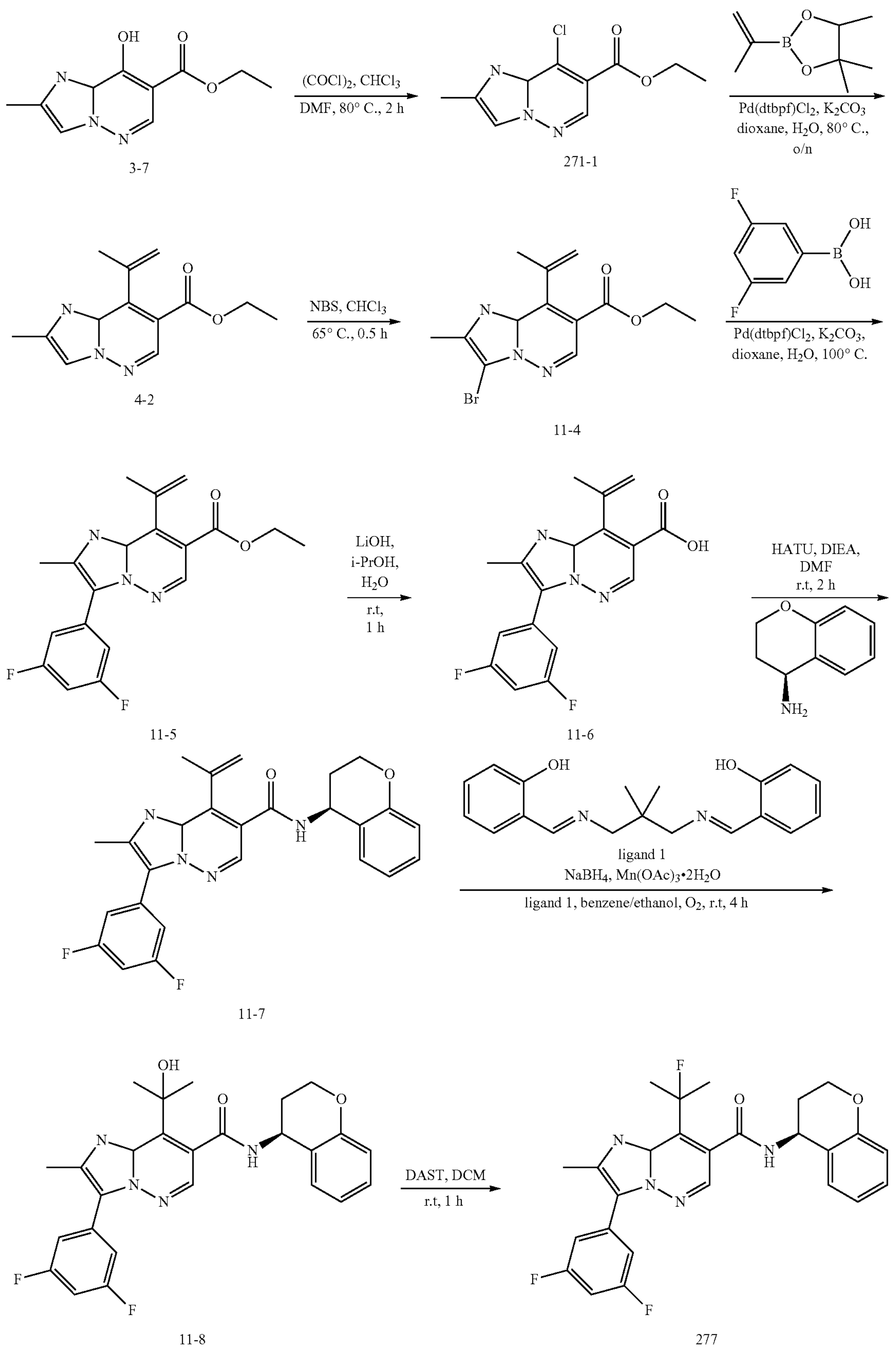

1. Synthesis of ethyl 8-chloro-2-methylimidazo[1,2-b]pyridazine-7-carboxylate (271-1)

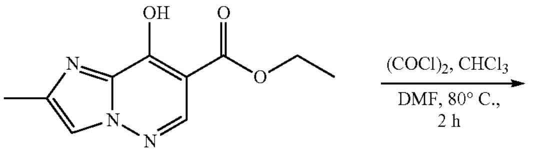

3-7

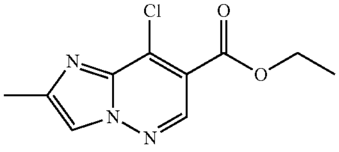

271-1

Into a 100-mL round-bottom flask, was placed ethyl 8-hydroxy-2-methylimidazo[1,2-b]pyridazine-7-carboxylate (3-7, 2.8 g, 12.6 mmol, 1.0 equiv), DMF (8.0 uL, 103.4 mmol, 8.2 equiv), $CHCl_3$ (55.0 mL). This was followed by the addition of $(COCl)_2$ (8.0 g, 63.1 mmol, 5.0 equiv) dropwise with stirring at room temperature. The resulting solution was stirred for 2 hrs at 80° C. The resulting mixture was concentrated. The crude product was purified by Prep-Flash with the following conditions: Column, $C^{18}$ silica gel; mobile phase, 0.1% FA in water and $CH_3CN$ (10% $CH_3CN$ increasing to 70% within 12 min). Detector, UV 254 nm, 220 nm. This resulted in 537 mg (17.2%) of ethyl 8-chloro-2-methylimidazo[1,2-b]pyridazine-7-carboxylate (271-1) as a yellow solid.

2. Synthesis of ethyl 2-methyl-8-(prop-1-en-2-yl)imidazo[1,2-b]pyridazine-7-carboxylate (4-2)

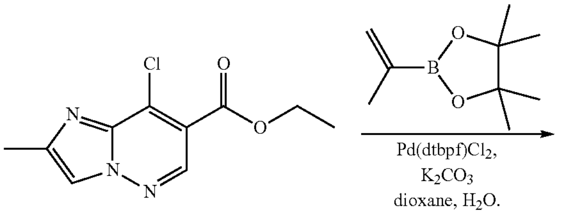

271-1

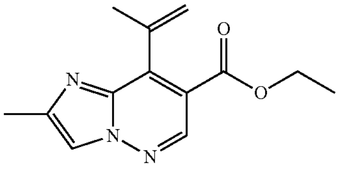

4-2

Into a 50-mL 3-necked round-bottom flask purged and maintained with an inert atmosphere of nitrogen, was placed ethyl 8-chloro-2-methylimidazo[1,2-b]pyridazine-7-carboxylate (271-1, 480.0 mg, 2.0 mmol, 1.0 equiv), dioxane (19.0 mL), $H_2O$ (4.8 mL), 4,4,5,5-tetramethyl-2-(prop-1-en-2-yl)-1,3,2-dioxaborolane (673.1 mg, 4.0 mmol, 2.0 equiv), $Pd(dtbpf)Cl_2$ (130.5 mg, 0.20 mmol, 0.1 equiv), $K_2CO_3$ (553.6 mg, 4.0 mmol, 2.0 equiv). The resulting solution was stirred for overnight at 80° C. The resulting solution was diluted with 10 mL of water. The resulting solution was extracted with 2×20 mL of ethyl acetate and the organic layers combined. The resulting mixture was washed with 2×20 ml of brine. The mixture was dried over anhydrous sodium sulfate and concentrated. The residue was applied onto a silica gel column with ethyl acetate/petroleum ether (0-20%). This resulted in 370 mg (73.0%) of ethyl 2-methyl-8-(prop-1-en-2-yl)imidazo[1,2-b]pyridazine-7-carboxylate (4-2) as a brown solid.

3. Synthesis of ethyl 3-bromo-2-methyl-8-(prop-1-en-2-yl)imidazo[1,2-b]pyridazine-7-carboxylate (11-4)

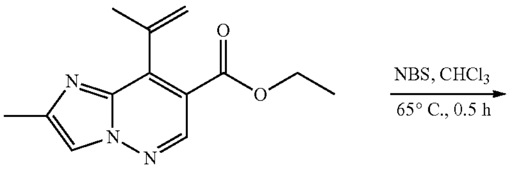

4-2

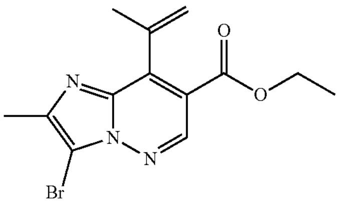

11-4

Into a 40-mL round-bottom flask, was placed ethyl 2-methyl-8-(prop-1-en-2-yl)imidazo[1,2-b]pyridazine-7-carboxylate (4-2, 370.0 mg, 1.5 mmol, 1.0 equiv), $CHCl_3$ (7.0 mL, 86.8 mmol), NBS (295.3 mg, 1.7 mmol, 1.1 equiv). The resulting solution was stirred for 30 min at 65° C. The resulting solution was diluted with 20 mL of water. The resulting solution was extracted with 2×20 mL of dichloromethane and the organic layers combined. The resulting mixture was washed with 2×20 ml of water. The mixture was dried over anhydrous magnesium sulfate and concentrated. This resulted in 491 mg (95.4%) of ethyl 3-bromo-2-methyl-8-(prop-1-en-2-yl)imidazo[1,2-b]pyridazine-7-carboxylate (11-4) as a brown solid.

4. Synthesis of ethyl 3-(3,5-difluorophenyl)-2-methyl-8-(prop-1-en-2-yl)imidazo[1,2-b]pyridazine-7-carboxylate (11-5)

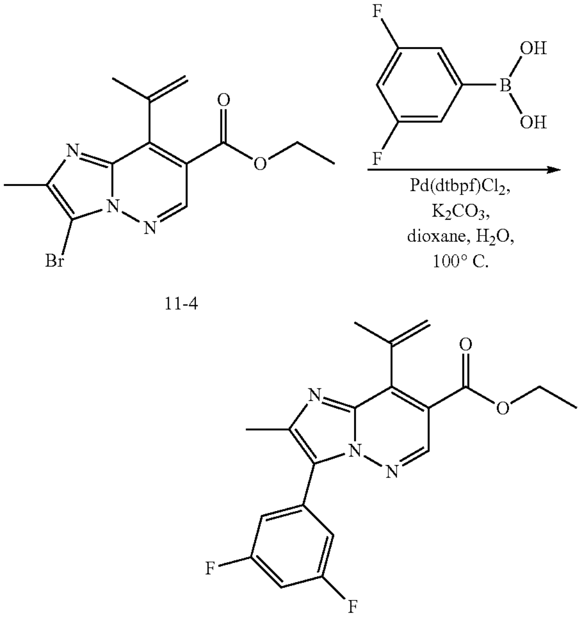

11-4

11-5

Into a 50-mL 3-necked round-bottom flask purged and maintained with an inert atmosphere of nitrogen, was placed ethyl 3-bromo-2-methyl-8-(prop-1-en-2-yl)imidazo[1,2-b]pyridazine-7-carboxylate (11-4, 490.0 mg, 1.5 mmol, 1.0 equiv), dioxane (10.0 mL), $H_2O$ (2.5 mL), 3,5-difluorophenylboronic acid (477.4 mg, 3.0 mmol, 2.0 equiv), $K_2CO_3$ (626.7 mg, 4.535 mmol, 3.0 equiv), Pd(dtbpf)$Cl_2$ (98.5 mg, 0.15 mmol, 0.1 equiv). The resulting solution was stirred for 30 min at 100° C. The resulting solution was diluted with 10 mL of water. The resulting solution was extracted with 2×50 mL of ethyl acetate and the organic layers combined and dried over anhydrous sodium sulfate and concentrated. The residue was applied onto a silica gel column with ethyl acetate/petroleum ether (0-15%). This resulted in 442 mg (80.2%) of ethyl 3-(3,5-difluorophenyl)-2-methyl-8-(prop-1-en-2-yl)imidazo[1,2-b]pyridazine-7-carboxylate (11-5) as a yellow green solid.

5. Synthesis of 3-(3,5-difluorophenyl)-2-methyl-8-(prop-1-en-2-yl)imidazo[1,2-b]pyridazine-7-carboxylic Acid (11-6)

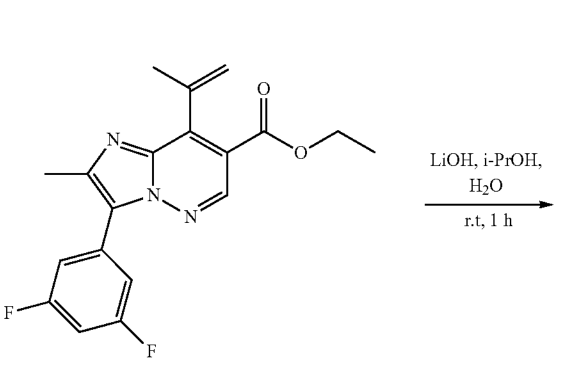

11-5

-continued

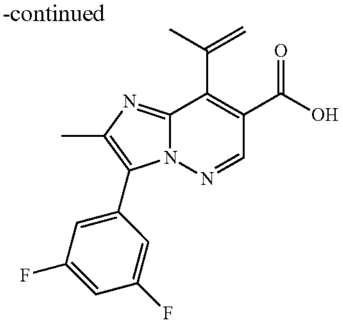

11-8

Into a 50-mL 3-necked round-bottom flask, was placed ethyl 3-(3,5-difluorophenyl)-2-methyl-8-(prop-1-en-2-yl)imidazo[1,2-b]pyridazine-7-carboxylate (11-5, 440.0 mg, 1.2 mmol, 1.0 equiv), i-PrOH (15.0 mL), $H_2O$ (8.0 mL), LiOH·$H_2O$ (155.0 mg, 3.7 mmol, 3.0 equiv). The resulting solution was stirred for 1 hr at room temperature. The resulting mixture was concentrated. The pH value of the solution was adjusted to 3 with HCl (2 mol/L). The resulting solution was extracted with 2×20 mL of ethyl acetate and the organic layers combined and dried over anhydrous sodium sulfate and concentrated. This resulted in 401 mg (89.0%) of 3-(3,5-difluorophenyl)-2-methyl-8-(prop-1-en-2-yl)imidazo[1,2-b]pyridazine-7-carboxylic acid (11-6) as a yellow solid.

6. Synthesis of 3-(3,5-difluorophenyl)-N-[(4S)-3,4-dihydro-2H-1-benzopyran-4-yl]-2-methyl-8-(prop-1-en-2-yl)imidazo[1,2-b]pyridazine-7-carboxamide (11-7)

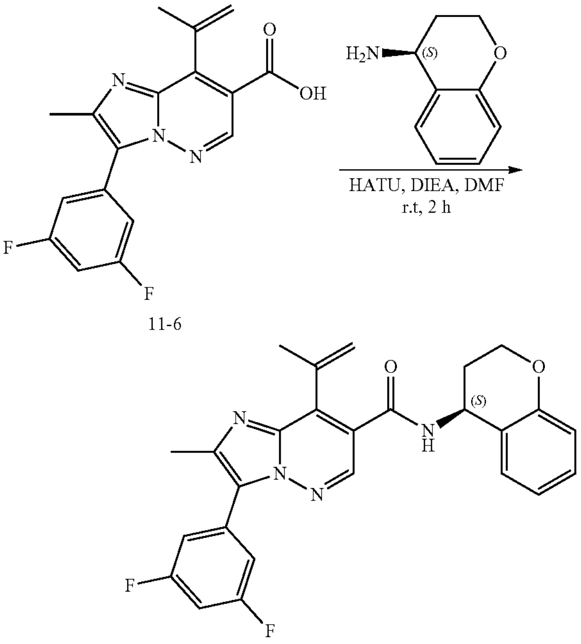

11-6

11-7

Into a 50-mL 3-necked round-bottom flask, was placed 3-(3,5-difluorophenyl)-2-methyl-8-(prop-1-en-2-yl)imidazo[1,2-b]pyridazine-7-carboxylic acid (11-6, 400.0 mg, 1.2 mmol, 1.0 equiv), DMF (12.0 mL), (4S)-3,4-dihydro-2H-1-benzopyran-4-amine (362.4 mg, 2.4 mmol, 2.0 equiv), DIEA (471.0 mg, 3.6 mmol, 3.0 equiv), HATU (692.8 mg, 1.8 mmol, 1.5 equiv). The resulting solution was stirred for 2 hrs at room temperature. The crude product was purified by Prep-Flash with the following conditions: Column, C18 silica gel; mobile phase, 0.1% $NH_4HCO_3$ in water and $CH_3CN$ (30% $CH_3CN$ increasing to 80% within 10 min). Detector, UV 254 nm, 220 nm. This resulted in 520 mg (92.0%) of 3-(3,5-difluorophenyl)-N-[(4S)-3,4-dihydro-2H-1-benzopyran-4-yl]-2-methyl-8-(prop-1-en-2-yl)imidazo[1,2-b]pyridazine-7-carboxamide (11-7) as a green solid.

7. Synthesis of 3-(3,5-difluorophenyl)-N-[(4S)-3,4-dihydro-2H-1-benzopyran-4-yl]-8-1 hydroxypropan-2-yl)-2-methylimidazo[1,2-b]pyridazine-7-carboxamide (11-8)

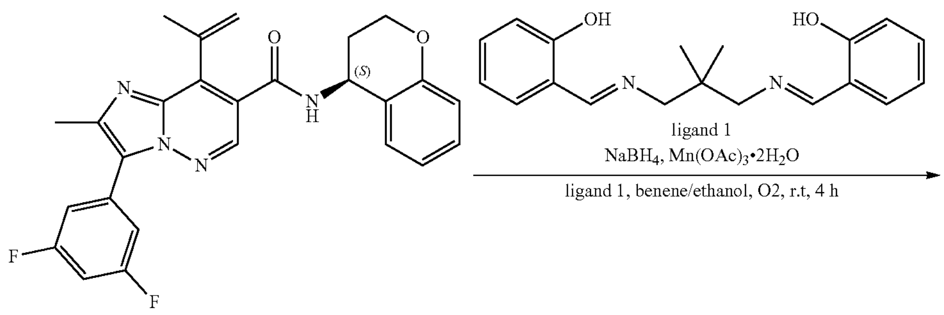

11-7

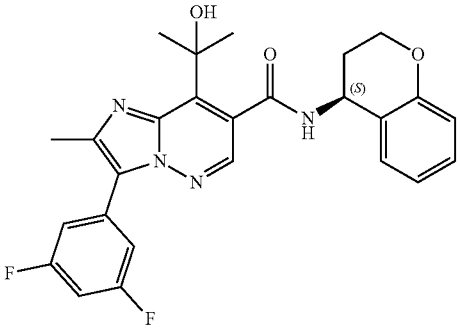

11-8

Into a 50-mL 3-necked round-bottom flask, was placed 3-(3,5-difluorophenyl)-N-[(4S)-3,4-dihydro-2H-1-benzopyran-4-yl]-2-methyl-8-(prop-1-en-2-yl)imidazo[1,2-b]pyridazine-7-carboxamide (11-7, 200.0 mg, 0.4 mmol, 1.0 equiv), ethanol (8.0 mL), toluene (8.0 mL), $NaBH_4$ (32.9 mg, 0.9 mmol, 2.0 equiv), $Mn(OAc)_{3.2}H_2O$ (9.3 mg, 0.03 mmol, 0.08 equiv), 2-[(1E)-([3-[(E)-[(2-hydroxyphenyl)methylidene]amino]-2,2-dimethylpropyl]imino)methyl]phenol (10.8 mg, 0.03 mmol, 0.08 equiv). To the above 02 (g) was introduced in. The resulting solution was stirred for 4 hrs at room temperature. The resulting solution was diluted with 10 mL of water. The resulting solution was extracted with 2×20 mL of ethyl acetate and the organic layers combined. The resulting mixture was washed with 2×20 ml of brine. The mixture was dried over anhydrous sodium sulfate and concentrated. This resulted in 250 mg (crude) of 3-(3,5-difluorophenyl)-N-[(4S)-3,4-dihydro-2H-1-benzopyran-4-yl]-8-(2-hydroxypropan-2-yl)-2-methylimidazo[1,2-b]pyridazine-7-carboxamide (11-8) as yellow oil.

8. Synthesis of 3-(3,5-difluorophenyl)-N-[(4S)-3,4-dihydro-2H-1-benzopyran-4-yl]-8-(2-fluoropropan-2-yl)-2-methylimidazo[1,2-b]pyridazine-7-carboxamide (Compound 277)

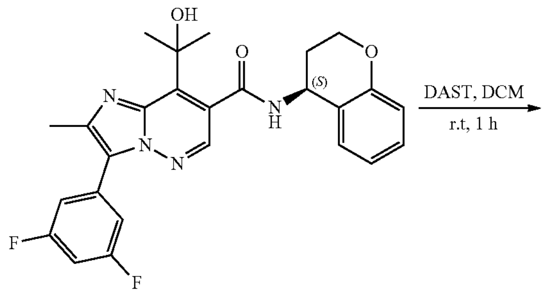

11-8

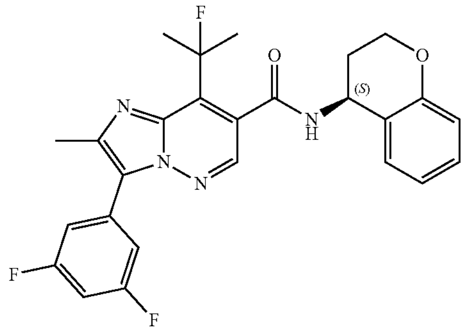

277

Into a 25-mL 3-necked round-bottom flask, was placed 3-(3,5-difluorophenyl)-N-[(4S)-3,4-dihydro-2H-1-benzopyran-4-yl]-8-(2-hydroxypropan-2-yl)-2-methylimidazo[1,2-b]pyridazine-7-carboxamide (11-8, 200.0 mg, 0.4 mmol, 1.0 equiv), DCM (10.0 mL). This was followed by the addition of DAST (134.7 mg, 0.8 mmol, 2.0 equiv) dropwise with stirring at room temperature. The resulting solution was stirred for 1 hr at room temperature. The resulting mixture was concentrated. The crude product was purified by Prep-Flash with the following conditions: Column, $C^{18}$ silica gel; mobile phase, 0.1% TFA in water and $CH_3CN$ (50% $CH_3CN$ increasing to 100% within 10 min). Detector, UV 254 nm, 220 nm. This resulted in 9.5 mg (4.6%) of 3-(3,5-difluorophenyl)-N-[(4S)-3,4-dihydro-2H-1-benzopyran-4-yl]-8-(2-fluoropropan-2-yl)-2-methylimidazo[1,2-b]pyridazine-7-carboxamide (277) as a white solid. (300 MHz, $CDCl_3$, ppm) δ 8.26 (s, 1H), 7.35-7.33 (m, 1H), 7.29-7.19 (m, 3H), 6.98-6.85 (m, 3H), 5.94 (d, J=7.5 Hz, 1H), 5.32-5.29 (m, 1H), 4.38-4.33 (m, 1H), 4.23-4.18 (m, 1H), 2.62 (s, 3H), 2.40-2.24 (m, 2H), 2.15 (d, J=6.3 Hz, 3H), 2.08 (d, J=6.3 Hz, 3H).

Preparation Example 7: Compounds 306, 297, 298, 298-0, 299, 299-0, 418, 420, 523, 524, 525, 526, 571, 572, 573, 574, A472 may be prepared by utilizing the process shown in Scheme 12 shown below.

Scheme 12

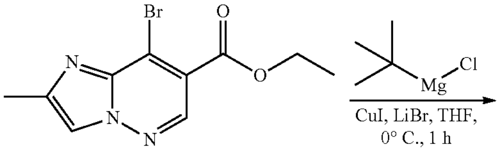

12-1

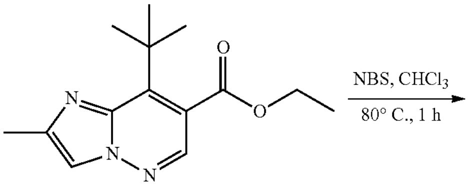

12-2

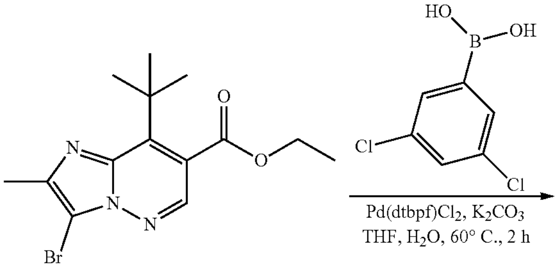

12-3

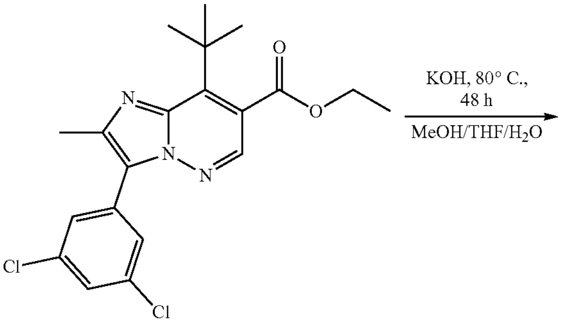

12-4

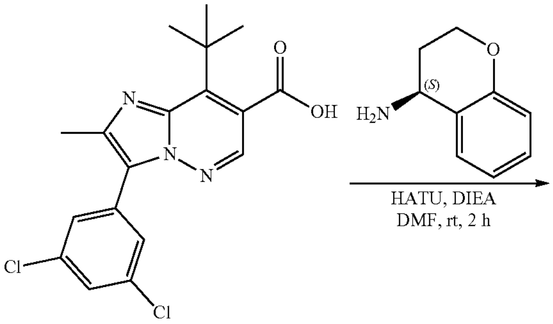

12-5

-continued

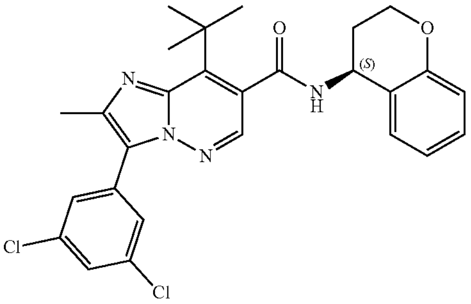

306

1. Synthesis of 8-tert-butyl-3-(3,5-dichlorophenyl)-2-methylimidazo[1,2-b]pyridazine-7-carboxylic Acid (12-2)

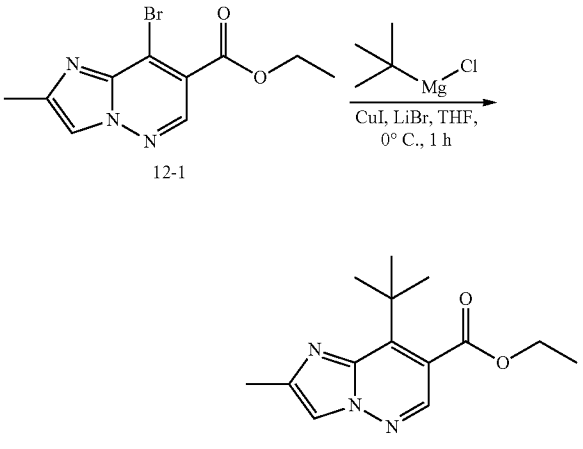

12-1

12-2

To a stirred mixture of ethyl 8-bromo-2-methylimidazo[1,2-b]pyridazine-7-carboxylate (12-1, 30.0 g, 105.6 mmol, 1.0 equiv) in THF (750.00 mL) was added LiBr (6.9 g, 791.9 mmol, 7.5 equiv) at 0° C. under nitrogen atmosphere. To the above mixture was added CuI (150.8 g, 791.9 mmol, 7.5 equiv) in portions over 30 min at 0° C. The resulting mixture was stirred for additional 30 min at 0° C. To the above mixture was added tert-butyl(chloro)magnesium (310.5 mL, 527.9 mmol, 5.0 equiv) dropwise over 1 h at 0° C. The resulting mixture was stirred for additional 5 min at 0 degrees C. The reaction was quenched by the addition of sat. $NH_4Cl$ (aq.) (400 mL) at 0 degrees C. The resulting mixture was extracted with EtOAc (2×800 mL). The combined organic layers were washed with brine (2×50 mL), dried over anhydrous $Na_2SO_4$. After filtration, the filtrate was concentrated under reduced pressure. The resulting mixture ethyl 8-tert-butyl-2-methylimidazo[1,2-b]pyridazine-7-carboxylate (12-2, 33 g, crude) was used in the next step directly without further purification.

2. Synthesis of ethyl 3-bromo-8-tert-butyl-2-methylimidazo[1,2-b]pyridazine-7-carboxylate (12-3)

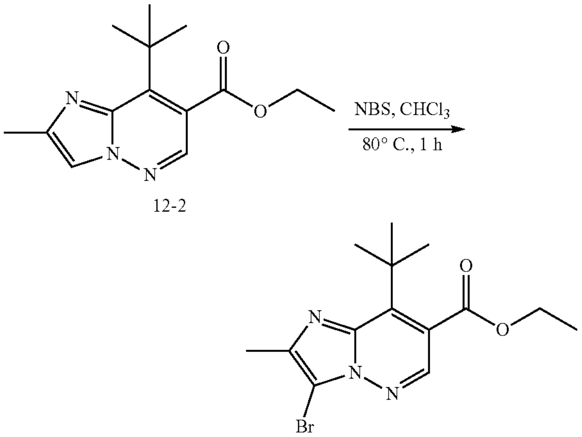

12-2

12-3

To a stirred solution of ethyl 8-tert-butyl-2-methylimidazo[1,2-b]pyridazine-7-carboxylate (12-2, 28.0 g, 107.1 mmol, 1.0 equiv) in $CHCl_3$ (300.0 mL) was added NBS (19.0 g, 107.1 mmol, 1.0 equiv) at room temperature. The resulting mixture was stirred for 1 h at 80 degrees C. under nitrogen atmosphere. The mixture was allowed to cool down to room temperature. The resulting mixture was concentrated under vacuum. The residue was purified by silica gel column chromatography, eluted with PE/EtOAc (3:1) to afford ethyl 3-bromo-8-tert-butyl-2-methylimidazo[1,2-b]pyridazine-7-carboxylate (12-3, 29.5 g, 80.9%) as a yellow solid.

Synthesis of ethyl 8-tert-butyl-3-(3,5-dichlorophenyl)-2-methylimidazo[1,2-b]pyridazine-7-carboxylate (12-4)

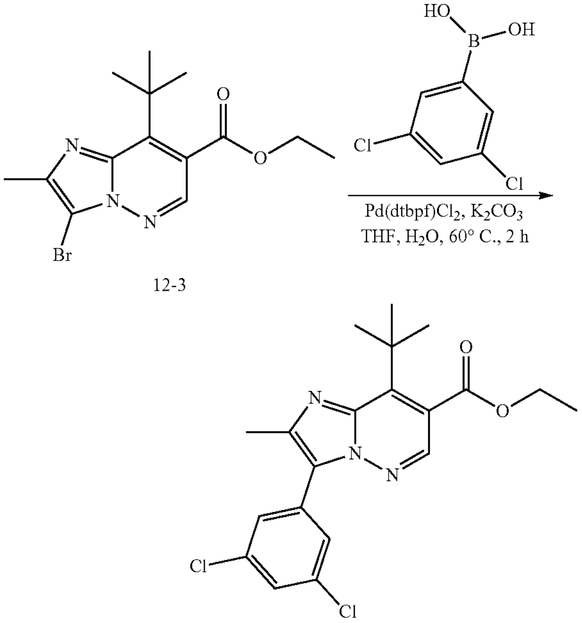

12-3

12-4

To a stirred mixture of ethyl 3-bromo-8-tert-butyl-2-methylimidazo[1,2-b]pyridazine-7-carboxylate (12-3, 26.0 g, 76.4 mmol, 1.0 equiv) and 3,5-dichlorophenylboronic acid (14.5 g, 76.4 mmol, 1.0 equiv) in THF (240.0 mL) and $H_2O$ (60.0 mL) were added $K_2CO_3$ (31.7 g, 229.2 mmol, 3.0 equiv) and Pd(dtbpf)$Cl_2$ (4980.7 mg, 7.6 mmol, 0.1 equiv) at room temperature under nitrogen atmosphere. The resulting mixture was stirred for 2 h at 60 degrees C. under nitrogen atmosphere. The mixture was allowed to cool down to room temperature. The resulting mixture was concentrated under vacuum. The resulting mixture was diluted with water (800 mL). The resulting mixture was extracted with EtOAc (2×800 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EtOAc (8:1) to afford ethyl 8-tert-butyl-3-(3,5-dichlorophenyl)-2-methylimidazo[1,2-b]pyridazine-7-carboxylate (12-4, 19 g, 61.2%) as an off-white solid.

3. Synthesis of 8-tert-butyl-3-(3,5-dichlorophenyl)-2-methylimidazo[1,2-b]pyridazine-7-carboxylic Acid (12-5)

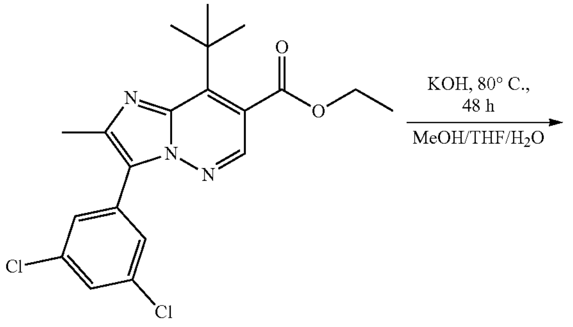

12-4

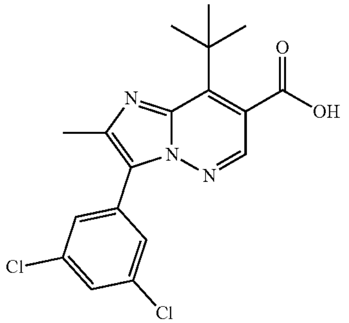

12-5

Into a 250-mL round-bottom flask, was placed ethyl 8-tert-butyl-3-(3,5-dichlorophenyl)-2-methylimidazo[1,2-b]pyridazine-7-carboxylate (12-4, 18.0 g, 44.3 mmol, 1.0 equiv), MeOH (100.0 mL, 344.3 mmol, 28.0 equiv), THF (100.0 mL), $H_2O$ (200.0 mL) and KOH (53.1 g, 1329.0 mmol, 30.0 equiv). The resulting solution was stirred for 48 hr at 80° C. The resulting mixture was concentrated under vacuum. The resulting solution was diluted with 50 mL of Water. The pH value of the solution was adjusted to 4 with HCl (2 mol/L). The solids were collected by filtration. The solid was dried in an oven under reduced pressure. This resulted in 8-tert-butyl-3-(3,5-dichlorophenyl)-2-methylimidazo[1,2-b]pyridazine-7-carboxylic acid (12-5, 18 g, crude) as an off-white solid.

4. Synthesis of 8-tert-butyl-3-(3,5-dichlorophenyl)-N-[(4S)-3,4-dihydro-2H-1-benzopyran-4-yl]-2-methylimidazo[1,2-b]pyridazine-7-carboxamide (Compound 306)

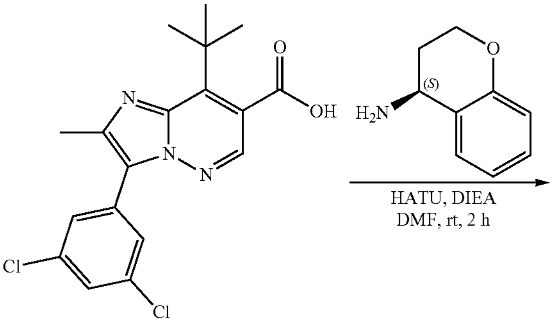

12-5

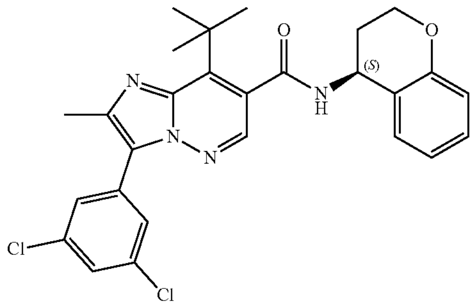

306

To a stirred mixture of 8-tert-butyl-3-(3,5-dichlorophenyl)-2-methylimidazo[1,2-b]pyridazine-7-carboxylic acid (12-5, 17.0 g, 44.9 mmol, 1.0 equiv) and (4S)-3,4-dihydro-2H-1-benzopyran-4-amine (8046.4 mg, 53.9 mmol, 1.2 equiv) in DMF (80.0 mL) were added DIEA (17.4 g, 134.8 mmol, 3.0 equiv) and HATU (20.5 g, 53.9 mmol, 1.2 equiv) at room temperature. The resulting mixture was stirred for 2 h at room temperature. The reaction mixture was added dropwise into 300 mL of $H_2O$. The precipitated solids were collected by filtration and washed with water (2×20 mL). The residue was dissolved in MeCN (200 mL). Then 800 mL of $H_2O$ was added dropwise. The precipitated solids were collected by filtration. The resulting solid was dried under infrared light to afford 8-tert-butyl-3-(3,5-dichlorophenyl)-N-[(4S)-3,4-dihydro-2H-1-benzopyran-4-yl]-2-methylimidazo[1,2-b]pyridazine-7-carboxamide (306, 17.2 g, 75.1%) as a light green solid. (300 MHz, CDCl3, ppm) δ: 8.08 (s, 1H), 7.57 (d, J=1.8 Hz, 2H), 7.41 (s, 1H), 7.32-7.18 (m, 2H), 6.99-6.95 (m, 1H), 6.88 (dd, J=8.1, 1.2 Hz, 1H), 6.21 (d, J=6.6 Hz, 1H), 5.32-5.29 (m, 1H), 4.41-4.34 (m, 1H), 4.24-4.16 (m, 1H), 2.61 (s, 3H), 2.41-2.34 (m, 1H), 2.27-2.21 (m, 1H), 1.78 (s, 9H)

| Compound | ¹H NMR Spectra |
|---|---|
| 297 | (300 MHz, CDCl3, ppm): δ 8.04 (s, 1H), 7.55 (d, J = 1.8 Hz, 2H), 7.38 (s, 1H), 6.98-6.88 (m, 2H), 6.12 (d, J = 6.9 Hz, 1H), 5.29 (t, J = 5.4 Hz, 1H), 4.34-4.29 (m, 1H), 4.18-4.11 (m, 1H), 2.59 (s, 1H), 2.38-2.31 (m, 1H), 2.19-2.14 (m, 1H), 1.75 (s, 9H) |
| 298 | (300 MHz, CDCl3, ppm) δ 8.16 (s, 1H), 7.50-7.46 (m, 3H), 7.26-7.19 (m, 2H), 6.97-6.91 (m, 1H), 6.87 (d, J = 8.4 Hz, 1H), 6.06 (d, J = 7.2 Hz, 1H), 5.33-5.31 (m, 1H), 4.38-4.33 (m, 1H), 4.21-4.13 (m, 1H), 2.39-2.34 (m, 1H), 2.26-2.21 (m, 1H), 1.76 (s, 9H) |
| 298-0 | (300 MHz, CDCl3, ppm) δ 8.16 (s, 1H), 7.60 (d, J = 1.8 Hz, 1H), 7.52-7.47 (m, 3H), 6.99-6.93 (m, 2H), 6.90-6.79 (m, 1H), 6.05 (d, J = 7.5 Hz, 1H), 5.34 (q, J = 5.7 Hz, 1H), 4.37-4.34 (m, 1H), 4.19-4.16 (m, 1H), 2.48-2.32 (m, 1H), 2.28-2.12 (m, 1H), 1.79 (s, 9H) |
| 299 | (300 MHz, CDCl3, ppm) δ 8.18 (s, 1H), 7.53-7.49 (m, 3H), 6.99-6.93 (m, 2H), 6.87-6.82 (m, 1H), 6.09 (d, J = 7.5 Hz, 1H), 5.37-5.31 (m, 1H), 4.39-4.32 (m, 1H), 4.22-4.14 (m, 1H), 2.42-2.36 (m, 1H), 2.24-2.18 (m, 1H), 1.79 (s, 9H) |
| 299-0 | (300 MHz, CDCl3, ppm) 8.16 (s, 1H), 7.60 (s, 1H), 7.57-7.44 (m, 3H), 6.96 (t, J = 8.1 Hz, 2H), 6.92-6.79 (m, 1H), 6.07 (d, J = 7.8 Hz, 1H), 5.35 (q, J = 5.7 Hz, 1H), 4.37-4.34 (m, 1H), 4.24-4.11 (m, 1H), 2.44-2.40 (m, 1H), 2.30-2.13 (m, 1H), 1.79 (s, 9H) |
| 418 | (300 MHz, DMSO-d6, ppm) δ 8.33 (s, 1H), 8.11 (s, 1H), 7.95 (s, 1H), 7.35 (s, 1H) 7.25-7.15 (m, 3H), 6.99-6.85 (m, 1H), 6.84-6.80 (m, 1H), 6.25-6.20 (m, 1H), 5.35-5.30 (m, 1H), 4.36-4.15 (m, 2H), 2.50-2.22 (m, 2H), 1.73 (s, 9H) |
| 420 | (300 MHz DMSO-d6, ppm): δ 8.15 (s, 1H), 7.75 (s, 2H) 7.44 (s, 1H), 7.00-6.79 (m, 2H), 6.15-6.30 (m, 1H), 5.25-5.32 (m, 1H), 4.30-4.47 (m, 1H), 4.10-4.15 (m, 1H), 2.40-2.38 (m, 1H), 2.25-2.10 (m, 1H), 1.80 (bs, 9H) |
| 523 | (300 MHz DMSO-d6, ppm): δ 8.08 (s, 1H), 7.15-7.44 (m, 3H), 7.00-6.79 (m, 2H), 6.10-6.21 (m, 1H), 5.36-5.43 (m, 1H), 4.30-4.49 (m, 1H), 4.10-4.18 (m, 1H), 2.40-2.38 (m, 4H), 2.28-2.26 (m, 1H), 1.80 (bs, 9H) |
| 524 | (300 MHz DMSO-d6, ppm): δ 9.20 (d, J = 7.9 Hz, 1H), 8.30 (s, 1H), 7.48-7.42 (m, 2H), 7.36-7.34 (m, 1H), 7.20-7.15 (m, 1H), 6.92 (t, J = 7.5, 1H), 6.80 (d, J = 8.2 Hz, 1H), 5.19-5.16 (m, 1H), 4.28-4.19 (m, 2H), 2.35 (s, 3H), 2.20-2.18 (m, 1H), 2.10-2.00 (m, 1H), 1.68 (s, 9H) |
| 525 | 300 MHz DMSO-d6, ppm): δ 9.20 (d, J = 8.0 Hz, 1H), 8.33 (s, 1H), 7.74-7.68 (m, 1H), 7.47-7.42 (m, 1H), 7.37-7.34 (m, 1H), 7.21-7.15 (m, 1H), 6.94-6.90 (m, 1H), 6.80 (d, J = 8.2 Hz, 1H), 5.20-5.17 (m, 1H), 4.28-4.19 (m, 3H), 2.43 (s, 3H), 2.19-2.16 (m, 1H), 2.05-1.99 (m, 1H), 1.68 (s, 9H) |
| 526 | (300 MHz DMSO-d6, ppm): δ 8.31 (s, 1H), 7.47-7.44 (m, 2H), 7.26-6.79 (m, 5H), 5.41 (bss, 1H), 4.36 (bs, 2H), 2.55 (bs, 3H), 2.40-2.38 (m, 1H), 2.28-2.26 (m, 1H), 1.80 (bs, 9H) |
| 571 | (300 MHz, CDCl3, ppm) δ 8.11 (s, 1H), 7.28-7.21 (m, 2H), 6.97-6.85 (m, 4H), 6.12-6.10 (m, 1H), 5.35-5.32 (m, 1H), 4.39-4.33 (m, 1H), 4.22-4.14 (m, 1H), 2.42-2.35 (m, 1H), 2.27-2.21 (m, 1H), 1.78 (s, 9H) |
| 572 | (400 MHz, CD3OD, ppm) δ 8.21 (s, 1H), 7.48 (d, J = 6.3 Hz, 2H), 7.31 (d, J = 5.7 Hz, 1H), 7.16 (t, J = 5.7 Hz, 1H), 6.94 (t, J = 5.7 Hz, 1H), 6.82 (d, J = 5.7 Hz, 1H), 5.28 (bt, J = 3.6 Hz, 1H), 4.33-4.28 (m, 1H), 4.23-4.17 (m, 1H), 2.30-2.23 (m, 1H), 2.19-2.14 (m, 1H), 1.75 (s, 9H) |
| 573 | (300 MHz, CDCl3, ppm) δ 8.11 (s, 1H), 7.24-7.17 (m, 2H), 7.13-7.03 (m, 2H), 6.94 (t, J = 7.5 Hz, 1H), 6.86 (d, J = 8.2 Hz, 1H), 6.09-6.08 (m, 1H), 5.32-5.30 (m, 1H), 4.36-4.33 (m, 1H), 4.19-4.14 (m, J = 10.5 Hz, 1H), 2.39-2.36 (m, 1H), 2.23-2.20 (m, 1H), 1.75 (s, 9H) |
| 574 | (300 MHz, CDCl3, ppm) δ 8.12 (d, J = 3.3 Hz, 1H), 7.44-7.40 (m, 1H), 7.25-7.10 (m, 2H), 6.99-6.93 (m, 1H), 6.90-6.87 (m, 1H), 6.10 (m, 1H), 5.35-5.34 (m, 1H), 4.39-4.36 (m, 1H), 4.22-4.15 (m, 1H), 2.43-2.36 (m, 1H), 1.79 (s, 9H) |
| A472 | (400 MHz, DMSO-d6, ppm) δ 9.02 (d, J = 8.49 Hz, 1H), 8.53 (s, 1H), 7.78 (d, J = 1.90 Hz, 2H), 7.68 (t, J = 1.84 Hz, 1H), 7.36 (d, J = 7.73 Hz, 1H), 7.17 (t, J = 7.71 Hz, 1H), 6.92 (t, J = 7.26 Hz, 1H), 6.76 (d, J = 8.11 Hz, 1H), 5.32 (m, 1H), 3.52-3.62 (m, 1H), 2.52-2.58 (m, 3H), 2.21 (m, 1H), 1.80-1.89 (m, 1H), 1.23-1.61 (m, 12H) |

Preparation Example 8: The following compounds can be synthesized by adopting the process shown in scheme 13 below: 320, 320-0, 513, 513-0, 514, 514-0.

Scheme 13

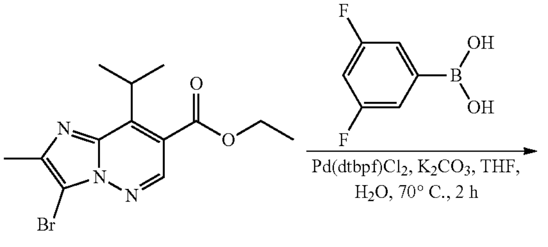

4-4

-continued

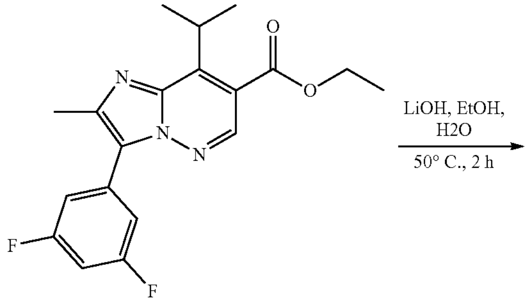

4-5

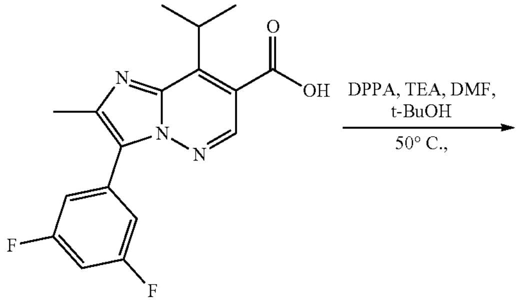

4-6

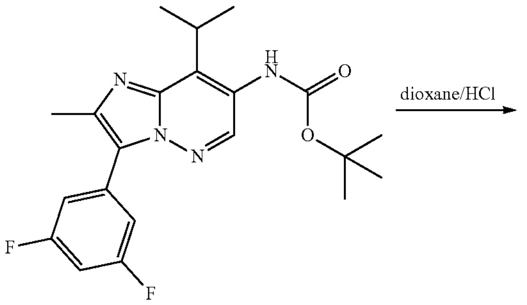

13-1

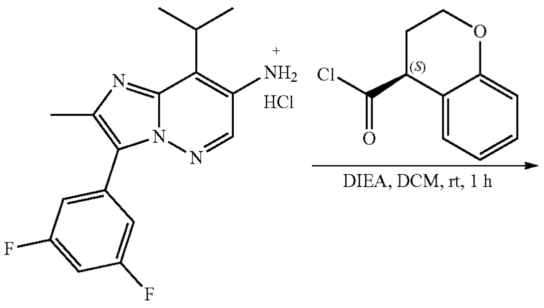

13-2

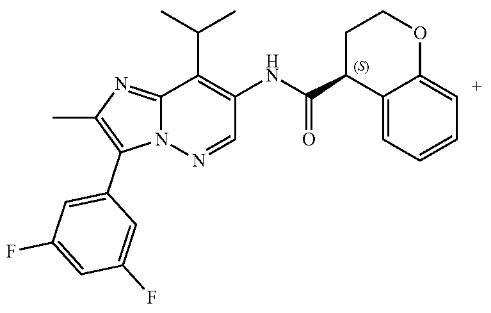

320

-continued

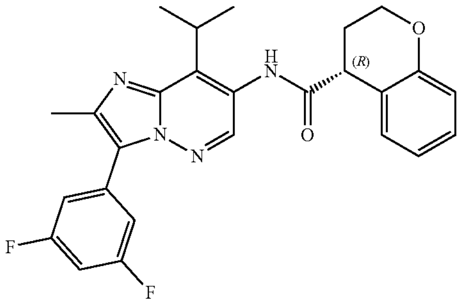

320-0

1. Synthesis of ethyl 3-(3,5-difluorophenyl)-8-isopropyl-2-methylimidazo[1,2-b]pyridazine-7-carboxylate (4-5)

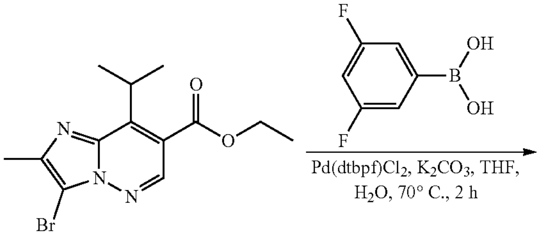

4-4

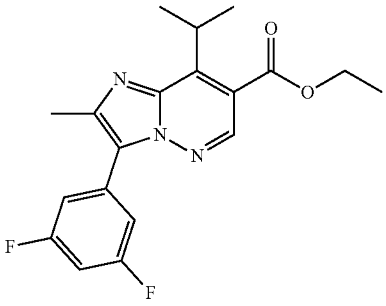

4-5

Into a 40-mL round-bottom flask, was placed THE (5.0 mL), $H_2O$ (1.0 mL, 0.06 mmol, 0.18 equiv), ethyl 3-bromo-8-isopropyl-2-methylimidazo[1,2-b]pyridazine-7-carboxylate (4-4, 100.0 mg, 0.3 mmol, 1.0 equiv), 3,5-difluorophenylboronic acid (145.0 mg, 0.9 mmol, 3.0 equiv), Pd(dtbpf)$Cl_2$ (20.0 mg, 0.03 mmol, 0.1 equiv), $K_2CO_3$ (85.0 mg, 0.6 mmol, 2.0 equiv). The resulting solution was stirred for 2 hr at 70° C. The resulting mixture was concentrated under vacuum. The residue was applied onto a silica gel column with ethyl acetate/petroleum ether (1:6). This resulted in 90 mg (81.7%) of ethyl 3-(3,5-difluorophenyl)-8-isopropyl-2-methylimidazo[1,2-b]pyridazine-7-carboxylate (4-5) as a white solid.

2. Synthesis of 3-(3,5-difluorophenyl)-8-isopropyl-2-methylimidazo[1,2-b]pyridazine-7-carboxylic Acid (4-6)

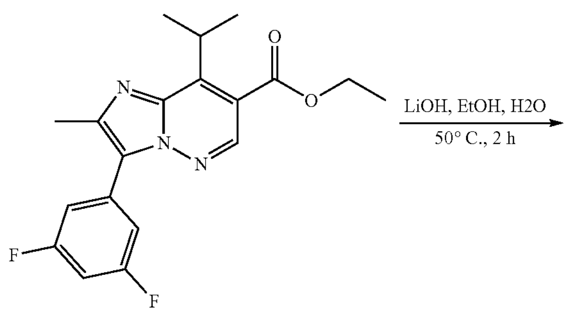

4-5

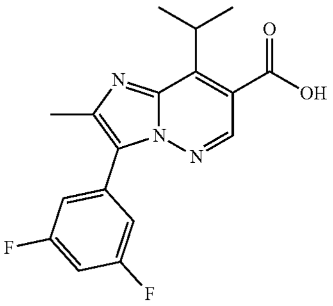

4-6

Into a 40-mL round-bottom flask, was placed $H_2O$ (1.0 mL), EtOH (5.0 mL), ethyl 3-(3,5-difluorophenyl)-8-isopropyl-2-methylimidazo[1,2-b]pyridazine-7-carboxylate (4-5, 90.0 mg, 0.25 mmol, 1.0 equiv), LiOH (60.0 mg, 2.5 mmol, 10.0 equiv). The resulting solution was stirred for 2 hr at 50° C. HCl (6 mol/L) was employed to adjust the pH to 4. The resulting solution was extracted with 3×20 mL of ethyl acetate and the organic layers combined and dried over anhydrous sodium sulfate and concentrated under vacuum. This resulted in 70 mg (84.4%) of 3-(3,5-difluorophenyl)-8-isopropyl-2-methylimidazo[1,2-b]pyridazine-7-carboxylic acid (4-6) as a white solid.

3. Synthesis of tert-butyl N-[3-(3,5-difluorophenyl)-8-isopropyl-2-methylimidazo[1,2-b]pyridazin-7-yl] carbamate (13-1)

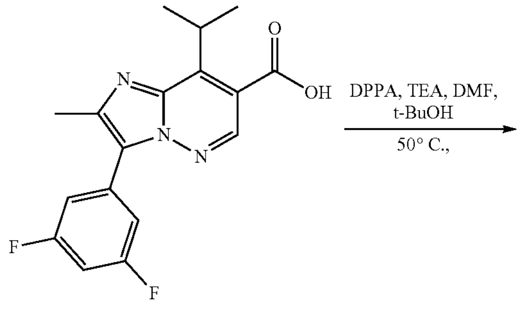

4-6

-continued

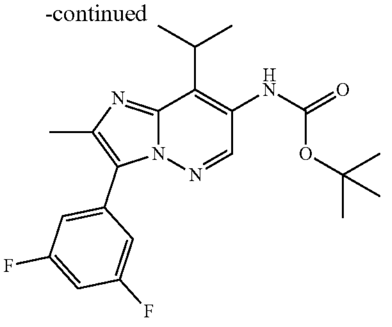

13-1

Into a 40-mL round-bottom flask, was placed DMF (1.0 mL, 0.01 mmol, 0.06 equiv), t-BuOH (1.0 mL, 0.01 mmol, 0.06 equiv), 3-(3,5-difluorophenyl)-8-isopropyl-2-methylimidazo[1,2-b]pyridazine-7-carboxylic acid (4-6, 70.0 mg, 0.2 mmol, 1.0 equiv), DPPA (70.0 mg, 0.25 mmol, 1.2 equiv), TEA (24.0 mg, 0.2 mmol, 1.1 equiv). The resulting solution was stirred for 3 hr at 50 degrees C. The mixture was purified by Flash-Prep-HPLC with the following conditions (IntelFlash-1): Column, C18 silica gel; mobile phase, $H_2O$:ACN=90:10 increasing to $H_2O$:ACN=20:80 within 15 min; Detector, 254 nm. This resulted in 65 mg (76.4%) of tert-butyl N-[3-(3,5-difluorophenyl)-8-isopropyl-2-methylimidazo[1,2-b]pyridazin-7-yl]carbamate (13-1) as a white solid.

4. Synthesis of 3-(3,5-difluorophenyl)-8-isopropyl-2-methylimidazo[1,2-b]pyridazin-7-amine (13-2)

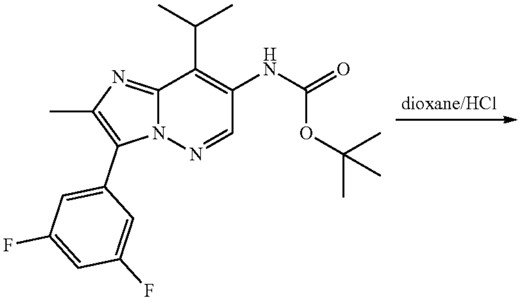

13-1

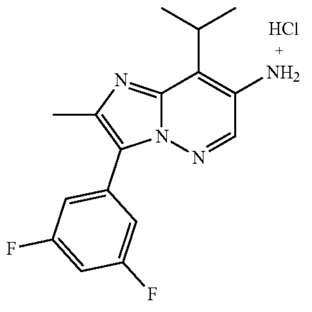

13-2

Into a 50-mL round-bottom flask, was placed HCl (gas) in 1,4-dioxane (4M, 5.00 mL), tert-butyl N-[3-(3,5-difluorophenyl)-8-isopropyl-2-methylimidazo[1,2-b]pyridazin-7-yl] carbamate (13-1, 65.0 mg, 0.2 mmol, 1.0 equiv). The resulting solution was stirred for 2 hr at 40 degrees C. The resulting mixture was concentrated under vacuum. This resulted in 40 mg (81.9%) of 3-(3,5-difluorophenyl)-8-isopropyl-2-methylimidazo[1,2-b]pyridazin-7-amine (13-2) as a white solid.

5. Synthesis of (4S)—N-[3-(3,5-difluorophenyl)-8-isopropyl-2-methylimidazo[1,2-b]pyridazin-7-yl]-3,4-dihydro-2H-1-benzopyran-4-carboxamide and (4R)—N-[3-(3,5-difluorophenyl)-8-isopropyl-2-methylimidazo[1,2-b]pyridazin-7-yl]-3,4-dihydro-2H-1-benzopyran-4-carboxamide (320 and 320-0)

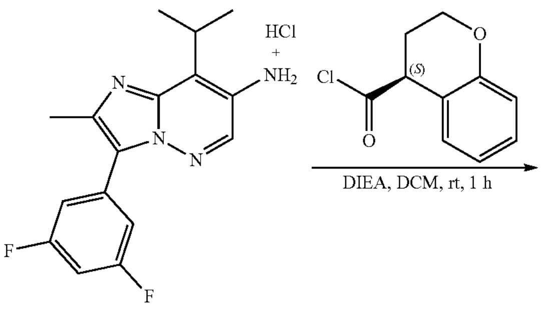

13-2

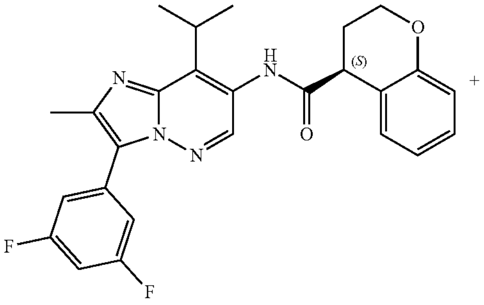

320

-continued

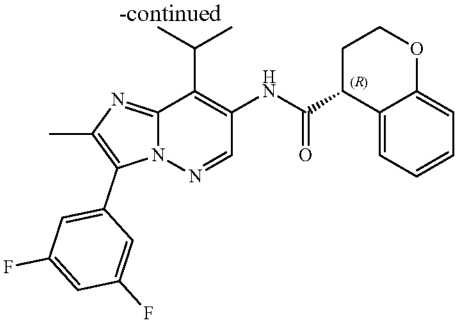

320-0

Into a 50-mL round-bottom flask, was placed DCM (2.0 mL), 3-(3,5-difluorophenyl)-8-isopropyl-2-methylimidazo[1,2-b]pyridazin-7-amine (13-2, 25.0 mg, 0.08 mmol, 1.0 equiv), (4S)-3,4-dihydro-2H-1-benzopyran-4-carbonyl chloride (50.0 mg, 0.2 mmol, 3.0 equiv), DIEA (0.5 mg, 0.004 mmol, 0.05 equiv). The resulting solution was stirred for 1 hr at room temperature. The resulting mixture was concentrated under vacuum. The crude product was purified by Flash-Prep-HPLC with the following conditions (Intel-Flash-1): Column, C18 silica gel; mobile phase, $H_2O$:ACN=50:50 increasing to $H_2O$:ACN=10:90 within 20; Detector, 254 nm. This resulted in 9.3 mg (24.3%) of (4S)—N-[3-(3,5-difluorophenyl)-8-isopropyl-2-methylimidazo[1,2-b]pyridazin-7-yl]-3,4-dihydro-2H-1-benzopyran-4-carboxamide (320) as a white solid and 11 mg (26.0%) of (4R)—N-[3-(3,5-difluorophenyl)-8-isopropyl-2-methylimidazo[1,2-b]pyridazin-7-yl]-3,4-dihydro-2H-1-benzopyran-4-carboxamide (320-0). $^1$H NMR for 320: (300 MHz Chloroform-d, ppm): δ 8.93 (s, 1H), 7.50-7.43 (m, 1H), 7.37-7.30 (m, 1H), 7.27-7.25 (m, 2H), 7.08-7.00 (m, 2H), 6.89-6.81 (m, 1H), 4.44-4.40 (m, 1H), 4.16-4.07 (m, 1H), 3.92 (brs, 1H), 3.70-3.66 (m, 1H), 2.70-2.63 (m, 1H), 2.61 (s, 3H), 2.34-2.28 (m, 1H), 1.20-1.14 (m, 6H); $^1$H NMR for 320-0: (300 MHz Chloroform-d, ppm): δ 8.94 (s, 1H), 7.50-7.44 (m, 1H), 7.36-7.31 (m, 1H), 7.27-7.20 (m, 2H), 7.15-7.00 (m, 2H), 6.94-6.82 (m, 1H), 4.44-4.40 (m, 1H), 4.14-4.07 (m, 1H), 3.92 (brs, 1H), 3.70-3.60 (m, 1H), 2.70-2.50 (m, 4H), 2.37-2.24 (m, 1H), 1.19-1.14 (m, 6H).

| Compound | $^1$H NMR Spectra |
|---|---|
| 514 | (300 MHz, CDCl3, ppm) δ 8.68 (s, 1H), 8.67 (bs, 1H), 8.44 (bs, 1H), 7.66 (bs, 1H), 7.63 (s, 1H), 7.60 (d, J = 1.8 Hz, 1H), 7.50 (s, 1H), 6.94 (bs, 1H), 4.54-4.50 (m, 1H), 4.35-4.27 (m, 1H), 4.05 (bs, 1H), 3.71-3.62 (m, 1H), 2.74-2.69 (m, 1H), 2.59 (s, 3H), 2.30-2.20 (m, 1H), 1.32-1.29 (m, 6H) |

Preparation Example 9: Compounds 323 and 323-0 can be synthesized according to the process depicted in Scheme 14 below.

Scheme 14

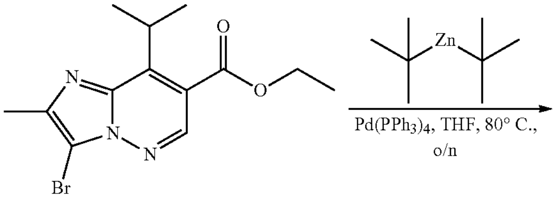

4-4

-continued

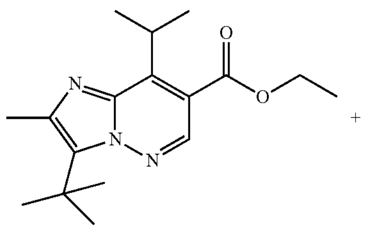

14-2a

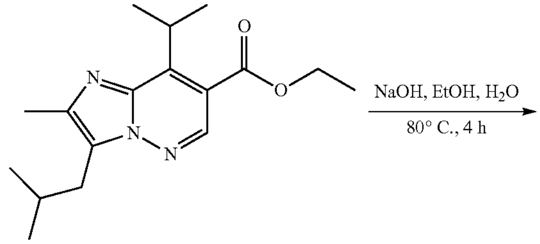

14-2b

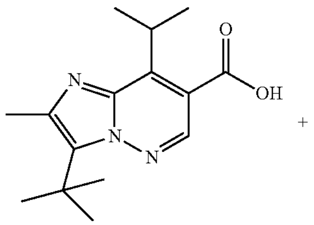

14-3a

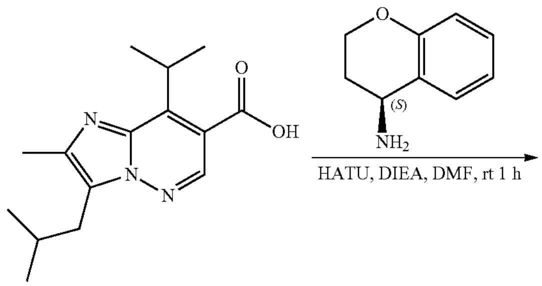

14-3b

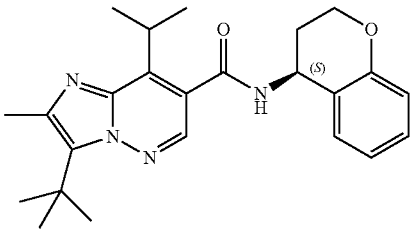

323

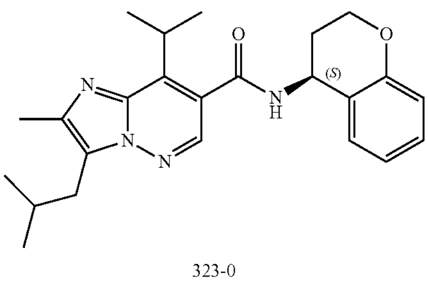

323-0

1. Synthesis of ethyl 3-tert-butyl-8-isopropyl-2-methylimidazo[1,2-b]pyridazine-7-carboxylate (14-2a) and ethyl 3-isobutyl-8-isopropyl-2-methylimidazo[1,2-b]pyridazine-7-carboxylate (14-2b)

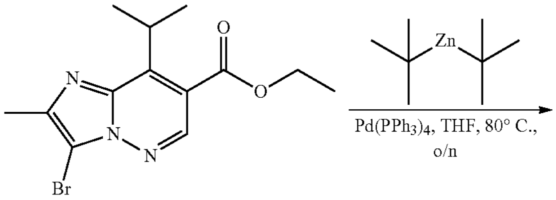

4-4

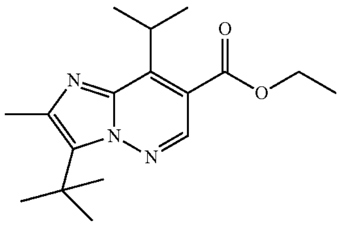

14-2a

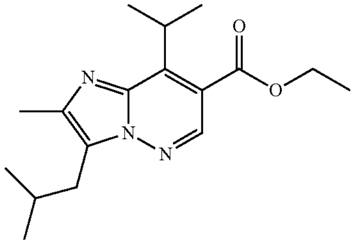

14-2b

Into a 8-mL round-bottom flask, was placed THE (3.0 mL), ethyl 3-bromo-8-isopropyl-2-methylimidazo[1,2-b] pyridazine-7-carboxylate (4-4, 100.0 mg, 0.3 mmol, 1.00 equiv), di-tert-butylzinc (4.0 mL, 2.0 mmol, 6.5 equiv), $Pd(PPh_3)_4$ (40.0 mg, 0.03 mmol, 0.1 equiv). The resulting solution was stirred for 1 overnight at 80° C. The resulting mixture was concentrated under vacuum. The residue was applied onto a silica gel column with ethyl acetate/petroleum ether (1:4). This resulted in 20 mg (mixture) of ethyl 3-tert-butyl-8-isopropyl-2-methylimidazo[1,2-b]pyridazine-7-carboxylate (14-2a) and ethyl 3-isobutyl-8-isopropyl-2-methylimidazo[1,2-b]pyridazine-7-carboxylate (14-2b) as a white solid.

2. Synthesis of 3-tert-butyl-8-isopropyl-2-methylimidazo[1,2-b]pyridazine-7-carboxylic acid (14-3a) and 3-isobutyl-8-isopropyl-2-methylimidazo[1,2-b]pyridazine-7-carboxylic Acid (14-3b)

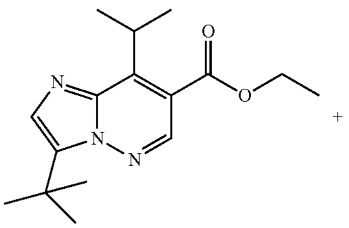

14-2a

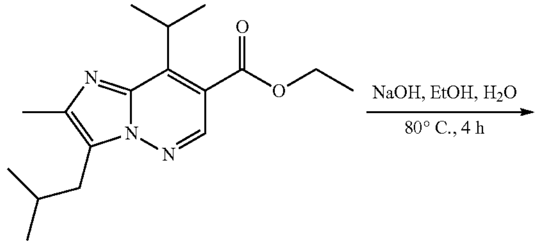

14-2b

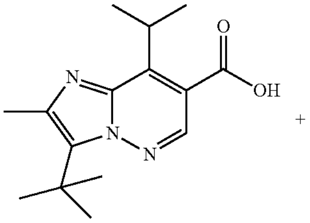

14-3a

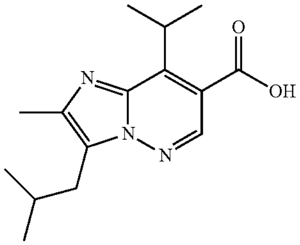

14-3b

Into a 50-mL round-bottom flask, was placed $H_2O$ (1.0 mL), EtOH (5.0 mL), mixture of ethyl 3-tert-butyl-8-isopropyl-2-methylimidazo[1,2-b]pyridazine-7-carboxylate and 3-isobutyl-8-isopropyl-2-methylimidazo[1,2-b]pyridazine-7-carboxylate (mix of 14-2a and 14-2b, 20.0 mg, 0.06 mmol, 1.00 equiv), NaOH (40.0 mg, 1.00 mmol, 15.2 equiv). The resulting solution was stirred for 2 hr at 80° C. HCl (6 mol/L) was employed to adjust the pH to 4. The resulting solution was extracted with 3×20 mL of ethyl acetate and the organic layers combined and dried over anhydrous sodium sulfate and concentrated under vacuum. This resulted in 12 mg (mixture) of 3-tert-butyl-8-isopropyl-2-methylimidazo[1,2-b]pyridazine-7-carboxylic acid (14-3a) and 3-isobutyl-8-isopropyl-2-methylimidazo[1,2-b]pyridazine-7-carboxylic acid (14-3b) as a white solid.

3. Synthesis of 3-tert-butyl-N-[(4S)-3,4-dihydro-2H-1-benzopyran-4-yl]-8-isopropyl-2-methylimidazo[1,2-b]pyridazine-7-carboxamide (323) and N-[(4S)-3,4-dihydro-2H-1-benzopyran-4-yl]-2-methyl-3-(2-methylpropyl)-8-(propan-2-yl)imidazo[1,2-b]pyridazine-7-carboxamide (323-0)

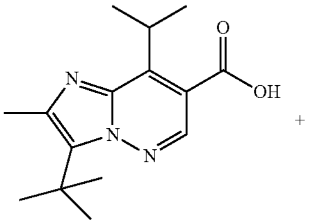

14-3a

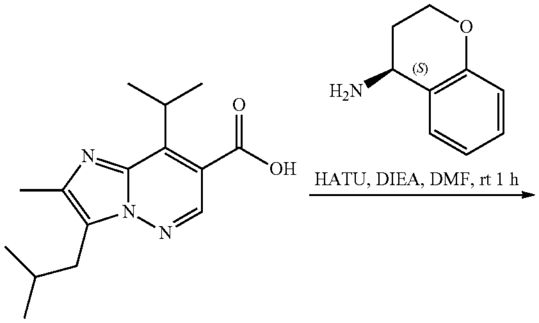

14-3b

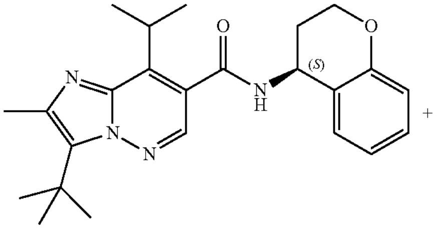

323

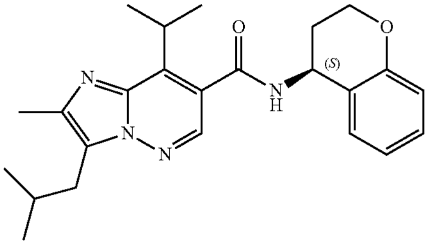

323-0

Into a 50-mL round-bottom flask, was placed DMF (1.0 mL, 12.9 mmol, 237.2 equiv), a mixture of 3-tert-butyl-8-isopropyl-2-methylimidazo[1,2-b]pyridazine-7-carboxylic acid and 3-isobutyl-8-isopropyl-2-methylimidazo[1,2-b]pyridazine-7-carboxylic acid (mix of 14-3a and 14-3b, 15.0 mg, 0.05 mmol, 1.0 equiv), (4S)-3,4-dihydro-2H-1-benzopyran-4-amine (10.0 mg, 0.06 mmol, 1.2 equiv), HATU (35.0 mg, 0.09 mmol, 1.7 equiv), DIEA (17.0 mg, 0.1 mmol, 2.4 equiv). The resulting solution was stirred for 1 hr at room temperature. The crude product was purified by Flash-Prep-HPLC with the following conditions (IntelFlash-1): Column, C18 silica gel; mobile phase, $H_2O$:ACN=50:50 increasing to $H_2O$:ACN=10:90 within 20 min; Detector, 254 nm. product was obtained. This resulted in 2.2 mg (9.9%) of 3-tert-butyl-N-[(4S)-3,4-dihydro-2H-1-benzopyran-4-yl]-8-isopropyl-2-methylimidazo[1,2-b]pyridazine-7-carboxamide (323) as a white solid and 5 mg (21%) of N-[(4S)-3,4-dihydro-2H-1-benzopyran-4-yl]-2-methyl-3-(2-methylpropyl)-8-(propan-2-yl)imidazo[1,2-b]pyridazine-7-carboxamide (323-0). $^1H$ NMR for 323: (300 MHz Chloroform-d, ppm): δ 8.22 (s, 1H), 7.40-7.30 (m, 1H), 7.25-7.20 (m, 1H), 6.99-6.96 (m, 1H), 6.91-6.88 (m, 1H), 6.11-5.90 (m, 1H), 5.45-5.30 (m, 1H), 4.41-4.37 (m, 1H), 4.30-4.14 (m, 1H), 3.90-0.70 (m, 1H), 2.68 (s, 3H), 2.50-2.30 (s, 1H), 2.30-2.15 (m, 1H), 1.75-1.70 (m, 6H), 1.55 (s, 9H); 1H NMR for 323-0: (300 MHz Chloroform-d, ppm): δ 8.24 (s, 1H), 7.40-7.31 (m, 1H), 7.27-7.21 (m, 1H), 6.99-6.90 (m, 1H), 6.88-6.85 (m, 1H), 6.10 (brs, 1H), 5.41-5.37 (m, 1H), 4.40-4.34 (m, 1H), 4.25-4.17 (m, 1H), 3.80 (brs, 1H), 2.85 (d, J=7.2 Hz, 2H), 2.53 (s, 3H), 2.44-2.38 (m, 1H), 2.28-2.10 (m, 2H), 1.60 (t, J=6.6 Hz, 6H), 0.95 (d, J=6.6 Hz, 6H).

Preparation Example 10: Compound 324 can be synthesized by the process shown in Scheme 15 shown below. Similarly, compounds 325, 369, 372-0, 373 can be prepared by an analogous methods by persons skilled in the art.

Scheme 15

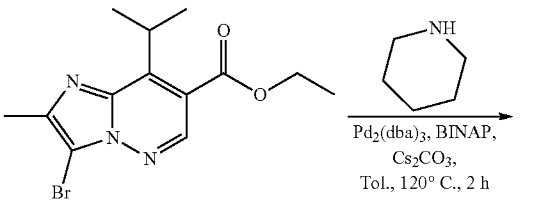

4-4

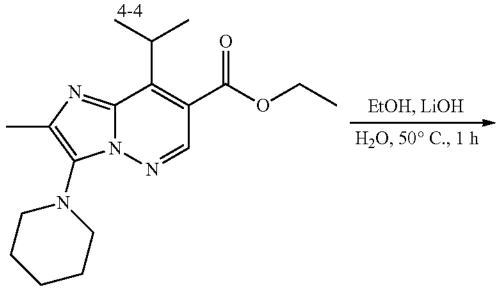

15-1

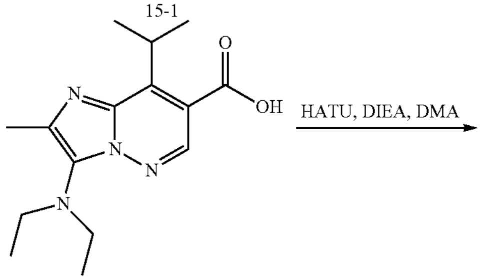

15-2

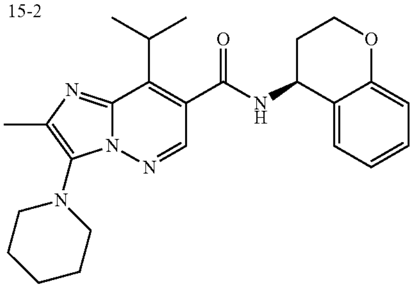

324

1. Synthesis of ethyl 8-isopropyl-2-methyl-3-(piperidin-1-yl)imidazo[1,2-b]pyridazine-7-carboxylic Acid (15-1)

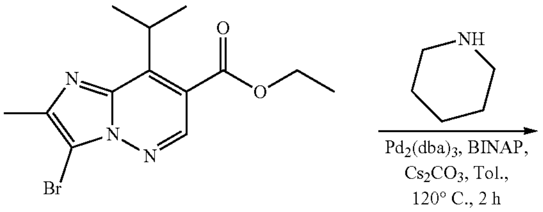

4-4

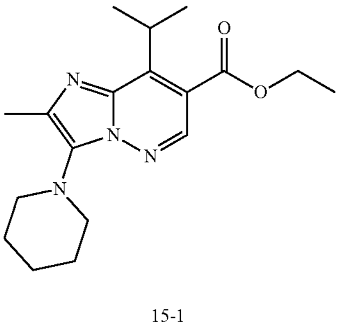

15-1

Into a 8-mL round-bottom flask purged and maintained with an inert atmosphere of nitrogen, was placed Toluene (2.0 mL), ethyl 3-bromo-8-isopropyl-2-methylimidazo[1,2-b]pyridazine-7-carboxylate (4-4, 70.0 mg, 0.2 mmol, 1.0 equiv), piperidine (120.0 mg, 1.4 mmol, 6.6 equiv), $Pd_2(dba)_3$ (35.0 mg, 0.04 mmol, 0.2 equiv), BINAP (38.0 mg, 0.06 mmol, 0.3 equiv), $Cs_2CO_3$ (200.0 mg, 0.6 mmol, 2.9 equiv). The resulting solution was stirred for 2 hr at 120° C. The resulting mixture was concentrated under vacuum. The residue was applied onto a silica gel column with ethyl acetate/petroleum ether (1:5). This resulted in 60 mg (84.6%) of ethyl 8-isopropyl-2-methyl-3-(piperidin-1-yl)imidazo[1,2-b]pyridazine-7-carboxylate (15-1) as a yellow solid.

2. Synthesis of 8-isopropyl-2-methyl-3-(piperidin-1-yl)imidazo[1,2-b]pyridazine-7-carboxylic Acid (15-2)

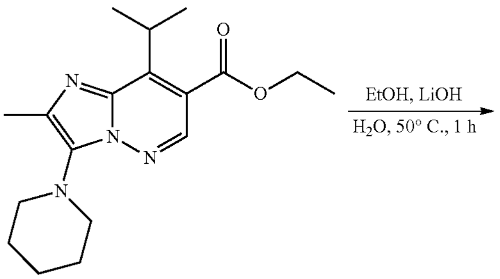

15-1

-continued

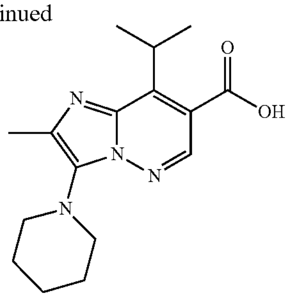

15-2

Into a 50-mL round-bottom flask, was placed i-PrOH (1.0 mL, 0.02 mmol), THE (1.0 mL), $H_2O$ (1.0 mL), ethyl 8-isopropyl-2-methyl-3-(piperidin-1-yl)imidazo[1,2-b]pyridazine-7-carboxylate (15-1, 70.0 mg, 0.2 mmol, 1.0 equiv), LiOH·$H_2O$ (30.0 mg, 0.7 mmol, 3.4 equiv). The resulting solution was stirred for 1 hr at 50° C. HCl (6 mol/L) was employed to adjust the pH to 4. The resulting solution was extracted with 3×20 mL of ethyl acetate and the organic layers combined and dried over anhydrous sodium sulfate and concentrated under vacuum. This resulted in 60 mg (93.7%) of 8-isopropyl-2-methyl-3-(piperidin-1-yl)imidazo[1,2-b]pyridazine-7-carboxylic acid (15-2) as a yellow solid.

3. Synthesis of N-[(4S)-3,4-dihydro-2H-1-benzopyran-4-yl]-8-isopropyl-2-methyl-3-(piperidin-1-yl)imidazo[1,2-b]pyridazine-7-carboxamide (324)

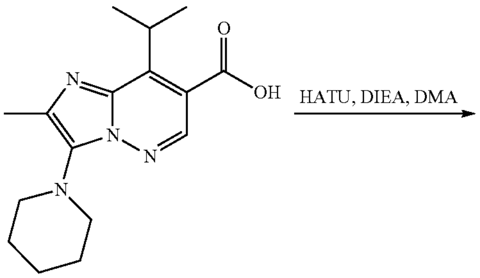

15-2

-continued

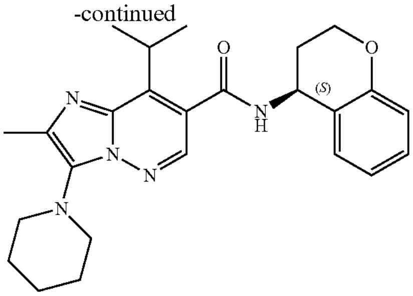

324

Into a 50-mL round-bottom flask, was placed DMA (3.0 mL), 8-isopropyl-2-methyl-3-(piperidin-1-yl)imidazo[1,2-b]pyridazine-7-carboxylic acid (15-2, 60.0 mg, 0.2 mmol, 1.0 equiv), (4S)-3,4-dihydro-2H-1-benzopyran-4-amine (44.0 mg, 0.3 mmol, 1.5 equiv), HATU (113.0 mg, 0.3 mmol, 1.5 equiv), DIEA (51.0 mg, 0.4 mmol, 2.0 equiv). The resulting solution was stirred for 1 hr at room temperature. The mixture was purified by Flash-Prep-HPLC with the following conditions (IntelFlash-1): Column, C18 silica gel; mobile phase, $H_2O$:ACN=50:50 increasing to $H_2O$:ACN=10:90 within 20; Detector, 254 nm. This resulted in 36.4 mg (42.3%) of N-[(4S)-3,4-dihydro-2H-1-benzopyran-4-yl]-8-isopropyl-2-methyl-3-(piperidin-1-yl)imidazo[1,2-b]pyridazine-7-carboxamide (324) as a yellow solid. (300 MHz, Chloroform-d, ppm): δ 8.19 (s, 1H), 7.33-7.30 (m, 1H), 7.25-7.20 (m, 1H), 6.97-6.90 (m, 1H), 6.89-6.80 (m, 1H), 6.10-6.02 (m, 1H), 5.40-5.30 (m, 1H), 4.38-4.34 (m, 1H), 4.22-4.10 (m, 1H), 3.79-3.76 (m, 1H), 3.30-3.20 (m, 4H), 2.52 (s, 3H), 2.50-2.35 (m, 1H), 2.30-2.15 (m, 1H), 1.80-1.70 (m, 4H), 1.65-1.58 (m, 8H).

| Compound | $^1$H NMR Spectra |
|---|---|
| 325 | (300 MHz, Chloroform-d, ppm): δ 8.20 (s, 1H), 7.34-7.27 (m, 1H), 7.25-7.21 (m, 1H), 6.98-6.90 (m, 1H), 6.90-6.80 (m, 1H), 6.15-6.00 (m, 1H), 5.40-5.30 (m, 1H), 4.45-4.34 (m, 1H), 4.24-4.15 (m, 1H), 3.91-3.83 (m, 4H), 3.80-3.70 (m, 1H), 3.40-3.20 (m, 4H), 2.52 (s, 3H), 2.49-2.32 (m, 1H), 2.30-2.15 (m, 1H), 1.70-1.50 (m, 6H) |
| 369 | (300 MHz, DMSO-d6, ppm) δ 8.98 (d, J = 7.8 Hz, 1H), 8.26 (d, J = 2.7 Hz, 1H), 7.31 (d, J = 7.2 Hz, 1H), 7.17 (t, J = 7.5 Hz, 1H), 6.92 (t, J = 7.2 Hz, 1H), 6.79 (d, J = 8.1 Hz, 1H), 5.30-5.15 (m, 1H), 4.25 (brs, 2H), 3.90 (s, 1H), 3.62-3.50 (m, 1H), 3.40-3.31 (m, 2H), 2.73 (brs, 1H), 2.42 (s, 3H), 2.30-2.15 (m, 1H), 2.10-2.00 (m, 1H), 1.90-1.80 (m, 1H), 1.75-1.40 (m, 11H) |
| 372-0 | (300 MHz, Chloroform-d, ppm): δ 8.20 (s, 1H), 7.35-7.30 (m, 1H),7.26-7.20 (m, 1H), 6.99-6.93 (m, 1H), 6.88 (dd, J = 7.2, 1.2 Hz, 1H), 6.05 (d, J = 7.5 Hz, 1H), 5.45-5.35 (m, 1H), 4.40-4.33 (m, 1H), 4.24-4.18 (m, 1H), 3.80-3.70 (m, 1H), 3.50-3.30 (m, 4H), 2.53 (s, 3H), 2.41-2.32 (m, 1H), 2.27-2.15 (m, 1H), 2.13-1.98 (m, 4H), 1.62 (t, J = 7.2 Hz, 6H) |
| 373 | (300 MHz, DMSO-d6, ppm): δ 9.01 (d, J = 8.4 Hz, 1H), 8.32 (s, 1H), 7.32 (d, J = 6.6 Hz, 1H), 7.20-7.14 (m, 1H), 6.95-6.89 (m, 1H), 6.80 (d, J = 6.6 Hz, 1H), 5.25-5.19 (m, 1H), 4.27-4.22 (m, 2H), 3.58-3.53 (m, 1H), 3.41-3.30 (m, 4H), 2.38 (s, 3H), 2.25-2.15 (m, 1H), 2.12-1.96 (m, 1H), 1.52-1.46 (m, 6H), 0.88 (t, J = 6.3 Hz, 4H), 0.14 (s, 6H) |

Preparation Example 11: Compounds 327, 326, 326-0, 365, 370, 371 may be prepared by the process shown in Scheme 16 below:
Scheme 16
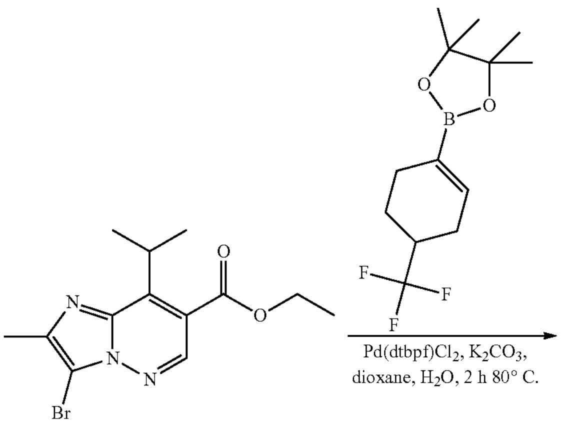
4-4
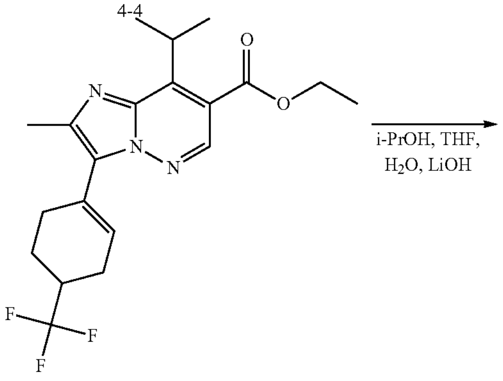
16-1
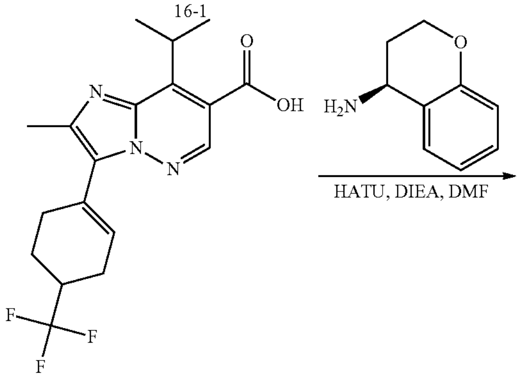
16-2
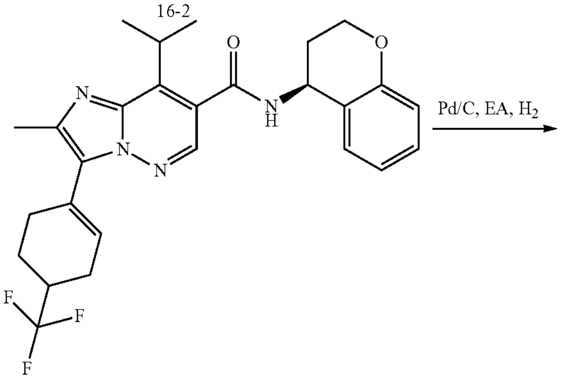
327
-continued
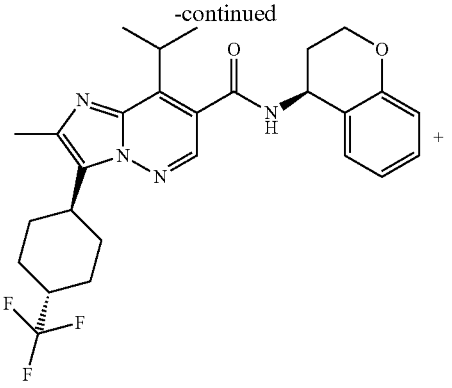
326
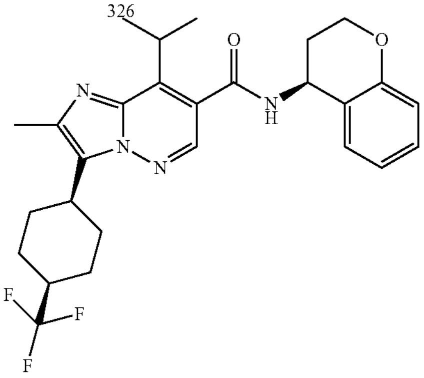
326-0
1. Synthesis of ethyl 8-isopropyl-2-methyl-3-[4-(trifluoromethyl)cyclohex-1-en-1-yl]imidazo[1,2-b]pyridazine-7-carboxylate (16-1)
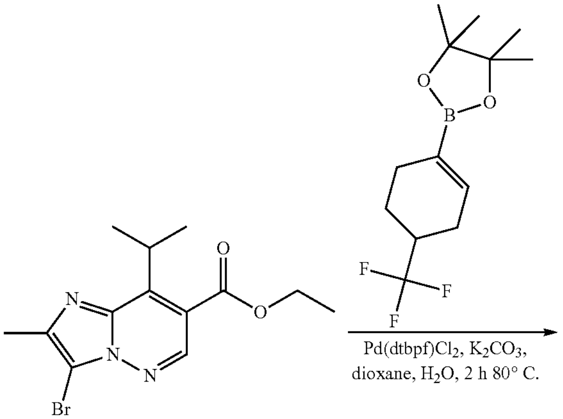
4-4
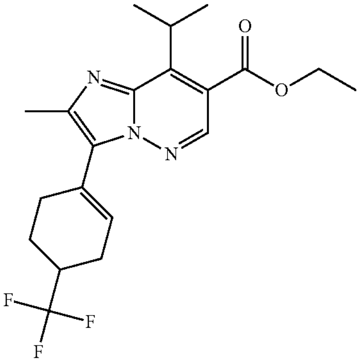
16-1

Into a 8-mL round-bottom flask, was placed dioxane (2.0 mL), $H_2O$ (0.4 mL), ethyl 3-bromo-8-isopropyl-2-methyl-imidazo[1,2-b]pyridazine-7-carboxylate (4-4, 100.00 mg, 0.3 mmol, 1.0 equiv), 4-(trifluoromethyl)cyclohex-1-en-1-ylboronic acid (120.0 mg, 0.6 mmol, 2.0 equiv), Pd(dtbpf)$Cl_2$ (20.0 mg, 0.03 mmol, 0.1 equiv), $K_2CO_3$ (100.0 mg, 0.7 mmol, 2.4 equiv). The resulting solution was stirred for 2 hr at 80° C. The resulting mixture was concentrated under vacuum. The residue was applied onto a silica gel column with ethyl acetate/petroleum ether (1:5). This resulted in 110 mg (90.7%) of ethyl 8-isopropyl-2-methyl-3-[4-(trifluoromethyl)cyclohex-1-en-1-yl]imidazo[1,2-b]pyridazine-7-carboxylate (16-1) as a yellow solid.

2. Synthesis of 8-isopropyl-2-methyl-3-[4-(trifluoromethyl)cyclohex-1-en-1-yl]imidazo[1,2-b]pyridazine-7-carboxylic Acid (16-2)

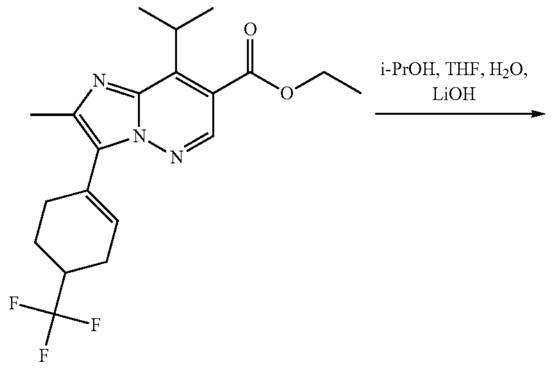

16-1

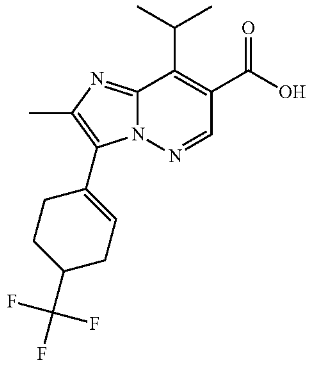

16-2

Into a 50-mL round-bottom flask, was placed i-PrOH (2.0 mL), THE (2.0 mL), $H_2O$ (1.0 mL), ethyl 8-isopropyl-2-methyl-3-[4-(trifluoromethyl)cyclohex-1-en-1-yl]imidazo[1,2-b]pyridazine-7-carboxylate (16-1, 110.0 mg, 0.3 mmol, 1.0 equiv), LiOH (70.0 mg, 2.9 mmol, 10.5 equiv). The resulting solution was stirred for 1 hr at 50° C. The pH value of the solution was adjusted to 4 with HCl (6 mol/L). The resulting solution was extracted with 3×20 mL of ethyl acetate and the organic layers combined and dried over anhydrous sodium sulfate and concentrated under vacuum. This resulted in 90 mg (88.0%) of 8-isopropyl-2-methyl-3-[4-(trifluoromethyl)cyclohex-1-en-1-yl]imidazo[1,2-b]pyridazine-7-carboxylic acid (16-2) as a white solid.

3. Synthesis of N-[(4S)-3,4-dihydro-2H-1-benzopyran-4-yl]-8-isopropyl-2-methyl-3-[4-(trifluoromethyl)cyclohex-1-en-1-yl]imidazo[1,2-b]pyridazine-7-carboxamide (327)

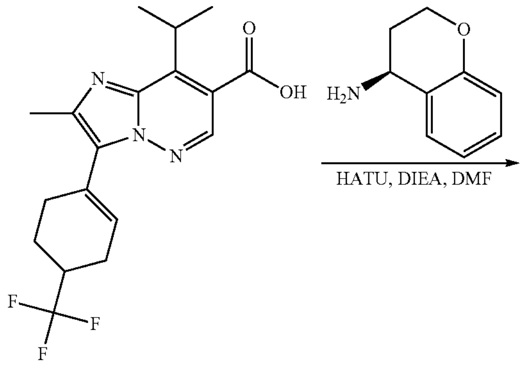

16-2

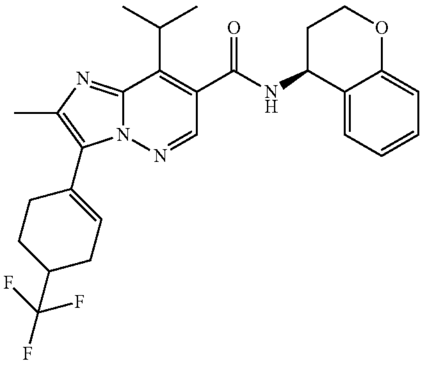

327

Into a 40-mL round-bottom flask, was placed DMF (5.0 mL), 8-isopropyl-2-methyl-3-[4-(trifluoromethyl)cyclohex-1-en-1-yl]imidazo[1,2-b]pyridazine-7-carboxylic acid (16-2, 130.0 mg, 0.3 mmol, 1.0 equiv), (4S)-3,4-dihydro-2H-1-benzopyran-4-amine (79.2 mg, 0.5 mmol, 1.5 equiv), HATU (200.5 mg, 0.5 mmol, 1.5 equiv), DIEA (137.2 mg, 1.0 mmol, 3.0 equiv). The resulting solution was stirred for 1 hr at room temperature. The mixture was purified by Flash-Prep-HPLC with the following conditions (IntelFlash-1): Column, C18 silica gel; mobile phase, $H_2O$:ACN=50:50 increasing to $H_2O$:ACN=10:90 within 20 min; Detector, 254 nm. This resulted in 130 mg (73.7%) of N-[(4S)-3,4-dihydro-2H-1-benzopyran-4-yl]-8-isopropyl-2-methyl-3-[4-(trifluoromethyl)cyclohex-1-en-1-yl]imidazo[1,2-b]pyridazine-7-carboxamide (327) as a white solid. (300 MHz, Chloroform-d, ppm): δ 8.20 (s, 1H), 7.35-7.30 (m, 1H), 7.25-7.17 (m, 1H), 7.10-6.84 (m, 2H), 6.15-5.90 (m, 2H), 5.45-5.30 (m, 1H), 4.44-4.31 (m, 1H), 4.23-4.19 (m, 1H), 3.83-3.72 (m, 1H), 2.75-2.55 (m, 3H), 2.53 (s, 3H), 2.50-2.35 (m, 3H), 2.29-2.13 (m, 3H), 1.63 (d, J=6.6 Hz, 6H).

4. Synthesis of N-[(4S)-3,4-dihydro-2H-1-benzopyran-4-yl]-8-isopropyl-2-methyl-3-[(1r,4r)-4-(trifluoromethyl)cyclohexyl]imidazo[1,2-b]pyridazine-7-carboxamide and N—((S)-chroman-4-yl)-8-isopropyl-2-methyl-3-((1s,4R)-4-(trifluoromethyl)cyclohexyl)imidazo[1,2-b]pyridazine-7-carboxamide (326 and 326-0)

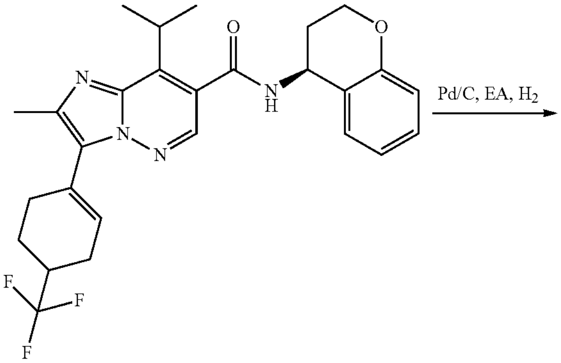

327

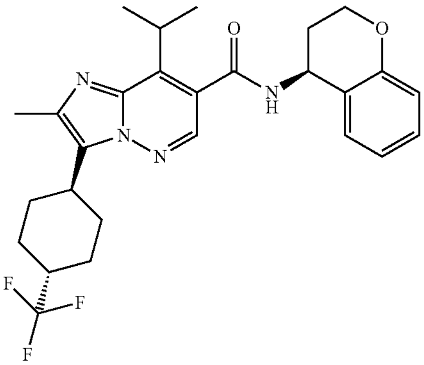

+

326

-continued

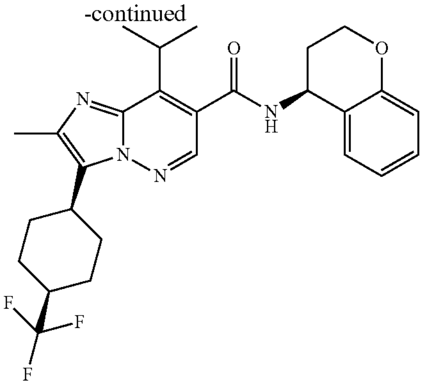

326-0

Into a 50-mL round-bottom flask, was placed EA (5.0 mL), N-[(4S)-3,4-dihydro-2H-1-benzopyran-4-yl]-8-isopropyl-2-methyl-3-[4-(trifluoromethyl)cyclohex-1-en-1-yl]imidazo[1,2-b]pyridazine-7-carboxamide (327, 50.0 mg, 0.10 mmol, 1.0 equiv), aqueous Pd/C (50.0 mg). To the above $H_2$(g) was introduced at rt. The resulting solution was stirred for 2 hr at room temperature. The solids were filtered out. The resulting mixture was concentrated under vacuum. The crude product was purified by Flash-Prep-HPLC with the following conditions (IntelFlash-1): Column, C18 silica gel; mobile phase, $H_2O$:ACN=50:50 increasing to $H_2O$:ACN=10:90 within 20 min; Detector, 254 nm. The racemic product was purified by Column: XA-YMC Cellulose-SC, 4.6*100 mm, 3 um; Mobile Phase A/Mobile Phase B: n-Hexane/EtOH=70/30; Flow rate:1 mL/min; Gradient:30B to 30 B in 10 min; 254 nm; Injection Volume: 1 ml; This resulted in 19.3 mg (38.4%) of N-[(4S)-3,4-dihydro-2H-1-benzopyran-4-yl]-8-isopropyl-2-methyl-3-[(1r,4r)-4-(trifluoromethyl)cyclohexyl]imidazo[1,2-b]pyridazine-7-carboxamide as a white solid and 8.0 mg (15.8%) of N—((S)-chroman-4-yl)-8-isopropyl-2-methyl-3-((1s,4R)-4-(trifluoromethyl)cyclohexyl)imidazo[1,2-b]pyridazine-7-carboxamide as a white solid (326 and 326-0). The stereochemical depictions are assumed. $^1$H NMR spectra for 326: (300 MHz Chloroform-d, ppm): δ 8.23 (s, 1H), 7.35-7.30 (m, 1H), 7.27-7.20 (m, 1H), 7.02-6.94 (m, 1H), 6.90-6.80 (m, 1H), 6.07 (brs, 1H), 5.44-5.34 (m, 1H), 4.44-4.31 (m, 1H), 4.28-4.14 (m, 1H), 3.90-3.80 (m, 1H), 3.45-3.25 (m, 1H), 2.58 (s, 3H), 2.55-2.40 (m, 2H), 2.45-2.15 (m, 4H), 1.85-1.65 (m, 5H), 1.62 (d, J=6.6 Hz, 6H); $^1$H NMR spectra for 326-0: (300 MHz, Chloroform-d, ppm): δ 8.17 (s, 1H), 7.30-7.28 (m, 1H), 7.25-7.15 (m, 1H), 6.94 (t, J=7.5 Hz, 1H), 6.86 (d, J=8.2 Hz, 1H), 6.15-5.90 (m, 1H), 5.45-5.20 (m, 1H), 4.40-4.30 (m, 1H), 4.25-4.10 (m, 1H), 3.81-3.65 (m, 1H), 3.30-3.10 (m, 1H), 2.53 (s, 3H), 2.46-2.31 (m, 1H), 2.30-2.00 (m, 6H), 2.00-1.85 (m, 2H), 1.65-1.55 (m, 6H), 1.50-1.45 (m, 1H).

| Compound | $^1$H NMR Spectra |
|---|---|
| 365 | (300 MHz, CDCl3, ppm): δ 8.25 (s, 1H), 7.31-7.28 (m, 1H),7.26-7.20 (m, 1H), 6.99-6.94 (m, 1H), 6.88 (d, J = 8.1 Hz, 1H), 6.06 (d, J = 7.2 Hz, 1H), 5.40-5.30 (m, 1H), 4.40-4.30 (m, 1H), 4.24-4.10 (m, 1H), 3.80-3.70 (m, 1H), 2.54 (s, 3H), 2.49-2.33 (m, 1H), 2.25-2.15 (m, 1H), 2.05-1.90 (m, 1H), 1.64-1.56 (m, 6H), 1.15-1.05 (m, 2H), 0.95-0.80 (m, 2H) |
| 370 | (300 MHz, CDCl3, ppm): δ 8.25 (s, 1H), 7.34-7.31 (m, 1H), 7.27-7.22 (m, 1H), 6.99-6.95 (m, 1H), 6.89 (d, J = 8.1 Hz 1H), 6.16 (brs, 1H), 5.45-5.35 (m, 1H), 4.40-4.34 (m, 1H), 4.28-4.18 (m, 1H), 4.16-4.09 (m, 2H), 3.80 (brs, 1H), 3.63-3.47 (m, 3H), 2.61 (s, 3H), 2.60-2.15 (m, 4H), 1.75-1.70 (m, 2H), 1.62 (t, J = 6.6 Hz, 6H) |
| 371 | (300 MHz, CDCl3, ppm): δ 8.22 (s, 1H), 7.31-7.28 (m, 1H), 7.24-7.21 (m, 1H), 6.99-6.94 (m, 1H), 6.90-6.87 (m, 1H), 6.07-6.05 (m, 1H), 5.41-5.35 (m, 1H), |

-continued
| Compound | $^1H$ NMR Spectra |
|---|---|
| | 4.41-4.34 (m, 1H), 4.27-4.17 (m, 1H), 3.78-3.74 (m, 1H), 3.38-3.29 (m, 1H), 2.56 (s, 3H), 2.54-2.22 (m, 6H), 2.03-1.86 (m, 4H), 1.62 (t, J = 6.9 Hz, 6H) |
Preparation Example 12: Compound 352 was prepared according to the process shown in scheme 17 below:
Scheme 17
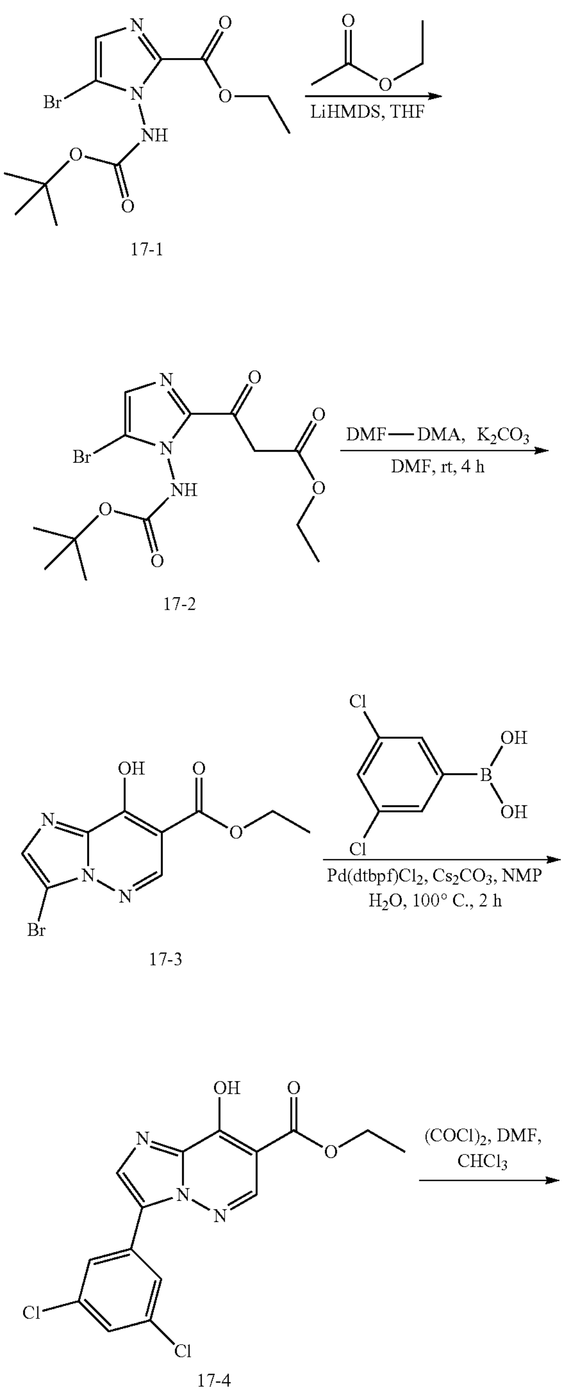
17-1
17-2
17-3
17-4
-continued
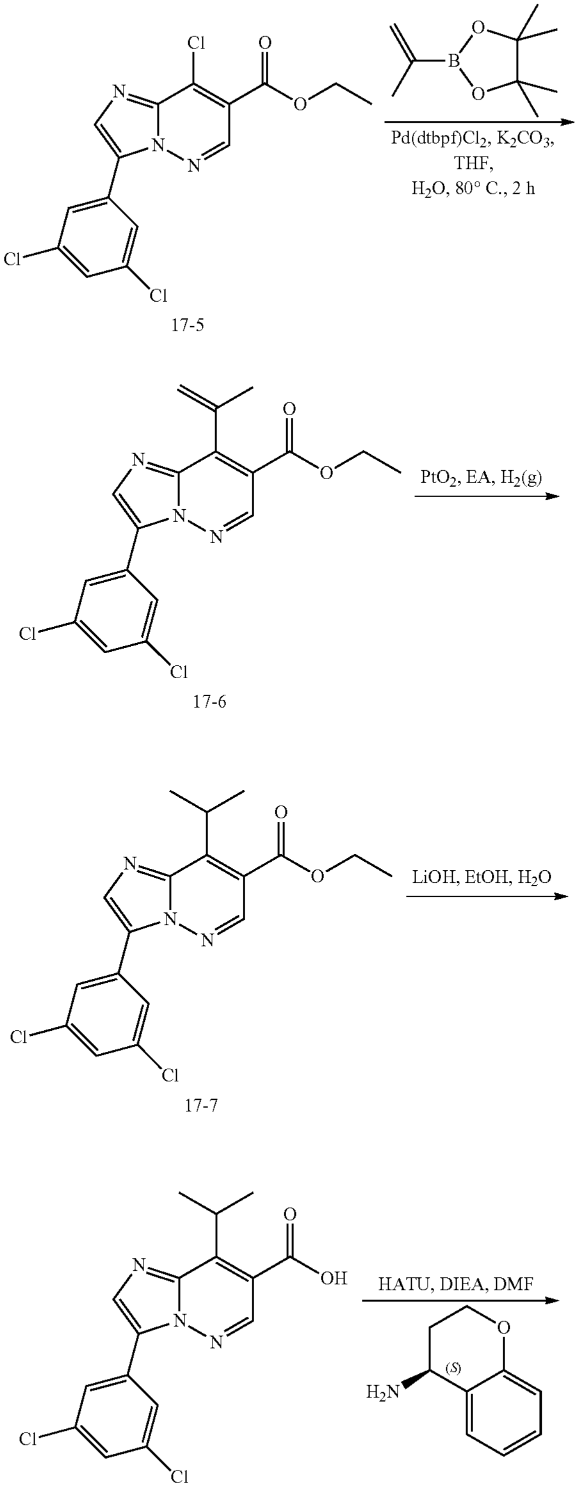
17-5
17-6
17-7
17-8

-continued

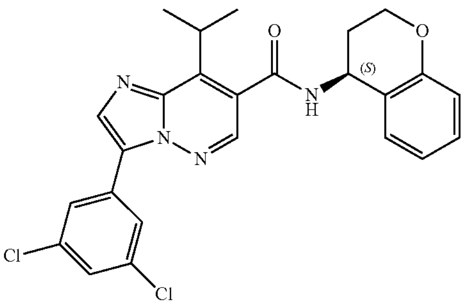

352

1. Synthesis of ethyl 3-[5-bromo-1-[(tert-butoxycarbonyl)amino]imidazol-2-yl]-3-oxopropanoate (17-2)

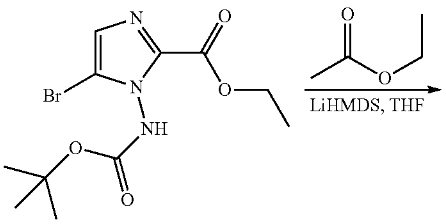

17-1

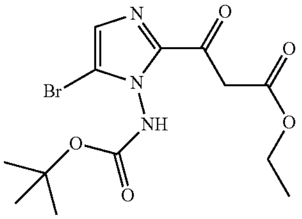

17-2

Into a 1000-mL round-bottom flask, was placed THE (85.0 g, 1178.8 mmol, 26.3 equiv), ethyl 5-bromo-1-[(tert-butoxycarbonyl)amino]imidazole-2-carboxylate (17-1, 15.0 g, 44.9 mmol, 1.0 equiv), ethyl acetate (50.0 g, 567.5 mmol, 12.6 equiv). This was followed by the addition of t-BuOK (500 mL), in portions at 0 degrees C. The resulting solution was stirred for 2 hr at room temperature. The reaction was then quenched by the addition of $NH_4Cl$ (aq). The resulting solution was extracted with 3×200 mL of ethyl acetate and the organic layers combined and dried over anhydrous sodium sulfate and concentrated under vacuum. The residue was applied onto a silica gel column with ethyl acetate/petroleum ether (1:4). This resulted in 13 g (77.0%) of ethyl 3-[5-bromo-1-[(tert-butoxycarbonyl)amino]imidazol-2-yl]-3-oxopropanoate (17-2) as colorless oil.

2. Synthesis of ethyl 3-bromo-8-hydroxyimidazo[1,2-b]pyridazine-7-carboxylate (17-3)

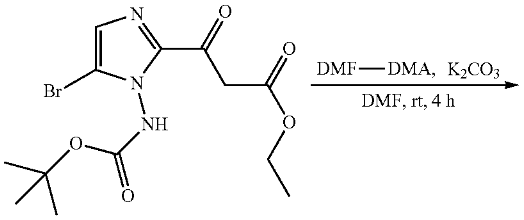

17-2

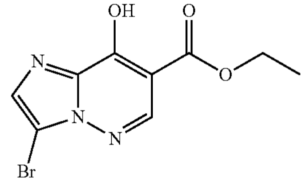

17-3

Into a 500-mL round-bottom flask, was placed DCM (100.0 mL, 1573.0 mmol, 59.2 equiv), ethyl 3-[5-bromo-1-[(tert-butoxycarbonyl)amino]imidazol-2-yl]-3-oxopropanoate (17-2, 10.0 g, 26.6 mmol, 1.0 equiv), DMF-DMA (9.0 g, 75.5 mmol, 2.8 equiv). The resulting solution was stirred for 2 hr at 40° C. The reaction was then quenched by the addition of water/ice. The resulting solution was extracted with 2×100 mL of MTBE and the aqueous layers combined. The pH value of the solution was adjusted to 4 with HCl (4 mol/L). The solids were collected by filtration. This resulted in 5 g (65.7%) of ethyl 3-bromo-8-hydroxyimidazo[1,2-b]pyridazine-7-carboxylate (17-3) as a white solid.

3. Synthesis of ethyl 3-(3,5-dichlorophenyl)-8-hydroxyimidazo[1,2-b]pyridazine-7-carboxylate (17-4)

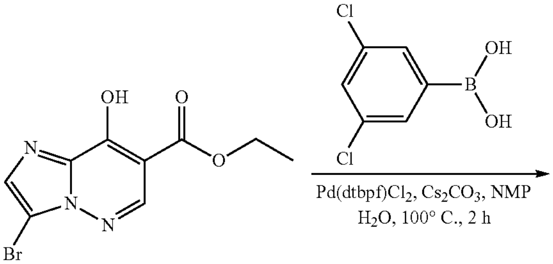

17-3

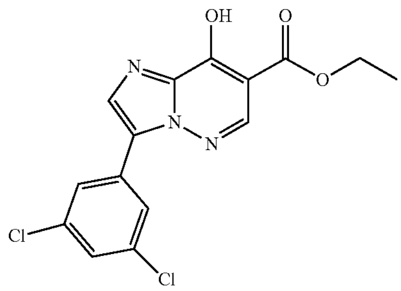

17-4

Into a 40-mL round-bottom flask purged and maintained with an inert atmosphere of nitrogen, was placed $H_2O$ (1.0 mL), NMP (5.0 mL), ethyl 3-bromo-8-hydroxyimidazo[1,2-b]pyridazine-7-carboxylate (17-3, 400.0 mg, 1.398 mmol, 1.0 equiv), 3,5-dichlorophenylboronic acid (320.1 mg, 1.7 mmol, 1.2 equiv), Pd(dtbpf)$Cl_2$ (70.0 mg, 0.1 mmol, 0.08 equiv), $Cs_2CO_3$ (1.2 g, 3.7 mmol, 2.6 equiv). The resulting solution was stirred for 2 hrs at 100° C. The mixture was cooled to rt, then added 5 ml $H_2O$. The solids were collected by filtration. This resulted in 300 mg (crude) of ethyl 3-(3,5-dichlorophenyl)-8-hydroxyimidazo[1,2-b]pyridazine-7-carboxylate (17-4) as a yellow solid.

4. Synthesis of ethyl 8-chloro-3-(3,5-dichlorophenyl)imidazo[1,2-b]pyridazine-7-carboxylate (17-5)

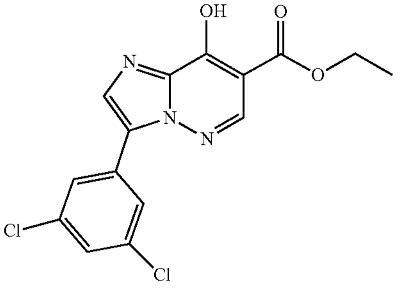

17-4

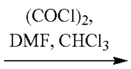

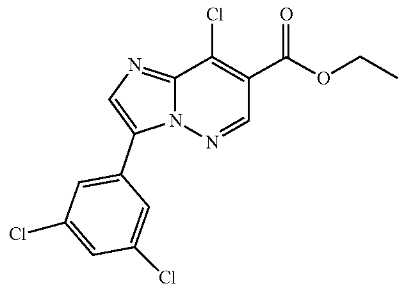

17-5

Into a 40-mL round-bottom flask, was placed $CHCl_3$ (5.0 mL, 0.04 mmol, 0.07 equiv), DMF (15.0 mg, 0.2 mmol, 0.4 equiv), ethyl 3-(3,5-dichlorophenyl)-8-hydroxyimidazo[1,2-b]pyridazine-7-carboxylate (17-4, 200.0 mg, 0.6 mmol, 1.0 equiv), $(COCl)_2$ (400.0 mg, 3.1 mmol, 5.5 equiv). The resulting solution was stirred for 22 hr at 80 degrees C. The resulting mixture was concentrated under vacuum. The resulting mixture was washed with 10×10 mL of ACN: $H_2O$=1:1. The solids were collected by filtration. This resulted in 110 mg (52.3%) of ethyl 8-chloro-3-(3,5-dichlorophenyl)imidazo[1,2-b]pyridazine-7-carboxylate (17-5) as a yellow solid.

5. Synthesis of ethyl 3-(3,5-dichlorophenyl)-8-(prop-1-en-2-yl)imidazo[1,2-b]pyridazine-7-carboxylate (17-6)

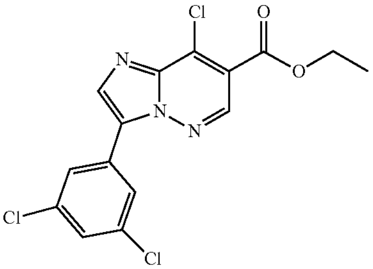

17-5

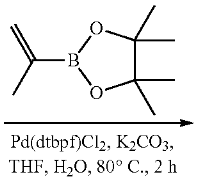

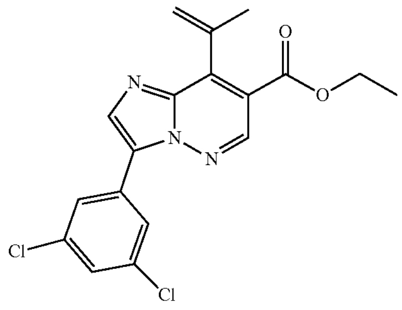

17-6

Into a 40-mL round-bottom flask purged and maintained with an inert atmosphere of nitrogen, was placed $H_2O$ (1.00 mL, 55.5 mmol, 187.0 equiv), THE (5.0 mL, 61.7 mmol, 207.9 equiv), ethyl 8-chloro-3-(3,5-dichlorophenyl)imidazo[1,2-b]pyridazine-7-carboxylate (17-5, 110.0 mg, 0.3 mmol, 1.0 equiv), 4,4,5,5-tetramethyl-2-(prop-1-en-2-yl)-1,3,2-dioxaborolane (72.0 mg, 0.43 mmol, 1.4 equiv), Pd(dtbpf)$Cl_2$ (40.0 mg, 0.06 mmol, 0.2 equiv), $K_2CO_3$ (160.0 mg, 1.2 mmol, 3.9 equiv). The resulting solution was stirred for 2 hr at 80° C. The resulting mixture was concentrated under vacuum. The residue was applied onto a silica gel column with ethyl acetate/petroleum ether (1:3). This resulted in 80 mg (71.6%) of ethyl 3-(3,5-dichlorophenyl)-8-(prop-1-en-2-yl)imidazo[1,2-b]pyridazine-7-carboxylate (17-6) as a yellow solid.

6. Synthesis of ethyl 3-(3,5-dichlorophenyl)-8-isopropylimidazo[1,2-b]pyridazine-7-carboxylate (17-7)

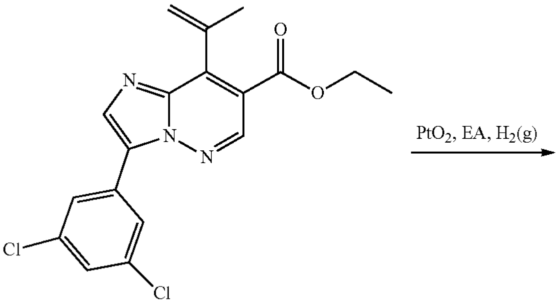

17-6

-continued

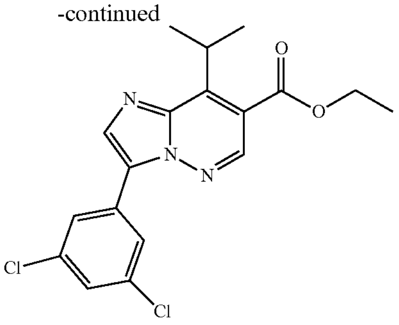

Into a 50-mL round-bottom flask, was placed EA (5.0 mL), ethyl 3-(3,5-dichlorophenyl)-8-(prop-1-en-2-yl)imidazo[1,2-b]pyridazine-7-carboxylate (17-6, 80.0 mg, 0.21 mmol, 1.0 equiv), $PtO_2$ (40.0 mg, 0.2 mmol, 0.8 equiv). To the above $H_2$(g) was introduced with a balloon. The resulting solution was stirred for 1 hr at 50° C. The solids were collected by filtration. The resulting mixture was concentrated under vacuum. This resulted in 60 mg of ethyl 3-(3,5-dichlorophenyl)-8-isopropylimidazo[1,2-b]pyridazine-7-carboxylate (17-7) as a yellow solid.

7. Synthesis of 3-(3,5-dichlorophenyl)-8-isopropylimidazo[1,2-b]pyridazine-7-carboxylic Acid (17-8)

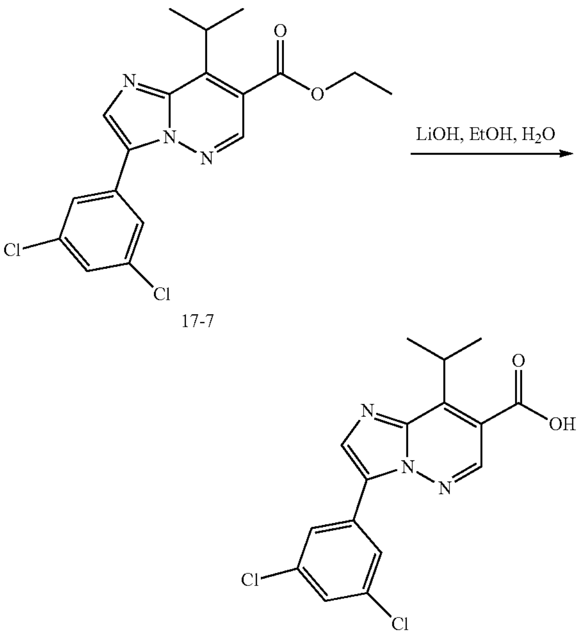

17-7

17-8

Into a 8-mL round-bottom flask, was placed EtOH (2.0 mL), $H_2O$ (0.50 mL), ethyl 3-(3,5-dichlorophenyl)-8-isopropylimidazo[1,2-b]pyridazine-7-carboxylate (17-7, 60.0 mg, 0.2 mmol, 1.0 equiv), LiOH (30.0 mg, 1.2 mmol, 7.9 equiv). The resulting solution was stirred for 1 hr at 50° C. The reaction was then quenched by the addition of water/ice. The pH value of the solution was adjusted to 4 with HCl (6 mol/L). The resulting solution was extracted with 3×20 mL of ethyl acetate and the organic layers combined and dried over anhydrous sodium sulfate and concentrated under vacuum. This resulted in 40 mg (72.0%) of 3-(3,5-dichlorophenyl)-8-isopropylimidazo[1,2-b]pyridazine-7-carboxylic acid (17-8) as a white solid.

8. Synthesis of 3-(3,5-dichlorophenyl)-N-[(4S)-3,4-dihydro-2H-1-benzopyran-4-yl]-8-isopropylimidazo[1,2-b]pyridazine-7-carboxamide (352)

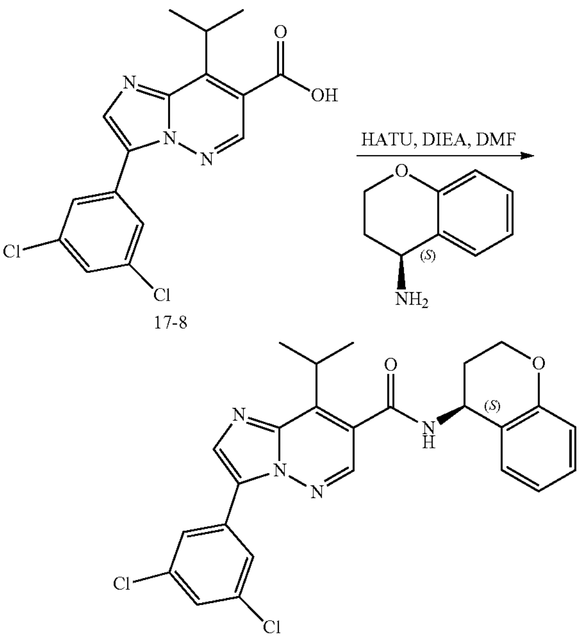

17-8

352

Into a 8-mL round-bottom flask, was placed DMF (4.0 mL), 3-(3,5-dichlorophenyl)-8-isopropylimidazo[1,2-b]pyridazine-7-carboxylic acid (17-8, 40.0 mg, 0.1 mmol, 1.0 equiv), (4S)-3,4-dihydro-2H-1-benzopyran-4-amine (22.0 mg, 0.15 mmol, 1.3 equiv), HATU (70.0 mg, 0.2 mmol, 1.6 equiv), DIEA (46.0 mg, 0.4 mmol, 3.1 equiv). The resulting solution was stirred for 1 hr at room temperature. The crude product was purified by Flash-Prep-HPLC with the following conditions (IntelFlash-1): Column, C18 silica gel; mobile phase, $H_2O$:ACN=50:50 increasing to $H_2O$:ACN=10:90 within 20 min; Detector, 254 nm. This resulted in 15.9 mg (28.9%) of 3-(3,5-dichlorophenyl)-N-[(4S)-3,4-dihydro-2H-1-benzopyran-4-yl]-8-isopropylimidazo[1,2-b]pyridazine-7-carboxamide (352) as a white solid. (300 MHz, Chloroform-d, ppm): δ 8.41 (s, 1H), 8.11 (s, 1H), 7.99 (d, J=1.8 Hz, 2H), 7.39 (s, 1H), 7.32-7.28 (m, 1H), 7.28-7.22 (m, 1H), 6.99-6.96 (m, 1H), 6.90 (d, J=8.4, 1H), 6.13 (d, J=7.5 Hz, 1H), 5.50-5.30 (m, 1H), 4.46-4.33 (m, 1H), 4.29-4.15 (m, 1H), 3.79-3.70 (m, 1H), 2.50-2.36 (m, 1H), 2.33-2.20 (m, 1H), 1.69-1.65 (m, 6H).

Preparation Example 13: Compound 366 was prepared according to scheme 18 shown below:

Scheme 18

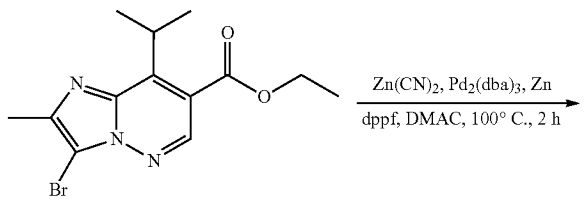

4-4

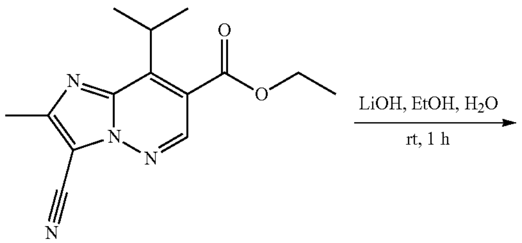

18-1

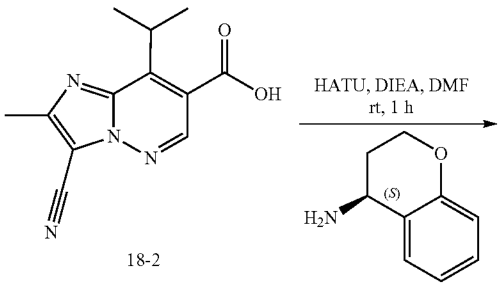

18-2

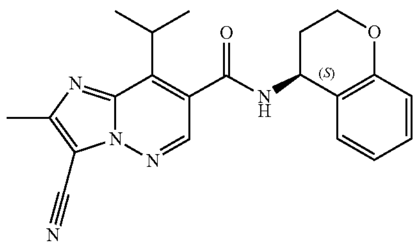

366

1. Synthesis of ethyl 3-cyano-8-isopropyl-2-methyl-imidazo[1,2-b]pyridazine-7-carboxylate

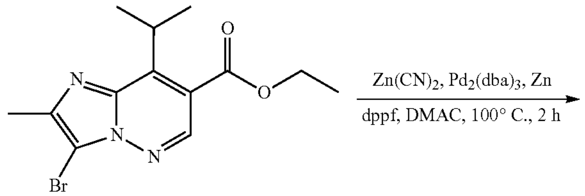

4-4

-continued

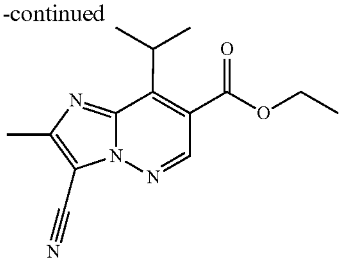

18-1

Into a 20-mL round-bottom flask purged and maintained with an inert atmosphere of nitrogen, was placed DMAC (5.0 mL), ethyl 3-bromo-8-isopropyl-2-methylimidazo[1,2-b]pyridazine-7-carboxylate (4-4, 100.0 mg, 0.3 mmol, 1.0 equiv), dppf (59.3 mg, 0.1 mmol, 0.3 equiv), $Zn(CN)_2$ (100.1 mg, 0.8 mmol, 2.8 equiv), $Pd_2(dba)_3$ (50.5 mg, 0.05 mmol, 0.2 equiv), Zn (100.1 mg, 1.5 mmol, 5.0 equiv). The resulting solution was stirred for 2 hr at 100° C. The reaction was then quenched by the addition of water. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:5). This resulted in 40 mg (47.9%) of ethyl 3-cyano-8-isopropyl-2-methylimidazo[1,2-b]pyridazine-7-carboxylate (18-1) as yellow oil.

2. Synthesis of 3-cyano-8-isopropyl-2-methylimidazo[1,2-b]pyridazine-7-carboxylic Acid (18-2)

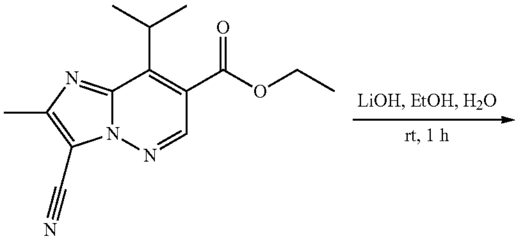

18-1

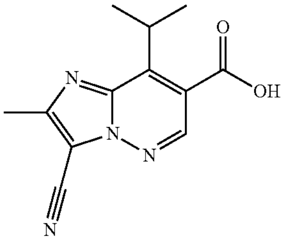

18-2

Into a 8-mL round-bottom flask, was placed EtOH (1.0 mL), $H_2O$ (0.5 mL), ethyl 3-cyano-8-isopropyl-2-methyl-imidazo[1,2-b]pyridazine-7-carboxylate (18-1, 40.0 mg, 0.15 mmol, 1.0 equiv), LiOH (30.0 mg, 1.2 mmol, 8.5 equiv). The resulting solution was stirred for 1 hr at room temperature. The pH value of the solution was adjusted to 4 with HCl (4 mol/L). The resulting solution was extracted with 3×20 mL of ethyl acetate and the organic layers combined and dried over anhydrous sodium sulfate and concentrated under vacuum. This resulted in 25 mg (69.7%)

of 3-cyano-8-isopropyl-2-methylimidazo[1,2-b]pyridazine-7-carboxylic acid (18-2) as yellow oil.

3. Synthesis of 3-cyano-N-[(4S)-3,4-dihydro-2H-1-benzopyran-4-yl]-8-isopropyl-2-methylimidazo[1,2-b]pyridazine-7-carboxamide (366)

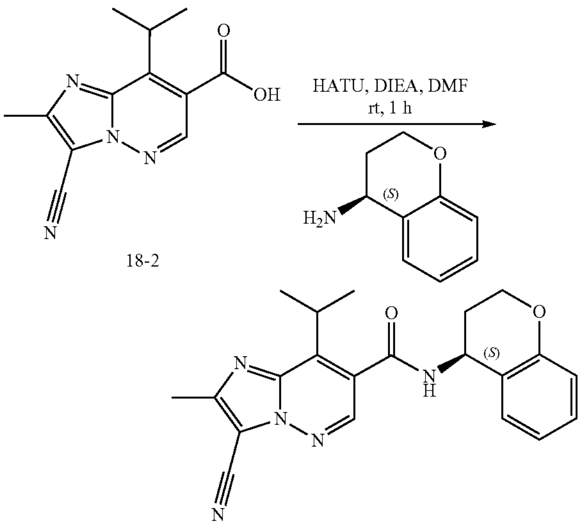

18-2

366

Into a 8-mL round-bottom flask, was placed DMF (2 mL), 3-cyano-8-isopropyl-2-methylimidazo[1,2-b]pyridazine-7-carboxylic acid (18-2, 25.0 mg, 0.1 mmol, 1.0 equiv), (4S)-3,4-dihydro-2H-1-benzopyran-4-amine (16.9 mg, 0.1 mmol, 1.1 equiv), HATU (47.0 mg, 0.1 mmol, 1.21 equiv), DIEA (28.0 mg, 0.2 mmol, 2.1 equiv). The resulting solution was stirred for 1 hr at room temperature. The mixture was purified by Flash-Prep-HPLC with the following conditions (IntelFlash-1): Column, C18 silica gel; mobile phase, $H_2O$: ACN=70:30 increasing to $H_2O$:ACN=10:90 within 20 min; Detector, 254 nm. This resulted in 16.5 mg (42.9%) of 3-cyano-N-[(4S)-3,4-dihydro-2H-1-benzopyran-4-yl]-8-isopropyl-2-methylimidazo[1,2-b]pyridazine-7-carboxamide (366) as a white solid. (300 MHz, $CDCl_3$, ppm): δ 8.35 (s, 1H), 7.25-7.20 (m, 2H), 6.97-6.92 (m, 1H), 6.86 (d, J=8.1 Hz, 1H), 6.20-6.10 (m, 1H), 5.39-5.33 (m, 1H), 4.41-4.32 (m, 1H), 4.27-4.14 (m, 1H), 3.69-3.59 (m, 1H), 2.62 (s, 3H), 2.45-2.35 (m, 1H), 2.29-2.18 (m, 1H), 1.65-1.55 (m, 6H).

Preparation Example 14: Compounds 394, 397-0, 395 and 398 may be synthesized according to scheme 19 shown below:

Scheme 19

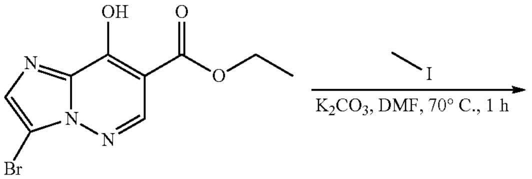

17-3

-continued

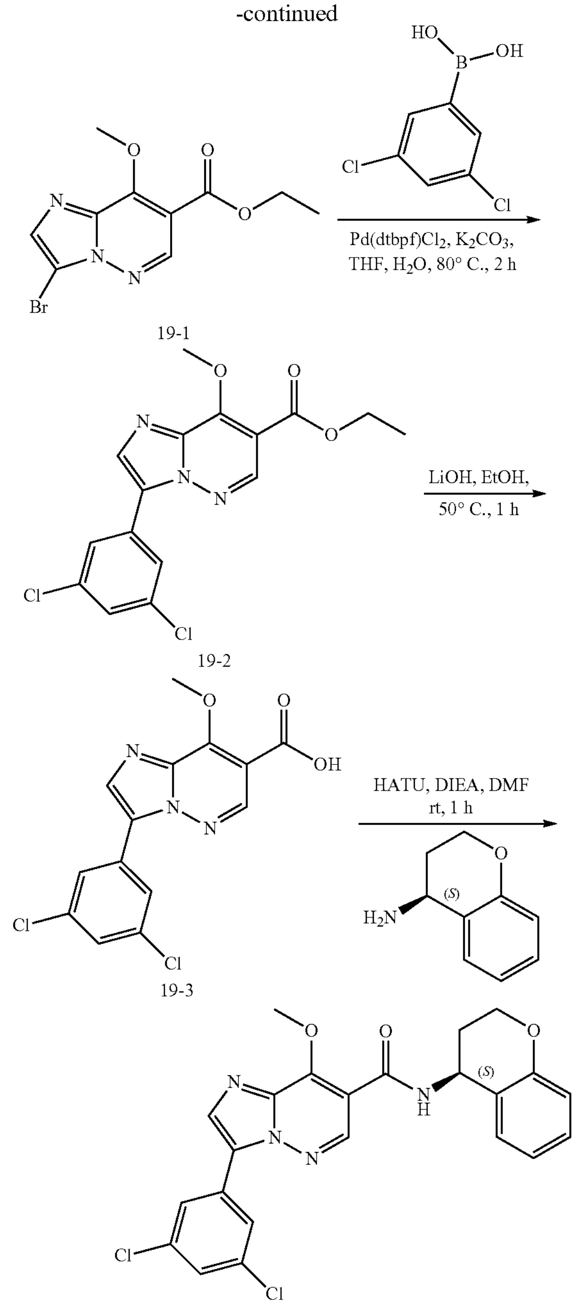

19-1

19-2

19-3

394

1. Synthesis of methyl 3-bromo-8-ethoxyimidazo[1,2-b]pyridazine-7-carboxylate (19-1)

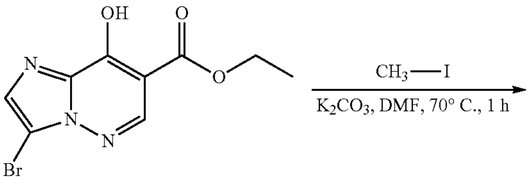

17-3

-continued

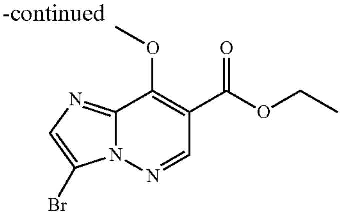

19-1

Into a 40-mL round-bottom flask, was placed DMF (5.0 mL), ethyl 3-bromo-8-hydroxyimidazo[1,2-b]pyridazine-7-carboxylate (17-3, 150.0 mg, 0.5 mmol, 1.0 equiv), methyl iodide (200.0 mg, 1.3 mmol, 2.4 equiv), $K_2CO_3$ (210.0 mg, 1.5 mmol, 2.9 equiv). The resulting solution was stirred for 1 hr at 70° C. The mixture was purified by Flash-Prep-HPLC with the following conditions (IntelFlash-1): Column, C18 silica gel; mobile phase, $H_2O$:ACN=90:10 increasing to $H_2O$:ACN=40:60 within 15 min; Detector, 254 nm. This resulted in 80 mg (48.6%) of methyl 3-bromo-8-ethoxyimidazo[1,2-b]pyridazine-7-carboxylate (19-1) as a white solid.

2. Synthesis of methyl 3-(3,5-dichlorophenyl)-8-ethoxyimidazo[1,2-b]pyridazine-7-carboxylate (19-2)

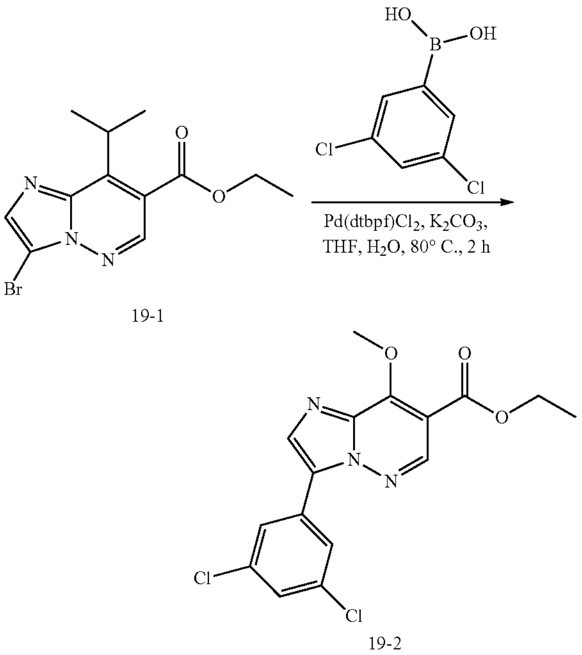

19-1

19-2

Into a 8-mL round-bottom flask purged and maintained with an inert atmosphere of nitrogen, was placed THF (5.0 mL), $H_2O$ (1.0 mL), methyl 3-bromo-8-ethoxyimidazo[1,2-b]pyridazine-7-carboxylate (19-1, 80.0 mg, 0.25 mmol, 1.0 equiv), 3,5-dichlorophenylboronic acid (56.0 mg, 0.3 mmol, 1.1 equiv), Pd(dtbpf)$Cl_2$ (30.0 mg, 0.05 mmol, 0.2 equiv), $K_2CO_3$ (100.0 mg, 0.7 mmol, 2.8 equiv). The resulting solution was stirred for 2 hr at 80° C. The resulting mixture was concentrated under vacuum. The residue was applied onto a silica gel column with ethyl acetate/petroleum ether (1:3). This resulted in 20 mg (20.6%) of methyl 3-(3,5-dichlorophenyl)-8-ethoxyimidazo[1,2-b]pyridazine-7-carboxylate (19-2) as a white solid.

3. Synthesis of 3-(3,5-dichlorophenyl)-8-methoxyimidazo[1,2-b]pyridazine-7-carboxylic Acid (19-3)

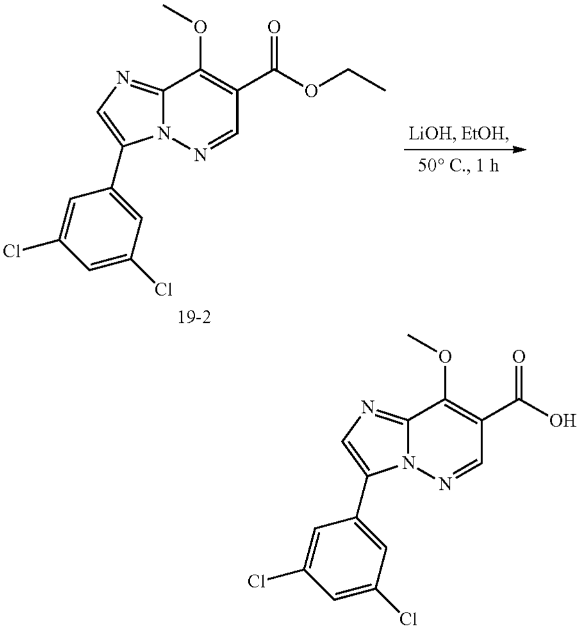

19-2

19-3

Into a 40-mL round-bottom flask, was placed EtOH (5.0 mL), $H_2O$ (2.0 mL), ethyl 3-(3,5-dichlorophenyl)-8-methoxyimidazo[1,2-b]pyridazine-7-carboxylate (19-2, 70.0 mg, 0.2 mmol, 1.0 equiv), LiOH (40.0 mg, 1.7 mmol, 8.7 equiv). The resulting solution was stirred for 1 hr at 50° C. The pH value of the solution was adjusted to 4 with HCl (4 mol/L). The resulting solution was extracted with 3×20 mL of ethyl acetate and the organic layers combined and dried over anhydrous sodium sulfate and concentrated under vacuum. This resulted in 40 mg (61.9%) of 3-(3,5-dichlorophenyl)-8-methoxyimidazo[1,2-b]pyridazine-7-carboxylic acid (19-3) as a white solid.

4. Synthesis of 3-(3,5-dichlorophenyl)-N-[(4S)-3,4-dihydro-2H-1-benzopyran-4-yl]-8-methoxyimidazo[1,2-b]pyridazine-7-carboxamide (394)

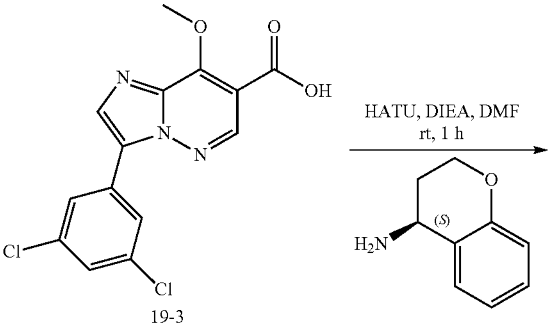

19-3

-continued

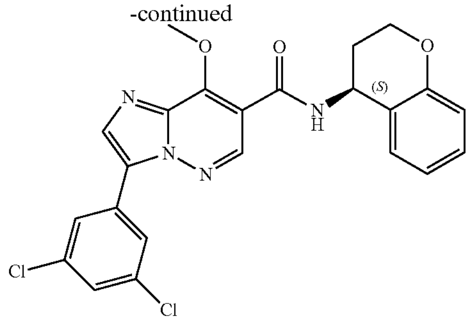

394

Into a 8-mL round-bottom flask, was placed DMF (3.0 mL), 3-(3,5-dichlorophenyl)-8-methoxyimidazo[1,2-b]pyridazine-7-carboxylic acid 19-3, (40.0 mg, 0.1 mmol, 1.0 equiv), (4S)-3,4-dihydro-2H-1-benzopyran-4-amine (19.5 mg, 0.1 mmol, 1.1 equiv), HATU (75.1 mg, 0.2 mmol, 1.7 equiv), DIEA (35.9 mg, 0.3 mmol, 2.3 equiv). The resulting solution was stirred for 1 hr at room temperature. The mixture was purified by Flash-Prep-HPLC with the following conditions (IntelFlash-1): Column, C18 silica gel; mobile phase, $H_2O$:ACN=70:30 increasing to $H_2O$:ACN=10:90 within 20 min; Detector, 254 nm. This resulted in 12 mg (21.6%) of 3-(3,5-dichlorophenyl)-N-[(4S)-3,4-dihydro-2H-1-benzopyran-4-yl]-8-methoxyimidazo[1,2-b]pyridazine-7-carboxamide (394) as a white solid. (300 MHz, $CDCl_3$, ppm): δ 10.08 (d, J=7.8 Hz, 1H), 9.10 (s, 1H), 7.92 (s, 2H), 7.51 (s, 1H), 7.37 (d, J=7.8 Hz, 1H), 7.41-7.33 (m, 1H), 7.21-7.15 (m, 1H), 6.94-6.84 (m, 2H), 5.48-5.46 (m, 1H), 4.46 (s, 3H), 4.37-4.29 (m, 2H), 2.39-2.30 (m, 1H), 2.25-2.17 (m, 1H).

| Compound | $^1$H NMR Spectra |
|---|---|
| 397-0 | (300 MHz, DMSO-d6, ppm) δ 10.1 (s, 1H), 9.15 (s, 1H), 7.95 (s, 2H), 7.65-7.60 (m, 2H), 7.35-7.40 (m, 1H) 7.20-7.15 (m, 1H), 6.99-6.85 (m, 2H), 6.20-6.00 (m, 1H), 5.70-5.30 (m, 3H), 4.36-4.25 (m, 2H), 3.20 (br, 1H), 2.45-2.20 (m, 2H) |
| 395 | (300 MHz, DMSO-d6, ppm) δ 10.05 (d, J = 15 Hz, 1H), 9.25 (s, 1H), 8.95 (s, 1H), 8.25 (s, 2H), 7.85-7.80 (m, 1H), 7.35-7.15 (m, 1H) 7.00-6.80 (m, 2H), 5.25-5.18 (m, 1H), 4.36-4.15 (m, 2H), 2.25-2.02 (m, 2H) |
| 398 | (300 MHz, CDCl3, ppm): δ 10.11 (d, J = 7.8 Hz, 1H), 9.12 (s, 1H), 7.93 (d, J = 1.9 Hz, 2H), 7.53 (s, 1H), 7.53-7.50 (m, 2H), 7.37 (d, J = 7.8 Hz, 1H), 7.21-7.16 (m, 1H), 6.94-6.85 (m, 2H), 5.48-5.44 (m, 1H), 4.97-4.88 (m, 2H), 4.37-4.30 (m, 2H), 2.37-2.32 (m, 1H), 2.24-2.19 (m, 1H), 1.64 (t, J = 7.2 Hz, 3H) |

Preparation Example 15: Compounds 450, 451, A408, A409, A421, A422, A460, A461, A462, A463 and A464 can be prepared adopting the process in schemes 20 and 21 shown below:

Scheme 20

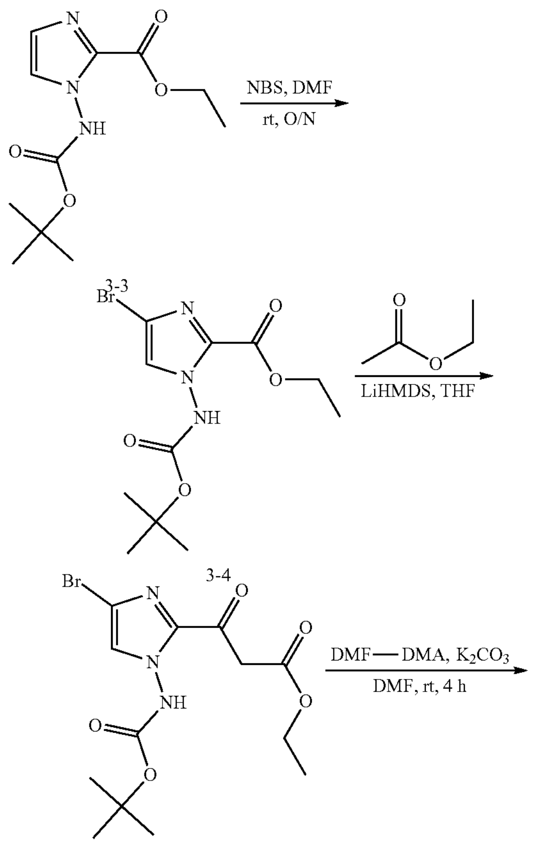

3-3

3-4

3-5

-continued

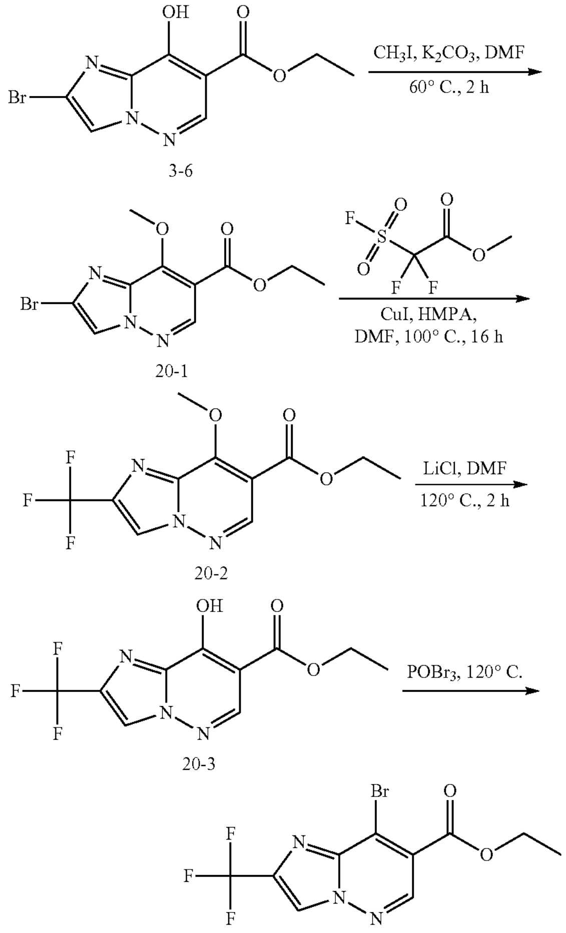

3-6

20-1

20-2

20-3

20-4

Scheme 21

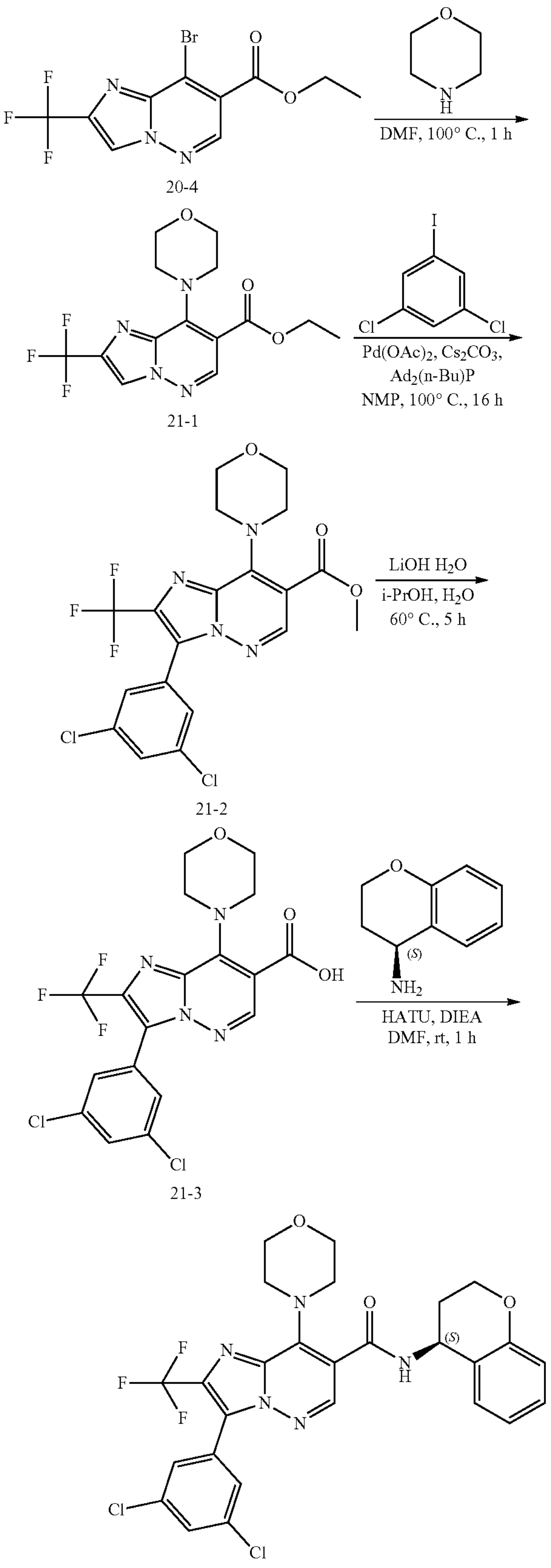

20-4

21-1

21-2

21-3

450

1. Synthesis of ethyl 4-bromo-1-[(tert-butoxycarbonyl)amino]imidazole-2-carboxylate (3-4)

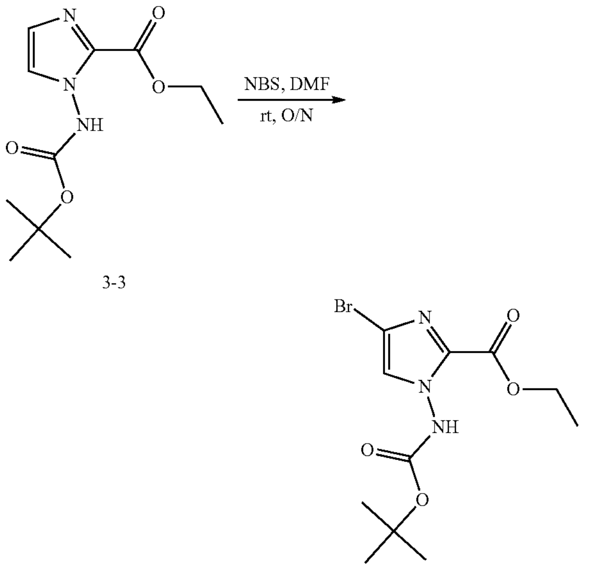

3-3

3-4

Into a 500-mL 3-necked round-bottom flask purged and maintained with an inert atmosphere of nitrogen, was placed ethyl 1-[(tert-butoxycarbonyl)amino]imidazole-2-carboxylate (3-3, 20.0 g, 78.4 mmol, 1.0 equiv), DMF (200.0 mL). This was followed by the addition of NBS (15.3 g, 86.2 mmol, 1.1 equiv) in several batches. The resulting solution was stirred for 1 overnight at room temperature. The reaction was then quenched by the addition of 1 L of water. The resulting solution was extracted with 3×300 mL of ethyl acetate and the organic layers combined. The resulting mixture was washed with 2×200 ml of brine. The mixture was dried over anhydrous sodium sulfate and concentrated. The residue was applied onto a silica gel column with ethyl acetate/petroleum ether (1:8). This resulted in 15 g (56.2%) of ethyl 4-bromo-1-[(tert-butoxycarbonyl)amino]imidazole-2-carboxylate (3-4) as a white solid.

2. Synthesis of ethyl 3-[4-bromo-1-[(tert-butoxycarbonyl)amino]imidazol-2-yl]-3-oxopropanoate (3-5)

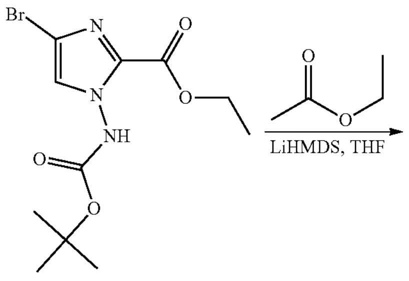

3-4

-continued

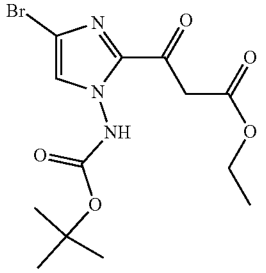

3-5

Into a 1-L 3-necked round-bottom flask purged and maintained with an inert atmosphere of nitrogen, was placed ethyl 4-bromo-1-[(tert-butoxycarbonyl)amino]imidazole-2-carboxylate (3-4, 14 g, 41.9 mmol, 1.0 equiv), THE (140.0 mL, 1728.0 mmol, 41.2 equiv), ethyl acetate (18.5 g, 209.5 mmol, 5.0 equiv). This was followed by the addition of LiHMDS (209.5 mL, 209.5 mmol, 5.0 equiv) dropwise with stirring at 0° C. The resulting solution was stirred for 30 min at 0° C. The reaction was then quenched by the addition of 200 mL of sat. $NH_4Cl$. The resulting solution was extracted with 3×200 mL of ethyl acetate and the organic layers combined. The resulting mixture was washed with 1×200 ml of brine. The mixture was dried over anhydrous sodium sulfate and concentrated. The residue was applied onto a silica gel column with ethyl acetate/petroleum ether (1:3). This resulted in 11.5 g (65.7%) of ethyl 3-[4-bromo-1-[(tert-butoxycarbonyl)amino]imidazol-2-yl]-3-oxopropanoate (3-5) as a yellow solid.

3. Synthesis of ethyl 2-bromo-8-hydroxyimidazo[1,2-b]pyridazine-7-carboxylate (3-6)

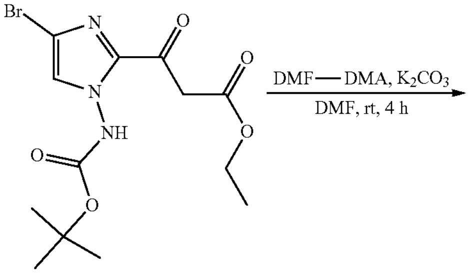

3-5

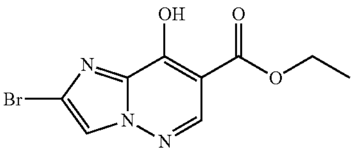

3-6

Into a 250-mL 3-necked round-bottom flask, was placed ethyl 3-[4-bromo-1-[(tert-butoxycarbonyl)amino]imidazol-2-yl]-3-oxopropanoate (3-5, 10.0 g, 26.6 mmol, 1.0 equiv), DMF (100.0 mL), $K_2CO_3$ (3.7 g, 26.6 mmol, 1.0 equiv), DMF-DMA (7.9 g, 66.5 mmol, 2.5 equiv). The resulting solution was stirred for 1 hr at room temperature. The reaction was then quenched by the addition of 300 mL of water. The solids were collected by filtration. The crude product was re-crystallized from ACN in the ratio of 10 v.

This resulted in 7.5 g (98.6%) of ethyl 2-bromo-8-hydroxyimidazo[1,2-b]pyridazine-7-carboxylate (3-6) as a white solid.

4. Synthesis of ethyl 2-bromo-8-methoxyimidazo[1,2-b]pyridazine-7-carboxylate (20-1)

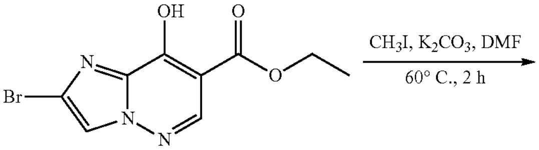

3-6

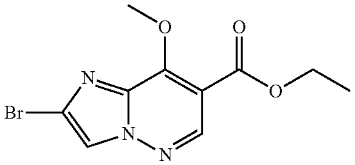

20-1

Into a 250-mL 3-necked round-bottom flask purged and maintained with an inert atmosphere of nitrogen, was placed ethyl 2-bromo-8-hydroxyimidazo[1,2-b]pyridazine-7-carboxylate (3-6, 8.0 g, 28.0 mmol, 1.0 equiv), DMF (80.0 mL), $K_2CO_3$ (7.7 g, 55.9 mmol, 2.0 equiv), $CH_3I$ (11.9 g, 83.891 mmol, 3.0 equiv). The resulting solution was stirred for 2 hr at 60° C. The residue was applied onto a C18 column with (25%~45% 8 min ACN in water). This resulted in 2.9 g (34.0%) of ethyl 2-bromo-8-methoxyimidazo[1,2-b]pyridazine-7-carboxylate (20-1) as a white solid.

5. Synthesis of ethyl 8-methoxy-2-(trifluoromethyl)imidazo[1,2-b]pyridazine-7-carboxylate (20-2)

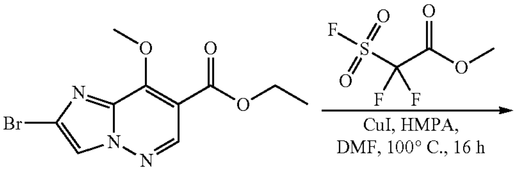

20-1

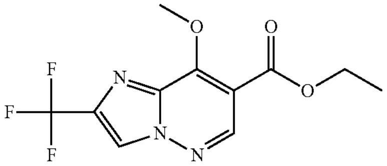

20-2

Into a 40-mL vial purged and maintained with an inert atmosphere of nitrogen, was placed ethyl 2-bromo-8-methoxyimidazo[1,2-b]pyridazine-7-carboxylate (20-1, 300.0 mg, 1.0 mmol, 1.0 equiv), DMF (6.0 mL), methyl 2,2-difluoro-2-sulfoacetate (960.2 mg, 5.0 mmol, 5.0 equiv), HMPA (895.7 mg, 5.0 mmol, 5.0 equiv), CuI (761.5 mg, 4.0 mmol, 4.0 equiv). The resulting solution was stirred for 16 hr at 100° C. The solids were filtered out. The residue was applied onto a C18 column with (25%~45% 8 min ACN in $H_2O$ (0.1% TFA)). This resulted in 170 mg (56.6%) of ethyl 8-methoxy-2-(trifluoromethyl)imidazo[1,2-b]pyridazine-7-carboxylate (20-2) as a yellow solid.

6. Synthesis of ethyl 8-hydroxy-2-(trifluoromethyl) imidazo[1,2-b]pyridazine-7-carboxylate (20-3)

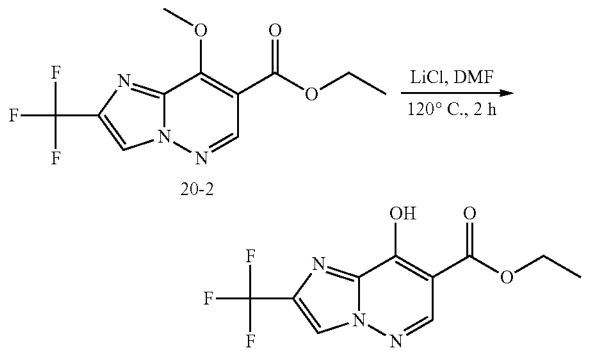

20-2

20-3

Into a 40-mL vial purged and maintained with an inert atmosphere of nitrogen, was placed ethyl 8-methoxy-2-(trifluoromethyl)imidazo[1,2-b]pyridazine-7-carboxylate (20-2, 1.8 g, 6.2 mmol, 1.0 equiv), LiCl (2.6 g, 62.2 mmol, 10.0 equiv), DMF (18.0 mL). The resulting solution was stirred for 2 hr at 120 degrees C. The residue was applied onto a C18 column with (75%~83% 8 min ACN in $H_2O$ (0.1% TFA)). This resulted in 900 mg (52.5%) of ethyl 8-hydroxy-2-(trifluoromethyl)imidazo[1,2-b]pyridazine-7-carboxylate (20-3) as a yellow solid.

7. Synthesis of ethyl 8-bromo-2-(trifluoromethyl) imidazo[1,2-b]pyridazine-7-carboxylate (20-4)

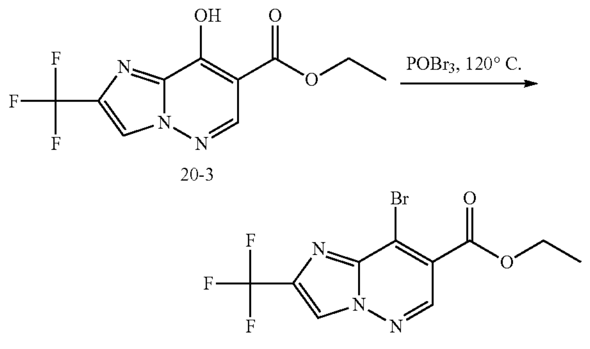

20-3

20-4

Into a 40-mL vial purged and maintained with an inert atmosphere of nitrogen, was placed ethyl 8-hydroxy-2-(trifluoromethyl)imidazo[1,2-b]pyridazine-7-carboxylate (20-3, 400.0 mg, 1.4 mmol, 1.0 equiv), $POBr_3$ (3333.7 mg, 11.6 mmol, 8.0 equiv). The resulting solution was stirred for 30 min at 120° C. The reaction was then quenched by the addition of 10 mL of water/ice. The pH value of the solution was adjusted to 8 with $Na_2CO_3$. The resulting solution was extracted with 3×10 mL of ethyl acetate and the organic layers combined. The resulting mixture was washed with 1×20 ml of brine. The mixture was dried over anhydrous sodium sulfate and concentrated. This resulted in 520 mg (97.3%) of ethyl 8-bromo-2-(trifluoromethyl)imidazo[1,2-b]pyridazine-7-carboxylate (20-4) as a yellow solid.

8. Synthesis of ethyl 8-(morpholin-4-yl)-2-(trifluoromethyl)imidazo[1,2-b]pyridazine-7-carboxylate (21-1)

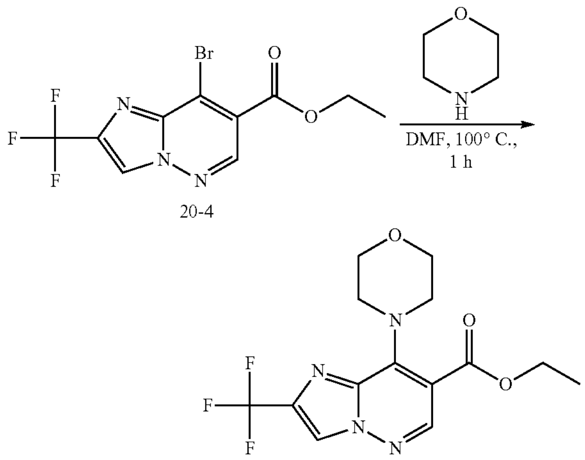

20-4

21-1

Into a 8-mL vial, was placed ethyl 8-bromo-2-(trifluoromethyl)imidazo[1,2-b]pyridazine-7-carboxylate (20-4, 150.0 mg, 0.4 mmol, 1.0 equiv), DMF (1.5 mL), morpholine (193.3 mg, 2.2 mmol, 5.0 equiv). The resulting solution was stirred for 1 hr at 100° C. The residue was applied onto a C18 column with (80%~90% 6 min ACN in $H_2O$ (0.1% FA)). This resulted in 110 mg (72.0%) of ethyl 8-(morpholin-4-yl)-2-(trifluoromethyl)imidazo[1,2-b]pyridazine-7-carboxylate (21-1) as a white solid.

9. Synthesis of ethyl 3-(3,5-dichlorophenyl)-8-(morpholin-4-yl)-2-(trifluoromethyl)imidazo[1,2-b] pyridazine-7-carboxylate (21-2)

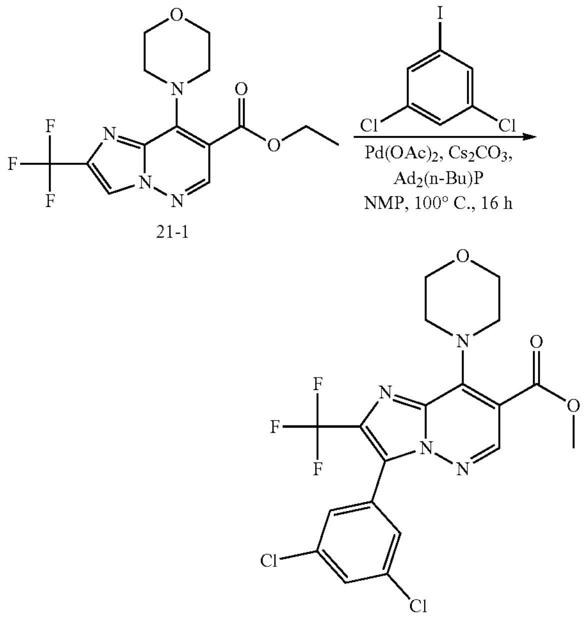

21-1

21-2

Into a 8-mL vial purged and maintained with an inert atmosphere of nitrogen, was placed ethyl 8-(morpholin-4-yl)-2-(trifluoromethyl)imidazo[1,2-b]pyridazine-7-carboxylate (21-1, 90.00 mg, 0.3 mmol, 1.0 equiv), NMP (1.8 mL), 1,3-dichloro-5-iodobenzene (214.0 mg, 0.8 mmol, 3.0 equiv), $Cs_2CO_3$ (170.3 mg, 0.5 mmol, 2.0 equiv), $Pd(AcO)_2$ (11.7 mg, 0.05 mmol, 0.2 equiv), $Ad_2$(n-Bu)P (28.0 mg, 0.08 mmol, 0.3 equiv). The resulting solution was stirred overnight at 100° C. The residue was applied onto a silica gel column with ethyl acetate/petroleum ether (1:5). This resulted in 110 mg (72.2%) of ethyl 3-(3,5-dichlorophenyl)-8-(morpholin-4-yl)-2-(trifluoromethyl)imidazo[1,2-b] pyridazine-7-carboxylate (21-2) as a white solid.

10. Synthesis of 3-(3,5-dichlorophenyl)-8-(morpholin-4-yl)-2-(trifluoromethyl)imidazo[1,2-b] pyridazine-7-carboxylic Acid (21-3)

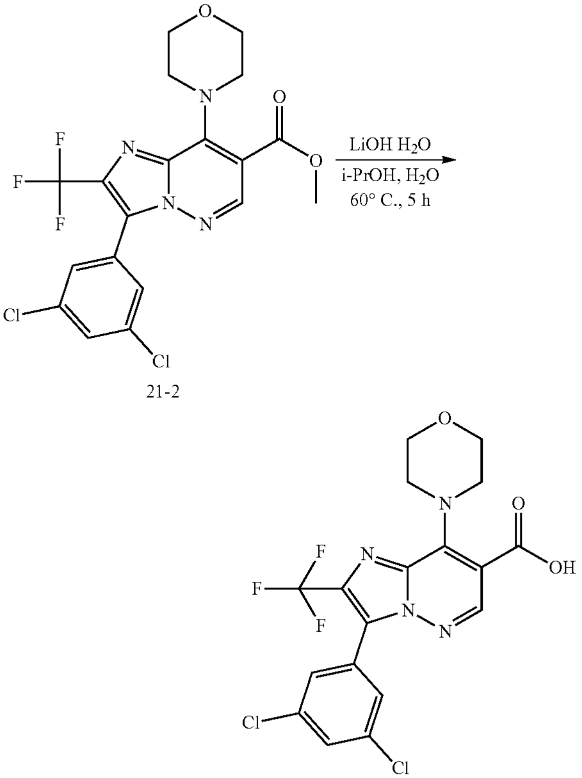

21-2

21-3

Into a 8-mL vial, was placed ethyl 3-(3,5-dichlorophenyl)-8-(morpholin-4-yl)-2-(trifluoromethyl)imidazo[1,2-b] pyridazine-7-carboxylate (21-2, 110.0 mg, 0.2 mmol, 1.0 equiv), i-PrOH (2.1 mL), $H_2O$ (0.7 mL), LiOH·$H_2O$ (75.4 mg, 1.8 mmol, 8.0 equiv). The resulting solution was stirred for 5 hr at 60 degrees C. The residue was applied onto a C18 column with (80%~90% 6 min ACN in $H_2O$ (0.1% FA)). This resulted in 70 mg (65.3%) of 3-(3,5-dichlorophenyl)-8-(morpholin-4-yl)-2-(trifluoromethyl)imidazo[1,2-b] pyridazine-7-carboxylic acid (21-3) as a white solid.

11. Synthesis of 3-(3,5-dichlorophenyl)-N-[(4S)-3,4-dihydro-2H-1-benzopyran-4-yl]-8-(morpholin-4-yl)-2-(trifluoromethyl)imidazo[1,2-b]pyridazine-7-carboxamide (450)

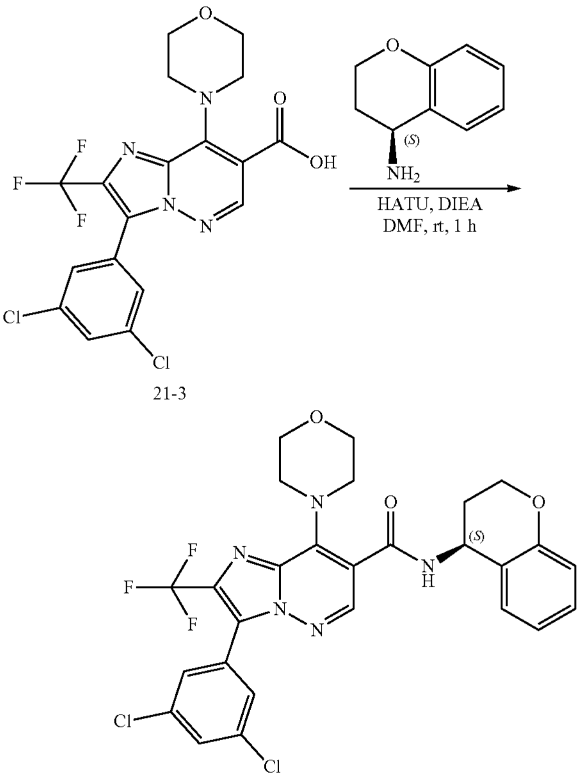

21-3

450

Into a 8-mL vial, was placed 3-(3,5-dichlorophenyl)-8-(morpholin-4-yl)-2-(trifluoromethyl)imidazo[1,2-b] pyridazine-7-carboxylic acid (21-3, 66.0 mg, 0.1 mmol, 1.0 equiv), DMF (2.0 mL), (4S)-3,4-dihydro-2H-1-benzopyran-4-amine (32.0 mg, 0.2 mmol, 1.5 equiv), DIEA (55.5 mg, 0.4 mmol, 3.0 equiv), HATU (81.6 mg, 0.2 mmol, 1.5 equiv). The resulting solution was stirred for 1 hr at room temperature. The residue was applied onto a C18 column with (90%~98% 6 min ACN in $H_2O$ (0.1% FA)). This resulted in 35.1 mg (41.4%) of 3-(3,5-dichlorophenyl)-N-[(4S)-3,4-dihydro-2H-1-benzopyran-4-yl]-8-(morpholin-4-yl)-2-(trifluoromethyl)imidazo[1,2-b]pyridazine-7-carboxamide (450) as a white solid. (300 MHz, DMSO-d6, ppm): δ 9.08 (d, J=8.0 Hz, 1H), 8.36 (s, 1H), 7.83 (t, J=1.9 Hz, 1H), 7.66 (d, J=1.9 Hz, 2H), 7.32 (d, J=7.8 Hz, 1H), 7.21-7.15 (m, 1H), 6.94-6.89 (m, 1H), 6.82-6.79 (m, 1H), 5.23-5.16 (m, 1H), 4.30-4.20 (m, 2H), 3.94-3.81 (m, 8H), 2.27-2.16 (m, 1H), 2.08-2.01 (m, 1H).

| Compound | $^1H$ NMR Spectra |
|---|---|
| 451 | (300 MHz, DMSO-d6, ppm): δ 9.01 (d, J = 8.1 Hz, 1H), 8.23 (s, 1H), 7.82 (t, J = 1.9 Hz, 1H), 7.64 (d, J = 1.9 Hz, 2H), 7.31-7.28 (m, 1H), 7.20-7.14 (m, 1H), 6.93-6.88 (m, 1H), 6.80 (d, J = 8.1, Hz, 1H), 5.20-5.14 (m, 1H), 4.27-4.21 (m, 2H), 3.43 (s, 6H), 2.27-2.13 (m, 1H), 2.14-1.98 (m, 1H) |

-continued

| Compound | $^1$H NMR Spectra |
|---|---|
| A408 | (400 MHz, DMSO-d6) δ ppm 8.99 (d, J = 8.11 Hz, 1H) 8.20 (s, 1 H) 7.73 (d, J = 1.90 Hz, 2H) 7.62-7.69 (m, 1H) 7.32 (d, J = 6.97 Hz, 1H) 7.12-7.21 (m, 1H) 6.91 (td, J = 7.45, 0.95 Hz, 1H) 6.80 (d, J = 8.24 Hz, 1H) 5.15-5.24 (m, 1H) 4.18-4.31 (m, 2H) 3.80-3.94 (m, 4H) 3.71-3.80 (m, 4H) 2.47 (s, 3H) 2.11-2.27 (m, 1H) 1.98-2.11 (m, 1H) |
| A409 | (400 MHz, DMSO-d6) δ ppm 8.93 (d, J = 8.11 Hz, 1H) 8.12 (s, 1H) 7.73 (d, J = 1.90 Hz, 2H) 7.64 (t, J = 1.90 Hz, 1H) 7.31 (d, J = 7.10 Hz, 1H) 7.16 (t, J = 7.40 Hz, 1H) 6.91 (td, J = 7.48, 1.01 Hz, 1H) 6.79 (dd, J = 8.24, 0.76 Hz, 1H) 5.14-5.21 (m, 1H) 4.16-4.31 (m, 2H) 3.30 (s, 6H) 2.47 (s, 3H) 2.09-2.25 (m, 1H) 1.96-2.09 (m, 1H) |
| A421 | (400 MHz, DMSO-d6, ppm) δ 8.99 (d, J = 7.98 Hz, 1H), 8.06 (s, 1H), 7.74 (d, J = 8.62 Hz, 2H), 7.30 (d, J = 7.60 Hz, 1H), 7.15 (t, J = 7.30 Hz, 1H), 6.89 (t, J = 7.41 Hz, 1H), 6.78 (d, J = 8.11 Hz, 1H), 5.18 (br d, J = 7.73 Hz, 1H), 4.19-4.29 (m, 2H), 3.69-3.93 (m, 8H), 2.52-2.55 (m, 1H), 2.22 (s, 3H), 1.20-1.24 (m, 1H) |
| A422 | (400 MHz, DMSO-d6, ppm) δ 8.99 (d, J = 8.11 Hz, 1H), 8.14 (s, 1H), 7.65-7.73 (m, 1H), 7.29-7.39 (m, 2H), 7.17 (t, J = 7.60 Hz, 1H), 6.91 (t, J = 7.10 Hz, 1H), 6.79 (d, J = 8.11 Hz, 1H), 5.16-5.22 (m, 1H), 4.20-4.30 (m, 2H), 3.72-3.92 (m, 8H), 2.16-2.38 (m, 4H), 1.99-2.08 (m, 1H) |
| A460 | (400 MHz, DMSO-d6, ppm) δ 8.93 (d, 1H), 8.06 (s, 1H), 7.67 (m, 1H), 7.36 (m, 1H), 7.30 (d, 1H), 7.16 (t, 1H), 6.90 (t, 1H), 6.79 (d, 1H), 5.17 (q, 1H), 4.24 (m, 2H), 3.41 (s, 6H), 2.35 (s, 3H), 1.97-2.20 (m, 2H) |
| A461 | (400 MHz, DMSO-d6, ppm) δ 8.92 (d, 1H), 8.02 (s, 1H), 8.00 (d, 1H), 7.64 (m, 1H), 7.28 (d, 1H), 7.16 (t, 1H), 6.89 (t, 1H), 6.79 (d, 1H), 5.17 (q, 1H), 4.24 (m, 2H), 3.41 (s, 6H), 2.27 (s, 3H), 1.96-2.19 (m, 2H) |
| A462 | 400 MHz, DMSO-d6) δ ppm 8.91 (d, J = 8.1 Hz, 1H), 8.02 (s, 1H), 7.27-7.44 (m, 3H), 7.16 (t, J = 7.4 Hz, 1H), 6.89 (td, J = 7.5, 1.1 Hz, 1H), 6.79 (dd, J = 8.2, 1.1 Hz, 1H), 5.14-5.21 (m, 1H), 3.49 (s, 6H), 2.52-2.52 (m, 2H), 2.21 (s, 3H), 2.10-2.21 (m, 1H), 1.95-2.05 (m, 1H) |
| A463 | (400 MHz, DMSO-d6) δ ppm 8.92 (dd, J = 8.1, 2.3 Hz, 1H), 8.01 (s, 1H), 7.86 (dd, J = 8.3, 3.0 Hz, 1H), 7.50 (ddd, J = 8.6, 7.2, 3.0 Hz, 1H), 7.28 (d, J = 7.7 Hz, 1H), 7.16 (t, J = 7.4 Hz, 1H), 6.89 (t, J = 7.5 Hz, 1H), 6.79 (d, J = 8.3 Hz, 1H), 5.13-5.20 (m, 1H), 3.52 (s, 6H), 2.52-2.56 (m, 2H), 2.28 (s, 3H), 2.10-2.21 (m, 1H), 1.95-2.05 (m, 1H) |
| A464 | (400 MHz, DMSO-d6) δ ppm 8.95 (d, J = 8.1 Hz, 1H), 8.00 (s, 1H), 7.30-7.41 (m, 3H), 7.00-7.30 (m, 2H), 6.91 (td, J = 7.6, 1.1 Hz, 1H), 6.75 (dd, J = 8.1, 1.1 Hz, 1H), 5.15-5.20 (m, 1H), 4.20-4.25 (m, 2H), 3.51 (s, 6H), 2.21 (s, 3H), 2.11-2.21 (m, 1H), 1.95-2.05 (m, 1H) |

Preparation Example 16: Compounds 511 and 512 can be prepared adopting the process in scheme 22 below:

Scheme 22

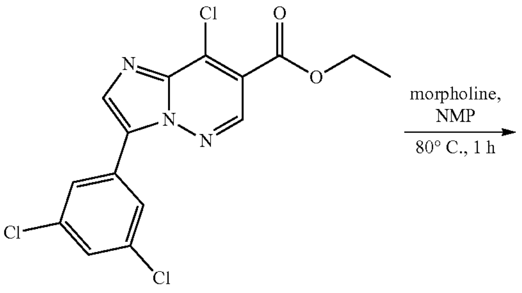

17-5

-continued

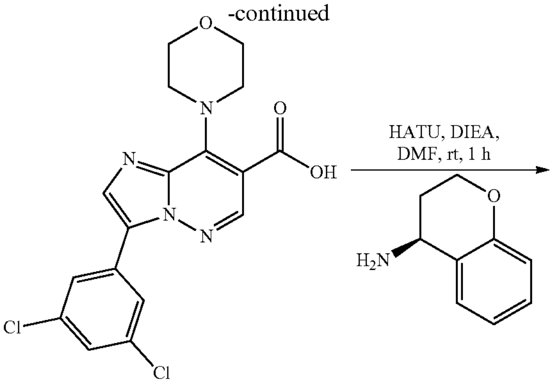

22-2

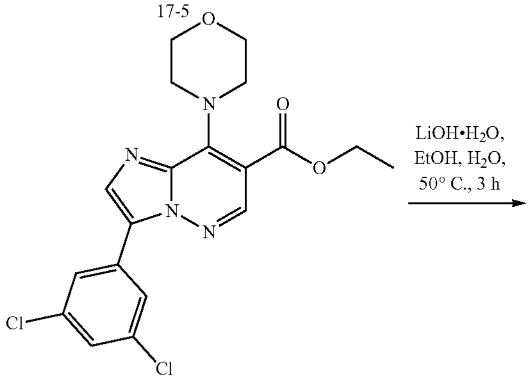

22-1

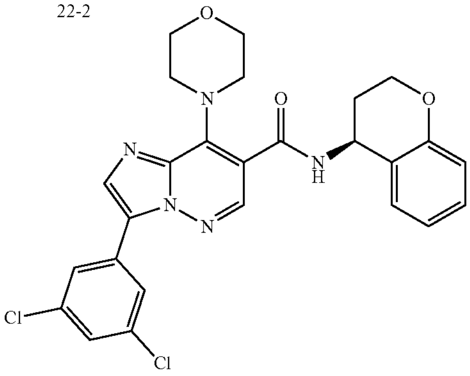

511

1. Synthesis of ethyl 3-(3,5-dichlorophenyl)-8-(morpholin-4-yl)imidazo[1,2-b]pyridazine-7-carboxylate (22-1)

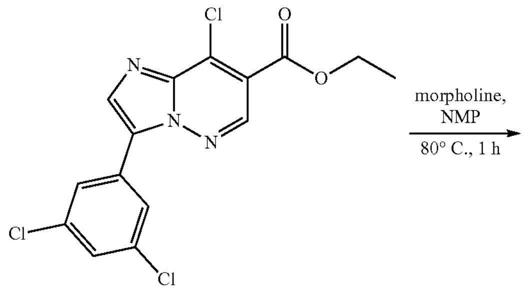

17-5

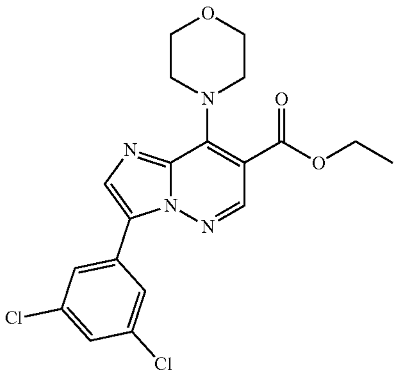

22-1

Into a 40-mL round-bottom flask, was placed NMP (5.0 mL), ethyl 8-chloro-3-(3,5-dichlorophenyl)imidazo[1,2-b]pyridazine-7-carboxylate (17-5, 100.0 mg, 0.2 mmol, 1.0 equiv), morpholine (0.5 mL, 5.7 mmol, 23.6 equiv). The resulting solution was stirred for 1 hr at 80° C. The reaction was then quenched by the addition of 10 mL of water. The resulting solution was extracted with 3×20 mL of ethyl acetate and the organic layers combined and dried over anhydrous sodium sulfate and concentrated under vacuum. This resulted in 65 mg (64.0%) of ethyl 3-(3,5-dichlorophenyl)-8-(morpholin-4-yl)imidazo[1,2-b]pyridazine-7-carboxylate (22-1) as a yellow solid.

2. Synthesis of 3-(3,5-dichlorophenyl)-8-(morpholin-4-yl)imidazo[1,2-b]pyridazine-7-carboxylic Acid (22-2)

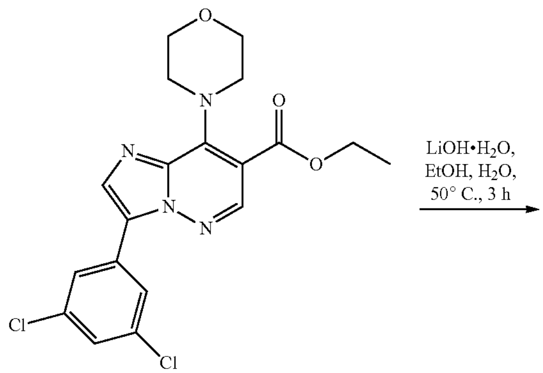

22-1

-continued

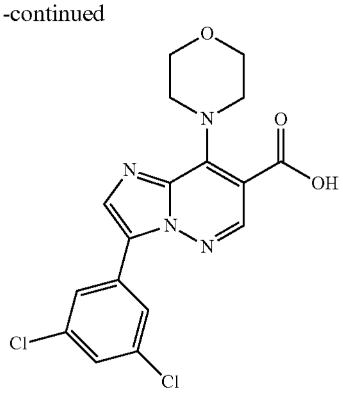

22-2

Into a 40-mL round-bottom flask, was placed EtOH (2.0 mL), $H_2O$ (1.5 mL), ethyl 3-(3,5-dichlorophenyl)-8-(morpholin-4-yl)imidazo[1,2-b]pyridazine-7-carboxylate (22-1, 65.0 mg, 0.1 mmol, 1.0 equiv), LiOH·$H_2O$ (50.0 mg, 1.2 mmol, 7.7 equiv). The resulting solution was stirred for 3 hr at 50° C. HCl (6 mol/L) was employed to adjust the pH to 4. The resulting solution was extracted with 3×20 mL of ethyl acetate and the organic layers combined and dried over anhydrous sodium sulfate and concentrated under vacuum. This resulted in 40 mg (65.9%) of 3-(3,5-dichlorophenyl)-8-(morpholin-4-yl)imidazo[1,2-b]pyridazine-7-carboxylic acid (22-2) as a yellow solid.

3. Synthesis of 3-(3,5-dichlorophenyl)-N-[(4S)-3,4-dihydro-2H-1-benzopyran-4-yl]-8-(morpholin-4-yl)imidazo[1,2-b]pyridazine-7-carboxamide (511)

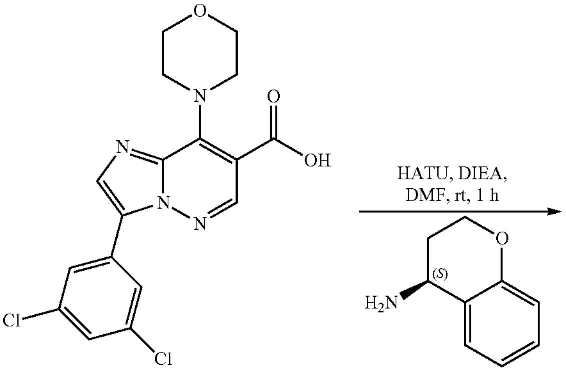

22-2

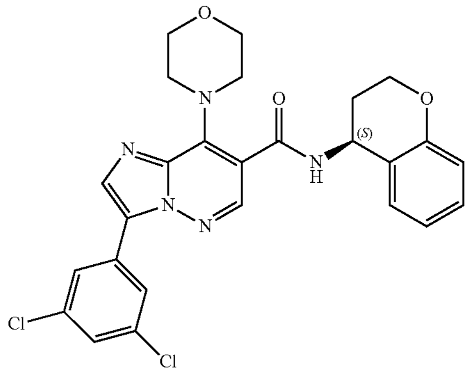

511

Into a 40-mL round-bottom flask, was placed DMF (5.0 mL), 3-(3,5-dichlorophenyl)-8-(morpholin-4-yl)imidazo[1, 2-b]pyridazine-7-carboxylic acid (22-2, 40.0 mg, 0.1 mmol, 1.0 equiv), (4S)-3,4-dihydro-2H-1-benzopyran-4-amine (17.0 mg, 0.1 mmol, 1.12 equiv), HATU (65.0 mg, 0.2 mmol, 1.7 equiv), DIEA (38.0 mg, 0.3 mmol, 2.9 equiv). The resulting solution was stirred for 1 hr at room temperature. The crude product was purified by Flash-Prep-HPLC with the following conditions (IntelFlash-1): Column, C18 silica gel; mobile phase, $H_2O$:ACN=50:50 increasing to $H_2O$:ACN=10:90 within 20 min; Detector, 254 nm. product was obtained. This resulted in 37.8 mg (70.9%) of 3-(3,5-dichlorophenyl)-N-[(4S)-3,4-dihydro-2H-1-benzopyran-4-yl]-8-(morpholin-4-yl)imidazo[1,2-b]pyridazine-7-carboxamide (511) as a white solid. (300 MHz, $CDCl_3$, ppm) δ 9.03 (d, J=8.1 Hz, 1H), 8.37 (s, 1H), 8.31 (s, 1H), 8.27 (d, J=1.8 Hz, 1H), 7.60 (t, J=1.8 Hz, 1H), 7.34 (d, J=1.8 Hz, 1H), 7.21-7.15 (m, 1H), 6.95-6.90 (m, 1H), 6.80-6.80 (m, 1H), 5.23-5.20 (m, 1H), 4.27-4.24 (m, 2H), 3.93-3.78 (m, 8H), 2.23-2.21 (m, 1H), 2.10-2.07 (m, 1H).

$^1H$ NMR spectra for 512: (300 MHz, $CDCl_3$, ppm) δ 8.36 (s, 1H), 7.98 (d, J=1.9 Hz, 2H), 7.90 (s, 1H), 7.37-7.35 (m, 1H), 7.32-7.22 (m, 2H), 7.03-6.86 (m, 2H), 6.67 (d, J=7.6 Hz, 1H), 5.42-5.34 (m, 1H), 4.43-4.31 (m, 1H), 4.29-4.16 (m, 1H), 3.46 (s, 6H), 2.43-2.36 (m, 1H), 2.27-2.14 (m, 1H) Preparation Example 17: Compound 558 was prepared according to the scheme 23 shown below. Compound 559 can be prepared by adopting the process described in scheme 23 by someone skilled in the art.

Scheme 23

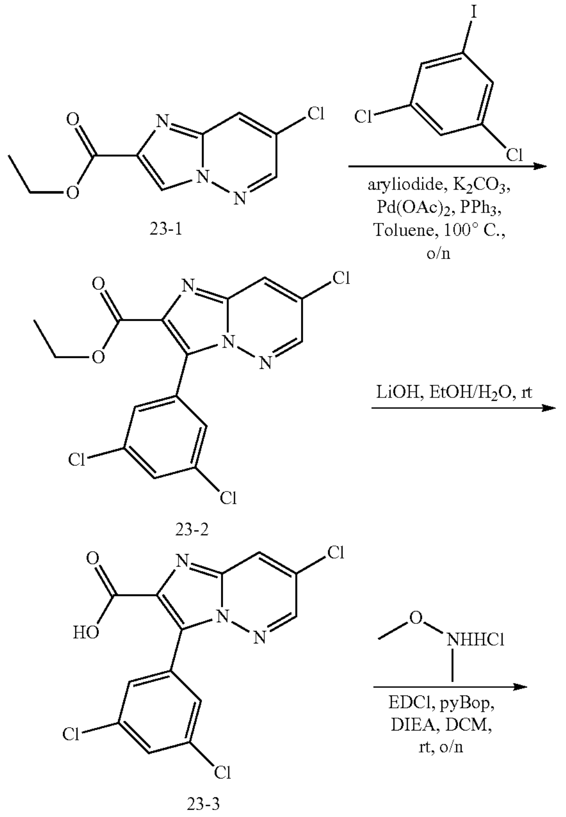

-continued

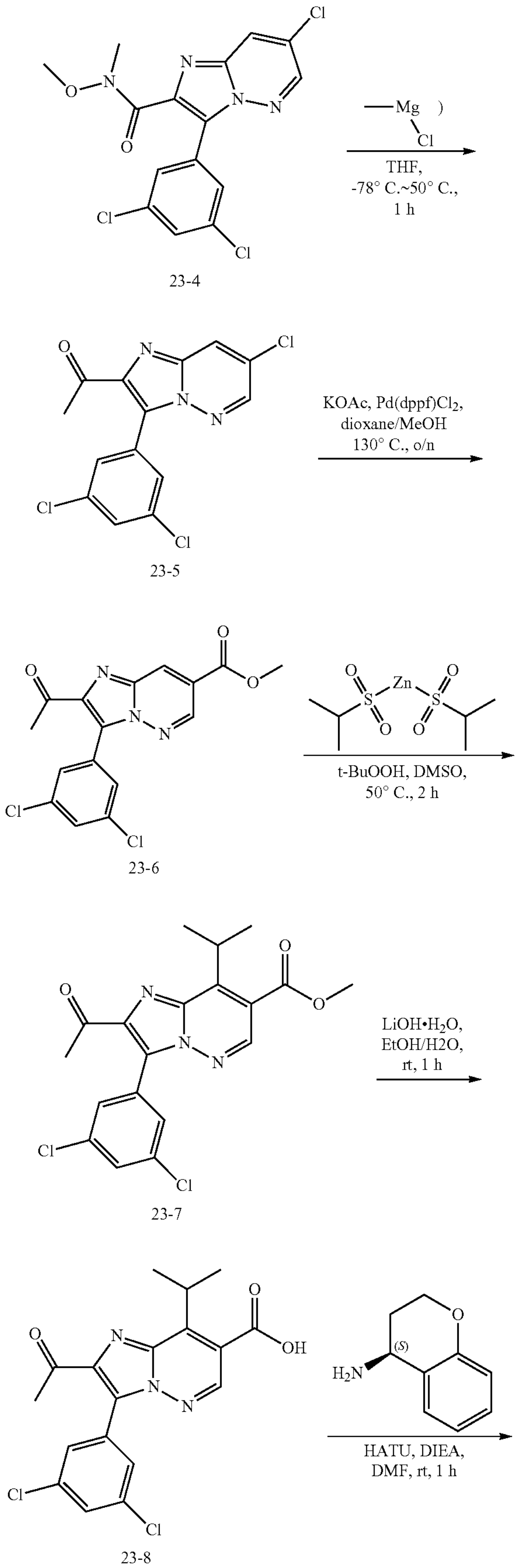

-continued

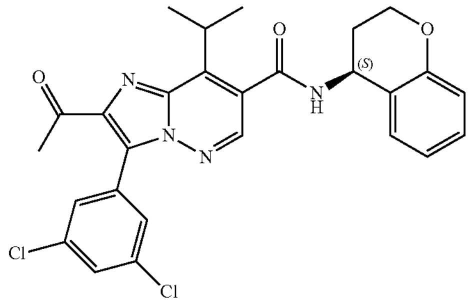

558

1. Synthesis of ethyl 7-chloro-3-(3,5-dichlorophenyl)imidazo[1,2-b]pyridazine-2-carboxylate (23-2)

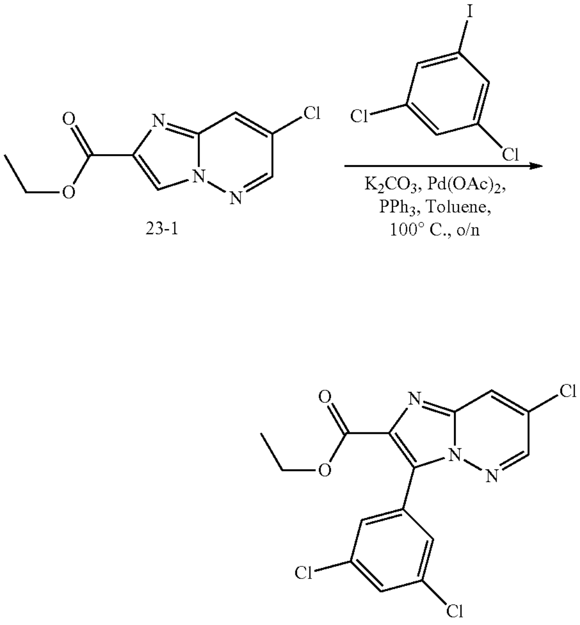

23-1

23-2

To a stirred mixture of ethyl 7-chloroimidazo[1,2-b]pyridazine-2-carboxylate (23-1, 1.0 g, 4.4 mmol, 1.0 equiv) and 1,3-dichloro-5-iodobenzene (1.8 g, 6.6 mmol, 1.5 equiv) in toluene (10 mL, 105.0 mmol, 23.7 equiv) were added $K_2CO_3$ (1.2 g, 8.9 mmol, 2.0 equiv) and $Pd(OAc)_2$ (0.1 g, 0.4 mmol, 0.1 equiv) and $PPh_3$ (0.2 g, 0.9 mmol, 0.2 equiv) at room temperature under nitrogen atmosphere. The resulting mixture was stirred for overnight at 100° C. under nitrogen atmosphere. The mixture was allowed to cool down to room temperature. The resulting mixture was concentrated under vacuum. The residue was purified by silica gel column chromatography, eluted with PE/EA (5:1) to afford ethyl 7-chloro-3-(3,5-dichlorophenyl)imidazo[1,2-b]pyridazine-2-carboxylate (23-2, 1.2 g, 73.0%) as a yellow oil.

2. Synthesis of 7-chloro-3-(3,5-dichlorophenyl)imidazo[1,2-b]pyridazine-2-carboxylic Acid (23-3)

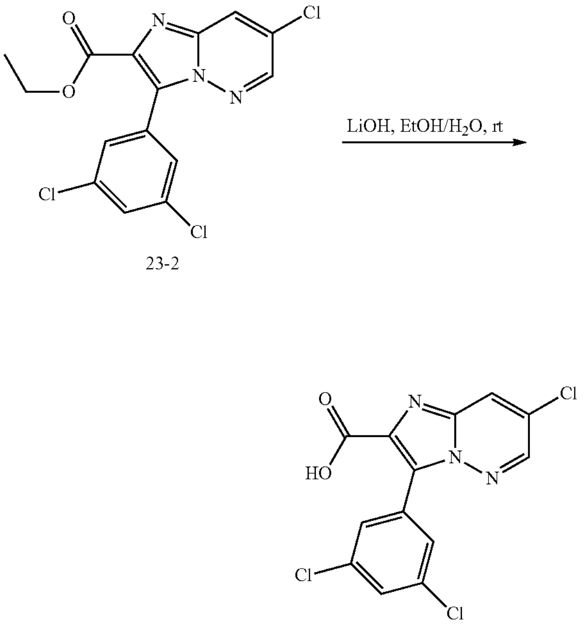

23-2

23-3

To a stirred mixture of ethyl 7-chloro-3-(3,5-dichlorophenyl)imidazo[1,2-b]pyridazine-2-carboxylate (23-2, 1.0 g, 2.7 mmol, 1.0 equiv) in EtOH (8 mL) and $H_2O$ (4 mL) was added $LiOH{\cdot}H_2O$ (1.13 g, 27.0 mmol, 10.0 equiv) at room temperature. The resulting mixture was stirred for 2 h at room temperature. The resulting mixture was concentrated under vacuum. The resulting mixture was diluted with water (50 mL). The mixture was acidified to pH 4 with HCl (aq.). The precipitated solids were collected by filtration and washed with water (2×10 mL). The resulting solid was dried under infrared light.

3. Synthesis of 7-chloro-3-(3,5-dichlorophenyl)-N-methoxy-N-methylimidazo[1,2-b]pyridazine-2-carboxamide (23-4)

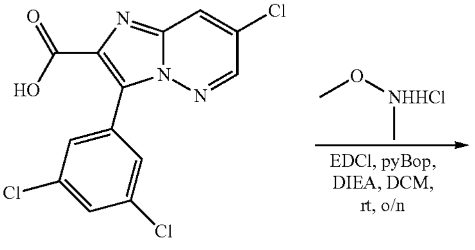

23-3

-continued

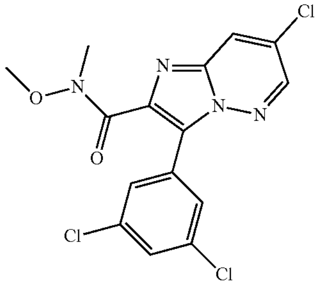

23-4

To a stirred mixture of 7-chloro-3-(3,5-dichlorophenyl) imidazo[1,2-b]pyridazine-2-carboxylic acid (23-3, 1.0 g, 3.0 mmol, 1.0 equiv) and N,O-dimethylhydroxylamine (0.3 g, 4.4 mmol, 1.5 equiv) in DCM (10 mL, 157.3 mmol, 53.9 equiv) were added EDCI (0.6 g, 2.9 mmol, 1.0 equiv) and PyBOP (1.5 g, 2.9 mmol, 1.0 equiv) and DIEA (1.1 g, 8.7 mmol, 3.0 equiv) at room temperature. The resulting mixture was stirred for overnight at room temperature. The resulting mixture was concentrated under vacuum. The residue was purified by reverse flash chromatography with the following conditions: column, silica gel; mobile phase, MeCN in water, 50% to 90% gradient in 10 min; detector, UV 254 nm to afford 400 mg of 7-chloro-3-(3,5-dichlorophenyl)-N-methoxy-N-methylimidazo[1,2-b]pyridazine-2-carboxamide (23-4, 35.5%) as a yellow oil.

4. Synthesis of afford 1-[7-chloro-3-(3,5-dichlorophenyl)imidazo[1,2-b]pyridazin-2-yl]ethenone (23-5)

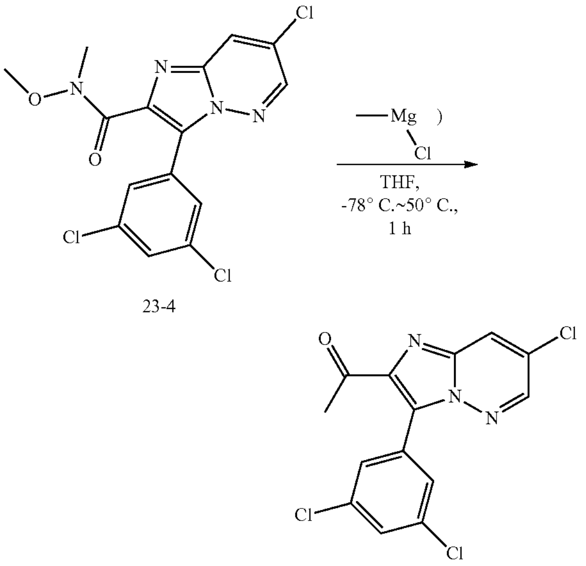

23-4

23-5

To a stirred mixture of 7-chloro-3-(3,5-dichlorophenyl)-N-methoxy-N-methylimidazo[1,2-b]pyridazine-2-carboxamide (23-4, 80.0 mg, 0.2 mmol, 1.0 equiv) in THF (2 mL, 24.7 mmol, 119.0 equiv) was added chloromethylmagnesium (77.6 mg, 1.0 mmol, 5.0 equiv) at −78° C. under nitrogen atmosphere. The resulting mixture was stirred for 60 min at 50° C. under nitrogen atmosphere. The reaction was quenched with sat. $NH_4Cl$ (aq.) at room temperature. The resulting mixture was extracted with EtOAc (2×20 mL). The combined organic layers were washed with brine (2×4 mL), dried over anhydrous $Na_2SO_4$. After filtration, the filtrate was concentrated under reduced pressure. The residue was purified by Prep-TLC (PE/EA 4:1) to afford 1-[7-chloro-3-(3,5-dichlorophenyl)imidazo[1,2-b]pyridazin-2-yl]ethanone (23-5, 40 mg, 56.6%) as a light yellow solid.

5. Synthesis of methyl 2-acetyl-3-(3,5-dichlorophenyl)imidazo[1,2-b]pyridazine-7-carboxylate (23-6)

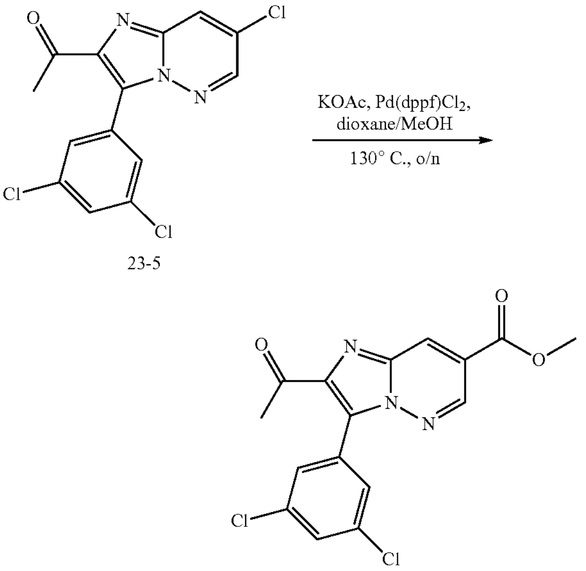

23-5

23-6

To a solution of 1-[7-chloro-3-(3,5-dichlorophenyl)imidazo[1,2-b]pyridazin-2-yl]ethanone (23-5, 40.0 mg, 0.1 mmol, 1.0 equiv) in 1 mL MeOH and dioxane (2 mL) was added KOAc (34.6 mg, 0.4 mmol, 3.0 equiv) and Pd(dppf) $Cl_2CH_2Cl_2$ (9.6 mg, 0.01 mmol, 0.1 equiv) in a pressure tank. The mixture was purged with nitrogen for 2 min and then was pressurized to 30 atm with carbon monoxide at 130 degrees C. for overnight. The reaction mixture was cooled to room temperature and filtered to remove insoluble solids. The residue was purified by Prep-TLC (PE/EA 3:1) to afford 20 mg of methyl 2-acetyl-3-(3,5-dichlorophenyl)imidazo[1,2-b]pyridazine-7-carboxylate (23-6, 46.8%) as a yellow solid.

6. Synthesis of afford methyl 2-acetyl-3-(3,5-dichlorophenyl)-8-isopropylimidazo[1,2-b]pyridazine-7-carboxylate (23-7)

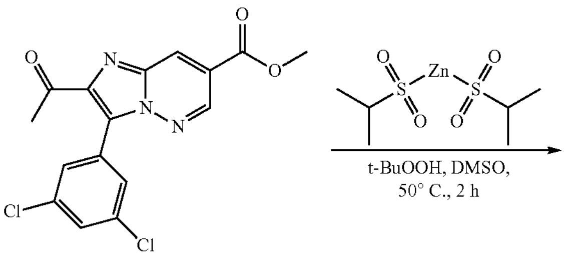

23-6

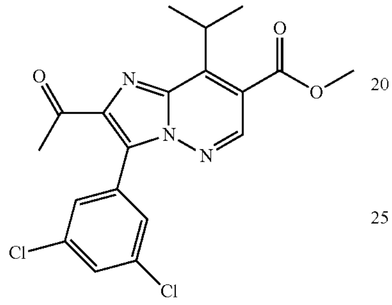

23-7

To a stirred mixture of methyl 2-acetyl-3-(3,5-dichlorophenyl)imidazo[1,2-b]pyridazine-7-carboxylate (23-6, 20.0 mg, 0.05 mmol, 1.0 equiv) and 2-[(propane-2-sulfonyl)zinciosulfonyl]propane (46.1 mg, 0.2 mmol, 3.0 equiv) in DMSO (2 mL) was added t-BuOOH (28.6 mg, 0.3 mmol, 5.0 equiv) at room temperature. The resulting mixture was stirred for 2 h at 50° C. The mixture was allowed to cool down to room temperature. The resulting mixture was diluted with water (10 mL). The resulting mixture was extracted with EtOAc (2×10 mL). The combined organic layers were washed with brine (2×5 mL), dried over anhydrous $Na_2SO_4$. After filtration, the filtrate was concentrated under reduced pressure. The residue was purified by Prep-TLC (PE/EA 2:1) to afford methyl 2-acetyl-3-(3,5-dichlorophenyl)-8-isopropylimidazo[1,2-b]pyridazine-7-carboxylate (23-7, 10 mg, 44.8%) as a yellow oil.

7. Synthesis of 2-acetyl-3-(3,5-dichlorophenyl)-8-(propan-2-yl)imidazo[1,2-b]pyridazine-7-carboxylic Acid (23-8)

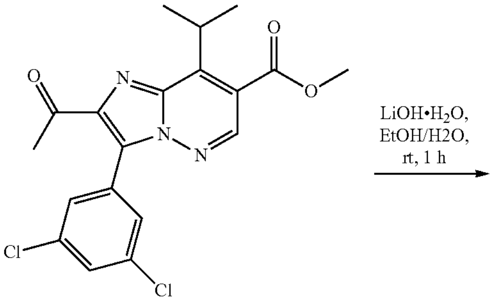

23-7

-continued

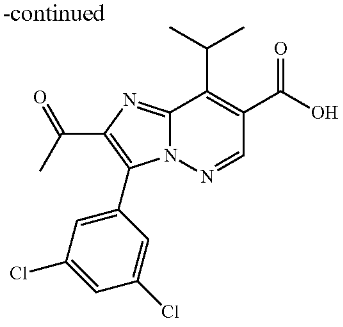

23-8

To a stirred mixture of methyl 2-acetyl-3-(3,5-dichlorophenyl)-8-isopropylimidazo[1,2-b]pyridazine-7-carboxylate (23-7, 10.0 mg, 0.02 mmol, 1.0 equiv) in EtOH (1 mL) and $H_2O$ (0.5 mL) was added $LiOH \cdot H_2O$ (10.3 mg, 0.25 mmol, 10.0 equiv) at room temperature. The resulting mixture was stirred for 1 h at room temperature. The resulting mixture was concentrated under vacuum. The resulting mixture was diluted with water (5 mL). The mixture was acidified to pH 4 with HCl (aq.). The resulting mixture was extracted with EtOAc (2×5 mL). The combined organic layers were washed with brine (1×5 mL), dried over anhydrous $Na_2SO_4$. After filtration, the filtrate was concentrated under reduced pressure. The crude product (23-8) was used in the next step directly without further purification.

8. Synthesis of 2-acetyl-3-(3,5-dichlorophenyl)-N-[(4S)-3,4-dihydro-2H-1-benzopyran-4-yl]-8-isopropylimidazo[1,2-b]pyridazine (558)

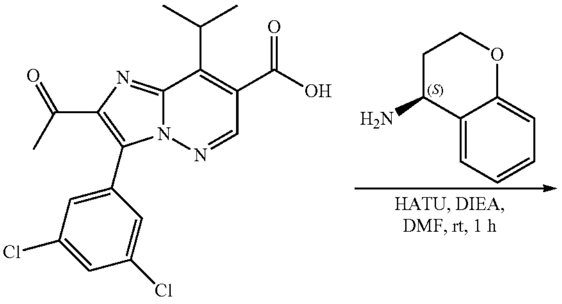

23-8

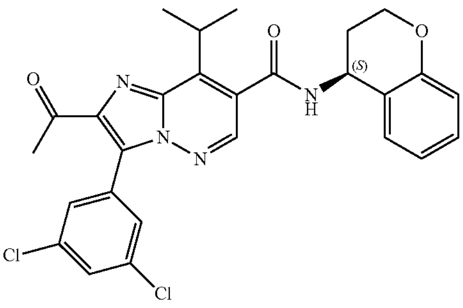

558

To a stirred mixture of 2-acetyl-3-(3,5-dichlorophenyl)-8-isopropylimidazo[1,2-b]pyridazine-7-carboxylic acid (23-8, 10.0 mg, 0.02 mmol, 1.0 equiv) and (4S)-3,4-dihydro-2H-1-benzopyran-4-amine (5.7 mg, 0.04 mmol, 1.5 equiv)

in DMF (1 mL, 12.9 mmol, 506.8 equiv) were added DIEA (9.9 mg, 0.07 mmol, 3.0 equiv) and HATU (14.5 mg, 0.04 mmol, 1.5 equiv) at room temperature. The resulting mixture was stirred for 1 h at room temperature. The crude product was purified by Prep-HPLC with the following conditions (Gradient: isocratic) to afford 11 mg of 2-acetyl-3-(3,5-dichlorophenyl)-N-[(4S)-3,4-dihydro-2H-1-benzopyran-4-yl]-8-isopropylimidazo[1,2-b]pyridazine (558, 95.0%) as a solid. (400 MHz, Chloroform-d, ppm) δ: 8.31 (s, 1H), 7.56 (s, 2H), 7.45 (s, 1H), 7.225-7.21 (m, 1H), 6.97-6.93 (m, 1H), 6.88-6.86 (m, 1H), 6.06-6.05 (m, 1H), 5.38-5.36 (m, J=4.5 Hz, 1H), 4.38-4.34 (m, 1H), 4.21-4.16 (m, 1H), 3.73-3.67 (m 1H), 2.75 (s, 3H), 2.43-2.38 (m, 1H), 2.23-2.20 (m, 1H), 1.68 (t, J=7.4 Hz, 6H).

$^1$H NMR spectra for 559: (400 MHz, Chloroform-d, ppm) δ: 8.44 (s, 1H), 7.88 (s, 2H), 7.50 (s, 1H), 7.26-7.21 (m, 2H), 6.98-6.94 (m, 1H), 6.90 (d, J=8.3 Hz, 1H), 6.08-6.07 (m, 1H), 5.40-5.36 (m, 1H), 4.39-4.34 (m, 1H), 4.21-4.15 (m, 1H), 3.71-3.64 (m, 1H), 2.44-2.39 (m, 1H), 2.26-2.20 (m, 1H), 1.65-1.54 (m, 6H)

Preparation Example 18: Compound 614 can be prepared according to the process described in Scheme 24.

Scheme 24

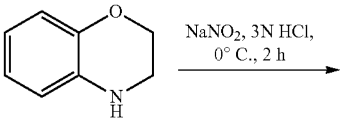

24-1

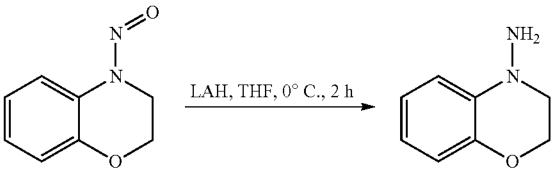

24-2

24-3

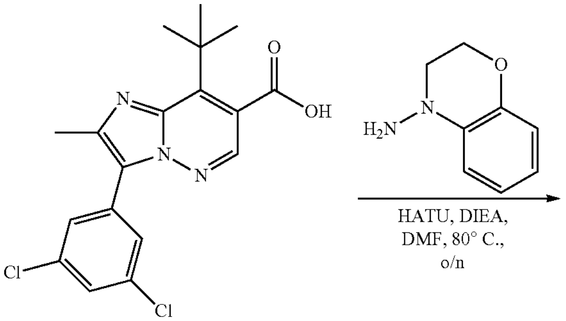

12-5

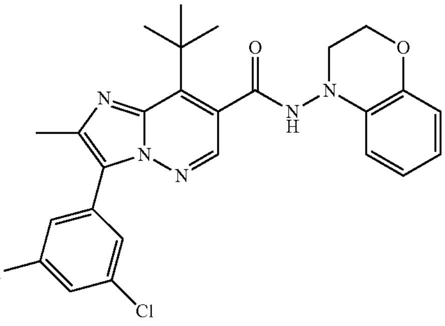

614

1. Synthesis of 4-nitroso-3,4-dihydro-2H-1,4-benzoxazine

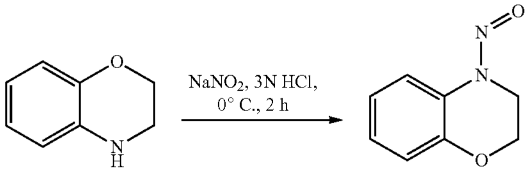

24-1

24-2

Into a 500 mL round-bottom flask. were added methyl 3,4-dihydro-2H-1,4-benzoxazine (24-1, 3.0 g, 22.2 mmol, 1.0 equiv) and 3M/HCl (300 ml) and $NaNO_2$ (1.8 g, 26.1 mmol, 1.2 equiv) was added dropwise/in portions at 2 hr at 0° C. under nitrogen atmosphere. The resulting mixture was concentrated under reduced pressure. The residue was purified by silica gel column chromatography, eluted with PE/EA (10:01) to afford 4-nitroso-3,4-dihydro-2H-1,4-benzoxazine (24-2, 2.7 g, 75.1%) as a yellow oil.

2. Synthesis of 3,4-dihydro-2H-1,4-benzoxazin-4-amine

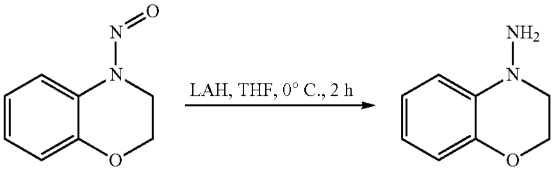

24-2

24-3

Into a 500 mL round-bottom flask. were added methyl 4-nitroso-2,3-dihydro-1,4-benzoxazine (24-2, 2.7 g, 19.2 mmol, 1.0 equiv) and THF (300 ml) and LAH (1.35 g, 1.9 mmol, 2.0 equiv) was added dropwise/in portions at 2 hr at 0° C. under nitrogen atmosphere. The resulting mixture was concentrated under reduced pressure. The residue was purified by silica gel column chromatography, eluted with PE/EA (10:01) to afford 3,4-dihydro-2H-1,4-benzoxazin-4-amine (24-3, 2.2 g, 44.9%) as a yellow oil.

3. Synthesis of 8-tert-butyl-3-(3,5-dichlorophenyl)-N-(2,3-dihydro-1,4-benzoxazin-4-yl)-2-methylimidazo[1,2-b]pyridazine-7-carboxamide (614)

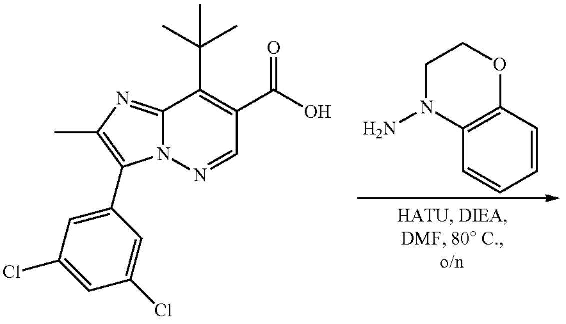

12-5

-continued

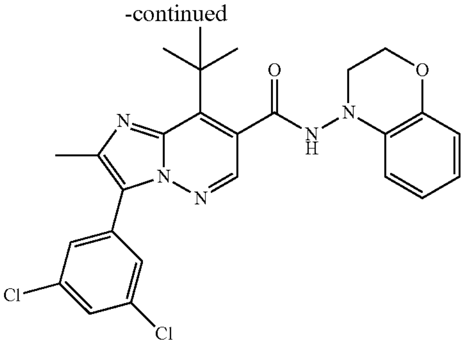

614

To a stirred mixture of 8-tert-butyl-3-(3,5-dichlorophenyl)-2-methylimidazo[1,2-b]pyridazine-7-carboxylic acid (12-5, 100.0 mg, 0.3 mmol, 1.0 equiv) and 2,3-dihydro-1,4-benzoxazin-4-amine (119.1 mg, 0.8 mmol, 3.0 equiv) in DMF (5 mL) were added DIEA (170.8 mg, 1.3 mmol, 5.0 equiv) and HATU (301.6 mg, 0.8 mmol, 3.0 equiv) at room temperature. The resulting mixture was stirred for overnight at 80 degrees C. The mixture was allowed to cool down to room temperature. The residue was purified by reverse flash chromatography with the following conditions: column, C18 silica gel; mobile phase, ACN in water, 40% to 95% gradient in 10 min; detector, UV 254 nm to afford 8-tert-butyl-3-(3,5-dichlorophenyl)-N-(2,3-dihydro-1,4-benzoxazin-4-yl)-2-methylimidazo[1,2-b]pyridazine-7-carboxamide (614, 43.8 mg, 32.5%) as an off-white solid. (300 MHz, DMSO-d6, ppm) δ 10.44 (s, 1H), 8.39 (s, 1H), 7.76 (d, J=1.8 Hz, 2H), 7.61 (t, J=2.1 Hz, 1H), 7.05-6.96 (m, 1H), 6.88-6.82 (m, 1H), 6.79-6.66 (m, 2H), 4.36-4.33 (m, 2H), 3.65-3.62 (m, 2H), 2.55 (s, 3H), 1.73 (s, 9H).

BIOLOGICAL EXAMPLES

The disclosure is further illustrated by the following biological examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Biological Example 1: Screening Method to Test Activity of Compounds Against Microfilaria of *Dirofilaria immitis*

Four hundred to six hundred microfilariae of *Dirofilaria immitis* were added to wells of a microtiter plate containing RPMI media and the test compound formulated in 100% DMSO. Plates were held for three days at 37° C. and 5% $CO_2$. The efficacy of a compound was determined based on the motility of the microfilaria as compared to average motility of control wells containing DMSO only. A dose response assay was conducted to determine an $EC_{50}$ value. Compounds 298-0, 304, 295, 296, A412, A406, A405, A411, A400, A401, 325, A419, 513-0, 450, A435, A439 and A442 exhibited $EC_{50}$ values of between 0.1 μM and 1 μM. Compounds 279, 273, 276, 294, 322, 323, 326-0, 323-0, 352, 364, 371, 373, 298, 419, A403, A413, A407, A414, A449, A448, A447, A441, 512, 511, 513, 418, A428, A427, 305, 451 and 558 exhibited $EC_{50}$ values between 0.01 μM and 0.1 μM. Compounds 308, 271, 274, 306, 297, A410, 277, 299-0, 293, 275, 175, 573, 614, 572, 528, 560, 420, A422, 523 and 527 exhibited $EC_{50}$ values of between 0.001 μM and 0.01 μM; and Compounds 307, 324, 345, 524, 526 and A421 exhibited $EC_{50}$ values of less than 0.001 μM.

Biological Example 2: Screening Method to Test Activity of Compounds Against *Haemonchus contortus*

Twenty L1 *Haemonchus contortus* larvae were added to wells of a microtitre plate containing a nutrient medium and the test compound in DMSO. An analysis was conducted at 4 days to determine the extent of development of the larvae from L1 to L3. Larvae exposed to DMSO alone served as controls. A dose response assay was conducted to determine an $EC_{50}$ value. Compounds 174, 366, 320-0, 369, 365, 321, 394, 298-0, 323-0, 323, 325, 296, 304-0, 373, 398, A404, 370, 326 and 299 were found to be active with $EC_{50}$ values of between 1 μM and 10 μM. Compounds 304, A405, A414, A403, A401, 371, 364, 352, 308, 320, 298, 299-0, 327, 324, 279 and 275 exhibited $EC_{50}$ values of between 0.1 μM and 1 μM. Compounds 175, 272, 273, 295, 326-0, 277, 294, 344, A408, A410, A412, A409, A413 and A400 exhibited $EC_{50}$ values of between 0.01 μM and 0.1 μM; and compounds 297, 306, 271, 345 and 274 exhibited $EC_{50}$ values of less than 0.01 μM.

Biological Example 3: Screening Method to Test Activity of Compounds Against L4 Stage Larvae of *Dirofilaria immits*

Four to six L4 stage *Dirofilaria immitis* worms are added to wells of a microtiter plate containing maintenance nutrient media and the test compound formulated in 100% DMSO. Plates are held at 37° C. and 5% $CO_2$ for three days and then assessed to determine the motility of the larvae. Efficacy of a compound is determined by comparison of the treated L4 motility of the relative to the average motility of worms in control wells containing DMSO only. A dose response assay is conducted to determine an $EC_{50}$ value. Compounds 366, 320-0, 365, 321, 304-0 and 329 exhibited EC50 values of between 1 μM and 10 μM, compounds 325, 323 and 370 were found to have EC50 values of between 0.1 μM and 1 μM. Compounds 276, 322, 320, 364, 326, 298-0, 299, 323-0, 296, 295 and 307 exhibited EC50 values of from 0.01 μM to 0.1 μM. Compounds 304, 175, 272, 294, 273, 344, 275, 327, 326-0, 299-0, 298, 277, 324 and 297 exhibited EC50 values of between 0.001 μM to 0.01 μM. Compounds 308, 271, 293, 345, 371 and 306 exhibited an EC50 of <0.001 μM.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of Formula (I):

(I)

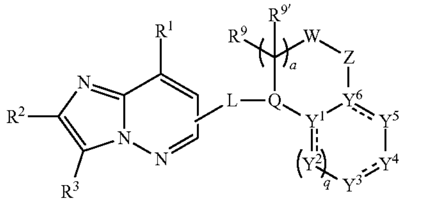

wherein:

L is L1, L2, L3, L4, L5, L6, L7, L8, L9, L10, L11, L12, L13, L14 or L15:

(L1)

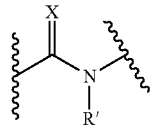

, (L2)

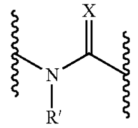

, (L3)

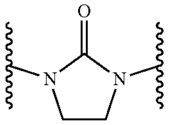

, (L4)

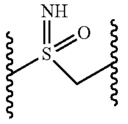

, (L5)

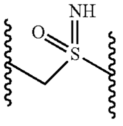

, (L6)

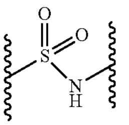

,

-continued (L7)

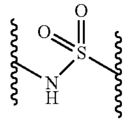

, (L8)

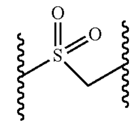

(L9)

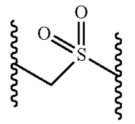

, (L10)

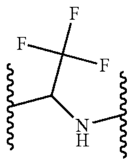

, (L11)

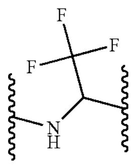

(L12)

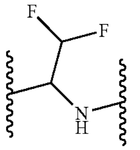

, (L13)

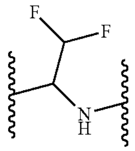

(L14)

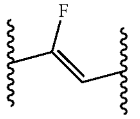

, (L15)

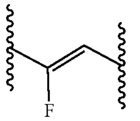

;

R' is hydrogen, optionally substituted alkyl, optionally substituted cycloalkyl, or optionally substituted aryl;

$R^1$ is hydrogen, cyano, halogen, hydroxyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkyl, optionally substituted aminoalkyl, optionally substituted alkylaminoalkyl, optionally substituted dialkylaminoalkyl, optionally substituted aryl, optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, —$SO_p$ (optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^2$ is hydrogen, cyano, halogen, hydroxyl, optionally substituted alkyl, optionally substituted alkoxy, optionally substituted alkenyl, optionally substituted alkynyl, optionally substituted aryl; optionally substituted aryloxy, optionally substituted heteroaryl, optionally substituted cycloalkyl, optionally substituted cycloalkenyl, optionally substituted cycloalkoxy, optionally substituted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —$SO_p$ (optionally substituted alkyl or haloalkyl), —$SF_5$, or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^3$ is optionally substituted alkyl, optionally substituted cycloalkyl, optionally substituted cycloalkenyl, optionally substituted alkylcarbonyl, optionally substituted alkoxycarbonyl, aminocarbonyl, optionally substituted alkylaminocarbonyl, optionally substituted dialkylaminocarbonyl, —$S(O)_p$ (optionally substituted alkyl), —$SF_5$, optionally substituted heterocyclyl, optionally substituted 6- to 10-membered aryl, optionally substituted 5- to 10-membered heteroaryl, a spirocyclic heterocyclyl-carbocyclyl group, a spirocyclic heterocyclyl-heterocyclyl group, a spirocyclic carbocyclyl-carbocyclyl group, a spirocyclic carbocyclyl-heterocyclyl group or —$NR^aR^b$, wherein $R^a$ and $R^b$ are independently H or optionally substituted alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^4$ and $R^{4'}$ are independently in each occurrence, hydrogen, halogen, cyano, nitro, hydroxyl, optionally substituted alkyl, optionally substituted alkoxy, optionally substituted cycloalkyl, optionally substituted cycloalkoxy, optionally substituted alkylcarbonyl, optionally substituted alkoxycarbonyl, optionally substituted aminocarbonyl, optionally substituted alkylaminocarbonyl, or optionally substituted di(alkyl)aminocarbonyl, optionally substituted alkylcarbonyloxy, optionally substituted alkylcarbonylamino, optionally substituted aryl, optionally substituted heteroaryl, —$SF_5$, —$SO_p$ (optionally substituted alkyl or haloalkyl); or $R^4$ together with $R^{4'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H or optionally substituted alkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O, Si and S and may be optionally substituted;

$R^8$ is hydrogen, halogen, alkyl, haloalkyl, cycloalkyl, alkenyl or alkynyl;

$R^9$ and $R^{9'}$ are independently hydrogen, halogen, $C_1$-$C_4$-alkyl, $C_1$-$C_4$-haloalkyl, $C_1$-$C_4$-alkoxy, $C_1$-$C_4$-haloalkoxy or cycloalkoxy, or $R^9$ together with $R^{9'}$ form a 2-6-membered chain optionally containing one or two heteroatoms selected from the group consisting of N, O, Si and S to form carbocyclic or heterocyclic ring together with the carbon atom to which they are attached;

Q is N or C—$R^8$;

X is O, S or N—R';

$Y^1$ and $Y^6$ are each independently N, C, or —$CR^4$—;

$Y^2$, $Y^3$, $Y^4$ and $Y^5$ are each independently N, NR', S, O, —$CR^4$— or $CR^4R^{4'}$;

W is $CR^5R^6$, O, $SO_p$, or N—$R^7$,

Z is $CR^5R^6$, O, $SO_p$, or N—$R^7$, wherein $R^5$ and $R^6$ are independently in each occurrence hydrogen, halogen, $C_1$-$C_4$-alkyl, $C_1$-$C_4$-haloalkyl, $C_1$-$C_4$-alkoxy, $C_1$-$C_4$-haloalkoxy or cycloalkoxy; or $R^5$ together with $R^6$ form a 2-6-membered chain optionally containing one or two heteroatoms selected from the group consisting of N, O, Si and S to form carbocyclic or heterocyclic ring together with the carbon atom to which they are attached;

$R^7$ is hydrogen or $C_1$-$C_4$-alkyl; and wherein at most three of $Y^1$, $Y^2$, $Y^3$, $Y^4$, $Y^5$ and $Y^6$ are heteroatoms;

a is 0 or 1;

q is 0 or 1;

p is independently in each occurrence is 0, 1, or 2; and the dashed bonds ( (- - - -) ) signifies a single or double bond;

or a pharmaceutically acceptable salt thereof.

2. The compound of Formula (I) of claim 1, wherein:

$R^1$ is hydrogen, cyano, halogen, hydroxyl, $C_1$-$C_6$-alkyl, $C_1$-$C_6$-haloalkyl, hydroxy-$C_1$-$C_6$-alkyl, hydroxy-$C_1$-$C_6$-haloalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, optionally substituted aryl, optionally substituted aryloxy, optionally substituted heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl, —$SF_5$, —$SO_p$ (optionally substituted $C_1$-$C_6$-alkyl or $C_1$-$C_6$-haloalkyl), or —$NR^aR^b$ wherein $R^a$ and $R^b$ are independently H or optionally substituted $C_1$-$C_6$-alkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^2$ is hydrogen, cyano, halogen, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkenyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$ (optionally substituted $C_1$-$C_6$-alkyl or $C_1$-$C_6$-haloalkyl), $SF_5$, or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^3$ is $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkenyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SF_5$, —S(O)p($C_1$-$C_6$-alkyl or $C_1$-$C_6$-haloalkyl), optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$, wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^4$ and $R^{4'}$ are independently in each occurrence, hydrogen, halogen, cyano, nitro, hydroxyl, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted $C_1$-$C_6$-alkylcarbonyl, optionally substituted $C_1$-$C_6$-alkoxycarbonyl, optionally substituted aminocarbonyl, optionally substituted $C_1$-$C_6$-alkylaminocarbonyl, optionally substituted di($C_1$-$C_6$-alkyl)aminocarbonyl, optionally substituted $C_1$-$C_6$-alkylcarbonyloxy, optionally substituted $C_1$-$C_6$-alkylcarbonylamino, optionally substituted phenyl, optionally substituted 5- or 6-membered heteroaryl, —$SF_5$, —$SO_p$ (optionally substituted $C_1$-$C_6$-alkyl or $C_1$-$C_6$-haloalkyl); or $R^4$ together with $R^{4'}$ together form a 2-6-membered chain optionally containing one or two heteroatoms selected from the group consisting of N, O, Si and S to form carbocyclic or heterocyclic ring together with the carbon atom to which they are attached; or —$NR^cR^d$, wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^8$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl;

$R^9$ and $R^{9'}$ are independently hydrogen, halogen, $C_1$-$C_4$-alkyl, $C_1$-$C_4$-haloalkyl, $C_1$-$C_4$-alkoxy, $C_1$-$C_4$-haloalkoxy or $C_3$-$C_8$-cycloalkoxy, or $R^9$ together with $R^{9'}$ form a 2-6-membered chain optionally containing one or two heteroatoms selected from the group consisting of N, O, Si and S to form carbocyclic or heterocyclic ring together with the carbon atom to which they are attached; and R' is hydrogen, $C_1$-$C_6$-alkyl, $C_1$-$C_6$-haloalkyl, optionally substituted $C_3$-$C_8$-cycloalkyl, or optionally substituted phenyl.

3. The compound of Formula (I) according to claim 1 or 2, wherein $R^1$ is hydrogen, cyano, optionally substituted $C_1$-$C_4$-alkyl, optionally substituted $C_1$-$C_4$-alkoxy, optionally substituted $C_2$-$C_4$-alkenyl, optionally substituted $C_2$-$C_4$-alkynyl, optionally substituted $C_3$-$C_8$-cycloalkyl, optionally substituted, saturated or unsaturated 5-, 6-, or 7-membered heterocycle, optionally substituted aryl, optionally substituted heteroaryl, optionally substituted aryloxy, optionally substituted $C_1$-$C_4$-alkylcarbonyl, optionally substituted $C_1$-$C_4$-alkoxycarbonyl, aminocarbonyl, optionally substituted $C_1$-$C_4$-alkylaminocarbonyl, optionally substituted $C_1$-$C_4$-dialkylaminocarbonyl, optionally substituted $SO_p$(optionally substituted alkyl or haloalkyl), amino, —NH-optionally substituted $C_1$-$C_4$-alkyl, or —$NR^aR^b$, wherein $R^a$ and $R^b$ are independently optionally substituted alkyl; or $R^a$ and $R^b$ may form, with the nitrogen to which they are attached, a 3-, 4-5-, 6-, 7-, or 8-membered-heterocyclyl group, which may be optionally substituted, and may include one or two additional heteroatoms selected from the group consisting of N, O and S;

R' is hydrogen or $C_1$-$C_4$-alkyl;

$R^2$ is hydrogen, halogen, cyano, nitro, —OH, optionally substituted $C_1$-$C_4$-alkyl, optionally substituted $C_1$-$C_4$-alkoxy, optionally substituted $C_3$-$C_8$-cycloalkyl, amino, NH-optionally substituted $C_1$-$C_4$-alkyl, —$SF_5$, or —$NR^aR^b$, wherein $R^a$ and $R^b$ are independently optionally substituted $C_1$-$C_4$-alkyl; or $R^a$ and $R^b$ may form, with the nitrogen to which they are attached, a 3, 4, 5, 6, 7, or 8 membered-heterocyclyl group, which may be optionally substituted, and may include one or two additional heteroatoms selected from the group consisting of N, O and S; —$SO_p$ (optionally substituted $C_1$-$C_4$-alkyl or haloalkyl);

$R^3$ is optionally substituted $C_1$-$C_4$-alkyl, optionally substituted phenyl, optionally substituted 5- to 10-membered heteroaryl, optionally substituted $C_3$-$C_8$-cycloalkyl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, or a 5- to 11-membered spirocyclic carbocyclyl-heterocyclyl group; and each $R^4$ is independently hydrogen, halogen, cyano, nitro, hydroxyl, optionally substituted $C_1$-$C_4$-alkyl, optionally substituted $C_1$-$C_4$-alkoxy, optionally substituted $C_3$-$C_8$-cycloalkyl, amino, NH-optionally substituted $C_1$-$C_4$-alkyl, —$SF_5$, or —$NR^cR^d$, wherein $R^c$ and $R^d$ are independently optionally substituted $C_1$-$C_4$-alkyl; or $R^c$ and $R^d$ may form, with the nitrogen to which they are attached, a 3, 4, 5, 6, 7, or 8 membered-heterocyclyl group, which may be optionally substituted and may include one or two additional heteroatoms selected from the group consisting of N, O and S, $SO_p$ (optionally substituted $C_1$-$C_4$-alkyl or haloalkyl.

4. The compound of Formula (I) according to claim 1 or 2, wherein Q is N.

5. The compound of Formula (I) according to claim 1 or 2, wherein Q is C—$R^8$.

6. The compound of Formula (I) according to claim 1 or 2, wherein X is O.

7. The compound of Formula (I) according to claim 1 or 2, wherein X is S.

8. The compound of Formula (I) according to claim 1 or 2, wherein a is 1 and q is 1.

9. The compound of Formula (I) according to claim 1 or 2, wherein a is 0 and q is 0.

10. The compound of Formula (I) according to claim 1 or 2, wherein a is 1 and q is 0.

11. The compound of Formula (I) according to claim 1 or 2, wherein:

L is L1;

R' is hydrogen or $C_1$-$C_4$-alkyl;

$R^1$ is halogen, $C_1$-$C_4$-alkyl, $C_1$-$C_4$-haloalkyl, hydroxy-$C_1$-$C_4$-alkyl, hydroxy-$C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, $C_1$-$C_4$-haloalkylaminocarbonyl, di-$C_1$-$C_4$-alkylaminocarbonyl, di-$C_1$-$C_6$-haloalkylaminocarbonyl, optionally substituted 5- or 6-membered heteroaryl or optionally substituted 5- or 6-membered heterocyclyl containing 1 to 3 N, S or O heteroatoms or —$NR^aR^b$ wherein $R^a$ and $R^b$ are independently H, $C_1$-$C_4$-alkyl or $C_1$-$C_4$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted;

$R^2$ is hydrogen, halogen, —$SF_5$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, optionally substituted $C_3$-$C_6$-cycloalkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, $C_1$-$C_4$-haloalkylaminocarbonyl, di-$C_1$-$C_4$-alkylaminocarbonyl, di-$C_1$-$C_4$-haloalkylaminocarbonyl, —$SO_p$ (optionally substituted $C_1$-$C_4$-alkyl or $C_1$-$C_4$-haloalkyl), or —$NR^aR^b$ wherein $R^a$ and $R^b$ are independently H, $C_1$-$C_4$-alkyl or $C_1$-$C_4$-haloalkyl;

$R^3$ is $C_1$-$C_6$-alkyl, $C_1$-$C_6$-haloalkyl, optionally substituted $C_3$-$C_8$-cycloalkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, $C_1$-$C_4$-haloalkylaminocarbonyl, di-$C_1$-$C_4$-alkylaminocarbonyl, di-$C_1$-$C_4$-haloalkylaminocarbonyl, —$SO_p$ (optionally substituted $C_1$-$C_4$-alkyl or $C_1$-$C_4$-haloalkyl), —$SF_5$, optionally substituted 3- to 7-membered heterocyclyl containing from one to three heteroatoms selected from the group consisting of N, O and S; optionally substituted phenyl, optionally substituted 5- or 6-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, wherein each ring of said spirocyclic group contains 3, 4, 5 or 6 ring atoms; or —$NR^aR^b$ wherein $R^a$ and $R^b$ are independently H, $C_1$-$C_4$-alkyl or $C_1$-$C_4$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^4$ is independently in each occurrence, hydrogen, halogen, —$SF_5$, $C_1$-$C_6$-alkyl, $C_1$-$C_4$-haloalkyl, $C_1$-$C_4$-alkoxy, $C_1$-$C_4$-haloalkoxy, —$SO_p$ (optionally substituted $C_1$-$C_4$-alkyl or $C_1$-$C_4$-haloalkyl), or —$NR^cR^d$ wherein $R^c$ and $R^d$ are independently H, $C_1$-$C_4$-alkyl or $C_1$-$C_4$-haloalkyl;

$R^8$ is hydrogen, halogen, $C_1$-$C_4$-alkyl or $C_1$-$C_4$-haloalkyl;

X is O or S;

Z is O; and

W is $CR^5R^6$.

12. The compound of Formula (I) according to claim 11, wherein a is 1 and q is 1.

13. The compound of Formula (I) according to claim 11, wherein a is 0 or 1 and q is 0.

14. The compound of Formula (I) according to claim 11, which is represented by the compound of formula (Ie):

(Ie)

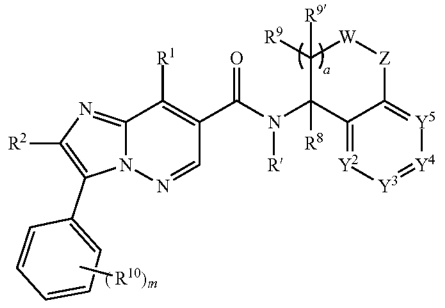

wherein:

each $R^{10}$ is independently halogen, cyano, hydroxyl, optionally substituted $C_3$-$C_8$-cycloalkyl, $C_1$-$C_4$-alkyl, $C_1$-$C_4$-haloalkyl, $C_1$-$C_4$-alkoxy, $C_1$-$C_4$-haloalkoxy, $C_1$-$C_6$-alkoxy-$C_1$-$C_6$-alkyl, $C_1$-$C_6$-haloalkoxy-$C_1$-$C_6$-alkyl, optionally substituted phenyl, optionally substituted phenyloxy, optionally substituted 5- or 6-membered heteroaryl, optionally substituted 5- to 6-membered heterocyclyl containing from one to three heteroatoms selected from the group consisting of N, O, Si and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, $C_1$-$C_6$-alkylthio, $C_a$-$C_6$haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, amino, $C_1$-$C_6$-alkylamino, di-$C_1$-$C_6$-alkylamino, or $SF_5$;

$R^1$ is halogen, $C_1$-$C_4$-alkyl, $C_1$-$C_4$-haloalkyl, hydroxy-$C_1$-$C_4$-alkyl, alkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, $C_1$-$C_4$-haloalkylaminocarbonyl, di-$C_1$-$C_4$-alkylaminocarbonyl, di-$C_1$-$C_6$-haloalkylaminocarbonyl, optionally substituted 5- or 6-membered heterocyclyl containing 1 to 3 N, S or O heteroatoms or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted;

$R^2$ is hydrogen, halogen, $C_1$-$C_4$-alkyl, $C_1$-$C_4$-haloalkyl, $C_1$-$C_4$-alkoxy, $C_1$-$C_4$-haloalkoxy, —$SO_p$ (optionally substituted $C_1$-$C_4$-alkyl or $C_1$-$C_4$-haloalkyl), —$SF_5$, or —$NR^aR^b$ wherein $R^a$ and $R^b$ are independently H, $C_1$-$C_4$-alkyl or $C_1$-$C_4$-haloalkyl;

$R^4$ is hydrogen, halogen, $C_1$-$C_4$-alkyl, $C_1$-$C_4$-haloalkyl, $C_1$-$C_4$-alkoxy, $C_1$-$C_4$-haloalkoxy, —$SO_p$ (optionally substituted $C_1$-$C_4$-alkyl or $C_1$-$C_4$-haloalkyl), —$SF_5$, or —$NR^cR^d$ wherein $R^c$ and $R^d$ are independently H, $C_1$-$C_4$-alkyl or $C_1$-$C_4$-haloalkyl;

$R^5$ and $R^6$ are independently hydrogen, halogen, $C_1$-$C_3$-alkyl or $C_1$-$C_3$-haloalkyl;

R' is hydrogen or $C_1$-$C_3$-alkyl;

$R^8$ is hydrogen;

$R^9$ and $R^{9'}$ are independently hydrogen, halogen, $C_1$-$C_3$-alkyl or $C_1$-$C_3$-haloalkyl;

$Y^2$, $Y^3$, $Y^4$, $Y^5$ are independently $CR^4$ or N;

a is 0 or 1; and m is 0, 1, 2, or 3.

15. The compound according to claim 14, wherein each $R^{10}$ is independently halogen and m is 2 or 3.

16. The compound according to claim 14, wherein each $R^{10}$ is independently chloro or fluoro and m is 2 or 3.

17. The compound according to claim 14, wherein:

each $R^{10}$ is independently chloro or fluoro;

m is 2 or 3;

$R^1$ is $C_1$-$C_4$-alkyl or —$NR^aR^b$;

$R^2$ is hydrogen, halogen, $C_1$-$C_3$-alkyl or $C_1$-$C_3$-haloalkyl;

W is $CH_2$;

Z is O; and $R^9$ and $R^{9'}$ are each hydrogen.

18. The compound according to claim 14, wherein $R^1$ $C_1$-$C_4$-alkyl, $C_2$-$C_4$-alkenyl, amino, $C_1$-$C_4$-alkylamino, di($C_1$-$C_4$-alkyl)amino, morpholino, pyranyl, tetrahydropyranyl, or dihydropyranyl;

$R^2$ is hydrogen, halogen, $C_1$-$C_4$-alkyl, $C_1$-$C_4$ haloalkyl; and $R^4$ is independently in each occurrence hydrogen, halogen, $C_1$-$C_4$-alkyl or $C_1$-$C_4$ haloalkyl.

19. The compound according to claim 18, wherein $R^1$ $C_1$-$C_4$-alkyl, di($C_1$-$C_4$-alkyl)amino, morpholino, pyranyl, tetrahydropyranyl, or dihydropyranyl;

$R^2$ is hydrogen, halogen, $C_1$-$C_3$-alkyl or $C_1$-$C_3$haloalkyl; and $R^4$ is independently in each occurrence hydrogen, halogen, $C_1$-$C_3$-alkyl or $C_1$-$C_3$-haloalkyl;

$R^{10}$ is chloro or fluoro; and m is 2 or 3.

20. The compound of any of claims 14 to 17, wherein each of $Y^2$, $Y^3$, $Y^4$ and $Y^5$ are independently —C—$R^4$.

21. The compound of any of claims 14 to 17, wherein $Y^2$ is N; and $Y^3$, $Y^4$ and $Y^5$ are independently —C—$R^4$.

22. The compound of any of claims 14 to 17, wherein $Y^3$ is N; and $Y^2$, $Y^4$ and $Y^5$ are independently —$CR^4$.

23. The compound of any of claims 14 to 17, wherein $Y^4$ is N and $Y^2$, $Y^3$ and $Y^5$ are independently —$CR^4$.

24. The compound of any of claims 14 to 17, wherein $Y^5$ is N and $Y^2$, $Y^3$ and $Y^4$ are independently —$CR^4$.

25. The compound of any of claims 14 to 17, wherein $Y^2$ and $Y^3$ are N; and $Y^4$ and $Y^5$ are independently —$CR^4$.

26. The compound of any of claims 14 to 17, wherein $Y^3$ and $Y^4$ are N; and $Y^2$ and $Y^5$ are independently —$CR^4$.

27. The compound of any of claims 14 to 17, wherein $Y^4$ and $Y^5$ are N; and $Y^2$ and $Y^3$ are independently —$CR^4$.

28. The compound of any of claims 14 to 17, wherein $Y^2$ and $Y^4$ are N; and $Y^3$ and $Y^5$ are independently —$CR^4$.

29. The compound of any of claims 14 to 17, wherein $Y^3$ and $Y^5$ are N; and $Y^2$ and $Y^4$ are independently —$CR^4$.

30. The compound of any of claims 14 to 17, wherein $Y^3$ and $Y^4$ are N; and $Y^2$ and $Y^5$ are independently —$CR^4$.

31. A compound of formula (I);

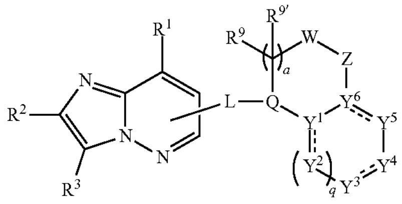

wherein $R^1$, $R^2$, $R^3$ and L are shown in the table below;

L1 is:

(L1)

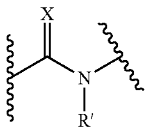

wherein X is oxygen and R' is hydrogen;

L2 is:

(L2)

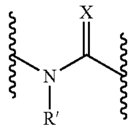

wherein X is oxygen and R' is hydrogen;

"Me" is methyl;

"i-Pr" is isopropyl;

"t-Bu" is tert-butyl;

prop-1-en-2-yl is

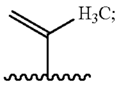

2-F-prop-2-yl represents the group

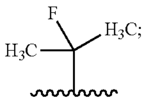

1, 1-difluoroethyl represents the group

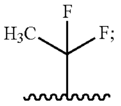

and the group
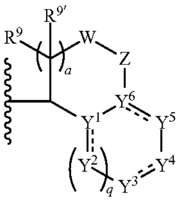
represents the following groups:
Ring System A
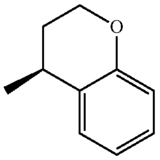
;
Ring System B
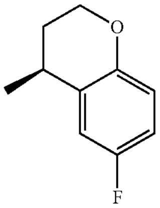
;
Ring System C
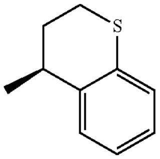
;
Ring System D
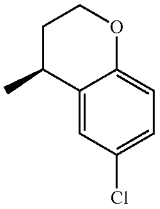
;
Ring System E
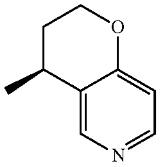
;
Ring System F
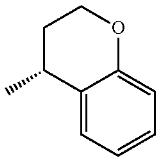
;
Ring System G
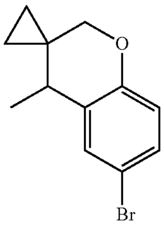
;
-continued
Ring System H
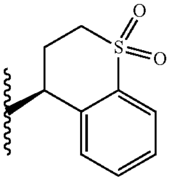
;
Ring System I
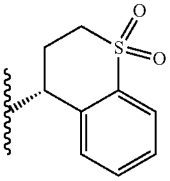
;
Ring System J
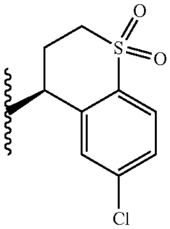
;
Ring System K
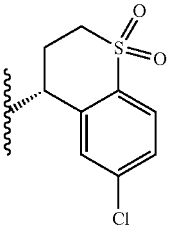
;
Ring System L
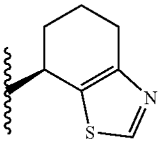
;
Ring System M
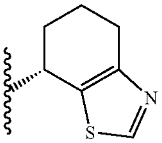
;
Ring System N
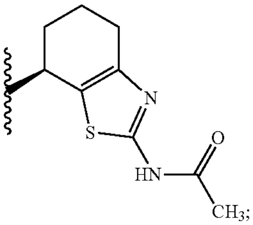
Ring System O
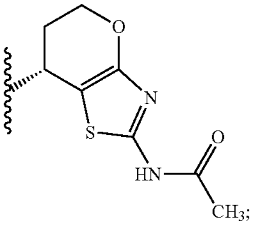

-continued
Ring System P
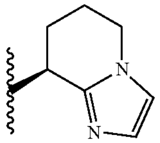
;
Ring System Q
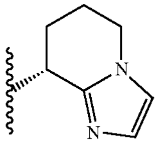
;
Ring System R
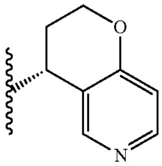
;
Ring System S
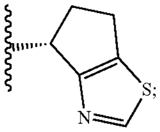
Ring System T
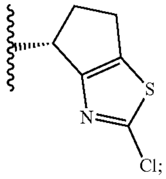
Ring System U
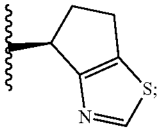
Ring System V
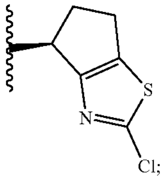
Ring System X
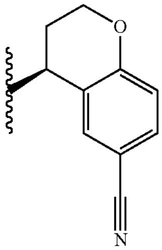
;
-continued
Ring System Y
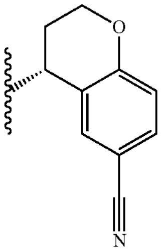
;
Ring System Z
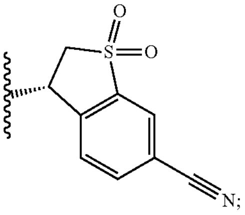
Ring System AA
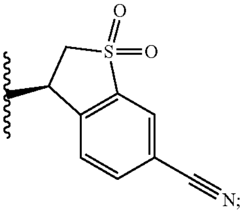
Ring System AB
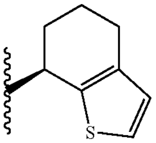
;
Ring System AC
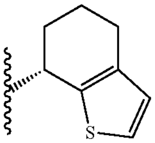
;
Ring System AD
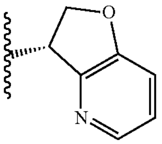
;
Ring System AE
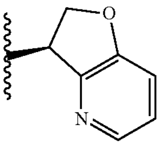
;
Ring System AF
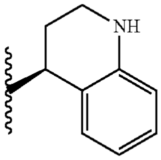
;

-continued
Ring System AG
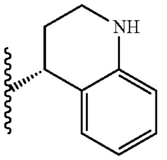
;
Ring System AH
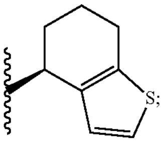
Ring System AJ
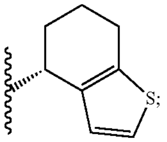
Ring System AK
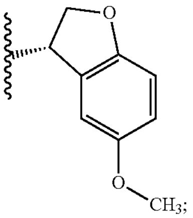
Ring System AL
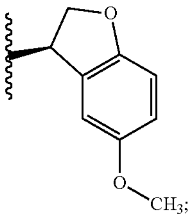
Ring System AM
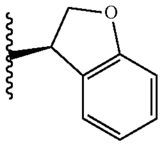
;
Ring System AN
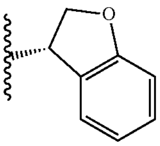
;
Ring System AO
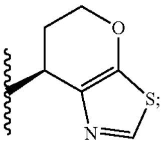
Ring System AP
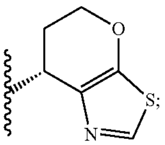
-continued
Ring System AQ
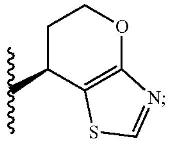
Ring System AR
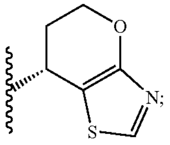
Ring System AS
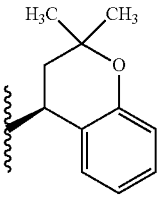
;
Ring System AT
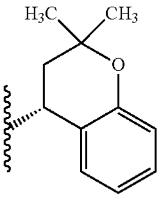
;
Ring System AU
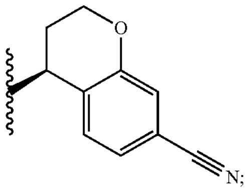
Ring System AV
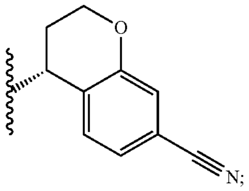
Ring System AW
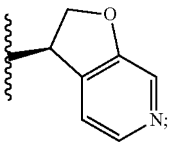
Ring System AX
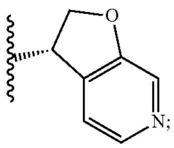
Ring System AY
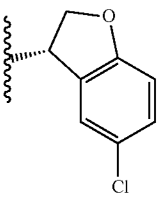
;

Ring System AZ

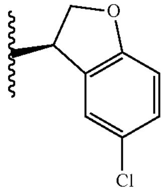

;

Ring System AAA

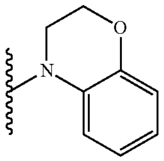

;

Formula (I)

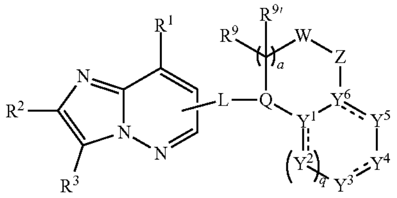

Formula (I)

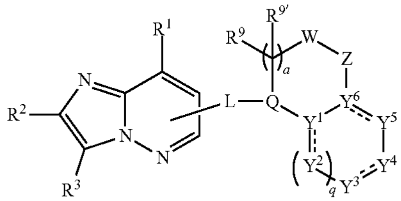

| Cmpd. # | L | R3 | R2 | R3 | Ring System |
|---|---|---|---|---|---|
| 271 | L1 | i-Pr | Me | 3,5-di-Cl—Ph | A |
| 326 | L1 | i-Pr | Me | 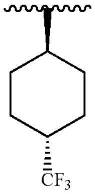 | A |
| 327 | L1 | i-Pr | Me | 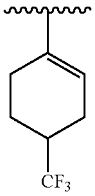 | A |

| Cmpd. # | L | R3 | R2 | R3 | Ring System |
|---|---|---|---|---|---|
| 326-0 | L1 | i-Pr | Me | 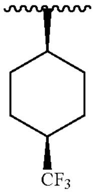 | A |
| 324 | L1 | i-Pr | Me | 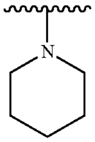 | A |
| 325 | L1 | i-Pr | Me | 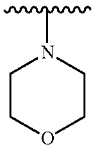 | A |
| 323 | L1 | i-Pr | Me | t-Bu | A |
| 175 | L1 | i-Pr | Me | 3,5-di-F—Ph | A |
| A407 | L1 | i-Pr | Me | 2,6-di-F—Ph | A |
| A406 | L1 | i-Pr | Me | 2,6-di-Cl—Ph | A |
| A413 | L1 | i-Pr | Me | 2,4-di-F—Ph | A |
| A408 | L1 | 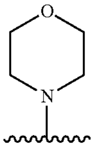 [SMILES: *N1CCOCC1] | Me | 3,5-di-Cl—Ph | A |
| A412 | L1 | i-Pr | Me | 4-F—Ph | A |
| A410 | L1 | i-Pr | Me | 3-Cl-4-F—Ph | A |
| A411 | L1 | i-Pr | Me | 3,5-di-Cl—Ph | C |
| A409 | L1 | —$N(CH_3)_2$ | Me | 3,5-di-Cl—Ph | A |
| A414 | L1 | i-Pr | Me | 3,5-di-Cl—Ph | D |
| 306 | L1 | t-Bu | Me | 3,5-di-Cl—Ph | A |
| 297 | L1 | t-Bu | Me | 3,5-di-Cl—Ph | B |
| 365 | L1 | i-Pr | Me | cyclopropyl | A |
| 371 | L1 | i-Pr | Me | 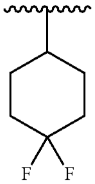 | A |
| 370 | L1 | i-Pr | Me | 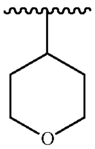 | A |
| 366 | L1 | i-Pr | Me | CN | A |
| 369 | L1 | i-Pr | Me | 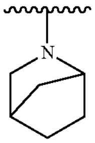 | A |

-continued

| Cmpd. # | L | R3 | R2 | R3 | Ring System |
|---|---|---|---|---|---|
| 308 | L1 | prop-1-en-2-yl | Me | 3,5-di-Cl—Ph | B |
| 364 | L1 | i-Pr | Me | 3,5-di-Cl—Ph | E |
| 352 | L1 | i-Pr | H | 3,5-di-Cl—Ph | A |
| 320-0 | L1 | i-Pr | Me | 3,5-di-F—Ph | F |
| 345 | L1 | i-Pr | Me | 2,3,5-tri-F—Ph | A |
| 344 | L1 | i-Pr | Me | 2,3,5-tri-F—Ph | B |
| 294 | L1 | i-Pr | Me | 3,5-di-Cl—Ph | B |
| 320 | L2 | i-Pr | Me | 3,5-di-F—Ph | A |
| 277 | L1 | 2-F-prop-2-yl | Me | 3,5-di-F—Ph | A |
| 323-0 | L1 | i-Pr | Me | $—CH_2CH(CH_3)_2$ | A |
| 298-0 | L1 | t-Bu | $CF_3$ | 3-Cl—Ph | B |
| 299-0 | L1 | t-Bu | $CF_3$ | 3-Cl—Ph | A |
| 299 | L1 | t-Bu | $CF_3$ | 3,5-di-Cl—Ph | B |
| 298 | L1 | t-Bu | $CF_3$ | 3,5-di-Cl—Ph | A |
| 304-0 | L1 | i-Pr | 3,5-di-Cl—Ph | Cl | B |
| 321 | L1 | i-Pr | 4-F—Ph | 3,5-di-F—Ph | A |
| 322 | L1 | i-Pr | Me | 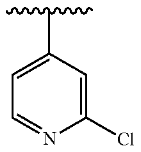 [SMILES: *c1ccnc(Cl)c1] | A |
| 304 | L1 | i-Pr | Cl | 3,5-di-Cl—Ph | B |
| 307 | L1 | prop-1-en-2-yl | Me | 3,5-di-F—Ph | B |
| 296 | L1 | i-Pr | $CF_3$ | 3,5-di-Cl—Ph | B |
| 295 | L1 | i-Pr | $CF_3$ | 3,5-di-Cl—Ph | A |
| 293 | L1 | i-Pr | Me | 2,3-di-Cl—Ph | B |
| 276 | L1 | i-Pr | $CF_3$ | 3,5-di-F—Ph | A |
| 274 | L1 | i-Pr | Me | 2,3-di-Cl—Ph | A |
| 273 | L1 | i-Pr | Me | 3-F—Ph | A |
| 272 | L1 | i-Pr | Me | 3-Cl-5-F—Ph | A |
| 275 | L1 | i-Pr | Me | 3,5-di-F—Ph | B |
| 279 | L1 | prop-1-en-2-yl | Me | 3,5-di-F—Ph | A |
| 174 | L1 | H | H | 2,6-di-F—Ph | A |
| A400 | L1 | 1,1-difluoroethyl | Me | 3,5-di-Cl—Ph | A |
| A401 | L1 | $CF_3$ | Me | 3,5-di-Cl—Ph | A |
| 373 | L1 | i-Pr | Me | 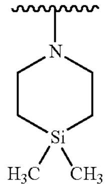 | A |
| 372-0 | L1 | i-Pr | Me | 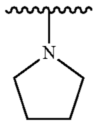 | A |
| A402 | L1 | i-Pr | Me | 3,5-di-Cl—Ph | G |
| A403 | L1 | i-Pr | $—CH_2OH$ | 3,5-di-Cl—Ph | A |
| A404 | L1 | i-Pr | $—CF_2CF_3$ | 3,5-di-Cl—Ph | A |
| 394 | L1 | $—OCH_3$ | H | 3,5-di-Cl—Ph | A |
| 398 | L1 | $—OCH_2CH_3$ | H | 3,5-di-Cl—Ph | A |
| A405 | L1 | $—CHF_2$ | Me | 3,5-di-Cl—Ph | A |
| 573 | L1 | t-Bu | Cl | 2,3,5-tri-F—Ph | A |
| 559 | L1 | i-Pr | —CN | 3,5-di-Cl—Ph | A |
| 614 | L1 | t-Bu | Me | 3,5-di-Cl—Ph | AAA |
| 451 | L1 | $—N(CH_3)_2$ | $CF_3$ | 3,5-di-Cl—Ph | A |
| 572 | L1 | t-Bu | Cl | 2,5-di-Cl-4-F—Ph | A |
| 528 | L1 | i-Pr | Me | 2,5-di-Cl-4-F—Ph | A |
| 571 | L1 | t-Bu | Cl | 2,4,5-tri-F—Ph | A |
| 574 | L1 | t-Bu | Cl | 2,3-di-Cl-5-F—Ph | A |
| A415 | L1 | i-Pr | Me | 3,5-di-Cl—Ph | H |

-continued

| Cmpd. # | L | R3 | R2 | R3 | Ring System |
|---|---|---|---|---|---|
| A416 | L1 | i-Pr | Me | 3,5-di-Cl—Ph | I |
| A417 | L1 | i-Pr | Me | 3,5-di-Cl—Ph | J |
| A418 | L1 | i-Pr | Me | 3,5-di-Cl—Ph | K |
| A419 | L1 | i-Pr | Me | 3,5-di-Cl—Ph | L |
| A420 | L1 | i-Pr | Me | 3,5-di-Cl—Ph | M |
| 560 | L1 | i-Pr | $—CHF_2$ | 3,5-di-Cl—Ph | A |
| 305 | L1 | i-Pr | $—CHF_2$ | 3,5-di-Cl—Ph | B |
| A421 | L1 | 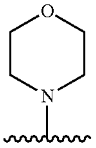 [SMILES: *N1CCOCC1] | Me | 2,6-di-Cl-4-F | A |
| A422 | L1 | 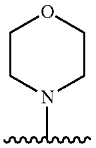 [SMILES: *N1CCOCC1] | Me | 2,3,5-tri-F—Ph | A |
| 420 | L1 | t-Bu | Cl | 3,5-di-Cl—Ph | A |
| A423 | L1 | i-Pr | Me | 3,5-di-Cl—Ph | N |
| A424 | L1 | i-Pr | Me | 3,5-di-Cl—Ph | 0 |
| 523 | L1 | t-Bu | Me | 2,6-di-Cl-4-F—Ph | A |
| A425 | L1 | i-Pr | Me | 3,5-di-Cl—Ph | P |
| A426 | L1 | i-Pr | Me | 3,5-di-Cl—Ph | Q |
| 526 | L1 | t-Bu | Me | 2,3-di-Cl-5-F—Ph | A |
| 527 | L1 | i-Pr | Me | 2,4,6-tri-F—Ph | A |
| 524 | L1 | t-Bu | Me | 2,4,6-tri-F—Ph | A |
| 525 | L1 | t-Bu | Me | 2,3,5-tri-F—Ph | A |
| 414-0 | L2 | i-Pr | Me | 3,5-di-Cl—Ph | R |
| 514 | L2 | i-Pr | Me | 3,5-di-Cl—Ph | E |
| A427 | L1 | i-Pr | Me | 3,5-di-Cl—Ph | S |
| A428 | L1 | i-Pr | Me | 3,5-di-Cl—Ph | T |
| A429 | L1 | i-Pr | Me | 3,5-di-Cl—Ph | U |
| A430 | L1 | i-Pr | Me | 3,5-di-Cl—Ph | V |
| 418 | L1 | t-Bu | H | 3,5-di-Cl—Ph | A |
| 513 | L2 | i-Pr | Me | 3,5-di-Cl—Ph | A |
| 513-0 | L2 | i-Pr | Me | 3,5-di-Cl—Ph | F |
| 511 | L1 | 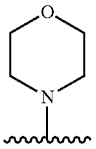 [SMILES: *N1CCOCC1] | H | 3,5-di-Cl—Ph | A |
| 512 | L1 | $—N(CH_3)_2$ | H | 3,5-di-Cl—Ph | A |
| A431 | L1 | i-Pr | Me | 3,5-di-Cl—Ph | W |
| 450 | L1 | 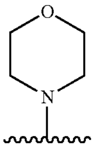 [SMILES: *N1CCOCC1] | $CF_3$ | 3,5-di-Cl—Ph | A |
| A432 | L1 | i-Pr | Me | 3,5-di-Cl—Ph | X |
| A473 | L1 | i-Pr | Me | 3,5-di-Cl—Ph | Y |
| A433 | L1 | i-Pr | Me | 3,5-di-Cl—Ph | Z |
| A434 | L1 | i-Pr | Me | 3,5-di-Cl—Ph | AA |
| A435 | L1 | i-Pr | Me | 3,5-di-Cl—Ph | AB |
| A436 | L1 | L1 | i-Pr | Me | N/A (H) |
| A437 | L1 | i-Pr | Me | 3,5-di-Cl—Ph | AC |
| A438 | L1 | i-Pr | Me | 3,5-di-Cl—Ph | AD |
| A439 | L1 | i-Pr | Me | 3,5-di-Cl—Ph | AF |
| A440 | L1 | i-Pr | Me | 3,5-di-Cl—Ph | AG |
| A441 | L1 | i-Pr | Me | 3,5-di-Cl—Ph | AH |
| A442 | L1 | i-Pr | Me | 3,5-di-Cl—Ph | AE |
| A443 | L1 | i-Pr | Me | 3,5-di-Cl—Ph | AJ |

-continued

| Cmpd. # | L | R3 | R2 | R3 | Ring System |
|---|---|---|---|---|---|
| A445 | L1 | i-Pr | Me | 3,5-di-Cl—Ph | AK |
| A446 | L1 | i-Pr | Me | 3,5-di-Cl—Ph | AL |
| A447 | L1 | i-Pr | Me | 3,5-di-Cl—Ph | AM |
| A448 | L1 | i-Pr | Me | 3,5-di-Cl—Ph | AO |
| A449 | L1 | i-Pr | Me | 3,5-di-Cl—Ph | AQ |
| A450 | L1 | i-Pr | Me | 3,5-di-Cl—Ph | AR |
| A451 | L1 | i-Pr | Me | 3,5-di-Cl—Ph | AP |
| A452 | L1 | i-Pr | Me | 3,5-di-Cl—Ph | AS |
| A472 | L1 | i-Pr | Me | 3,5-di-Cl—Ph | AT |
| A453 | L1 | i-Pr | Me | 3,5-di-Cl—Ph | AN |
| A454 | L1 | i-Pr | Me | 3,5-di-Cl—Ph | AU |
| 419 | L1 | i-Pr | Cl | 3,5-di-Cl—Ph | A |
| 397-0 | L1 | $OCH_2CH{=}CH_2$ | Me | 3,5-di-Cl—Ph | A |
| A455 | L1 | i-Pr | Me | 3,5-di-Cl—Ph | AW |
| A456 | L1 | i-Pr | Me | 3,5-di-Cl—Ph | AX |
| A457 | L1 | i-Pr | Me | 3,5-di-Cl—Ph | AY |
| A458 | L1 | i-Pr | Me | 3,5-di-Cl—Ph | AZ |
| 395 | L1 | $—OCHF_2$ | Me | 3,5-di-Cl—Ph | A |
| A459 | L1 | 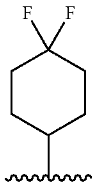 | Me | 3,5-di-Cl—Ph | A |
| A464 | L1 | $—N(CH_3)_2$ | Me | 2,6-di-Cl-4-F—Ph | A |
| A462 | L1 | $—N(CH_3)_2$ | Me | 2,4,6-tri-F—Ph | A |
| A463 | L1 | $—N(CH_3)_2$ | Me | 2,3-di-Cl-5-F—Ph | A |
| A460 | L1 | $—N(CH_3)_2$ | Me | 2,3,5-tri-F—Ph | A |
| A461 | L1 | $—N(CH_3)_2$ | Me | 2,3,5-tri-Cl—Ph | A |
| 558 | L1 | i-Pr | $—C(O)CH_3$ | 3,5-di-Cl—Ph | A. |

32. A veterinary composition comprising the compound of claim 1 or a pharmaceutically or a veterinarily acceptable salt thereof and a veterinarily acceptable carrier.

33. A veterinary composition comprising the compound of claim 1 or a pharmaceutically or a veterinarily acceptable salt thereof, one or more additional active agent(s), and a veterinarily acceptable carrier.

34. A method for the treatment, control and/or prevention of a parasitic infection or infestation in an animal in need thereof, which comprises administering to said animal an effective amount of the compound of claim 1, or a pharmaceutically or a veterinarily acceptable salt thereof.

35. A compound having the formula:

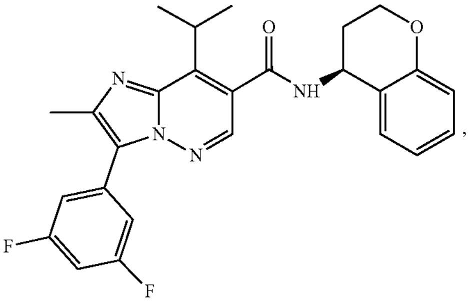

-continued

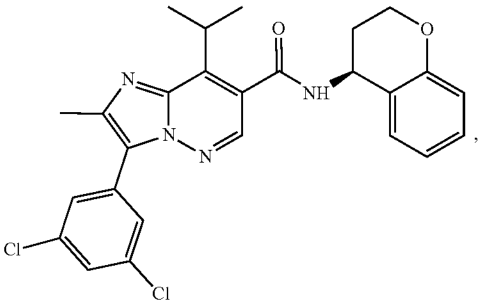

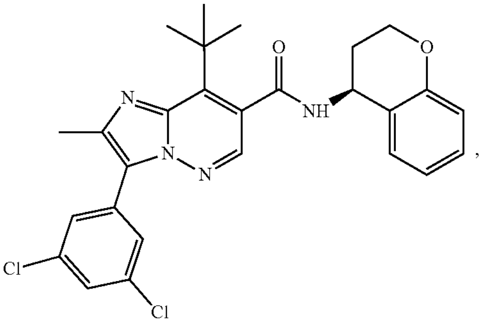 [SMILES: Cc1nc2c(C(C)(C)C)c(C(=O)N[C@H]3CCOc4ccccc43)cnn2c1-c1cc(Cl)cc(Cl)c1 ; "."]

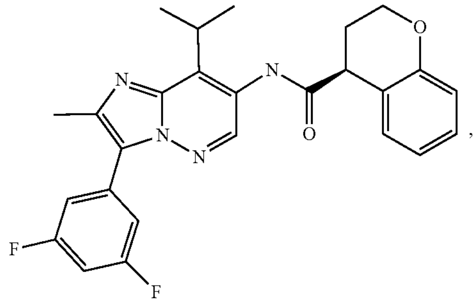

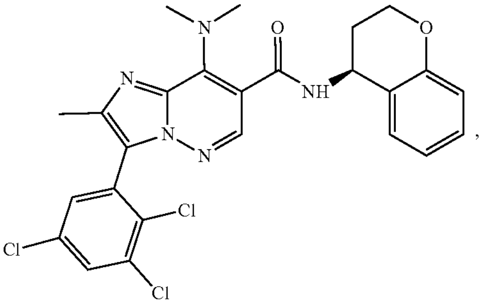

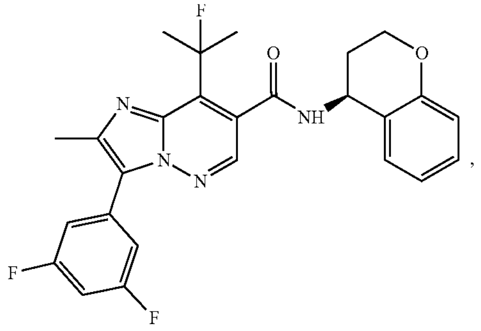

-continued
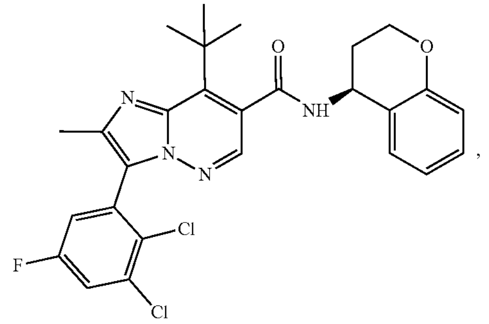 [SMILES: Cc1nc2c(C(C)(C)C)c(C(=O)N[C@H]3CCOc4ccccc43)cnn2c1-c1cc(F)cc(Cl)c1Cl ; "."]
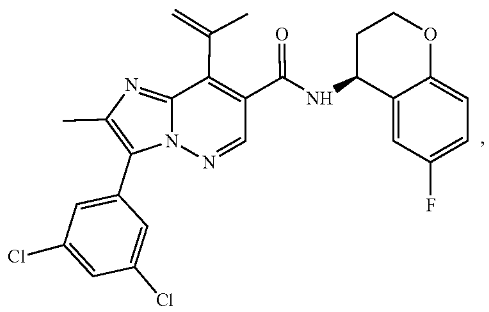
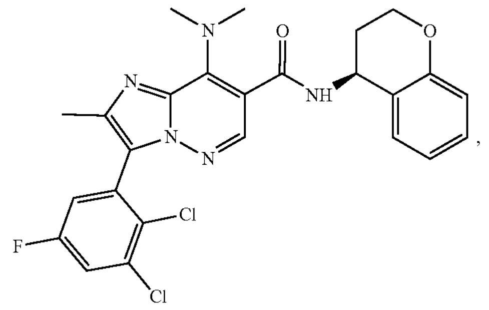
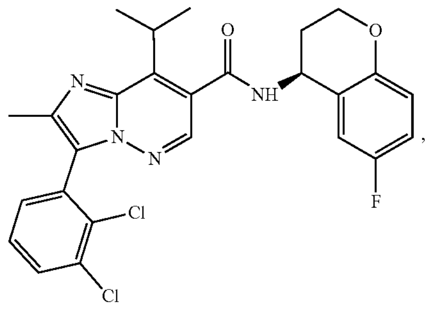
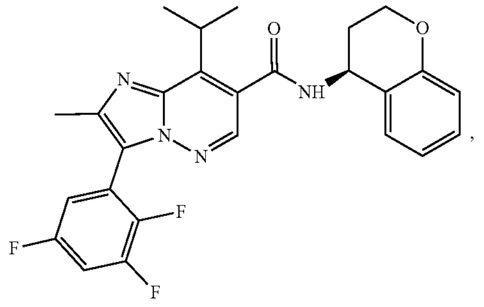
-continued
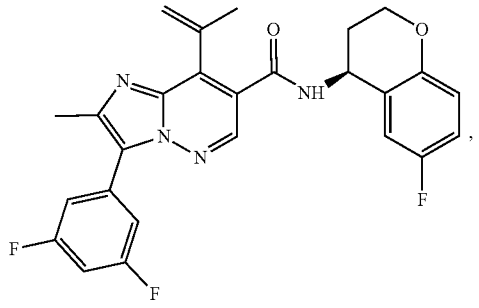
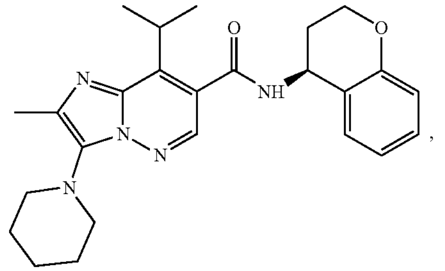
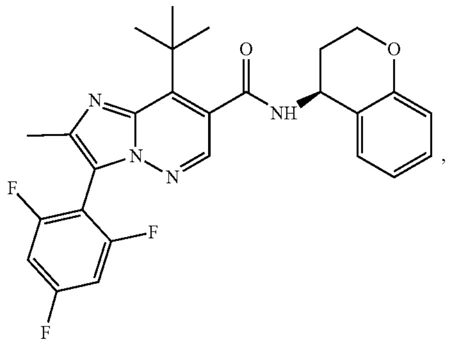
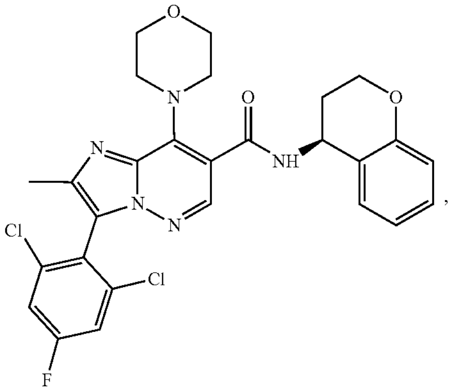
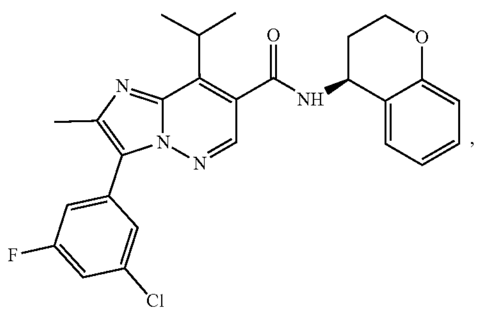 [SMILES: Cc1nc2c(C(C)C)c(C(=O)N[C@H]3CCOc4ccccc43)cnn2c1-c1cc(F)cc(F)c1 ; "."]

-continued
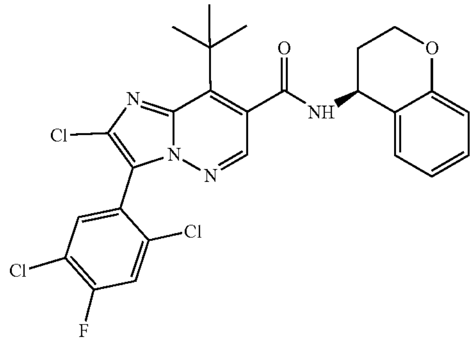
,
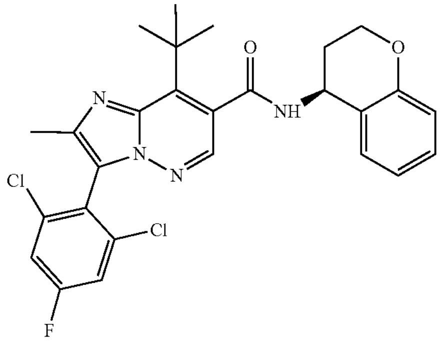
, or
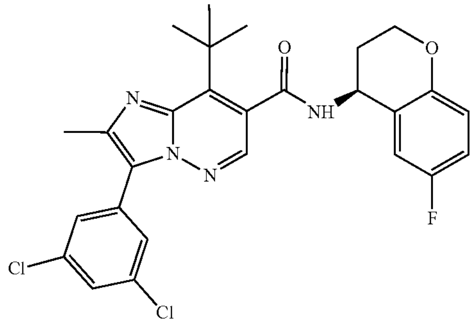
;
or a pharmaceutically acceptable salt thereof.
36. A compound of the formula
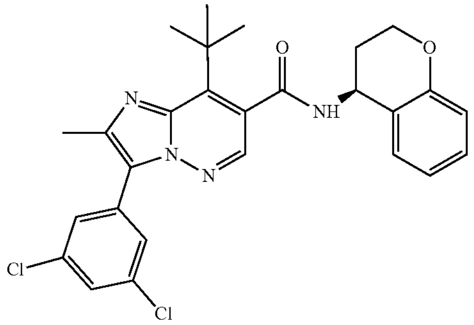
.
37. The compound according to claim 35 having the formula
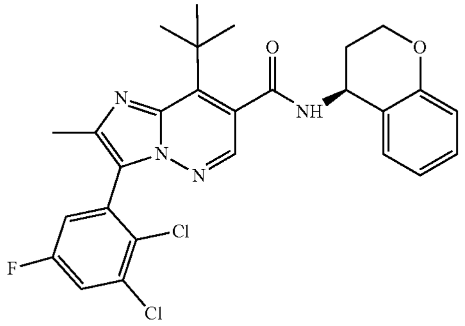
.
38. A compound of the formula
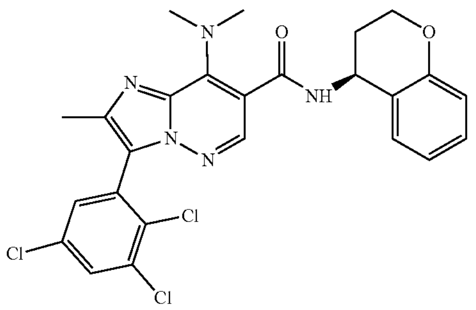
.
39. A compound of the formula
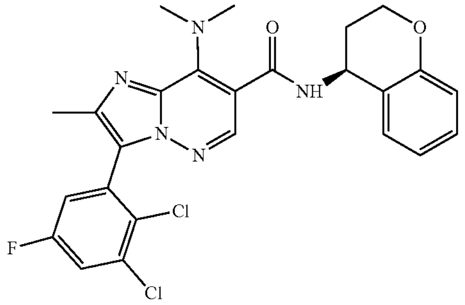
.
40. A compound of the formula
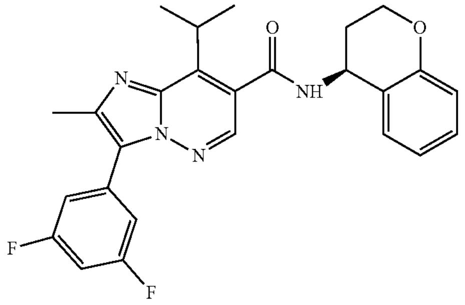
.

41. A compound of the formula
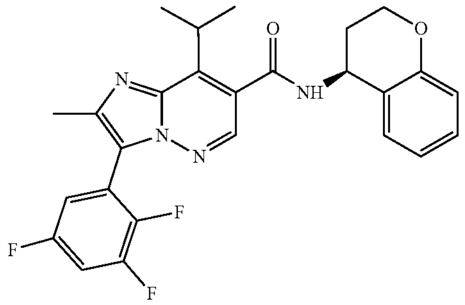
.
* * * * *

UNITED STATES PATENT AND TRADEMARK OFFICE

CERTIFICATE OF CORRECTION

PATENT NO. : 11,964,977 B2
APPLICATION NO. : 17/324288
DATED : April 23, 2024
INVENTOR(S) : Hannes Fiepko Koolman, Bart Herlé and Alan Long It is certified that error appears in the above-identified patent and that said Letters Patent is hereby corrected as shown below:

In the Specification

Column 31, Line 45, please correct formula " 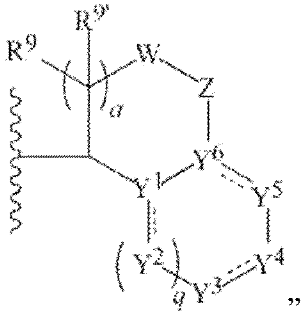 " to formula

-- 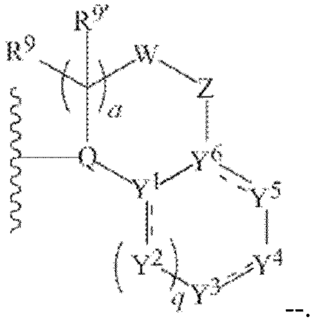 --.

Signed and Sealed this
Twenty-sixth Day of November, 2024

Katherine Kelly Vidal
*Director of the United States Patent and Trademark Office*

Column 37, Line 50, please correct formula “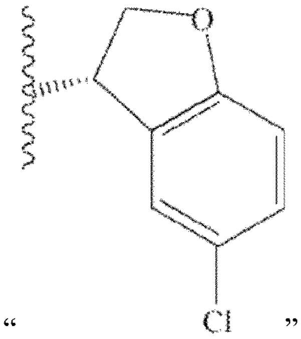” to formula
-- 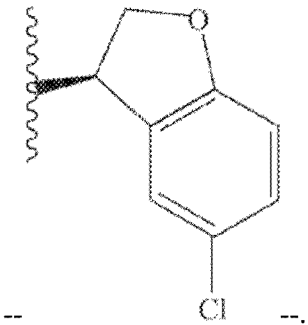 --.
Column 200, Line 50, “$C_a$-$C_6$haloalkylthio” should read --$C_1$-$C_6$-haloalkylthio--.
Column 203, Line 5, please correct “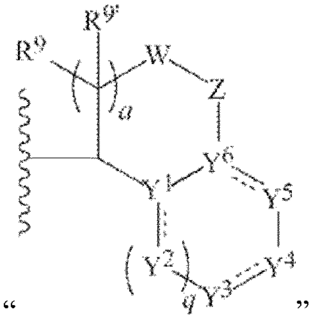” to -- 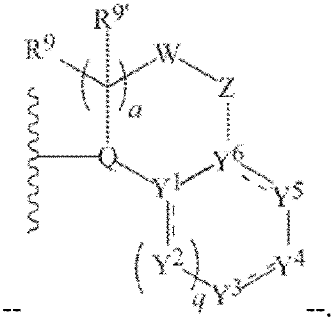 --.
Column 203, Line 10, “represents the following groups:” should read --represents one of the following Ring Systems:--.
Column 204, Line 60, please correct “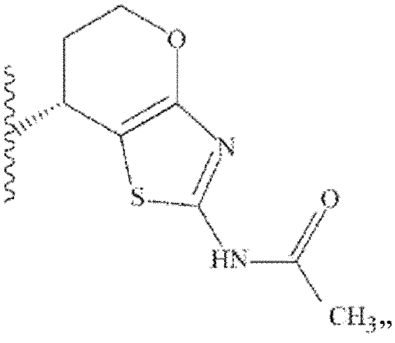” to --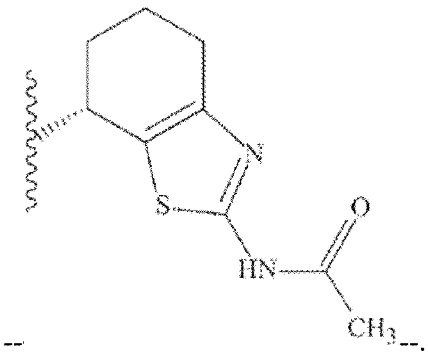--.

Column 209, Line 9, please insert --or-- after the ";" following the chemical structure of Ring System AZ; Column 209, Line 17, please insert the text --or is hydrogen;-- in the next line after the chemical structure of Ring System AAA.

Column 209, Lines 18-25, and Lines 30-37, please twice cancel the text:

Formula (I)

"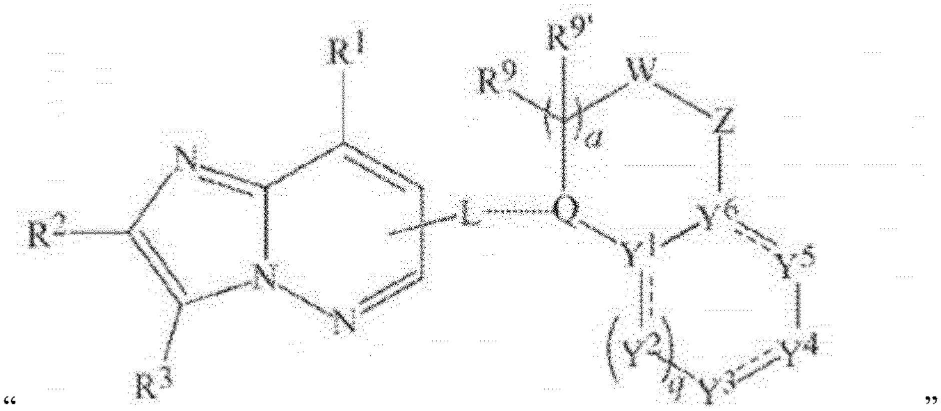".

Column 209, Line 43, the following text in the first line of the table:

"R3 R2 R3" should be changed to:

--$R^1$ $R^2$ $R^3$--.

Column 210, Line 60, please correct "CN" to --cyano--.

Column 213, Line 35, in the table entry for compound A461 "A" should read --A, or--.